US009828339B2

(12) United States Patent
Kim et al.

(10) Patent No.: US 9,828,339 B2
(45) Date of Patent: Nov. 28, 2017

(54) BIPHENYL DERIVATIVES AND METHODS FOR PREPARING SAME

(71) Applicant: DONG-A ST CO., LTD, Seoul (KR)

(72) Inventors: Soon-Hoe Kim, Gyeonggi-do (KR); Weon-Bin Im, Gyeonggi-do (KR); Chong-Hwan Cho, Gyeonggi-do (KR); Sun-Ho Choi, Seoul (KR); Jung-Sang Park, Gyeonggi-do (KR); Mi-Yeon Kim, Gyeonggi-do (KR); Sung-Hak Choi, Gyeonggi-do (KR); Min-Jung Lee, Gyeonggi-do (KR); Kang-Hun Cho, Gyeonggi-do (KR)

(73) Assignee: DONG-A ST CO., LTD, Seoul (KR)

( * ) Notice: Subject to any disclaimer, the term of this patent is extended or adjusted under 35 U.S.C. 154(b) by 0 days.

(21) Appl. No.: 14/909,096

(22) PCT Filed: Jul. 17, 2014

(86) PCT No.: PCT/KR2014/006483
§ 371 (c)(1),
(2) Date: Jan. 29, 2016

(87) PCT Pub. No.: WO2015/016511
PCT Pub. Date: Feb. 5, 2015

(65) Prior Publication Data
US 2016/0176816 A1  Jun. 23, 2016

(30) Foreign Application Priority Data

Jul. 30, 2013 (KR) .................. 10-2013-0090175

(51) Int. Cl.
*C07D 207/08* (2006.01)

(52) U.S. Cl.
CPC .................. *C07D 207/08* (2013.01)

(58) Field of Classification Search
CPC .................................................. C07D 207/08
See application file for complete search history.

(56) References Cited

U.S. PATENT DOCUMENTS

| | | | |
|---|---|---|---|
| 2008/0249127 A1 | 10/2008 | Laine et al. | 214/304 |
| 2010/0105658 A1 | 4/2010 | Nagashima et al. | 514/214.03 |
| 2014/0017345 A1 | 1/2014 | Kim et al. | 424/725 |
| 2014/0044817 A1 | 2/2014 | Kim et al. | 424/773 |
| 2015/0374641 A1 | 12/2015 | Kim et al. | 424/484 |

FOREIGN PATENT DOCUMENTS

| | | |
|---|---|---|
| EA | 13083 B1 | 2/2010 |
| EP | 0 747 355 | 11/1996 |
| KR | 10-2006-0129017 | 12/2006 |
| RU | 2472785 | 1/2013 |
| WO | WO 01/42212 | 6/2001 |
| WO | WO 2005/067537 | 7/2005 |
| WO | WO 2006/018708 | 2/2006 |
| WO | WO 2007/034325 | 3/2007 |

(Continued)

OTHER PUBLICATIONS

Mangialasche et al., LancetNeurol. 2010; 9: p. 702-716.*
Raedler (Psychiatric Times. (2008) vol. 25 (5); p. 1-8).*
Moulton et al. (British Journal of Pharmacology (2011) 163, p. 44-52).*
U.S. Appl. No. 14/392,160, filed Dec. 23, 2015.
U.S. Appl. No. 14/907,267, filed Jan. 22, 2016.
Letter/Written Disclosure of the Information Disclosure Statement for the above-referenced application, filed herewith on Apr. 28, 2016, 2 pages.
"Darifenacin" Drugs of the Future 21: 1105-1108 (1996).
Fisher "Muscarinic agonists for the treatment of Alzheimer's disease: progress and perspectives." Exp Opin Invest Drugs 6: 1395-1411 (1997).
"Revatropate" Drugs of the Future 22: 135-137 (1997).
"Tolterodine" Drugs of the Future 22: 733-737 (1997).

(Continued)

*Primary Examiner* — Valerie Rodriguez-Garcia
(74) *Attorney, Agent, or Firm* — Dentons US LLP; Stephanie Seidman; Frank J. Miskiel

(57) ABSTRACT

Provided are biphenyl derivatives having the structure of Formula 1:

stereoisomers thereof, and pharmaceutically acceptable salts thereof, wherein $R_1$ is hydrogen, halogen, hydroxy, substituted or unsubstituted $C_1$-$C_6$ alkyl, or $C_1$-$C_6$ alkoxy; $R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$; $R_5$ is hydrogen or $C_1$-$C_6$ alkyl; n is 0 or 1; and $R_6$ is hydrogen or amino, methods for preparing the same, and a pharmaceutical composition containing the same. The biphenyl derivatives having the structure of Formula 1 act as muscarinic M3 receptor antagonists, and thus are useful for the prevention or treatment of a disease selected from among chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, and hypersalivation syndromes.

13 Claims, No Drawings

(56) References Cited

FOREIGN PATENT DOCUMENTS

WO    WO 2009/004379    1/2009

OTHER PUBLICATIONS

International Search Report and Written Opinion, dated Oct. 28, 2014, in connection with International Patent Application No. PCT/KR2014/006483 [English translation], 9 pages.
International Preliminary Report on Patentability, dated Feb. 2, 2016, in connection with International Patent Application No. PCT/KR2014/006483 [English translation], 7 pages.
Letter/Written Disclosure of the Supplemental Information Disclosure Statement for the above-referenced application, filed herewith on Jul. 13, 2017, 3 pages.
Office Action, dated Apr. 20, 2017, in connection with corresponding Russian Patent Application No. 2016106977/04 [English translation and original document in Russian], 10 pages.
Letter/Written Disclosure of the Supplemental Information Disclosure Statement for the above-referenced application, filed herewith on Jul. 21, 2017, 3 pages.
Examination Report, dated Jun. 16, 2017, in connection with corresponding New Zealand Patent Application No. 716743, 6 pages.
Letter/Written Disclosure of the Supplemental Information Disclosure Statement for the above-referenced application, filed herewith on Jun. 22, 2017, 2 pages.
Examination Report, dated Jul. 1, 2016, in connection with corresponding Australian Patent Application No. 2014297144, 3 pages.
Examiner's Report, dated Nov. 4, 2016, in connection with corresponding Canadian Patent Application No. 2,919,624, 3 pages.
Extended European Search Report, dated Dec. 8, 2016, in connection with corresponding European Patent Application No. 14831249.9, 6 pages.
Response, submitted May 2, 2017, to Examination Report, dated Jul. 1, 2016, in connection with corresponding Australian Patent Application No. 2014297144, 26 pages.
Response, submitted May 4, 2017, to Examiner's Report, dated Nov. 4, 2016, in connection with Canadian Patent Application No. 2,919,624, 59 pages.
Notice of Acceptance, dated May 25, 2017, in connection with corresponding Australian Patent Application No. 2014297144, 3 pages.

\* cited by examiner

BIPHENYL DERIVATIVES AND METHODS FOR PREPARING SAME

RELATED APPLICATIONS

This application is the U.S. National Stage of International Application. No. PCT/KR2014/006483, filed 17 Jul. 2014, which claims benefit of priority to Korean Patent Application KR 10-2013-0090175, filed 30 Jul. 2013, the specification of which is incorporated by reference herein.

TECHNICAL FIELD

The present invention relates to novel muscarinic M3 receptor antagonists, and more particularly, to novel biphenyl derivatives having muscarinic M3 receptor antagonist activity, or isomers thereof, pharmaceutically acceptable salts thereof, or hydrates thereof, methods for preparing the same, and a pharmaceutical composition containing the same as an active ingredient.

BACKGROUND ART

Muscarinic receptors are found in all parts of the human body, including the brain and salivary glands. Such receptors are members of G-protein coupled receptors, and are further divided into five subtypes (M1 to M5). Among these subtypes, M1, M2 and M3 receptors are extensively found in tissues of animal and human, and their pharmacological properties have been elucidated. Muscarinic M1 receptor is expressed mainly in cerebral cortex, and is involved in the regulation of higher cognitive functions. The M2 receptor is found mainly in heart and bladder smooth muscles, and is involved in regulation of heart rate. It is known that the M3 receptor is extensively expressed in many peripheral tissues and is involved in stimulation of the gastrointestinal tract and the urinary tract, and salivation. The M4 and M5 receptors are found in the brain, and the M4 receptor is mainly involved in movement, but the role of the M5 receptor remains obscure.

Generally, it was found that muscarinic receptor antagonists are useful for the treatment of various diseases, for example, chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, and hyper-salivation syndromes (Invest. Drugs, 1997, 6 (10), 1395-1411, Drugs Future, 1997, 22 (2) 135-137, Drugs Future, 1996, 21 (11), 1105-1108, Drugs Future, 1997, 22 (7), 733-737).

Meanwhile, it is known that, among the muscarinic receptors, the M2 and M3 receptors are predominant in human bladder and play a role in the regulation of bladder contraction. The M2 receptor is present in the bladder in an amount that is at least three times larger than the M3 receptor, and it plays a role in inhibiting bladder relaxation by beta-receptor rather than being involved directly in bladder contraction. Thus, the M3 receptor appears to play the most important role in bladder contraction. Therefore, selective antagonists against the M3 receptor exhibit excellent inhibitory effects against muscarinic bladder contraction, but inhibit salivary secretion to cause dry mouth.

Accordingly, the present inventors have prepared novel derivatives that can exhibit functional activity by their selective binding to the muscarinic M3 receptor and have minimized side effects, thereby completing the present invention.

DISCLOSURE

Technical Problem

It is an object of the present invention to provide novel biphenyl derivatives or pharmaceutically acceptable salts thereof.

Another object of the present invention is to provide methods for preparing novel biphenyl derivatives or pharmaceutically acceptable salts thereof.

Still another object of the present invention is to provide a muscarinic M3 receptor antagonist containing novel biphenyl derivatives, pharmaceutically acceptable salts thereof, or hydrates thereof as an active ingredient.

Technical Solution

The present invention provides novel biphenyl derivatives or pharmaceutically acceptable salts thereof.

The present invention also provides methods for preparing novel biphenyl derivatives or pharmaceutically acceptable salts thereof.

The present invention also provides muscarinic M3 receptor antagonists containing novel biphenyl derivatives, pharmaceutically acceptable salts thereof, or hydrates thereof as an active ingredient.

As used herein, the term "alkyl" means a straight or branched hydrocarbon radical. For example, $C_1$-$C_6$ alkyl is an aliphatic hydrocarbon having 1 to 6 carbon atoms, and is intended to include all methyl, ethyl, propyl, n-butyl, n-pentyl, n-hexyl, isopropyl, isobutyl, sec-butyl, tert-butyl, neopentyl, isopentyl and the like.

As used herein, the term "alkoxy" means a radical wherein the hydrogen atom of a hydroxyl group is substituted with alkyl. For example, $C_1$-$C_6$ alkoxy is intended to include all methoxy, ethoxy, propoxy, n-butoxy, n-pentyloxy, isopropoxy, sec-butoxy, tert-butoxy, neopentyloxy, isopentyloxy and the like.

Novel Biphenyl Derivatives

The present invention provides novel biphenyl derivatives represented by the following Formula 1, or pharmaceutically acceptable salts thereof:

[Formula 1]

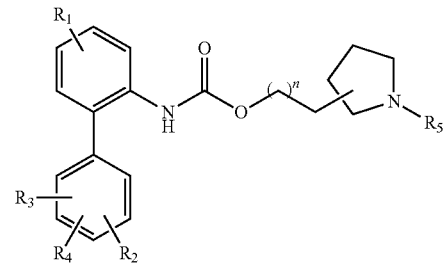

wherein:

$R_1$ is hydrogen, halogen, hydroxy, substituted or unsubstituted $C_1$-$C_6$ alkyl, or $C_1$-$C_6$ alkoxy;

$R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$;

$R_5$ is hydrogen or $C_1$-$C_6$ alkyl;
n is 0 or 1; and
$R_6$ is hydrogen or amino.

In a preferred embodiment of the present invention, $R_1$ in Formula 1 may be hydrogen or halogen; $R_2$, $R_3$ and $R_4$ may each independently be hydrogen, halogen, or $C_1$-$C_6$ alkyl; and $R_5$ may be $C_1$-$C_6$ alkyl.

In another preferred embodiment of the present invention, $R_1$ in Formula 1 may be hydrogen; $R_2$, $R_3$ and $R_4$ may each independently be hydrogen or halogen; $R_5$ may be $C_1$-$C_6$ alkyl; and n may be 0 or 1.

In the present invention, the pharmaceutically acceptable salts are preferably acid addition salts formed with pharmaceutically acceptable free acids. Free acids that may be used in the present invention include organic acids and inorganic acids. The inorganic acids include hydrochloric acid, hydrobromic acid, sulfuric acid, phosphoric acid, etc, and the organic acids include citric acid, acetic acid, lactic acid, maleic acid, coumaric acid, gluconic acid, methanesulfonic acid, glycolic acid, succinic acid, 4-toluenesulfonic acid, trifluoroacetic acid, galacturonic acid, embonic acid, glutamic acid, aspartic acid, etc.

In addition, the compounds of Formula 1 or pharmaceutically acceptable salts thereof can show polymorphism, and can also exist as solvates (e.g., hydrates, etc.). Furthermore, the compounds of the present invention can also exist as individual stereoisomers or mixtures of stereoisomers.

The present invention is also directed to novel biphenyl derivatives selected from the group consisting of the following compounds:
1) 2-(1-methylpyrrolidin-2-yl)ethyl(4'-fluoro-[1,1'-biphenyl]-2-yl)carbamate;
2) 2-(1-methylpyrrolidin-2-yl)ethyl(3',5'-difluoro-[1,1'-biphenyl]-2-yl)carbamate;
3) 2-(1-methylpyrrolidin-2-yl)ethyl(3',4',5'-trifluoro-[1,1'-biphenyl]-2-yl)carbamate;
4) 2-(1-methylpyrrolidin-2-yl)ethyl(3'-fluoro-[1,1'-biphenyl]-2-yl)carbamate;
5) 2-(1-methylpyrrolidin-2-yl)ethyl(4'-methoxy-[1,1'-biphenyl]-2-yl)carbamate;
6) 2-(1-methylpyrrolidin-2-yl)ethyl[1,1'-biphenyl]-2-ylcarbamate;
7) 2-(1-methylpyrrolidin-2-yl)ethyl(4'-chloro-[1,1'-biphenyl]-2-yl)carbamate;
8) 2-(1-methylpyrrolidin-2-yl)ethyl(3'-chloro-[1,1'-biphenyl]-2-yl)carbamate;
9) 2-(1-methylpyrrolidin-2-yl)ethyl(3',5'-dichloro-[1,1'-biphenyl]-2-yl)carbamate;
10) 2-(1-methylpyrrolidin-2-yl)ethyl(4'-trifluoromethoxy-[1,1'-biphenyl]-2-yl)carbamate;
11) 2-(1-methylpyrrolidin-2-yl)ethyl(4'-nitro-[1,1'-biphenyl]-2-yl)carbamate;
12) 2-(1-methylpyrrolidin-2-yl)ethyl(3'-trifluoromethyl-[1,1'-biphenyl]-2-yl)carbamate;
13) 2-(1-methylpyrrolidin-2-yl)ethyl(4'-trifluoromethyl-[1,1'-biphenyl]-2-yl)carbamate;
14) 2-(1-methylpyrrolidin-2-yl)ethyl((3'-fluoro-4'-methyl)-[1,1'-biphenyl]-2-yl)carbamate;
15) 2-(1-methylpyrrolidin-2-yl)ethyl(3'-methyl-[1,1'-biphenyl]-2-yl)carbamate;
16) 2-(1-methylpyrrolidin-2-yl)ethyl(3'-ethoxy-[1,1'-biphenyl]-2-yl)carbamate;
17) 2-(1-methylpyrrolidin-2-yl)ethyl(3'-chloro-5-fluoro-[1,1'-biphenyl]-2-yl)carbamate;
18) 2-(1-methylpyrrolidin-2-yl)ethyl(3',5-difluoro-[1,1'-biphenyl]-2-yl)carbamate;
19) 2-(1-methylpyrrolidin-2-yl)ethyl(4',5-difluoro-[1,1'-biphenyl]-2-yl)carbamate;
20) 2-(1-methylpyrrolidin-2-yl)ethyl(3',5,5'-trifluoro-[1,1'-biphenyl]-2-yl)carbamate;
21) 2-(1-methylpyrrolidin-2-yl)ethyl(5-fluoro-[1,1'-biphenyl]-2-yl)carbamate;
22) 2-(1-methylpyrrolidin-2-yl)ethyl(5-fluoro-3'-methyl-[1,1'-biphenyl]-2-yl)carbamate;
23) 2-(1-methylpyrrolidin-2-yl)ethyl(4-fluoro-[1,1'-biphenyl]-2-yl)carbamate;
24) 2-(1-methylpyrrolidin-2-yl)ethyl(3',4-difluoro-[1,1'-biphenyl]-2-yl)carbamate;
25) 2-(1-methylpyrrolidin-2-yl)ethyl(4-methoxy-[1,1'-biphenyl]-2-yl)carbamate;
26) 2-(1-methylpyrrolidin-2-yl)ethyl(5-methyl-[1,1'-biphenyl]-2-yl)carbamate;
27) 2-(1-methylpyrrolidin-2-yl)ethyl(3'-fluoro-5-methyl-[1,1'-biphenyl]-2-yl)carbamate;
28) 2-(1-methylpyrrolidin-2-yl)ethyl(4'-cyano-[1,1'-biphenyl]-2-yl)carbamate;
29) 2-(1-methylpyrrolidin-2-yl)ethyl(3'-(3-hydroxypropyl)-[1,1'-biphenyl]-2-yl)carbamate;
30) 2-(1-methylpyrrolidin-2-yl)ethyl(4'-(dimethylamino)-[1,1'-biphenyl]-2-yl)carbamate;
31) 2-(1-methylpyrrolidin-2-yl)ethyl(4'-(tert-butyl)-[1,1'-biphenyl]-2-yl)carbamate;
32) 2-(1-methylpyrrolidin-2-yl)ethyl(2'-amino-[1,1'-biphenyl]-2-yl)carbamate;
33) 2-(1-methylpyrrolidin-2-yl)ethyl(3'-amino-[1,1'-biphenyl]-2-yl)carbamate;
34) 2-(1-methylpyrrolidin-2-yl)ethyl(2'-fluoro-[1,1'-biphenyl]-2-yl)carbamate;
35) 2-(1-methylpyrrolidin-2-yl)ethyl(2'-chloro-[1,1'-biphenyl]-2-yl)carbamate;
36) 2-(1-methylpyrrolidin-2-yl)ethyl(2'-hydroxy-[1,1'-biphenyl]-2-yl)carbamate;
37) 2-(1-methylpyrrolidin-2-yl)ethyl(3'-tert-butyl-5'-methyl-[1,1'-biphenyl]-2-yl)carbamate;
38) 2-(1-methylpyrrolidin-2-yl)ethyl(4'-fluoro-3'-(trifluoromethyl)-[1,1'-biphenyl]-2-yl)carbamate;
39) 2-(1-methylpyrrolidin-2-yl)ethyl(4'-amino-3'-chloro-[1,1'-biphenyl]-2-yl)carbamate;
40) 2-(1-methylpyrrolidin-2-yl)ethyl(3'-hydroxy-[1,1'-biphenyl]-2-yl)carbamate;
41) 2-(1-methylpyrrolidin-2-yl)ethyl(3'-chloro-4'-fluoro-[1,1'-biphenyl]-2-yl)carbamate;
42) 2-(1-methylpyrrolidin-2-yl)ethyl(3',4',5-trifluoro-[1,1'-biphenyl]-2-yl)carbamate;
43) 2-(1-methylpyrrolidin-2-yl)ethyl(3',4'-dichloro-5-fluoro-[1,1'-biphenyl]-2-yl)carbamate;
44) 2-(1-methylpyrrolidin-2-yl)ethyl(3'-ethyl-5-fluoro-[1,1'-biphenyl]-2-yl)carbamate;
45) 2-(1-methylpyrrolidin-2-yl)ethyl(5-fluoro-3',5'-dimethyl-[1,1'-biphenyl]-2-yl)carbamate;
46) 2-(1-methylpyrrolidin-2-yl)ethyl(3'-amino-5-fluoro-[1,1'-biphenyl]-2-yl)carbamate;
47) 2-(1-methylpyrrolidin-2-yl)ethyl(5-(trifluoro-methyl)-[1,1'-biphenyl]-2-yl)carbamate;
48) 2-(1-methylpyrrolidin-2-yl)ethyl(4'-fluoro-5-(trifluoromethyl)-[1,1'-biphenyl]-2-yl)carbamate;
49) 2-(1-methylpyrrolidin-2-yl)ethyl(3'-fluoro-5-(trifluoromethyl)-[1,1'-biphenyl]-2-yl)carbamate;
50) 2-(1-methylpyrrolidin-2-yl)ethyl(3',5'-difluoro-5-(trifluoromethyl)-[1,1'-biphenyl]-2-yl)carbamate;
51) 2-(1-methylpyrrolidin-2-yl)ethyl(3'-chloro-5-(trifluoromethyl)-[1,1'-biphenyl]-2-yl)carbamate;

52) 2-(1-methylpyrrolidin-2-yl)ethyl(3'-chloro-5,5'-difluoro-[1,1'-biphenyl]-2-yl)carbamate;
53) 2-(1-methylpyrrolidin-2-yl)ethyl(3'-chloro-4',5-difluoro-[1,1'-biphenyl]-2-yl)carbamate;
54) 2-(1-methylpyrrolidin-2-yl)ethyl(4'-chloro-3',5-difluoro-[1,1'-biphenyl]-2-yl)carbamate;
55) 2-(1-methylpyrrolidin-2-yl)ethyl(3',5'-dichloro-5-fluoro-[1,1'-biphenyl]-2-yl)carbamate;
56) 2-(1-methylpyrrolidin-2-yl)ethyl(3',5-dichloro-4',5-difluoro-[1,1'-biphenyl]-2-yl)carbamate;
57) 2-(1-methylpyrrolidin-2-yl)ethyl(3'-chloro-5-fluoro-5'-hydroxy-[1,1'-biphenyl]-2-yl)carbamate;
58) 2-(1-methylpyrrolidin-2-yl)ethyl(3'-chloro-5-fluoro-4'-hydroxy-[1,1'-biphenyl]-2-yl)carbamate;
59) 2-(1-methylpyrrolidin-2-yl)ethyl(5-fluoro-3',4'-dimethyl-[1,1'-biphenyl]-2-yl)carbamate;
60) 2-(1-methylpyrrolidin-2-yl)ethyl(5-methoxy-[1,1'-biphenyl]-2-yl)carbamate;
61) 2-(1-methylpyrrolidin-2-yl)ethyl(3'-fluoro-5-methoxy-[1,1'-biphenyl]-2-yl)carbamate;
62) 2-(1-methylpyrrolidin-2-yl)ethyl(3',5'-difluoro-5-methoxy-[1,1'-biphenyl]-2-yl)carbamate;
63) 2-(1-methylpyrrolidin-2-yl)ethyl(3'-chloro-5-methoxy-[1,1'-biphenyl]-2-yl)carbamate;
64) 2-(1-methylpyrrolidin-2-yl)ethyl(3',5'-dichloro-5-methoxy-[1,1'-biphenyl]-2-yl)carbamate;
65) 2-(1-methylpyrrolidin-2-yl)ethyl(3'-chloro-4'-fluoro-5-methoxy-[1,1'-biphenyl]-2-yl)carbamate;
66) 2-(1-methylpyrrolidin-2-yl)ethyl(5-chloro-[1,1'-biphenyl]-2-yl)carbamate;
67) 2-(1-methylpyrrolidin-2-yl)ethyl(5-chloro-3'-fluoro-[1,1'-biphenyl]-2-yl)carbamate;
68) 2-(1-methylpyrrolidin-2-yl)ethyl(5-chloro-4'-fluoro-[1,1'-biphenyl]-2-yl)carbamate;
69) 2-(1-methylpyrrolidin-2-yl)ethyl(5-chloro-3',5'-difluoro-[1,1'-biphenyl]-2-yl)carbamate;
70) 2-(1-methylpyrrolidin-2-yl)ethyl(3',5-dichloro-[1,1'-biphenyl]-2-yl)carbamate;
71) 2-(1-methylpyrrolidin-2-yl)ethyl(3',5,5'-trichloro-[1,1'-biphenyl]-2-yl)carbamate;
72) 2-(1-methylpyrrolidin-2-yl)ethyl(3',5-dichloro-5'-fluoro-[1,1'-biphenyl]-2-yl)carbamate;
73) 2-(1-methylpyrrolidin-2-yl)ethyl(3',5-dichloro-4'-fluoro-[1,1'-biphenyl]-2-yl)carbamate;
74) (R)-(1-methylpyrrolidin-3-yl)methyl(3'-fluoro-4'-formyl-[1,1'-biphenyl]-2-yl)carbamate;
75) 2-(1-methylpyrrolidin-2-yl)ethyl(3',5'-difluoro-5-hydroxy-[1,1'-biphenyl]-2-yl)carbamate;
76) 2-(1-methylpyrrolidin-2-yl)ethyl(3',5'-dichloro-5-hydroxy-[1,1'-biphenyl]-2-yl)carbamate;
77) 2-(1-methylpyrrolidin-2-yl)ethyl(3'-chloro-4'-fluoro-5-hydroxy-[1,1'-biphenyl]-2-yl)carbamate;
78) (R)-pyrrolidin-3-ylmethyl[1,1'-biphenyl]-2-ylcarbamate;
79) (S)-pyrrolidin-3-ylmethyl[1,1'-biphenyl]-2-ylcarbamate;
80) (R)-pyrrolidin-3-ylmethyl(3',5'-difluoro-[1,1'-biphenyl]-2-yl)carbamate;
81) (S)-pyrrolidin-3-ylmethyl(3',5'-difluoro-[1,1'-biphenyl]-2-yl)carbamate;
82) (S)-pyrrolidin-3-ylmethyl(5-fluoro-[1,1'-biphenyl]-2-yl)carbamate;
83) (S)-pyrrolidin-3-ylmethyl(5-fluoro-3'-methyl-[1,1'-biphenyl]-2-yl)carbamate;
84) (R)-pyrrolidin-3-ylmethyl(3',5,5'-trifluoro-[1,1'-biphenyl]-2-yl)carbamate;
85) (S)-pyrrolidin-3-ylmethyl(3',5,5'-trifluoro-[1,1'-biphenyl]-2-yl)carbamate;
86) (R)-pyrrolidin-3-ylmethyl(5-methyl-[1,1'-biphenyl]-2-yl)carbamate;
87) (R)-pyrrolidin-3-ylmethyl(3'-fluoro-5-methyl-[1,1'-biphenyl]-2-yl)carbamate;
88) (S)-pyrrolidin-2-ylmethyl(4'-fluoro-[1,1'-biphenyl]-2-yl)carbamate;
89) (R)-(1-methylpyrrolidin-3-yl)methyl[1,1'-biphenyl]-2-ylcarbamate;
90) (S)-(1-methylpyrrolidin-3-yl)methyl[1,1'-biphenyl]-2-ylcarbamate;
91) (R)-(1-methylpyrrolidin-3-yl)methyl(3',5'-difluoro-[1,1'-biphenyl]-2-yl)carbamate;
92) (S)-(1-methylpyrrolidin-3-yl)methyl(3',5'-difluoro-[1,1'-biphenyl]-2-yl)carbamate;
93) (S)-(1-methylpyrrolidin-3-yl)methyl(5-fluoro-[1,1'-biphenyl]-2-yl)carbamate;
94) (S)-(1-methylpyrrolidin-3-yl)methyl(5-fluoro-3'-methyl-[1,1'-biphenyl]-2-yl)carbamate;
95) (R)-(1-methylpyrrolidin-3-yl)methyl(3',5,5'-trifluoro-[1,1'-biphenyl]-2-yl)carbamate;
96) (S)-(1-methylpyrrolidin-3-yl)methyl(3',5,5'-trifluoro-[1,1'-biphenyl]-2-yl)carbamate;
97) (R)-(1-methylpyrrolidin-3-yl)methyl(5-methyl-[1,1'-biphenyl]-2-yl)carbamate;
98) (R)-(1-methylpyrrolidin-3-yl)methyl(3'-fluoro-5-methyl-[1,1'-biphenyl]-2-yl)carbamate;
99) (S)-(1-methylpyrrolidin-2-yl)methyl(4'-fluoro-[1,1'-biphenyl]-2-yl)carbamate;
100) (R)-(1-methylpyrrolidin-3-yl)methyl(3'-methyl-[1,1'-biphenyl]-2-yl)carbamate;
101) (S)-(1-methylpyrrolidin-3-yl)methyl(3'-methyl-[1,1'-biphenyl]-2-yl)carbamate;
102) (R)-(1-ethylpyrrolidin-3-yl)methyl[1,1'-biphenyl]-2-ylcarbamate;
103) (S)-(1-ethylpyrrolidin-3-yl)methyl[1,1'-biphenyl]-2-ylcarbamate;
104) (R)-(1-ethylpyrrolidin-3-yl)methyl(3'-methyl-[1,1'-biphenyl]-2-yl)carbamate;
105) (S)-(1-ethylpyrrolidin-3-yl)methyl(3'-methyl-[1,1'-biphenyl]-2-yl)carbamate;
106) (S)-(1-ethylpyrrolidin-2-yl)methyl[1,1'-biphenyl]-2-ylcarbamate;
107) (S)-(1-isobutylpyrrolidin-2-yl)methyl[1,1'-biphenyl]-2-ylcarbamate;
108) (S)-(1-methylpyrrolidin-3-yl)methyl(3',5-difluoro-[1,1'-biphenyl]-2-yl)carbamate;
109) (R)-(1-methylpyrrolidin-2-yl)methyl[1,1'-biphenyl]-2-ylcarbamate;
110) (R)-(1-methylpyrrolidin-2-yl)methyl(3'-methyl-[1,1'-biphenyl]-2-yl)carbamate;
111) (R)-(1-methylpyrrolidin-2-yl)methyl(5-fluoro-3'-methyl-[1,1'-biphenyl]-2-yl)carbamate;
112) (S)-(1-isopropylpyrrolidin-2-yl)methyl[1,1'-biphenyl]-2-ylcarbamate;
113) (R)-(1-methylpyrrolidin-3-yl)methyl(3'-fluoro-[1,1'-biphenyl]-2-yl)carbamate;
114) (R)-(1-methylpyrrolidin-3-yl)methyl(4'-fluoro-[1,1'-biphenyl]-2-yl)carbamate;
115) (R)-(1-methylpyrrolidin-3-yl)methyl(3',4'-difluoro-[1,1'-biphenyl]-2-yl)carbamate;
116) (S)-(1-methylpyrrolidin-3-yl)methyl(3'-fluoro-[1,1'-biphenyl]-2-yl)carbamate;
117) (R)-(1-methylpyrrolidin-3-yl)methyl(3'-chloro-[1,1'-biphenyl]-2-yl)carbamate;

118) (S)-(1-methylpyrrolidin-3-yl)methyl(3'-chloro-[1,1'-biphenyl]-2-yl)carbamate;
119) (S)-(1-methylpyrrolidin-3-yl)methyl(3',5'-dichloro-[1,1'-biphenyl]-2-yl)carbamate;
120) (S)-(1-methylpyrrolidin-3-yl)methyl(3'-chloro-5'-fluoro-[1,1'-biphenyl]-2-yl)carbamate;
121) (S)-(1-methylpyrrolidin-3-yl)methyl(3'-chloro-4'-fluoro-[1,1'-biphenyl]-2-yl)carbamate;
122) (S)-(1-methylpyrrolidin-3-yl)methyl(5-fluoro-3',5'-dimethyl-[1,1'-biphenyl]-2-yl)carbamate;
123) (S)-(1-methylpyrrolidin-3-yl)methyl(3'-chloro-5-fluoro-5'-hydroxy-[1,1'-biphenyl]-2-yl)carbamate;
124) (S)-(1-methylpyrrolidin-3-yl)methyl(4',5-difluoro-[1,1'-biphenyl]-2-yl)carbamate;
125) (S)-(1-methylpyrrolidin-3-yl)methyl(3'-chloro-5-fluoro-[1,1'-biphenyl]-2-yl)carbamate;
126) (S)-(1-methylpyrrolidin-3-yl)methyl(3',5'-dichloro-5-fluoro-[1,1'-biphenyl]-2-yl)carbamate;
127) (S)-(1-methylpyrrolidin-3-yl)methyl(4'-chloro-5-fluoro-[1,1'-biphenyl]-2-yl)carbamate;
128) (S)-(1-methylpyrrolidin-3-yl)methyl(3',4'-dichloro-5-fluoro-[1,1'-biphenyl]-2-yl)carbamate;
129) (S)-(1-methylpyrrolidin-3-yl)methyl(3'-chloro-5,5'-difluoro-[1,1'-biphenyl]-2-yl)carbamate;
130) (R)-(1-methylpyrrolidin-3-yl)methyl(3',4'-dichloro-[1,1'-biphenyl]-2-yl)carbamate;
131) (R)-(1-methylpyrrolidin-3-yl)methyl(3',5'-dichloro-[1,1'-biphenyl]-2-yl)carbamate;
132) (R)-(1-methylpyrrolidin-3-yl)methyl(3'-chloro-5'-fluoro-[1,1'-biphenyl]-2-yl)carbamate;
133) (R)-(1-methylpyrrolidin-3-yl)methyl(5-fluoro-3'-amino-[1,1'-biphenyl]-2-yl)carbamate;
134) (R)-(1-methylpyrrolidin-3-yl)methyl(3'-chloro-5-fluoro-5'-hydroxy-[1,1'-biphenyl]-2-yl)carbamate;
135) (R)-(1-methylpyrrolidin-3-yl)methyl(3',5'-dichloro-5-fluoro-[1,1'-biphenyl]-2-yl)carbamate;
136) (R)-(1-methylpyrrolidin-3-yl)methyl(3'-chloro-4'-fluoro-[1,1'-biphenyl]-2-yl)carbamate;
137) (R)-(1-methylpyrrolidin-3-yl)methyl(3'-hydroxy-[1,1'-biphenyl]-2-yl)carbamate;
138) (R)-(1-methylpyrrolidin-3-yl)methyl(3'-chloro-5'-(trifluoromethyl)-[1,1'-biphenyl]-2-yl)carbamate;
139) (R)-(1-methylpyrrolidin-3-yl)methyl(3'-chloro-5-fluoro-5'-methoxy-[1,1'-biphenyl]-2-yl)carbamate;
140) (R)-(1-methylpyrrolidin-3-yl)methyl(3'-chloro-5-fluoro-5'-(trifluoromethyl)-[1,1'-biphenyl]-2-yl)carbamate;
141) (R)-(1-methylpyrrolidin-3-yl)methyl(4',5-difluoro-[1,1'-biphenyl]-2-yl)carbamate;
142) (R)-(1-methylpyrrolidin-3-yl)methyl(3'-chloro-5,5'-difluoro-[1,1'-biphenyl]-2-yl)carbamate;
143) (R)-(1-methylpyrrolidin-3-yl)methyl(3'-chloro-4',5-dlfluoro-[1,1'-biphenyl]-2-yl)carbamate;
144) (R)-(1-methylpyrrolidin-3-yl)methyl(2',5-difluoro-[1,1'-biphenyl]-2-yl)carbamate;
145) (R)-(1-methylpyrrolidin-3-yl)methyl(3',5-dichloro-[1,1'-biphenyl]-2-yl)carbamate;
146) (R)-(1-methylpyrrolidin-3-yl)methyl(3',5-dichloro-4'-fluoro-[1,1'-biphenyl]-2-yl)carbamate;
147) (R)-(1-methylpyrrolidin-3-yl)methyl(3'-chloro-4'-fluoro-5-methoxy-[1,1'-biphenyl]-2-yl)carbamate;
148) (S)-(1-methylpyrrolidin-2-yl)methyl(3'-chloro-5'-fluoro-[1,1'-biphenyl]-2-yl)carbamate;
149) (S)-(1-methylpyrrolidin-2-yl)methyl(3'-chloro-4'-fluoro-[1,1'-biphenyl]-2-yl)carbamate;
150) (R)-(1-ethylpyrrolidin-3-yl)methyl(3'-chloro-4'-fluoro-[1,1'-biphenyl]-2-yl)carbamate;
151) (R)-(1-isopropylpyrrolidin-3-yl)methyl(3'-chloro-4'-fluoro-[1,1'-biphenyl]-2-yl)carbamate;
152) (R)-(1-methylpyrrolidin-3-yl)methyl(3'-(hydroxymethyl)-[1,1'-biphenyl]-2-yl)carbamate;
153) (R)-(1-methylpyrrolidin-3-yl)methyl(3'-carbamoyl-[1,1'-biphenyl]-2-yl)carbamate;
154) (R)-(1-methylpyrrolidin-3-yl)methyl(3'-amino-[1,1'-biphenyl]-2-yl)carbamate;
155) (R)-(1-methylpyrrolidin-3-yl)methyl(3'-cyano-[1,1'-biphenyl]-2-yl)carbamate;
156) (R)-(1-methylpyrrolidin-3-yl)methyl(2'-fluoro-[1,1'-biphenyl]-2-yl)carbamate;
157) (R)-(1-methylpyrrolidin-3-yl)methyl(2',4'-difluoro-[1,1'-biphenyl]-2-yl)carbamate;
158) (R)-(1-methylpyrrolidin-3-yl)methyl(2',3'-difluoro-[1,1'-biphenyl]-2-yl)carbamate;
159) (R)-(1-methylpyrrolidin-3-yl)methyl(3'-chloro-6'-fluoro-[1,1'-biphenyl]-2-yl)carbamate;
160) (S)-(1-methylpyrrolidin-2-yl)methyl(3'-fluoro-[1,1'-biphenyl]-2-yl)carbamate;
161) (S)-(1-methylpyrrolidin-2-yl)methyl(3',5'-difluoro-[1,1'-biphenyl]-2-yl)carbamate;
162) (S)-(1-methylpyrrolidin-2-yl)methyl(3',4'-difluoro-[1,1'-biphenyl]-2-yl)carbamate;
163) (S)-(1-methylpyrrolidin-2-yl)methyl(2',4',5'-trifluoro-[1,1'-biphenyl]-2-yl)carbamate;
164) (S)-(1-methylpyrrolidin-2-yl)methyl(4'-chloro-[1,1'-biphenyl]-2-yl)carbamate;
165) (S)-(1-methylpyrrolidin-2-yl)methyl(3'-chloro-[1,1'-biphenyl]-2-yl)carbamate;
166) (S)-(1-methylpyrrolidin-2-yl)methyl(3',4'-dichloro-[1,1'-biphenyl]-2-yl)carbamate;
167) (S)-(1-methylpyrrolidin-2-yl)methyl(2',4'-dichloro-[1,1'-biphenyl]-2-yl)carbamate;
168) (S)-(1-methylpyrrolidin-2-yl)methyl(3'-hydroxy-[1,1'-biphenyl]-2-yl)carbamate;
169) (S)-(1-methylpyrrolidin-2-yl)methyl(3'-cyano-[1,1'-biphenyl]-2-yl)carbamate;
170) (S)-(1-methylpyrrolidin-2-yl)methyl(3'-amino-[1,1'-biphenyl]-2-yl)carbamate;
171) (S)-(1-methylpyrrolidin-2-yl)methyl(3',4',5-trifluoro-[1,1'-biphenyl]-2-yl)carbamate;
172) (S)-(1-methylpyrrolidin-2-yl)methyl(3',5,5'-trifluoro-[1,1'-biphenyl]-2-yl)carbamate;
173) (S)-(1-methylpyrrolidin-2-yl)methyl(2',4',5,5'-tetrafluoro-[1,1'-biphenyl]-2-yl)carbamate;
174) (S)-(1-methylpyrrolidin-2-yl)methyl(3'-chloro-5-fluoro-[1,1'-biphenyl]-2-yl)carbamate;
175) (S)-(1-methylpyrrolidin-2-yl)methyl(4'-chloro-5-fluoro-[1,1'-biphenyl]-2-yl)carbamate;
176) (S)-(1-methylpyrrolidin-2-yl)methyl(2',4'-dichloro-5-fluoro-[1,1'-biphenyl]-2-yl)carbamate;
177) (S)-(1-methylpyrrolidin-2-yl)methyl(3',4'-dichloro-5-fluoro-[1,1'-biphenyl]-2-yl)carbamate;
178) (S)-(1-methylpyrrolidin-2-yl)methyl(3'-cyano-5-fluoro-[1,1'-biphenyl]-2-yl)carbamate;
179) (S)-(1-methylpyrrolidin-2-yl)methyl(3'-hydroxy-5-fluoro-[1,1'-biphenyl]-2-yl)carbamate;
180) (S)-(1-methylpyrrolidin-2-yl)methyl(5-fluoro-3'-(trifluoromethyl)-[1,1'-biphenyl]-2-yl)carbamate;
181) (S)-(1-methylpyrrolidin-2-yl)methyl(3'-chloro-4,4',5-trifluoro-[1,1'-biphenyl]-2-yl)carbamate;
182) (R)-(1-methylpyrrolidin-2-yl)methyl(3'-chloro-4,5-difluoro-[1,1'-biphenyl]-2-yl)carbamate;
183) 2-(1-methylpyrrolidin-2-yl)ethyl(2',4'-difluoro-[1,1'-biphenyl]-2-yl)carbamate;

184) 2-(1-methylpyrrolidin-2-yl)ethyl(2',3'-difluoro-[1,1'-biphenyl]-2-yl)carbamate;
185) 2-(1-methylpyrrolidin-2-yl)ethyl(2',6'-difluoro-[1,1'-biphenyl]-2-yl)carbamate;
186) 2-(1-methylpyrrolidin-2-yl)ethyl(5'-chloro-2'-fluoro-[1,1'-biphenyl]-2-yl)carbamate;
187) (S)-(1-methylpyrrolidin-2-yl)methyl(2'-fluoro-[1,1'-biphenyl]-2-yl)carbamate;
188) (S)-(1-methylpyrrolidin-2-yl)methyl(2',4'-difluoro-[1,1'-biphenyl]-2-yl)carbamate;
189) (S)-(1-methylpyrrolidin-2-yl)methyl(2',3'-difluoro-[1,1'-biphenyl]-2-yl)carbamate;
190) (S)-(1-methylpyrrolidin-2-yl)methyl(3'-chloro-6'-fluoro-[1,1'-biphenyl]-2-yl)carbamate;
191) (R)-(1-methylpyrrolidin-3-yl)methyl(3',5'-dimethyl-[1,1'-biphenyl]-2-yl)carbamate;
192) (R)-(1-methylpyrrolidin-3-yl)methyl(5-fluoro-3'-methyl-[1,1'-biphenyl]-2-yl)carbamate;
193) (R)-(1-methylpyrrolidin-3-yl)methyl(5-fluoro-3',5'-dimethyl-[1,1'-biphenyl]-2-yl)carbamate;
194) (R)-(1-methylpyrrolidin-3-yl)methyl(3',5-difluoro-[1,1'-biphenyl]-2-yl)carbamate;
195) (R)-(1-methylpyrrolidin-3-yl)methyl(3'-chloro-5-fluoro-[1,1'-biphenyl]-2-yl)carbamate;
196) (R)-(1-ethylpyrrolidin-3-yl)methyl(3'-chloro-4',5-difluoro-[1,1'-biphenyl]-2-yl)carbamate;
197) (S)-(1-methylpyrrolidin-2-yl)methyl[1,1'-biphenyl]-2-ylcarbamate;
198) (S)-(1-methylpyrrolidin-2-yl)methyl(4'-fluoro-[1,1'-biphenyl]-2-yl)carbamate;
199) (S)-(1-methylpyrrolidin-2-yl)methyl(3'-methyl-[1,1'-biphenyl]-2-yl)carbamate;
200) (S)-(1-methylpyrrolidin-2-yl)methyl(5-fluoro-[1,1'-biphenyl]-2-yl)carbamate;
201) (S)-(1-methylpyrrolidin-2-yl)methyl(5-fluoro-3'-methyl-[1,1'-biphenyl]-2-yl)carbamate;
202) (S)-(1-methylpyrrolidin-2-yl)methyl(3',5-difluoro-[1,1'-biphenyl]-2-yl)carbamate;
203) (S)-(1-methylpyrrolidin-2-yl)methyl(4',5-difluoro-[1,1'-biphenyl]-2-yl)carbamate;
204) (S)-(1-methylpyrrolidin-2-yl)methyl(4-fluoro-[1,1'-biphenyl]-2-yl)carbamate;
205) (S)-(1-methylpyrrolidin-2-yl)methyl(3',4-difluoro-[1,1'-biphenyl]-2-yl)carbamate;
206) (S)-(1-methylpyrrolidin-2-yl)methyl(5-methyl-[1,1'-biphenyl]-2-yl)carbamate;
207) (S)-(1-methylpyrrolidin-2-yl)methyl(3'-fluoro-5-methyl-[1,1'-biphenyl]-2-yl)carbamate;
208) (S)-(1-methylpyrrolidin-2-yl)methyl(5-fluoro-3',5'-dimethyl-[1,1'-biphenyl]-2-yl)carbamate;
209) (S)-(1-methylpyrrolidin-2-yl)methyl(4'-(tert-butyl)-5-fluoro-[1,1'-biphenyl]-2-yl)carbamate;
210) (S)-(1-methylpyrrolidin-2-yl)methyl(3'-chloro-5,5'-difluoro-[1,1'-biphenyl]-2-yl)carbamate;
211) (S)-(1-methylpyrrolidin-2-yl)methyl(3'-chloro-4',5-difluoro-[1,1'-biphenyl]-2-yl)carbamate;
212) (S)-(1-methylpyrrolidin-2-yl)methyl(4'-chloro-3',5-difluoro-[1,1'-biphenyl]-2-yl)carbamate;
213) (S)-(1-methylpyrrolidin-2-yl)methyl(3'-amino-5-fluoro-[1,1'-biphenyl]-2-yl)carbamate;
214) (S)-(1-methylpyrrolidin-2-yl)methyl(2',5-difluoro-3'-(trifluoromethyl)-[1,1'-biphenyl]-2-yl)carbamate;
215) (S)-(1-methylpyrrolidin-2-yl)methyl(3'-chloro-5-fluoro-5'-(trifluoromethyl)-[1,1'-biphenyl]-2-yl)carbamate;
216) (S)-(1-methylpyrrolidin-2-yl)methyl(3'-chloro-5-fluoro-5'-hydroxy-[1,1'-biphenyl]-2-yl)carbamate;
217) (S)-(1-methylpyrrolidin-2-yl)methyl(3'-chloro-5-fluoro-5'-methoxy-[1,1'-biphenyl]-2-yl)carbamate;
218) (S)-(1-methylpyrrolidin-2-yl)methyl(5-fluoro-2',4'-bis(trifluoromethyl)-[1,1'-biphenyl]-2-yl)carbamate;
219) (S)-(1-methylpyrrolidin-2-yl)methyl(3'-ethoxy-5-fluoro-[1,1'-biphenyl]-2-yl)carbamate;
220) (S)-(1-methylpyrrolidin-2-yl)methyl(5-fluoro-3',4'-dimethoxy-[1,1'-biphenyl]-2-yl)carbamate;
221) (S)-(1-methylpyrrolidin-2-yl)methyl(5-fluoro-3',5'-dimethoxy-[1,1'-biphenyl]-2-yl)carbamate;
222) (S)-(1-methylpyrrolidin-2-yl)methyl(5-methoxy-[1,1'-biphenyl]-2-yl)carbamate;
223) (S)-(1-methylpyrrolidin-2-yl)methyl(3'-fluoro-5-methoxy-[1,1'-biphenyl]-2-yl)carbamate;
224) (S)-(1-methylpyrrolidin-2-yl)methyl(3'-chloro-5-methoxy-[1,1'-biphenyl]-2-yl)carbamate;
225) (S)-(1-methylpyrrolidin-2-yl)methyl(3',4'-dichloro-5-methoxy-[1,1'-biphenyl]-2-yl)carbamate; and
226) (S)-(1-methylpyrrolidin-2-yl)methyl(3',5'-dichloro-5-methoxy-[1,1'-biphenyl]-2-yl)carbamate.

Methods for Preparation of Novel Biphenyl Derivatives

The present invention provides methods for preparing the compounds of formula 1 or pharmaceutically acceptable salts thereof (Preparation Methods 1 to 4).

Preparation Method 1

The method for preparing the compounds of formula 1 or pharmaceutically acceptable salts thereof according to the present invention may comprise a step of reacting a compound of the following formula 2 with a compound of the following formula 3 in the presence of a carbamate synthesis reagent:

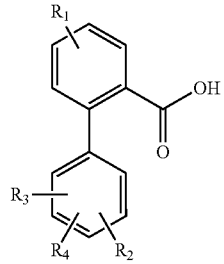

[Formula 2]

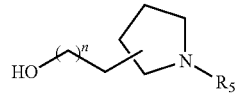

[Formula 3]

wherein $R_1$ to $R_5$ and n are the same as defined in formula 1.

The carbamate synthesis reagent preferably comprises an azide compound. Specifically, the carbamate synthesis reagent that is used in the present invention may be a mixture of diphenylphosphoryl azide (DPPA) and triethylamine, a mixture of propylphosphonic anhydride (T3P), trimethylsilyl azide (TMSN$_3$) and triethylamine, a mixture of sodium azide (NaN$_3$), tetrabutylammonium bromide and zinc(II) triflate, or the like.

In addition, the carbamate synthesis reaction may be performed at a temperature between 100° C. and 120° C. for 4 to 12 hours.

Preparation Method 2

In addition, the method for preparing the compounds of formula 1 or pharmaceutically acceptable salts thereof according to the present invention may comprise the steps of: reacting a compound of the following formula 2 with a compound of the following formula 3a in the presence of a carbamate synthesis reagent to prepare a compound of the following formula 4; removing an amine protecting group from the compound of formula 4 to prepare a compound of the following formula 1a; and introducing an $R_5$ substituent into the compound of formula 1a:

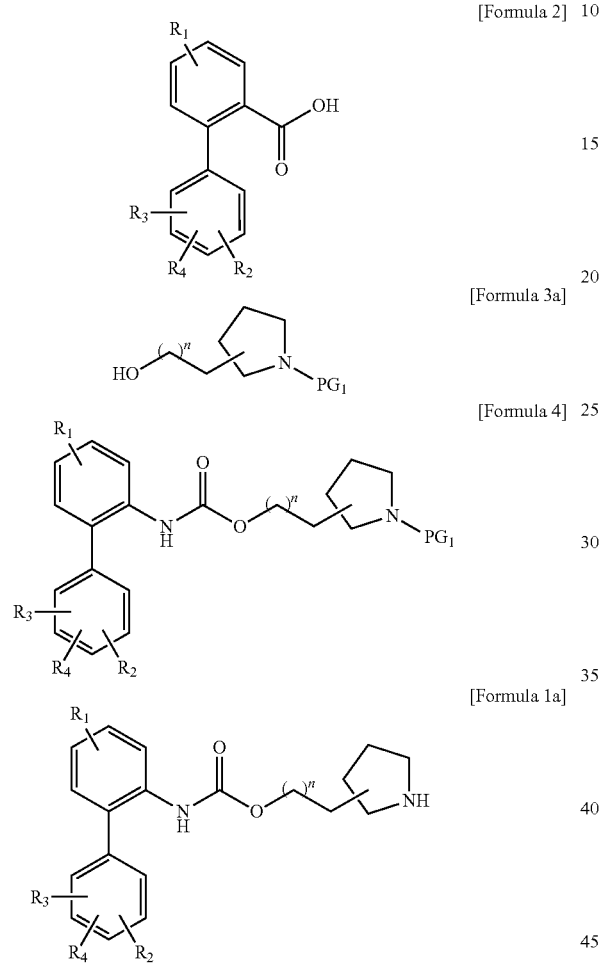

[Formula 2]

[Formula 3a]

[Formula 4]

[Formula 1a]

wherein $R_1$ to $R_4$ and n are the same as defined in formula 1, and $PG_1$ is an amine protecting group which may be selected from the group consisting of Boc (tert-butyloxycarbonyl), benzyl, tert-butyl, PMB (4-methoxybenzyl), Fmoc (fluorenylmethyloxycarbonyl), Ts (tosylate), MOM (methoxymethyl), THP (tetrahydropyranyl), TBDMS (tert-butyldimethylsilyl), and TBDPS (tert-butyldimethylsilyl).

The carbamate synthesis reagent and the reaction conditions are the same as described above for preparation method 1.

In addition, palladium-carbon (Pd—C), a strong acid such as trifluoroacetic acid, sulfuric acid, hydrobromic acid or the like; or a base such as piperidine; ammonium cerium (IV) nitrate; tetra-n-butyl ammonium fluoride or the like may be used in the reaction of removing amine protecting group. The reaction may be carried out at room temperature for 3 to 12 hours.

In addition, the reaction of introducing the $R_5$ substituent may be carried out using formaldehyde solution, acetic acid and zinc, or may be carried out using alkyl halide, potassium carbonate, potassium iodide or triethylamine. Water or dimethylformamide may be used as a solvent. The reaction may be performed at room temperature to 120° C. for 5-12 hours.

Meanwhile, the compound of formula 2 can be prepared by a method comprising the steps of: reacting a compound of the following formula 5 in the presence of an acid to prepare a compound of the following formula 6, which has a carboxylic acid protecting group introduced therein; coupling the compound of formula 6 with a compound of the following formula 7 to prepare a compound of the following formula 8; and de-esterifying the compound of formula 8 in the presence of a base:

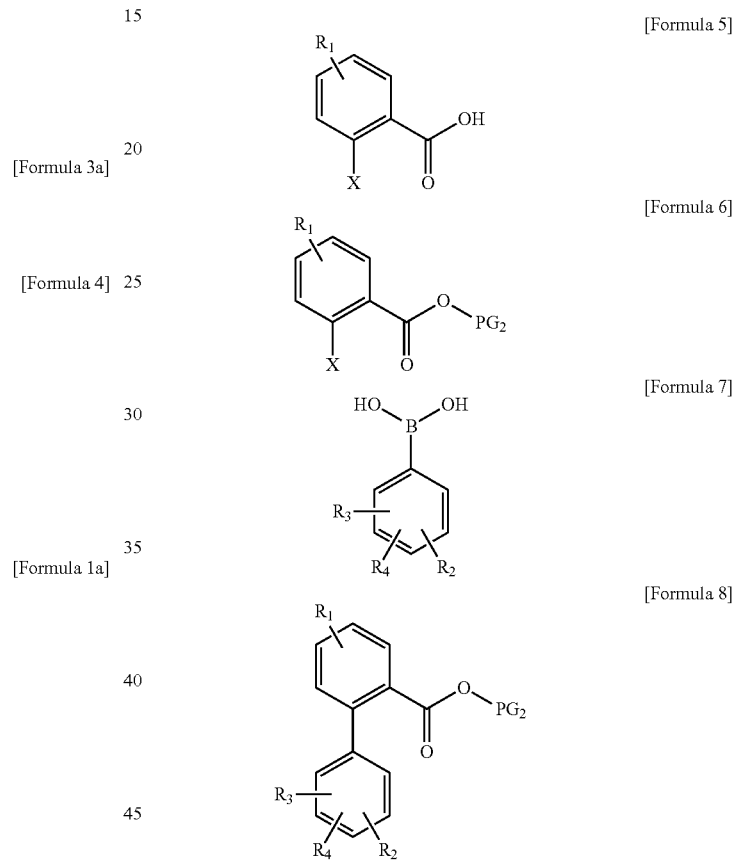

[Formula 5]

[Formula 6]

[Formula 7]

[Formula 8]

wherein $R_1$ to $R_5$ and n are the same as defined in formula 1; X is halogen; and $PG_2$ is a protecting group that may be selected from the group consisting of a $C_1$-$C_4$ alkyl group, benzyl, PMB (4-methoxybenzyl), THP (tetrahydropyranyl), TBDMS (tert-butyldimethylsilyl), and TBDPS (tert-butyldiphenylsilyl).

In the reaction of introducing the carboxylic acid protecting group, thionyl chloride or sulfuric acid is preferably used as the acid, and ethanol or methanol may be used as a solvent. The reaction may be performed at a temperature between 80° C. and 100° C. for 4 to 24 hours.

In addition, the base that is used in the coupling reaction is preferably selected from among potassium carbonate and sodium carbonate. A catalyst that is used in the coupling reaction may be tetrakistriphenylphosphine palladium or dichlorobistriphenylphosphine palladium, and a solvent that is used in the coupling reaction may be toluene, a mixture of toluene and ethanol, a mixture of ethanol and water, a mixture of acetonitrile and water, or the like. Furthermore, the coupling reaction may be performed at a temperature between 100° C. and 120° C. for 10 minutes to 12 hours.

Furthermore, the base that is used in the de-esterification reaction is preferably selected from among sodium hydroxide and potassium hydroxide, and a solvent that is used in the de-esterification reaction may be ethanol or a mixture of ethanol and water. The de-esterification reaction may be performed at a temperature between 100° C. and 120° C. for 2 to 12 hours.

Preparation Method 3

In addition, the method for preparing the compounds of formula 1 or pharmaceutically acceptable salts thereof according to the present invention may comprise the steps of: reacting a compound of the following formula 5 with a compound of the following formula 3 in the presence of a carbamate synthesis reagent to prepare a compound of the following formula 9; and coupling a compound of the following formula 7 to the compound of formula 9:

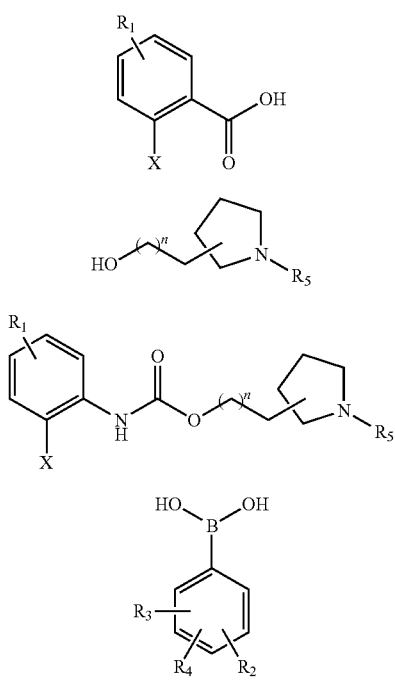

[Formula 5]

[Formula 3]

[Formula 9]

[Formula 7]

wherein $R_1$ to $R_5$ and n are the same as defined in formula 1, and X is halogen.

The carbamate synthesis reagent and the reaction conditions are the same as described above for preparation method 1.

In addition, the coupling reaction reagents and the reaction conditions are the same as described above for preparation method 2.

Preparation Method 4

In addition, the method for preparing the compounds of formula 1 or pharmaceutically acceptable salts thereof according to the present invention may comprise the steps of: reacting a compound of the following formula 5 with a compound of the following formula 3a in the presence of a carbamate synthesis reagent to prepare a compound of the following formula 9a; deprotecting the compound of formula 9a to obtain a compound of the following formula 9b; introducing an $R_5$ substituent into the compound of the formula 9b to prepare a compound of the following formula 9; and coupling a compound of the following formula 7 to the compound of formula 9:

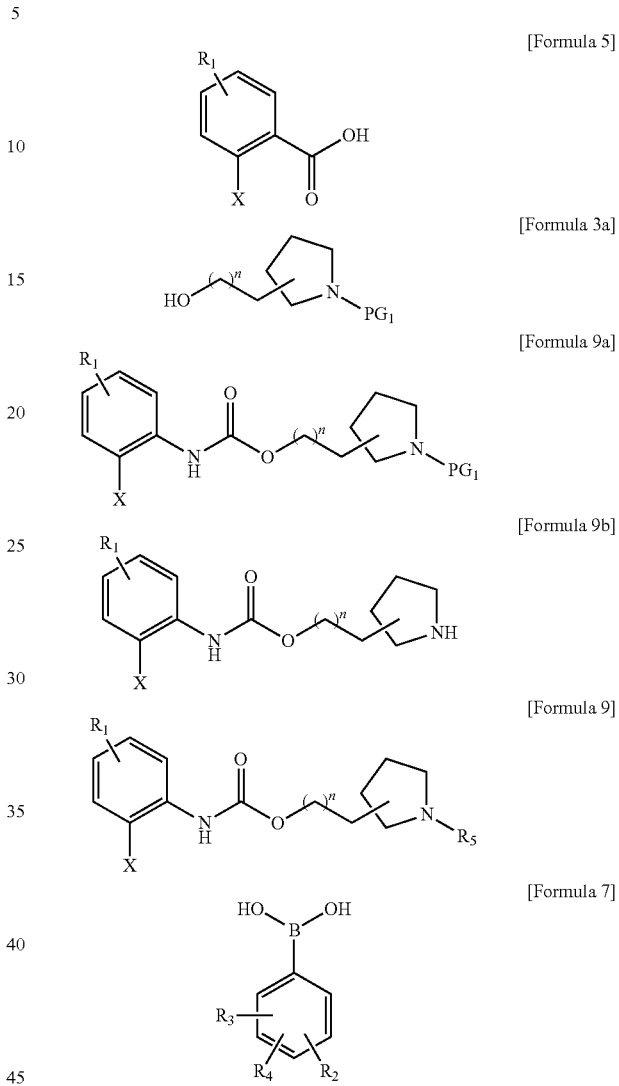

[Formula 5]

[Formula 3a]

[Formula 9a]

[Formula 9b]

[Formula 9]

[Formula 7]

wherein $R_1$ to $R_5$ and n are the same as defined in formula 1; X is halogen; and $PG_1$ is the same as defined in preparation method 2.

The carbamate synthesis reagent and the reaction conditions are as described above for preparation method 1.

In addition, the deprotection reaction, the reaction of introducing the $R_5$ substituent and the coupling reaction are as described above for preparation method 2.

Pharmaceutical Composition Containing Novel Biphenyl Derivatives

The present invention provides a muscarinic M3 receptor antagonist containing the compound of formula 1, an isomer thereof, a pharmaceutically acceptable salt thereof, or a hydrate thereof as an active ingredient.

In the present invention, the muscarinic M3 receptor antagonist may be a composition for the prevention or treatment of a disease selected from the group consisting of chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, and hyper-salivation syndromes.

In the present invention, the muscarinic M3 receptor antagonist may contain, in addition to the compound of formula 1 or a pharmaceutically acceptable salt thereof, one or more active ingredients showing a function equal or similar to the compound of formula 1 or a pharmaceutically acceptable salt thereof.

For administration, the composition of the present invention may further comprise at least one pharmaceutically acceptable carrier. The pharmaceutically acceptable carrier that is used in the composition of the present invention may be physiological saline, sterile water, Ringer's solution, buffered saline, dextrose solution, maltodextrin solution, glycerol, ethanol, or a mixture of one or more thereof. If necessary, other conventional additives such as antioxidants, buffers or bacteriostatic agents may be added to the composition of the present invention. In addition, diluents, dispersants, surfactants, binders and lubricants may further be added to the composition to formulate injectable formulations such as aqueous solutions, suspensions or emulsions, pills, capsules, granules or tablets. Furthermore, the composition of the present invention may preferably be formulated depending on particular diseases or their components, using a suitable method known in the art or the method described in Remington's Pharmaceutical Science, Merck Publishing Company, Easton Pa.

In addition, when the muscarinic M3 receptor antagonist of the present invention is for oral administration, the compound of formula 1 or a pharmaceutically acceptable salt thereof may be contained in an amount of 1-95 wt %, preferably 1-70 wt %, based on the total weight of the M3 receptor antagonist.

The pharmaceutical composition of the present invention may be administered orally or may be administered parenterally in the form of injectable solutions, suppositories, transdermal agents, inhalation agents or intravesical agents.

The present invention also provides a method for treating or alleviating a disease related to the activity on muscarinic M3 receptor, the method comprising administering a muscarinic M3 receptor antagonist containing the compound of formula 1 or a pharmaceutically acceptable salt as an active ingredient to mammals including humans in need of muscarinic M3 receptor antagonist activity.

The muscarinic M3 receptor antagonist of the present invention may be used alone or in combination with surgery, hormone therapy, drug therapy and a biological response modifier in order to prevent or treat a disease related to the activity on muscarinic M3 receptor.

Method for Prevention or Treatment of Muscarinic M3 Receptor-Related Diseases

The present invention also provides a method for preventing or treating a muscarinic M3 receptor-related disease, for example, a disease selected from among chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, and hyper-salivation syndromes, the method comprising administering to subjects in need thereof a composition containing, as an active ingredient, the compound of formula 1, or an isomer thereof, a pharmaceutically acceptable salt thereof, or a hydrate thereof.

The composition that is used in the preventing or treating method of the present invention includes the pharmaceutical composition as described herein.

In addition, the subjects in need of the preventing or treating method of the present invention include mammals, particularly humans.

Advantageous Effects

The biphenyl derivatives according to the present invention have affinity and selectivity for the muscarinic M3 receptor and less toxic. Thus, these biphenyl derivatives can be used as agents for preventing or treating various diseases, particularly urinary system diseases such as enuresis, nervous pollakiuria, neurogenic bladder, unstable bladder, chronic cystitis, cystospasm, urinary incontinence, or frequent urination, respiratory system diseases such as chronic obstructive pulmonary disease, chronic bronchitis, asthma, or rhinitis, and digestive diseases such as irritable bowel syndrome, spastic colitis or diverticulitis, in which the muscarinic M3 receptor is involved.

Particularly, because the biphenyl derivatives of the present invention have high selectivity for the muscarinic M2 receptor and the muscarinic M3 receptor that is present in smooth muscles, gland tissues and the like, these biphenyl derivatives are M3 receptor antagonists having less side effects, and thus are very useful as agents for preventing or treating urinary incontinence, frequent urination, chronic bronchitis, chronic obstructive pulmonary disease, asthma, rhinitis, and the like.

EXAMPLES

The present disclosure will be described more fully hereinafter with reference to the accompanying synthesis examples, examples and experimental examples. However, the Examples according to the present invention can be modified in various ways, and the scope of the present invention should not be interpreted as being limited to the following Examples. The Examples of the present invention are provided so that those skilled in the art can sufficiently understand the present invention.

Furthermore, agents stated hereinafter were purchased from Aldrich Korea, Acros, Lancaster, TCI unless otherwise specified. $^1$H NMR used herein was Varian 400 MHz, and Microwave oven used herein was Monowave 300 of Anton Paar company.

[Synthesis Example 1] Synthesis of 4'-fluoro-[1,1'-biphenyl]-2-carboxylic acid

[Step 1] Synthesis of ethyl-2-bromobenzoate

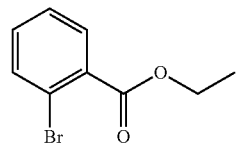

2-Bromobenzoic acid (5 g, 24.87 mmol) was dissolved in ethanol (100 mL). Sulfuric acid (5 mL) was added thereto and stirred under reflux for 24 hours. After reaction was terminated, the reactant was cooled to room temperature. The solvent was removed by concentrating the reactant under reduced pressure, and extracted with water and ethyl acetate. The organic layer was dried with anhydrous magnesium sulfate, filtered and concentrated. The resulting residue was purified with column chromatography to prepare the titled compound (4.9 g, 86%).

[Step 2] Synthesis of ethyl 4'-fluoro-[1,1'-biphenyl]-2-carboxylate

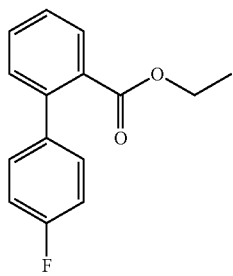 [SMILES: CCOC(=O)c1ccccc1-c1ccc(F)cc1]

Ethyl-2-bromobenzoate (1 g, 4.37 mmol) prepared in Step 1 was dissolved in a mixed solution of toluene (20 mL) and ethanol (4 mL), and then 4-fluorophenyl boronic acid (672 mg, 4.80 mmol), potassium carbonate (1.21 g, 8.73 mmol) and tetrakis triphenylphosphine palladium (504 mg, 0.44 mmol) were added thereto. The reactant was stirred at 100° C. for 6 hours, cooled to room temperature and filtered through celite. The solvent was removed by concentrating the reactant under reduced pressure. The same was extracted with water and ethyl acetate. The organic layer was dried with anhydrous magnesium sulfate, filtered and concentrated. The resulting residue was purified with column chromatography to prepare the titled compound (948 mg, 89%).

[Step 3] Synthesis of 4'-fluoro-[1,1'-biphenyl]-2-carboxylic acid

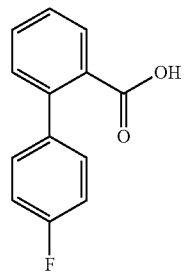 [SMILES: O=C(O)c1ccccc1-c1ccc(F)cc1]

Ethyl 4'-fluoro-[1,1'-biphenyl]-2-carboxylate (948 mg, 3.33 mmol) prepared in Step 2 was dissolved in ethanol (20 mL). 2N-sodium hydroxide solution (5.82 mL, 11.64 mmol) was added thereto and stirred under reflux for 12 hours. The reactant was cooled to room temperature. The solvent was removed by concentrating the reactant under reduced pressure. The same was extracted with 1N-hydrochloric acid and dichloromethane. The organic layer was dried with anhydrous magnesium sulfate, filtered and concentrated to prepare the titled compound (747 mg, 89%).

Synthesis Examples 2-15

2-Bromobenzoic acid as a starting material and reacting materials in Table 1 were used to prepare compounds of Synthesis Examples 2-15 in the same manner as Synthesis Example 1.

TABLE 1

Synthesis Examples 1-15

| Synthesis Example | Chemical Name | Reacting Material |
|---|---|---|
| 1 | 4'-Fluoro-[1,1'-biphenyl]-2-carboxylic acid | 4-Fluorophenyl boronic acid |
| 2 | 3',5'-Difluoro-[1,1'-biphenyl]-2-carboxylic acid | 3,5-Difluorophenyl boronic acid |
| 3 | 3',4',5'-Trifluoro-[1,1'-biphenyl]-2-carboxylic acid | 3,4,5-Trifluorophenyl boronic acid |
| 4 | 3'-Fluoro-[1,1'-biphenyl]-2-carboxylic acid | 3-Fluorophenyl boronic acid |
| 5 | 4'-Methoxy-[1,1'-biphenyl]-2-carboxylic acid | 4-Methoxyphenyl boronic acid |
| 6 | 4'-Chloro-[1,1'-biphenyl]-2-carboxylic acid | 4-Chlorophenyl boronic acid |
| 7 | 3'-Chloro-[1,1'-biphenyl]-2-carboxylic acid | 3-Chlorophenyl boronic acid |
| 8 | 3',5'-Dichloro-[1,1'-biphenyl]-2-carboxylic acid | 3,5-Dichlorophenyl boronic acid |
| 9 | 4'-Trifluoromethoxy-[1,1'-biphenyl]-2-carboxylic acid | 4-Trifluoromethoxyphenyl boronic acid |
| 10 | 4'-Nitro-[1,1'-biphenyl]-2-carboxylic acid | 4-Nitrophenyl boronic acid |
| 11 | 3'-Trifluoromethyl-[1,1'-biphenyl]-2-carboxylic acid | 3-Trifluoromethylphenyl boronic acid |
| 12 | 4'-Trifluoromethyl-[1,1'-biphenyl]-2-carboxylic acid | 4-Trifluoromethylphenyl boronic acid |
| 13 | 3'-Fluoro-4'-methyl-[1,1'-biphenyl]-2-carboxylic acid | 3-Fluoro-4-methylphenyl boronic acid |
| 14 | 3'-Methyl-[1,1'-biphenyl]-2-carboxylic acid | 3-Methylphenyl boronic acid |
| 15 | 3'-Ethoxy-[1,1'-biphenyl]-2-carboxylic acid | 3-Ethoxyphenyl boronic acid |

[Synthesis Example 16] Synthesis of 3'-chloro-5-fluoro-[1,1'-biphenyl]-2-carboxylic acid

[Step 1] Ethyl 2-bromo-4-fluorobenzoate

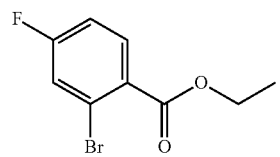

2-Bromo-4-fluorobenzoic acid (2.37 g, 10.82 mmol) was dissolved in ethanol (100 mL). Thionyl chloride (1.57 mL, 21.64 mmol) was added thereto and stirred under reflux for 24 hours. The reactant was cooled to room temperature after the reaction was terminated. The solvent was removed by concentrating the reactant under reduced pressure. The same was extracted with water and ethyl acetate. The organic layer was dried with anhydrous magnesium sulfate, filtered and concentrated. The resulting residue was purified with column chromatography to prepare the titled compound (2.29 g, 87%).

[Step 2] Ethyl 3'-chloro-5-fluoro-[1,1'-biphenyl]-2-carboxylate

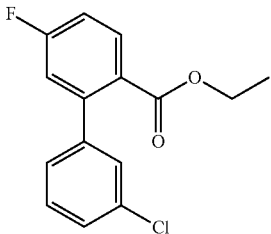 [SMILES: CCOC(=O)c1ccc(F)cc1-c1cccc(Cl)c1]

Ethyl 2-bromo-4-fluorobenzoate (1.1 g, 4.47 mmol) prepared in Step 1 was dissolved in toluene (20 mL). 3-Chlorophenyl boronic acid (766 mg, 4.90 mmol), potassium carbonate (1.23 g, 8.90 mmol) and tetrakis triphenylphosphine palladium (520 mg, 0.44 mmol) were added thereto. The reactant was stirred at 100° C. for 6 hours and cooled to room temperature. The same was filtered through celite and the solvent was removed by concentrating the reactant under reduced pressure. The same was extracted with water and ethyl acetate. The organic layer was dried with anhydrous magnesium sulfate, filtered and concentrated. The resulting residue was purified with column chromatography to prepare the titled compound (850 mg, 69%).

[Step 3] 3'-Chloro-5-fluoro-[1,1'-biphenyl]-2-carboxylic acid

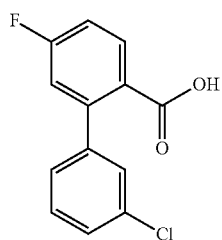 [SMILES: O=C(O)c1ccc(F)cc1-c1cccc(Cl)c1]

Ethyl 3'-chloro-5-fluoro-[1,1'-biphenyl]-2-carboxylate (850 mg, 3.05 mmol) prepared in Step 2 was dissolved in ethanol (20 mL). 2N-sodium hydroxide solution (4.57 mL, 9.15 mmol) was added thereto and stirred under reflux for 12 hours. The reactant was cooled to room temperature. The solvent was removed by concentrating the reactant under reduced pressure and extracted with 1N-hydrochloric acid and dichloromethane. The organic layer was dried with anhydrous magnesium sulfate, filtered and concentrated to prepare the titled compound (650 mg, 85%).

Synthesis Examples 17-26

The starting materials and reacting materials in Table 2 were used to prepare compounds of Synthesis Examples 17-26 in the same manner as Synthesis Example 16.

TABLE 2

Synthesis Examples 16-26

| Synthesis Example | Chemical Name | Starting Material | Reacting Material |
|---|---|---|---|
| 16 | 3'-Chloro-5-fluoro-[1,1'-biphenyl]-2-carboxylic acid | 2-Bromo-4-fluorobenzoic acid | 3-Chlorophenyl boronic acid |
| 17 | 3',5-Difluoro-[1,1'-biphenyl]-2-carboxylic acid | 2-Bromo-4-fluorobenzoic acid | 3-Fluorophenyl boronic acid |
| 18 | 4',5-Difluoro-[1,1'-biphenyl]-2-carboxylic acid | 2-Bromo-4-fluorobenzoic acid | 4-Fluorophenyl boronic acid |
| 19 | 3',5,5'-Trifluoro-[1,1'-biphenyl]-2-carboxylic acid | 2-Bromo-4-fluorobenzoic acid | 3,5-Difluorophenyl boronic acid |
| 20 | 5-Fluoro-[1,1'-biphenyl]-2-carboxylic acid | 2-Bromo-4-fluorobenzoic acid | Phenyl boronic acid |
| 21 | 5-Fluoro-3'-methyl-[1,1'-biphenyl]-2-carboxylic acid | 2-Bromo-4-fluorobenzoic acid | 3-Methylphenyl boronic acid |
| 22 | 4-Fluoro-[1,1'-biphenyl]-2-carboxylic acid | 2-Bromo-5-fluorobenzoic acid | Phenyl boronic acid |
| 23 | 3',4-Difluoro-[1,1'-biphenyl]-2-carboxylic acid | 2-Bromo-5-fluorobenzoic acid | 3-Fluorophenyl boronic acid |
| 24 | 4-Methoxy-[1,1'-biphenyl]-2-carboxylic acid | 2-Bromo-5-methoxybenzoic acid | Phenyl boronic acid |
| 25 | 5-Methyl-[1,1'-biphenyl]-2-carboxylic acid | 2-Bromo-4-methylbenzoic acid | Phenyl boronic acid |
| 26 | 3'-Fluoro-5-methyl-[1,1'-biphenyl]-2-carboxylic acid | 2-Bromo-4-methylbenzoic acid | 3-Fluorophenyl boronic acid |

[Synthesis Example A] Synthesis of 2-(1-methylpyrrolidin-2-yl)ethyl (2-iodophenyl)carbamate

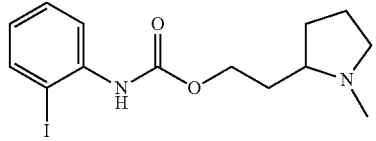 [SMILES: CN1CCCC1CCOC(=O)Nc1ccccc1I]

2-Iodobenzoic acid (1 g, 4.03 mmol) was dissolved in toluene (50 mL). Biphenylphosphoryl azide (1.04 mL, 4.84 mmol) and triethylamine (566 μL, 4.03 mmol) were added thereto. The same was stirred at room temperature for 30 minutes, and then stirred under reflux for 1 hour. The reactant was cooled to room temperature. 2-(2-Hydroxyethyl)-1-methylpyrrolidine (651 μL, 4.84 mmol) was added thereto and stirred under reflux for 12 hours. The reactant was cooled to room temperature. The solvent was removed by concentrating the reactant under reduced pressure and the same was extracted with water and ethyl acetate. The organic layer was dried with anhydrous magnesium sulfate, filtered and concentrated. The resulting residue was purified with column chromatography to prepare the titled compound (1.16 g, 77%).

Synthesis Examples B-E

The starting materials in Table 3 were used instead of 2-iodobenzoic acid to prepare compounds of Synthesis Examples B-E in the same manner as Synthesis Example A.

TABLE 3

Synthesis Examples A-E

| Synthesis Example | Chemical Name | Starting Material |
|---|---|---|
| A | 2-(1-Methylpyrrolidin-2-yl)ethyl (2-iodophenyl)-carbamate (1.16 g, 77%) | 2-Iodobenzoic acid (1 g, 4.03 mmol) |
| B | 2-(1-Methylpyrrolidin-2-yl)ethyl (2-bromo-4-fluorophenyl)carbamate (3.7 g, 94%) | 2-Bromo-4-fluoro-benzoic acid (2.5 g, 11.42 mmol) |
| C | 2-(1-Methylpyrrolidin-2-yl)ethyl (2-bromo-4-(trifluoromethyl)phenyl)-carbamate (1.72 g, 94%) | 2-Bromo-4-(trifluoromethyl)-benzoic acid (2 g, 7.43 mmol) |
| D | 2-(1-Methylpyrrolidin-2-yl)ethyl (2-bromo-4-methoxyphenyl)carbamate (2.5 g, 81%) | 2-Bromo-4-methoxy-benzoic acid (2 g, 7.43 mmol) |
| E | 2-(1-Methylpyrrolidin-2-yl)ethyl (2-bromo-4-chlorophenyl)carbamate (38 g, 99%) | 2-Bromo-4-chloro-benzoic acid (2.5 g, 10.62 mmol) |

[Synthesis Example F] Synthesis of (R)-(1-methyl-pyrrolidin-3-yl)methyl (2-bromophenyl)carbamate

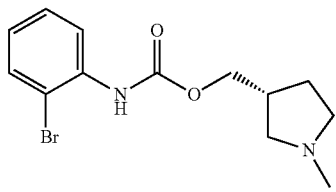 [SMILES: CN1CC[C@@H](COC(=O)Nc2ccccc2Br)C1]

[Step 1] Synthesis of (R)-tert-butyl 3-((((2-bromophenyl) carbamoyl)oxy)methyl)pyrrolidine-1-carboxylate

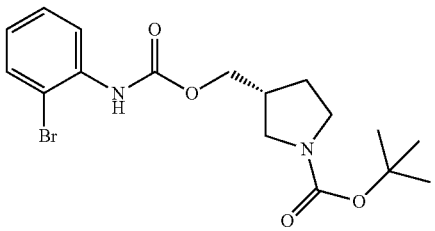 [SMILES: CC(C)(C)OC(=O)N1CC[C@@H](COC(=O)Nc2ccccc2Br)C1]

2-Bromobenzoic acid (4.5 g, 22.4 mmol) was dissolved in toluene (100 mL) and biphenylphosphoryl azide (5.8 mL, 26.9 mmol) and triethylamine (3.15 mL, 22.4 mmol) were added thereto. The same was stirred at room temperature for 30 minutes, and then stirred under reflux for 1 hour. The reactant was cooled to room temperature, (R)-tert-butyl 3-(hydroxymethyl)pyrrolidine-1-carboxylate (5.41 g, 26.9 mmol) was added thereto, and stirred under reflux for 12 hours. The reactant was cooled to room temperature. The solvent was removed by concentrating the reactant under reduced pressure. The same was extracted with water and dichloromethane. The organic layer was dried with anhydrous magnesium sulfate, filtered and concentrated. The resulting residue was purified with column chromatography to prepare the titled compound (8.1 g, 91%).

[Step 2] Synthesis of ((R)-pyrrolidin-3-ylmethyl (2-bromo-phenyl)carbamate

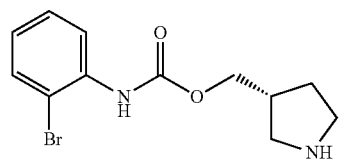 [SMILES: O=C(Nc1ccccc1Br)OC[C@@H]1CCNC1]

(R)-tert-butyl-3-((((2-bromophenyl)carbamoyl)oxy)-methyl)-pyrrolidine-1-carboxylate (8.1 g, 20.29 mmol) prepared in Step 1 was dissolved in dichloromethane (100 mL). Trifluoroacetic acid (50 mL) was added thereto and stirred at room temperature for 2 hours. The solvent was removed by concentrating the reactant under reduced pressure, and the same was extracted with 2N-sodium hydroxide solution and dichloromethane. The organic layer was dried with anhydrous magnesium sulfate, filtered and concentrated. The resulting residue was purified with column chromatography to prepare the titled compound (3.94 g, 65%).

[Step 3] Synthesis of (R)-(1-methylpyrrolidin-3-yl) methyl (2-bromophenyl)carbamate

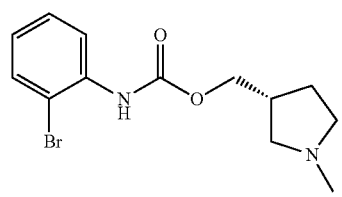 [SMILES: CN1CC[C@@H](COC(=O)Nc2ccccc2Br)C1]

(R)-pyrrolidin-3-ylmethyl(2-bromophenyl)carbamate (3.94 g, 13.13 mmol) prepared in Step 2 was dissolved in water (100 mL). Acetic acid (5 mL), formaldehyde solution (15 mL) and zinc powder (1.5 g) were sequentially added thereto and stirred at room temperature for 12 hours. The reactant was filtered, neutralized with 2N-sodium hydroxide solution and extracted with water and dichloromethane. The organic layer was dried with anhydrous magnesium sulfate, filtered and concentrated. The resulting residue was purified with column chromatography to prepare the titled compound (3.06 g, 75%).

Synthesis Examples G-L

The starting materials and reacting materials in Table 4 were used to prepare compounds of Synthesis Examples G-L in the same manner as Synthesis Example F.

TABLE 4

Synthesis Examples F-L

| Synthesis Example | Chemical Name | Starting Material | Reacting Material |
|---|---|---|---|
| F | (R)-(1-methyl-pyrrolidin-3-yl)-methyl (2-bromo-phenyl)carbamate (3.06 g, 75%) | 2-Bromobenzoic acid (4.5 g, 22.4 mmol) | (R)-tert-butyl 3-(hydroxymethyl)pyrrolidine-1-carboxylate (5.41 g, 26.9 mmol) |
| G | (S)-(1-methyl-pyrrolidin-3-yl)methyl (2-bromophenyl)-carbamate | 2-Bromobenzoic acid | (S)-tert-butyl 3-(hydroxymethyl)-pyrrolidine-1-carboxylate |
| H | (R)-(1-methyl-pyrrolidin-3-yl)methyl (2-bromo-4-fluoro-phenyl)carbamate (2.29 g, 30%) | 2-Bromo-4-fluorobenzoic acid (5 g, 22.83 mmol) | (R)-tert-butyl 3-(hydroxymethyl)-pyrrolidine-1-carboxylate (5.51 g, 27.4 mmol) |
| I | Synthesis of (S)-(1-methyl-pyrrolidin-3-yl)-methyl (2-bromo-4-fluoro-phenyl)carbamate | 2-Bromo-4-fluorobenzoic acid | (S)-tert-butyl 3-(hydroxymethyl)-pyrrolidine-1-carboxylate |
| J | (R)-(1-methylpyrrolidin-3-yl)methyl (2-bromo-4-chlorophenyl)carbamate (2.5 g, 34%) | 2-Bromo-4-chlorobenzoic acid (5 g, 21.23 mmol) | (R)-tert-butyl 3-(hydroxymethyl)pyrrolidine-1-carboxylate (5.1 g, 25.48 mmol) |
| K | (R)-(1-methyl-pyrrolidin-3-yl)-methyl (2-bromo-4-methoxy-phenyl)carbamate (2.3 g, 52%) | 2-Bromo-4-methoxybenzoic acid (3 g, 12.98 mmol) | (R)-tert-butyl 3-(hydroxymethyl)-pyrrolidine-1-carboxylate (3.9 g, 19.47 mmol) |
| L | (R)-(1-methyl-pyrrolidin-3-yl)-methyl (2-bromo-4,5-difluoro-phenyl)carbamate (884 mg, 40%) | 2-Bromo-4,5-difluorobenzoic acid (1.5 g, 6.33 mmol) | (R)-tert-butyl 3-(hydroxymethyl)-pyrrolidine-1-carboxylate (2.55 g, 12.65 mmol) |

[Synthesis Example M] Synthesis of (S)-(1-methyl-pyrrolidin-2-yl)methyl (2-bromophenyl)carbamate

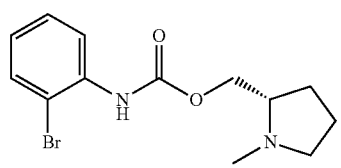 [SMILES: CN1CCC[C@H]1COC(=O)Nc1ccccc1Br]

2-Bromobenzoic acid (2 g, 9.95 mmol) was dissolved in toluene (75 mL), and then biphenylphosphoryl azide (2.57 mL, 11.94 mmol) and triethylamine (1.4 mL, 9.95 mmol) were added thereto. The same was stirred at room temperature for 30 minutes, and then stirred under reflux for 1 hour. The reactant was cooled to room temperature. (S)-(1-methylpyrrolidin-2-yl)methanol (1.42 mL, 11.94 mmol) was added thereto and stirred under reflux for 4 hours. The reactant was cooled to room temperature. The solvent was removed by concentrating the reactant under reduced pressure. The same was extracted with water and dichloromethane. The organic layer was dried with anhydrous magnesium sulfate, filtered and concentrated. The resulting residue was purified with column chromatography to prepare the titled compound (1.4 g, 45%).

Synthesis Examples N-P

The starting materials and reacting materials in Table 5 were used to prepare compounds of Synthesis Examples N-P in the same manner as Synthesis Example M.

TABLE 5

Synthesis Examples M-P

| Synthesis Example | Chemical Name | Starting Material | Reacting Material |
|---|---|---|---|
| M | (S)-(1-methyl-pyrrolidin-2-yl)methyl(2-bromophenyl)-carbamate (1.4 g, 45%) | 2-Bromobenzoic acid (2 g, 9.95 mmol) | (S)-(1-methyl-pyrrolidin-2-yl)-methanol (1.42 mL, 11.94 mmol) |
| N | (S)-(1-methyl-pyrrolidin-2-yl)methyl (2-bromo-4-fluoro-phenyl)-carbamate (2.86 g, 47%) | 2-Bromo-4-fluorobenzoic acid (4 g, 18.26 mmol) | (S)-(1-methyl-pyrrolidin-2-yl)-methanol (2.6 mL, 21.91 mmol) |

TABLE 5-continued

Synthesis Examples M-P

| Synthesis Example | Chemical Name | Starting Material | Reacting Material |
|---|---|---|---|
| O | (S)-(1-methyl-pyrrolidin-2-yl)methyl (2-bromo-4-methoxyphenyl)-carbamate (600 mg, 67%) | 2-Bromo-4-methoxybenzoic acid (600 mg, 2.60 mmol) | (S)-(1-methyl-pyrrolidin-2-yl)-methanol (463 µL, 3.90 mmol) |
| P | (S)-(1-methyl-pyrrolidin-2-yl)methyl(2-bromo-4,5-difluorophenyl)-carbamate (737 mg, 50%) | 2-Bromo-4,5-difluorobenzoic acid (1 g, 4.22 mmol) | (S)-(1-methyl-pyrrolidin-2-yl)-methanol (730 mg, 6.33 mmol) |

Example

TABLE 6

Compounds of Examples

| Example | Compound | NMR Value |
|---|---|---|
| 1 | 2-(1-Methylpyrrolidin-2-yl)-ethyl (4'-fluoro-[1,1'-biphenyl]-2-yl)carbamate | $^1$H NMR (CDCl$_3$): δ 8.10-7.99(m, 1H), 7.38-7.26(m, 3H), 7.20-7.06(m, 4H), 6.52-6.41(bs, 1H), 4.21-4.08(m, 2H), 3.12-2.99(m, 1H), 2.29(m, 3H), 2.20-1.87(m, 4H), 1.83-1.61(m, 2H), 1.61-1.40(m, 2H) |
| 2 | 2-(1-Methylpyrrolidin-2-yl)-ethyl (3',5'-difluoro-[1,1'-biphenyl]-2-yl)carbamate | $^1$H NMR (CDCl$_3$): δ 8.11-7.96(m, 1H), 7.45-7.32(m, 1H), 7.21-7.07(m, 2H), 6.98-6.79(m, 3H), 6.55-6.39(bs, 1H), 4.27-4.10(m, 2H), 3.14-2.99(m, 1H), 2.30(s, 3H), 2.21-1.85(m, 4H), 1.85-1.41(m, 4H) |
| 3 | 2-(1-Methylpyrrolidin-2-yl)-ethyl (3',4',5'-trifluoro-[1,1'-biphenyl]-2-yl)-carbamate | $^1$H NMR (CDCl$_3$): δ 8.00-7.88(m, 1H), 7.43-7.30(m, 1H), 7.29-7.08(m, 2H), 7.05-6.91(m, 2H), 6.69-6.52(bs, 1H), 4.25-4.06(m, 2H), 3.25-3.08(m, 1H), 2.47-2.17(m, 5H), 2.14-1.91(m, 2H), 1.90-1.45(m, 4H) |

TABLE 6-continued

Compounds of Examples

| Example | Compound | NMR Value |
|---|---|---|
| 4 | 2-(1-Methylpyrrolidin-2-yl)-ethyl (3'-fluoro-[1,1'-biphenyl]-2-yl)carbamate 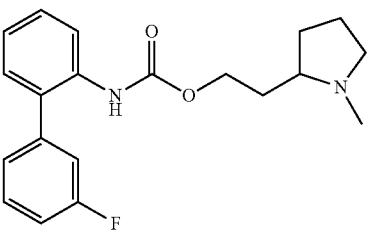 | $^1$H NMR (CDCl$_3$): δ 8.13-7.96(m, 1H), 7.50-7.28(m, 2H), 7.22-7.00(m, 5H), 6.60-6.45(bs, 1H), 4.25-4.07(m, 2H), 3.13-2.99(m, 1H), 2.31(s, 3H), 2.22-1.41(m, 8H) |
| 5 | 2-(1-Methylpyrrolidin-2-yl)-ethyl (4'-methoxy-[1,1'-biphenyl]-2-yl)carbamate 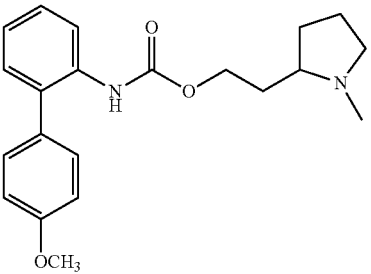 [SMILES: COc1ccc(-c2ccccc2NC(=O)OCCC2CCCN2C)cc1] | $^1$H NMR (CDCl$_3$): δ 8.13-7.99(m, 1H), 7.35-7.22(m, 4H), 7.20-7.14(m, 1H), 7.12-7.06(m, 1H), 7.03-6.95(m, 2H), 6.63-6.56(bs, 1H), 4.23-4.10(m, 2H), 3.85(s, 3H), 3.10-3.01(m, 1H), 2.28(s, 3H), 2.17-1.88(m, 4H), 1.84-1.62(m, 2H), 1.62-1.41(m, 2H) |
| 6 | 2-(1-Methylpyrrolidin-2-yl)-ethyl [1,1'-biphenyl]-2-yl-carbamate 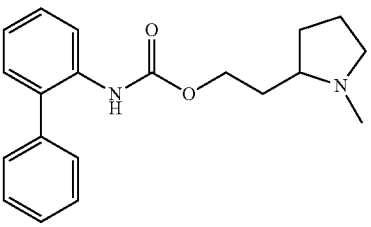 [SMILES: CN1CCCC1CCOC(=O)Nc1ccccc1-c1ccccc1] | $^1$H NMR (CDCl$_3$): δ 8.11(s, 1H), 7.45(t, 1H), 7.38(d, 1H), 7.34(dd, 2H), 7.21(dd, 2H), 7.12(t, 1H), 6.99(t, 1H), 6.64(s, 1H), 4.18-4.14(m, 2H), 3.09-3.01(m, 1H), 2.40(s, 3H), 2.34(m, 3H), 2.12-2.06(m, 2H), 1.91-1.82(m, 1H), 1.78-1.66(m, 2H), 1.60-1.56(m, 1H) |
| 7 | 2-(1-Methylpyrrolidin-2-yl)-ethyl (4'-chloro-[1,1'-biphenyl]-2-yl)carbamate 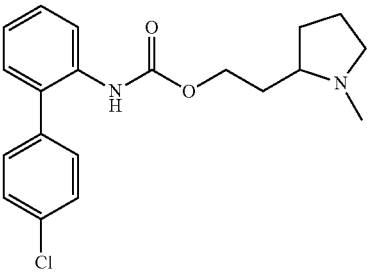 | $^1$H NMR (CDCl$_3$): δ 8.11-7.94(m, 1H), 7.55-6.97(m, 7H), 6.55-6.35(bs, 1H), 4.25-3.98(m, 2H), 3.14-2.94(m, 1H), 2.29(s, 3H), 2.20-1.84(m, 4H), 1.81-1.37(m, 4H) |

TABLE 6-continued

Compounds of Examples

| Example | Compound | NMR Value |
|---|---|---|
| 8 | 2-(1-Methylpyrrolidin-2-yl)-ethyl (3'-chloro-[1,1'-biphenyl]-2-yl)carbamate 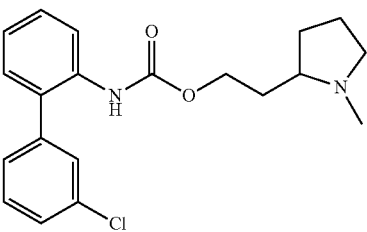 | $^1$H NMR (CDCl$_3$): δ 8.06(s, 1H), 7.41-7.35(m, 4H), 7.26-7.22(m, 1H), 7.19-7.16(m, 1H), 7.14-7.10(m, 1H), 6.47(s, 1H), 4.22-4.15(m, 2H), 3.07-3.02(m, 1H), 2.29(s, 3H), 2.16-2.06(m, 2H), 2.03-1.91(m, 2H), 1.78-1.62(m, 2H), 1.60-1.47(m, 2H) |
| 9 | 2-(1-Methylpyrrolidin-2-yl)-ethyl (3',5'-dichloro-[1,1'-biphenyl]-2-yl)carbamate 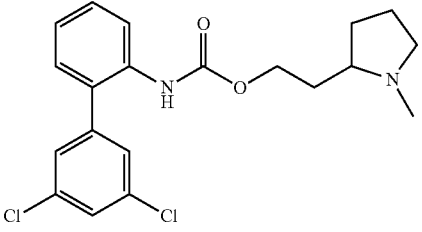 [SMILES: CN1CCCC1CCOC(=O)Nc1ccccc1-c1cc(Cl)cc(Cl)c1] | $^1$H NMR (CDCl$_3$): δ 8.01(s, 1H), 7.39-7.35(m, 2H), 7.22-7.20(m, 2H), 7.17-7.11(m, 2H), 6.42(s, 1H), 4.22-4.13(m, 2H), 3.10-3.01(s, 1H), 2.30(s, 3H), 2.08-2.04(m, 2H), 2.03-1.90(m, 2H), 1.78-1.60(m, 2H), 1.58-1.42(m, 2H) |
| 10 | 2-(1-Methylpyrrolidin-2-yl)-ethyl (4'-trifluoromethoxy-[1,1'-biphenyl]-2-yl)-carbamate 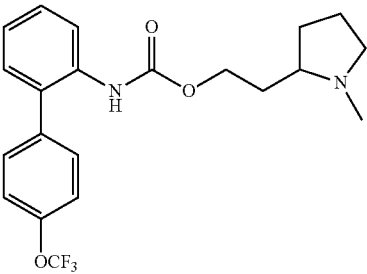 [SMILES: CN1CCCC1CCOC(=O)Nc1ccccc1-c1ccc(OC(F)(F)F)cc1] | $^1$H NMR (CDCl$_3$): δ 8.03(s, 1H), 7.39-7.34(m, 3H), 7.31-7.291(m, 2H), 7.19-7.11(m, 2H), 6.44(s, 1H), 4.24-4.15(m, 2H), 3.04-3.00(m, 1H), 2.27(s, 3H), 2.04-2.01(m, 2H), 2.00-1.88(m, 2H), 1.80-1.63(m, 2H), 1.59-1.44(m, 2H) |
| 11 | 2-(1-Methylpyrrolidin-2-yl)-ethyl (4'-nitro-[1,1'-biphenyl]-2-yl)carbamate 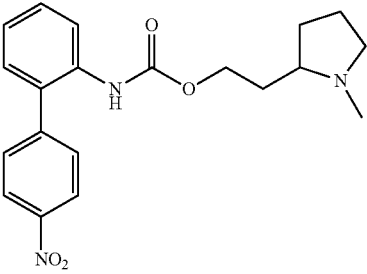 | $^1$H NMR (CDCl$_3$): δ 8.27-8.24(m, 1H), 7.55-7.52(m, 1H), 7.41-7.37(m, 1H), 7.22-7.00(m, 3H), 7.01-6.97(m, 1H), 4.14-4.05(m, 2H), 3.37-3.35(m, 1H), 2.50(s, 3H), 2.10-2.04(m, 2H), 1.93-1.88(m, 2H), 1.81-1.77(m, 2H), 1.66-1.62(m, 2H) |

TABLE 6-continued

Compounds of Examples

| Example | Compound | NMR Value |
|---|---|---|
| 12 | 2-(1-Methylpyrrolidin-2-yl)-ethyl (3-trifluoromethyl-[1,1'-biphenyl]-2-yl)-carbamate 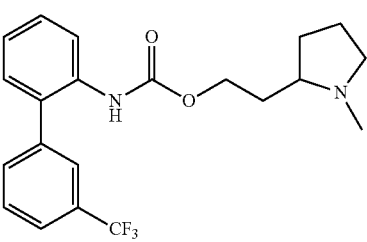 | $^1$H NMR (CDCl$_3$): δ 8.10-7.92(m, 1H), 7.73-7.46(m, 3H), 7.44-7.31(m, 1H), 7.31-7.05(m, 2H), 6.55-6.34(bs, 1H), 4.26-4.02(m, 2H), 3.20-3.00(m, 1H), 2.31(s, 3H), 2.25-1.88(m, 4H) 1.86-1.40(m, 4H) |
| 13 | 2-(1-Methylpyrrolidin-2-yl)-ethyl (4'-trifluoromethyl-[1,1'-biphenyl]-2-yl)-carbamate 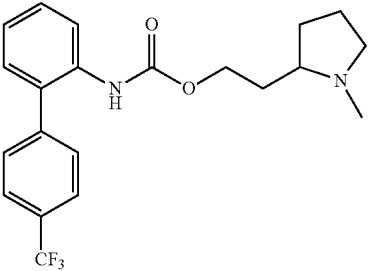 [SMILES: CN1CCCC1CCOC(=O)Nc1ccccc1-c1ccc(C(F)(F)F)cc1] | $^1$H NMR (CDCl$_3$): δ 8.04(s, 1H), 7.72(d, 2H, J = 8.0), 7.48(d, 2H, J = 8.4), 7.41-7.36(m, 1H), 7.20-7.13(m, 2H), 6.41(s, 1H), 4.18-4.14(m, 2H), 3.06-3.01(s, 1H), 2.27(s, 3H), 2.18-2.04(m, 2H), 2.02-1.87(m, 2H), 1.77-1.68(m, 2H), 1.57-1.43(m, 2H) |
| 14 | 2-(1-Methylpyrrolidin-2-yl)-ethyl ((3'-fluoro-4'-methyl)-[1,1'-biphenyl]-2-yl)carbamate 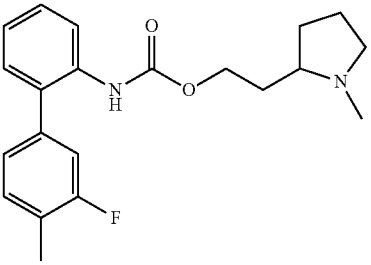 [SMILES: Cc1ccc(-c2ccccc2NC(=O)OCCC2CCCN2C)cc1F] | $^1$H NMR (CDCl$_3$): δ 8.11-7.99(m, 1H), 7.39-7.30(m, 1H), 7.30-7.14(m, 2H), 7.14-7.07(m, 1H), 7.06-6.95(m, 2H), 6.64-6.54(bs, 1H), 4.26-4.08(m, 2H), 3.30-3.09(m, 1H), 2.36(s, 3H), 2.32(s, 3H), 2.30-2.14(m, 2H), 2.13-1.92(m, 2H), 1.92-1.46(m, 4H) |
| 15 | 2-(1-Methylpyrrolidin-2-yl)-ethyl (3'-methyl-[1,1'-biphenyl]-carbamate 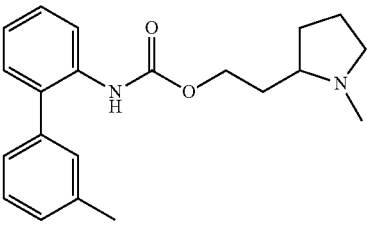 [SMILES: Cc1cccc(-c2ccccc2NC(=O)OCCC2CCCN2C)c1] | $^1$H NMR (CDCl$_3$): δ 8.10(s, 1H), 7.38-7.33(m, 2H), 7.26-7.17(m, 3H), 7.15-7.09(m, 1H), 6.66(s, 1H), 4.19-4.16(m, 2H), 3.21-3.01(s, 1H), 2.41(s, 3H), 2.28(s, 3H), 2.23-2.12(m, 2H), 2.10-1.91(m, 2H), 1.83-1.63(m, 2H), 1.60-1.43(m, 2H) |

TABLE 6-continued

Compounds of Examples

| Example | Compound | NMR Value |
|---|---|---|
| 16 | 2-(1-Methylpyrrolidin-2-yl)-ethyl (3'-ethoxy-[1,1'-biphenyl]-2-yl)carbamate | $^1$H NMR (CDCl$_3$): δ 8.10(s, 1H), 7.37-7.31(m, 2H), 7.23-7.18(m, 2H), 7.11-7.08(m, 1H), 7.00-6.86(m, 2H), 6.70(s, 1H), 4.17-4.01(m, 4H), 3.18-3.15(m, 1H), 2.36(s, 3H), 2.23-2.16(m, 2H), 2.08-1.91(m, 2H), 1.81-1.71(m, 2H), 1.63-1.41(m, 2H), 1.40-1.38(m, 3H) |
| 17 | 2-(1-Methylpyrrolidin-2-yl)-ethyl (3'-chloro-5-fluoro-[1,1'-biphenyl]-2-yl)-carbamate | $^1$H NMR (CDCl$_3$): δ 7.94(s, 1H), 7.41-7.36(m, 2H), 7.32(s, 1H), 7.22-7.20(m, 1H), 7.07-7.02(m, 1H), 6.92-6.89(m, 1H), 6.38(s, 1H), 4.17-4.13(m, 2H), 3.04-3.00(m, 1H), 2.27(s, 3H), 2.15-2.03(m, 2H), 2.00-1.87(m, 2H), 1.80-1.64(m, 2H), 1.56-1.40(m, 2H) |
| 18 | 2-(1-Methylpyrrolidin-2-yl)-ethyl (3',5-difluoro-[1,1'-biphenyl]-2-yl)carbamate | $^1$H NMR (CDCl$_3$): δ 7.86(s, 1H), 7.44-7.39(m, 1H), 7.26-7.22(m, 1H), 7.17-7.08(m, 1H), 7.06-7.02(m, 1H), 7.01-6.91(m, 2H), 6.75(s, 1H), 4.15-4.06(m, 2H), 3.30-3.27(m, 1H), 2.47(s, 3H), 2.10-1.93(m, 2H), 1.87-1.73(m, 2H), 1.70-1.54(m, 2H) |
| 19 | 2-(1-Methylpyrrolidin-2-yl)-ethyl (4',5-difluoro-[1,1'-biphenyl]-2-yl)carbamate | $^1$H NMR (CDCl$_3$): δ 7.97(s, 1H), 7.32-7.26(m, 1H), 7.24-7.21(m, 1H), 7.19-7.13(m, 2H), 7.07-7.00(m, 1H), 6.92-6.90(m, 1H), 6.48(s, 1H), 4.16-4.10(m, 2H), 3.20-3.17(m, 1H), 2.26(s, 3H), 2.17-2.15(m, 2H), 2.07-1.96(m, 2H), 1.83-1.72(m, 2H), 1.69-1.65(m, 2H) |

TABLE 6-continued

Compounds of Examples

| Example | Compound | NMR Value |
|---|---|---|
| 20 | 2-(1-Methylpyrrolidin-2-yl)-ethyl (3′,5,5′-trifluoro-[1,1′-biphenyl]-2-yl)-carbamate | $^1$H NMR (CDCl$_3$): δ 7.82-7.66(bs, 1H), 7.12-6.75(m, 5H), 4.27-3.99(m, 2H), 3.51-3.30(bs, 1H), 2.75-2.34(m, 5H), 2.20-1.55(m, 6H) |
| 21 | 2-(1-Methylpyrrolidin-2-yl)-ethyl (5-fluoro-[1,1′-biphenyl]-2-yl)carbamate | $^1$H NMR (CDCl$_3$): δ 7.98(s, 1H), 7.50-7.39(m, 3H), 7.34-7.27(m, 2H), 7.06-7.01(m, 1H), 6.98-6.92(m, 1H), 6.45(s, 1H), 4.17-4.07(m, 2H), 3.05-3.01(m, 1H), 2.27(s, 3H), 2.22-2.02(m, 2H), 2.01-1.80(m, 2H), 1.78-1.61(m, 2H), 1.58-1.40(m, 2H) |
| 22 | 2-(1-Methylpyrrolidin-2-yl)-ethyl (5-fluoro-3′-methyl-[1,1′-biphenyl]-2-yl)-carbamate | $^1$H NMR (CDCl$_3$): δ 8.01(s, 1H), 7.36-7.32(m, 1H), 7.27-7.21(m, 2H), 7.13-7.11(m, 1H), 7.05-7.00(m, 1H), 6.96-6.90(m, 1H), 6.51(s, 1H), 4.16-4.09(m, 2H), 3.06-3.02(m, 1H), 2.39(s, 3H), 2.28(s, 3H), 2.18-2.07(m, 2H), 2.05-1.88(m, 2H), 1.81-1.62(m, 2H), 1.58-1.44(m, 2H) |
| 23 | 2-(1-Methylpyrrolidin-2-yl)-ethyl (4-fluoro-[1,1′-biphenyl]-2-yl)carbamate | $^1$H NMR (CDCl$_3$): δ 7.97(s, 1H), 7.48-7.45(m, 2H), 7.42-7.40(m, 1H), 7.32-7.30(m, 2H), 7.15-7.11(m, 1H), 6.82-6.79(m, 1H), 6.66(s, 1H), 4.18-4.14(m, 2H), 3.06-3.04(m, 1H), 2.30(s, 3H), 2.15-2.00(m, 2H), 1.99-1.91(m, 2H), 1.69-1.58(m, 2H), 1.56-1.48(m, 2H) |

TABLE 6-continued

Compounds of Examples

| Example | Compound | NMR Value |
|---|---|---|
| 24 | 2-(1-Methylpyrrolidin-2-yl)ethyl (3',4-difluoro-[1,1'-biphenyl]-2-yl)carbamate | $^1$H NMR (CDCl$_3$): δ 7.97(s, 1H), 7.48-7.44(m, 1H), 7.28-7.17(m, 2H), 7.15-7.11(m, 1H), 7.05-6.97(m, 1H), 6.86-6.80(m, 1H), 6.68(s, 1H), 4.19-4.13(m, 2H), 3.31-3.28(m, 1H), 2.48(s, 3H), 2.19-2.07(m, 2H), 1.95-1.88(m, 2H), 1.85-1.70(m, 2H), 1.67-1.54(m, 2H) |
| 25 | 2-(1-Methylpyrrolidin-2-yl)ethyl (4-methoxy-[1,1'-biphenyl]-2-yl)carbamate | $^1$H NMR (CDCl$_3$): δ 7.80(s, 1H), 7.44-7.36(m, 1H), 7.34-7.29(m, 3H), 7.09-7.07(m, 1H), 6.68-6.64(m, 2H), 4.20-4.14(m, 2H), 3.82(s, 3H), 3.04-3.00(m, 1H), 2.26(s, 3H), 2.14-2.00(m, 2H), 2.13-1.87(m, 2H), 1.79-1.59(m, 2H), 1.56-1.40(m, 2H) |
| 26 | 2-(1-Methylpyrrolidin-2-yl)ethyl (5-methyl-[1,1'-biphenyl]-2-yl)carbamate | $^1$H NMR (CDCl$_3$): δ 7.91(s, 1H), 7.46-7.42(m, 2H), 7.38-7.29(m, 2H), 7.22-7.18(m, 1H), 7.02(s, 1H), 6.54(s, 1H), 4.18-4.10(m, 2H), 3.21-3.10(m, 1H), 2.32(s, 3H), 2.31(s, 3H), 2.22-2.16(m, 2H), 2.12-1.91(m, 2H), 1.81-1.68(m, 2H), 1.65-1.48(m, 2H) |
| 27 | 2-(1-Methylpyrrolidin-2-yl)ethyl (3'-fluoro-5-methyl-[1,1'-biphenyl]-2-yl)carbamate | $^1$H NMR (CDCl$_3$): δ 7.92(s, 1H), 7.44-7.38(m, 2H), 7.20-7.15(m, 1H), 7.13-7.09(m, 1H), 7.07-6.97(m, 2H), 6.55(s, 1H), 4.17-4.07(m, 2H), 3.30-3.23(m, 1H), 2.49(s, 3H), 2.37(s, 3H), 2.15-2.05(m, 2H), 1.93-1.90(m, 2H), 1.79-1.76(m, 2H), 1.63-1.61(m, 2H) |

TABLE 6-continued

Compounds of Examples

| Example | Compound | NMR Value |
|---|---|---|
| 28 | 2-(-Methylpyrrolidin-2-yl)-ethyl (4'-cyano[1,1'-biphenyl]-2-yl)carbamate | $^1$H NMR (CDCl$_3$): δ 8.06-7.93(m, 1H), 7.75(d, 8.4 Hz, 2H), 7.49(d, J = 8.0 Hz, 2H), 7.44-7.33(m, 1H), 7.21-7.09(m, 2H), 6.42-6.38(bs, 1H), 4.22-4.07(m, 2H), 3.11-2.98(m, 1H), 2.29(s, 3H), 2.19-1.85(m, 3H) 1.85-1.39(m, 5H) |
| 29 | 2-(1-Methylpyrrolidin-2-yl)-ethyl (3'-(3-hydroxypropyl)-[1,1'-biphenyl]-2-yl)-carbamate | $^1$H NMR (CDCl$_3$): δ 8.03(s, 1H), 7.39-7.28(m, 3H), 7.23-7.11(m, 3H), 7.05-7.01(m, 1H), 6.67(s, 1H), 4.23-4.14(m, 2H), 3.66-3.60(m, 2H), 3.17-3.03(m, 1H), 2.75-2.71(m, 2H), 2.32(s, 3H), 2.24-2.10(m, 2H), 2.05-1.96(m, 2H), 1.94-1.83(m, 2H), 1.81-1.69(m, 2H), 1.61-1.46(m, 2H) |
| 30 | 2-(1-Methylpyrrolidin-2-yl)-ethyl (4'-(dimethylamino)-[1,1'-biphenyl]-2-yl)-carbamate | $^1$H NMR (CDCl$_3$): δ 8.11(s, 1H), 7.28(t, 1H, J = 7.2 Hz), 7.23-7.19(m, 2H), 7.19-7.17(m, 1H), 7.07(t, 1H, J = 7.6 Hz), 6.81(t, 2H, J = 2.8 Hz), 6.74(s, 1H), 4.18-4.14(m, 2H), 3.09-3.01(m, 1H), 3.00(s, 9H), 2.14(s, 3H), 2.12-2.06(m, 2H), 2.01-1.92(m, 2H), 1.79-1.66(m, 2H), 1.58-1.46(m, 2H) |
| 31 | 2-(1-Methylpyrrolidin-2-yl)-ethyl (4'-(tert-butyl)-[1,1'-biphenyl]-2-yl)-carbamate | $^1$H NMR (CDCl$_3$): δ 8.04(s, 1H), 7.48-7.46(m, 2H), 7.35-7.27(m, 3H), 7.24-7.19(m, 1H), 7.12-7.08(m, 1H), 6.67(s, 1H), 4.17-4.13(m, 2H), 3.10-3.07(m, 1H), 2.30(s, 3H), 2.18-1.99(m, 2H), 1.98-1.90(m, 2H), 1.80-1.62(m, 2H), 1.44-1.36(m, 2H), 1.36(s, 9H) |

TABLE 6-continued

Compounds of Examples

| Example | Compound | NMR Value |
|---|---|---|
| 32 | 2-(1-Methylpyrrolidin-2-yl)-ethyl (2'-amino[1,1'-biphenyl]-2-yl)carbamate | $^1$H NMR (CDCl$_3$): δ 8.11(s, 1H), 7.37(t, 1H, J = 8.0 Hz), 7.22-7.20(m, 2H), 7.13(t, 1H, J = 7.6 Hz), 7.06(d, 1H, J = 7.6 Hz), 6.86-6.78(m, 2H), 4.15-4.11(m, 2H), 3.08-3.04(s, 1H), 2.25(s, 3H), 2.17-2.10(m, 2H), 2.02-1.90(m, 2H), 1.78-1.66(m, 2H), 1.58-1.46(m, 2H) |
| 33 | 2-(1-Methylpyrrolidin-2-yl)-ethyl (3'-amino[1,1'-biphenyl]-2-yl)carbamate | $^1$H NMR (CD$_3$OD): δ 7.83(s, 1H), 7.29-7.15(m, 3H), 7.06-7.00(m, 2H), 6.80-6.77(m, 2H), 4.14-4.10(m, 2H), 3.30(s, 3H), 3.20-3.15(m, 1H), 2.45-2.43(m, 2H), 2.10-2.00(m, 2H), 1.84-1.81(m, 2H), 1.62-1.47(m, 2H) |
| 34 | 2-(1-methylpyrrolidin-2-yl)-ethyl (2'-fluoro[1,1'-biphenyl]-2-yl)carbamate | $^1$H NMR (CDCl$_3$): δ 7.96(s, 1H), 7.42-7.36(m, 3H), 7.31-7.14(m, 3H), 6.99-6.97(m, 1H), 6.45(s, 1H), 4.15-4.08(m, 2H), 3.26-3.22(s, 1H), 2.39(s, 3H), 2.35-2.25(m, 2H), 2.09-1.96(m, 2H), 1.88-1.64(m, 2H), 1.60-1.53(m, 2H) |
| 35 | 2-(1-Methylpyrrolidin-2-yl)-ethyl (2'-chloro-[1,1'-biphenyl]-2-yl)carbamate | $^1$H NMR (CDCl$_3$): δ 8.01(s, 1H), 7.51-7.48(m, 1H), 7.41-7.34(m, 2H), 7.28-7.13(m, 3H), 6.96-6.93(m, 1H), 6.26(s, 1H), 4.18-4.05(m, 2H), 3.22-3.20(s, 1H), 2.37(s, 3H), 2.35-2.28(m, 2H), 2.07-1.93(m, 2H), 1.84-1.63(m, 2H), 1.57-1.52(m, 2H) |

TABLE 6-continued

Compounds of Examples

| Example | Compound | NMR Value |
|---|---|---|
| 36 | 2-(1-Methylpyrrolidin-2-yl)-ethyl (2'-hydroxy-[1,1'-biphenyl]-2-yl)carbamate | $^1$H NMR (CDCl$_3$): δ 7.84(s, 1H), 7.39-7.33(m, 1H), 7.31-7.12(m, 4H), 7.05-7.01(m, 1H), 6.96-6.90(m, 1H), 4.21-4.09(m, 2H), 3.21-3.14(s, 1H), 2.40(s, 3H), 2.36-2.26(m, 2H), 2.13-1.96(m, 2H) 1.84-1.66(m, 2H), 1.64-1.53(m, 2H) |
| 37 | 2-(1-Methylpyrrolidin-2-yl)-ethyl (3'-tert-butyl-5'-methyl-[1,1'-biphenyl]-2-yl)-carbamate | $^1$H NMR (CDCl$_3$): δ 8.11(s, 1H), 7.35-7.27(m, 1H), 7.23-7.21(m, 2H), 7.18(s, 1H), 7.13-7.09(m, 1H), 6.99(s, 1H), 6.74(s, 1H), 4.17-4.12(m, 2H), 3.12-3.09(m, 1H), 2.39(s, 3H), 2.30(s, 3H), 2.23-2.11(m, 2H), 2.01-1.98(m, 2H), 1.79-1.66(m, 2H), 1.58-1.46(m, 2H), 1.32(m, 9H) |
| 38 | 2-(1-Methylpyrrolidin-2-yl)-ethyl (4'-fluoro-3'-(trifluoromethyl)-[1,1'-biphenyl]-2-yl)carbamate | $^1$H NMR (CDCl$_3$): δ 7.99(s, 1H), 7.60-7.58(m, 1H), 7.56-7.53(m, 1H), 7.41-7.36(m, 1H), 7.32-7.27(m, 1H), 7.20-7.14(m, 2H), 6.37(s, 1H), 4.18-4.13(m, 2H), 3.14-3.12(m, 1H), 2.34(s, 3H), 2.34-2.21(m, 2H), 2.06-1.93(m, 2H), 1.76-1.68(m, 2H), 1.64-1.46(m, 2H) |
| 39 | 2-(1-Methylpyrrolidin-2-yl)-ethyl(4'-amino-3'-chloro-[1,1'-biphenyl]-2-yl)-carbamate | $^1$H NMR (CDCl$_3$): δ 8.04(s, 1H), 7.30(t, 1H, J = 8.0 Hz), 7.15-7.12(m, 2H), 7.07-7.03(m, 2H), 6.82(d, 1H, J = 8.4 Hz), 6.59(s, 1H), 4.18-4.09(m, 2H), 3.08-3.04(m, 1H), 2.30(s, 3H), 2.25-2.10(m, 2H), 2.08-1.91(m, 2H), 1.81-1.57(m, 2H), 1.56-1.43(m, 2H) |

TABLE 6-continued

Compounds of Examples

| Example | Compound | NMR Value |
|---|---|---|
| 40 | 2-(1-Methylpyrrolidin-2-yl)-ethyl (3'-hydroxy-[1,1'-biphenyl]-2-yl)carbamate | $^1$H NMR (CD$_3$OD): δ 7.84(s, 1H), 7.31-7.18(m, 3H), 7.06-7.02(m, 2H), 6.82-6.79(m, 2H), 4.11-4.08(m, 2H), 3.30(s, 3H), 3.21-3.18(m, 1H), 2.45-2.43(m, 2H), 2.08-2.01(m, 2H), 1.84-1.82(m, 2H), 1.61-1.45(m, 2H) |
| 41 | 2-(1-Methylpyrrolidin-2-yl)-ethyl (3'-chloro-4'-fluoro-[1,1'-biphenyl]-2-yl)-carbamate | $^1$H NMR (CDCl$_3$): δ 8.06-7.93(bs, 1H), 7.41-7.38(m, 1H), 7.38-7.34(m, 1H), 7.23-7.19(m, 3H), 7.17-7.10(m, 2H), 6.51-6.44(bs, 1H), 4.20-4.12(m, 2H), 3.16-3.07(bs, 1H), 2.33(s, 3H), 2.25-2.13(m, 2H), 2.07-1.92(m, 2H), 1.84-1.65(m, 2H), 1.65-1.46(m, 2H) |
| 42 | 2-(1-Methylpyrrolidin-2-yl)-ethyl(3',4',5-trifluoro-[1,1'-biphenyl]-2-yl)-carbamate | $^1$H NMR (CDCl$_3$): δ 7.98(s, 1H), 7.29-7.28(m, 1H), 7.17-7.14(m, 1H), 7.08-7.03(m, 2H), 6.90(dd, 1H, J = 8.8 Hz, J = 2.8 Hz), 6.33(s, 1H), 4.17-4.13(m, 2H), 3.05-3.03(m, 1H), 2.28(s, 3H), 2.08-2.03(m, 2H), 2.02-1.89(m, 2H), 1.79-1.63(m, 2H), 1.60-1.42(m, 2H) |
| 43 | 2-(1-Methylpyrrolidin-2-yl)-ethyl (3',4'-dichloro-5-fluoro-[1,1'-biphenyl]-2-yl)-carbamate | $^1$H NMR (CDCl$_3$): δ 7.94(s, 1H), 7.54(d, 1H, J = 8.4 Hz), 7.44(d, 1H, J = 2.0 Hz), 7.19(dd, 1H, J = 8.4 Hz, J = 2.0 Hz), 7.09-7.05(m, 1H), 6.91(dd, 1H, J = 8.4 Hz, J = 2.8 Hz), 6.38(s, 1H), 4.20-4.14(m, 2H), 3.17-3.16(m, 1H), 2.36(s, 3H), 2.07-1.96(m, 2H), 1.83-1.80(m, 2H), 1.77-1.71(m, 2H), 1.58-1.54(m, 2H) |

TABLE 6-continued

Compounds of Examples

| Example | Compound | NMR Value |
|---|---|---|
| 44 | 2-(1-Methylpyrrolidin-2-yl)-ethyl (3'-ethyl-5-fluoro-[1,1'-biphenyl]-2-yl)-carbamate | $^1$H NMR (CDCl$_3$): δ 8.01(s, 1H), 7.38(t, 1H, J = 8.0 Hz), 7.25-7.23(m, 1H), 7.16-7.13(m, 2H), 7.05-7.00(m, 1H), 6.95-6.92(m, 1H), 6.53(s, 1H), 4.17-4.12(m, 2H), 3.05-3.03(m, 1H), 2.68(q, 2H, J = 7.6 Hz), 2.28(s, 3H), 2.16-2.02(m, 2H), 2.00-1.88(m, 2H), 1.78-1.62(m, 2H), 1.59-1.41(m, 2H), 1.25(t, 3H, J = 7.6 Hz) |
| 45 | 2-(1-Methylpyrrolidin-2-yl)-ethyl (5-fluoro-3',5'-dimethyl-[1,1'-biphenyl]-2-yl)carbamate | $^1$H NMR (CDCl$_3$): δ 8.01(s, 1H), 7.03-6.98(m, 2H), 6.93-6.89(m, 2H), 6.55(s, 1H), 4.20-4.14(m, 2H), 3.03-3.01(m, 1H), 2.38(s, 6H), 2.35(s, 3H), 2.09-2.04(m, 2H), 2.03-1.90(m, 2H), 1.79-1.63(m, 2H), 1.59-1.44(m, 2H) |
| 46 | 2-(1-Methylpyrrolidin-2-yl)-ethyl (3'-amino-5-fluoro-[1,1'-biphenyl]-2-yl)-carbamate | $^1$H NMR (CDCl$_3$): δ 8.02(s, 1H), 7.25-7.21(m, 2H), 7.03-6.99(m, 1H), 6.92-6.89(m, 1H), 6.71-6.67(m, 2H), 6.60(s, 2H), 4.16-4.12(m, 2H), 3.04-3.01(m, 1H), 2.28(s, 3H), 2.02-1.97(m, 2H), 1.96-1.89(m, 2H), 1.78-1.63(m, 2H), 1.57-1.41(m, 2H) |
| 47 | 2-(1-Methylpyrrolidin-2-yl)-ethyl (5-(trifluoromethyl)-[1,1'-biphenyl]-2-yl)-carbamate | $^1$H NMR (CDCl$_3$): δ 8.29(d, 1H, J = 8.8 Hz), 7.59(d, 1H, J = 8.8 Hz), 7.52-7.49(m, 2H), 7.46-7.44(m, 2H), 7.36-7.34(m, 2H), 6.78(s, 1H), 4.19-4.16(m, 2H), 3.12-3.10(m, 1H), 2.33(s, 3H), 2.17-2.05(m, 2H), 2.03-1.93(m, 2H), 1.78-1.64(m, 2H), 1.53-1.51(m, 2H) |

TABLE 6-continued

Compounds of Examples

| Example | Compound | NMR Value |
|---|---|---|
| 48 | 2-(1-Methylpyrrolidin-2-yl)-ethyl (4'-fluoro-5-(trifluoromethyl)-[1,1'-biphenyl]-2-yl)carbamate | $^1$H NMR (CDCl$_3$): δ 8.27(d, 1H, J = 8.4 Hz), 7.59(d, 1H, J = 8.8 Hz), 7.41(d, 1H, J = 1.2 Hz), 7.34-7.31(m, 2H), 7.22-7.18(m, 2H), 6.70(s, 1H), 4.22-4.16(m, 2H), 3.26-3.24(m, 1H), 2.41(s, 3H), 2.35-2.29(m, 2H), 2.13-1.98(m, 2H), 1.88-1.77(m, 2H), 1.62-1.59(m, 2H) |
| 49 | 2-(1-Methylpyrrolidin-2-yl)-ethyl (3'-fluoro-5-(trifluoromethyl)-[1,1'-biphenyl]-2-yl)carbamate | $^1$H NMR (CDCl$_3$): δ 8.29(d, 1H, J = 8.8 Hz), 7.61(d, 1H, J = 8.8 Hz), 7.51-7.45(m, 1H), 7.43(s, 1H), 7.18-7.13(m, 2H), 7.08-7.06(m, 1H), 6.71(s, 1H), 4.21-4.17(m, 2H), 3.12-3.10(m, 1H), 2.33(s, 3H), 2.19-2.15(m, 2H), 2.07-1.92(m, 2H), 1.74-1.71(m, 2H), 1.53-1.50(m, 2H) |
| 50 | 2-(1-Methylpyrrolidin-2-yl)-ethyl (3',5'-difluoro-5-(trifluoromethyl)-[1,1'-biphenyl]-2-yl)carbamate | $^1$H NMR (CDCl$_3$): δ 8.26(d, 1H, J = 8.8 Hz), 7.62(d, 1H, J = 8.8 Hz), 7.43(s, 1H), 6.93-6.89(m, 3H), 6.78(s, 1H), 4.24-4.19(m, 2H), 3.28-3.21(m, 1H), 2.45(s, 3H), 2.15-2.04(m, 2H), 1.89-1.87(m, 2H), 1.82-1.80(m, 2H), 1.67-1.63(m, 2H) |
| 51 | 2-(1-Methylpyrrolidin-2-yl)-ethyl (3'-chloro-5-(trifluoromethyl)-[1,1'-biphenyl]-2-yl)carbamate | $^1$H NMR (CDCl$_3$): δ 8.27(d, 1H, J = 8.4 Hz), 7.61(d, 1H, J = 8.8 Hz), 7.47-7.43(m, 3H), 7.35(s, 1H), 7.25-7.23(m, 1H), 6.75(s, 1H), 4.23-4.17(m, 2H), 3.34-3.32(m, 1H), 2.42(s, 3H), 2.11-2.05(m, 2H), 2.02-1.91(m, 2H), 1.90-1.83(m, 2H), 1.83-1.80(m, 2H) |

TABLE 6-continued

Compounds of Examples

| Example | Compound | NMR Value |
|---|---|---|
| 52 | 2-(1-Methylpyrrolidin-2-yl)-ethyl (3'-chloro-5,5'-difluoro-[1,1'-biphenyl]-2-yl)carbamate | $^1$H NMR (CDCl$_3$): δ 7.91(s, 1H), 7.22-7.20(m, 1H), 7.15-7.13(m, 1H), 7.10-7.05(m, 1H), 6.99-6.97(m, 1H), 6.92(dd, 1H, J = 8.8 Hz, J = 2.8 Hz), 6.44(s, 1H), 4.21-4.14(m, 2H), 3.22-3.19(m, 1H), 2.40(s, 3H), 2.32-2.28(m, 2H), 2.10-2.02(m, 2H), 1.86-1.59(m, 2H), 1.26-1.22(m, 2H) |
| 53 | 2-(1-Methylpyrrolidin-2-yl)-ethyl (3'-chloro-4',5-difluoro-[1,1'-biphenyl]-2-yl)carbamate | $^1$H NMR (CDCl$_3$): δ 7.91(s, 1H), 7.39(dd, 1H, J = 7.2 Hz, J = 2.0 Hz), 7.23-7.19(m, 2H), 7.08-7.04(m, 1H), 6.90(dd, 1H, J = 8.4 Hz, J = 2.8 Hz), 6.37(s, 1H), 4.18-4.13(m, 2H), 3.14-3.10(m, 1H), 2.33(s, 3H), 2.23-2.16(m, 2H), 2.06-1.91(m, 2H), 1.82-1.65(m, 2H), 1.60-1.51(m, 2H) |
| 54 | 2-(1-Methylpyrrolidin-2-yl)-ethyl (4'-chloro-3',5-difluoro-[1,1'-biphenyl]-2-yl)carbamate | $^1$H NMR (CDCl$_3$): δ 7.81(s, 1H), 7.47-7.43(m, 1H), 7.19-7.11(m, 2H), 7.11-6.95(m, 1H), 6.90(dd, 1H, J = 8.8 Hz, J = 3.2 Hz), 6.62(s, 1H), 4.14-4.04(m, 2H), 3.21-3.16(m, 1H), 2.37(s, 3H), 2.04-1.95(m, 2H), 1.84-1.69(m, 2H), 1.67-1.61(m, 1H), 1.57-1.48(m, 2H) |
| 55 | 2-(1-Methylpyrrolidin-2-yl)-ethyl (3',5'-dichloro-5-fluoro-[1,1'-biphenyl]-2-yl)-carbamate | $^1$H NMR (CDCl$_3$): δ 7.90(s, 1H), 7.41-7.40(m, 1H), 7.25-7.22(m, 2H), 7.10-7.05(m, 1H), 6.91(dd, 1H, J = 8.8 Hz, J = 2.8 Hz), 6.38(s, 1H), 4.20-4.16(m, 2H), 3.16-3.12(m, 1H), 2.36(s, 3H), 2.23-2.21(m, 2H), 2.09-1.94(m, 2H), 1.80-1.64(m, 2H), 1.56-1.52(m, 2H) |

TABLE 6-continued

Compounds of Examples

| Example | Compound | NMR Value |
|---|---|---|
| 56 | 2-(1-Methylpyrrolidin-2-yl)-ethyl (3',5'-dichloro-4',5-difluoro-[1,1'-biphenyl]-2-yl)carbamate | $^1$H NMR (CDCl$_3$): δ 7.81(s, 1H), 7.31-7.30(m, 1H), 7.19-7.18(m, 1H), 7.09-7.04(m, 1H), 6.91-6.62(m, 1H), 6.61(s, 1H), 4.20-4.11(m, 2H), 3.26-3.22(m, 1H), 2.42-2.30(m, 4H), 2.11-1.93(m, 2H), 1.88-1.63(m, 2H), 1.61-1.54(m, 2H) |
| 57 | 2-(1-Methylpyrrolidin-2-yl)-ethyl (3'-chloro-5-fluoro-5'-hydroxy[1,1'-biphenyl]-2-yl)carbamate | $^1$H NMR (CDCl$_3$): δ 7.83(s, 1H), 7.03-6.95(m, 1H), 6.91-6.88(m, 1H), 6.80(s, 1H), 6.73-6.66(m, 2H), 4.12-4.07(m, 2H), 3.21-3.17(m, 1H), 2.35(s, 3H), 2.28-2.24(m, 2H), 1.82-1.65(m, 2H), 1.62-1.55(m, 2H), 1.25-1.21(m, 2H) |
| 58 | 2-(1-Methylpyrrolidin-2-yl)-ethyl (3'-chloro-5-fluoro-4'-hydroxy-[1,1'-biphenyl]-2-yl)carbamate | $^1$H NMR (CDCl$_3$): δ 7.83(s, 1H), 7.25-7.20(m, 1H), 7.05-6.92(m, 3H), 6.88(dd, 1H, J = 8.8 Hz, J = 2.8 Hz), 6.57(s, 1H), 4.14-4.06(m, 2H), 3.22-3.17(m, 1H), 2.40(s, 3H), 2.39-2.29(m, 2H), 2.10-1.97(m, 2H), 1.86-1.66(m, 2H), 1.65-1.54(m, 2H) |
| 59 | 2-(1-Methylpyrrolidin-2-yl)-ethyl (5-fluoro-3',4'-dimethyl-[1,1'-biphenyl]-2-yl)carbamate | $^1$H NMR (CDCl$_3$): δ 7.99(s, 1H), 7.22-7.20(m, 1H), 7.08-6.97(m, 3H), 6.90(dd, 1H, J = 9.2 Hz, J = 2.8 Hz), 6.57(s, 1H), 4.15-4.13(m, 2H), 3.16-3.12(m, 1H), 2.31(s, 3H), 2.29(s, 6H), 2.02-2.17(m, 2H), 2.00-1.89(m, 2H), 1.76-1.55(m, 2H), 1.53-1.42(m, 2H) |

TABLE 6-continued

Compounds of Examples

| Example | Compound | NMR Value |
|---|---|---|
| 60 | 2-(1-Methylpyrrolidin-2-yl)-ethyl(5-methoxy-[1,1'-biphenyl]-2-yl)carbamate | $^{1}$H NMR (CDCl$_3$): δ 7.93(s, 1H), 7.46-7.40(m, 2H), 7.39-7.36(m, 1H), 7.35-7.33(m, 2H), 6.89(dd, 1H, J = 8.8 Hz, J = 2.8 Hz), 6.77(d, 1H, J = 2.8 Hz), 6.38(s, 1H), 4.15-4.10(m, 2H), 3.86(s, 3H), 3.14-3.11(m, 1H), 2.35(m, 3H), 2.26-2.16(m, 2H), 2.06-1.91(m, 2H), 1.82-1.62(m, 2H), 1.60-1.45(m, 2H) |
| 61 | 2-(1-Methylpyrrolidin-2-yl)-ethyl(3'-fluoro-5-methoxy-[1,1'-biphenyl]-2-yl)-carbamate | $^{1}$H NMR (CDCl$_3$): δ 7.82(s, 1H), 7.42-7.39(m, 1H), 7.14-7.10(m, 1H), 7.07-7.05(m, 2H), 6.90(dd, 1H, J = 8.8 Hz, J = 3.2 Hz), 6.75(d, 1H, J = 3.2 Hz), 6.37(s, 1H), 4.17-4.13(m, 2H), 3.79(s, 3H), 3.21-3.18(m, 1H), 2.38(s, 3H), 2.30-2.26(m, 2H), 2.09-1.99(m, 2H), 1.74-1.70(m, 2H), 1.56-1.53(m, 2H) |
| 62 | 2-(1-Methylpyrrolidin-2-yl)-ethyl(3',5'-difluoro-5-methoxy-[1,1'-biphenyl]-2-yl)carbamate | $^{1}$H NMR (CDCl$_3$): δ 7.72(s, 1H), 7.28-7.26(m, 1H), 6.92-6.79(m, 3H), 6.74-6.73(m, 1H), 6.29(s, 1H), 4.15-4.10(m, 2H), 3.75(s, 3H), 3.15-3.10(m, 1H), 2.34(s, 3H), 2.27-2.25(m, 2H), 2.06-1.96(m, 2H), 1.78-1.69(m, 2H), 1.63-1.50(m, 2H) |
| 63 | 2-(1-Methylpyrrolidin-2-yl)-ethyl(3'-chloro-5-methoxy-[1,1'-biphenyl]-2-yl)-carbamate | $^{1}$H NMR (CDCl$_3$): δ 7.82(s, 1H), 7.38-7.34(m, 2H), 7.23-7.21(m, 2H), 6.90(dd, 1H, J = 9.2 Hz, J = 2.8 Hz), 6.74(d, 1H, J = 2.8 Hz), 6.28(s, 1H), 4.17-4.12(m, 2H), 3.78(s, 3H), 3.16-3.14(m, 1H), 2.35(s, 3H), 2.23-2.18(m, 2H), 2.21-1.93(m, 2H), 1.79-1.64(m, 2H), 1.60-1.50(m, 2H) |

TABLE 6-continued

Compounds of Examples

| Example | Compound | NMR Value |
|---|---|---|
| 64 | 2-(1-Methylpyrrolidin-2-yl)-ethyl(3',5'-dichloro-5-methoxy-[1,1'-biphenyl]-2-yl)carbamate | $^1$H NMR (CDCl$_3$): δ 7.70(s, 1H), 7.36-7.35(m, 1H), 7.23-7.20(m, 2H), 6.90(dd, 1H, J = 8.8 Hz, J = 2.8 Hz), 6.73-6.72(m, 1H), 6.58(s, 1H), 4.16-4.08(m, 2H), 3.75(s, 3H), 3.28-3.26(m, 1H), 2.43(s, 3H), 2.40-2.38(m, 2H), 2.08-2.02(m, 2H), 1.85-1.72(m, 2H), 1.60-1.57(m, 2H) |
| 65 | 2-(1-Methylpyrrolidin-2-yl)-ethyl(3'-chloro-4'-fluoro-5-methoxy-[1,1'-biphenyl]-2-yl)carbamate | $^1$H NMR (CDCl$_3$): δ 7.70(s, 1H), 7.39-7.38(m, 1H), 7.21-7.19(m, 2H), 6.90(dd, 1H, J = 8.8 Hz, J = 2.8 Hz), 6.72-6.71(m, 1H), 6.21(s, 1H), 4.15-4.09(m, 2H), 3.76(s, 3H), 3.13-3.11(m, 1H), 2.37(s, 3H), 2.30-2.23(m, 2H), 2.02-1.97(m, 2H), 1.79-1.71(m, 2H), 1.62-1.56(m, 2H) |
| 66 | 2-(1-Methylpyrrolidin-2-yl)-ethyl(5-chloro-[1,1'-biphenyl]-2-yl)carbamate | $^1$H NMR (CDCl$_3$): δ 8.04(s, 1H), 7.48-7.45(m, 2H), 7.43-7.39(m, 1H), 7.32-7.28(m, 3H), 7.23-7.18(m, 1H), 6.56(s, 1H), 4.16-4.12(m, 2H), 3.06-3.02(m, 1H), 2.28(s, 3H), 2.12-1.96(m, 2H), 1.94-1.87(m, 2H), 1.76-1.64(m, 2H), 1.57-1.44(m, 2H) |
| 67 | 2-(1-Methylpyrrolidin-2-yl)-ethyl(5-chloro-3'-fluoro-[1,1'-biphenyl]-2-yl)-carbamate | $^1$H NMR (CDCl$_3$): δ 8.03(s, 1H), 7.44(q, 1H, J = 8.0 Hz), 7.31(dd, 1H, J = 8.8 Hz, J = 2.4 Hz), 7.14-7.10(m, 2H), 7.05-7.03(m, 1H), 6.49(s, 1H), 4.17-4.13(m, 2H), 3.03-3.01(m, 2H), 2.29(s, 3H), 2.13-1.98(m, 2H), 1.97-1.88(m, 2H), 1.77-1.64(m, 2H), 1.59-1.42(m, 2H) |

TABLE 6-continued

Compounds of Examples

| Example | Compound | NMR Value |
|---|---|---|
| 68 | 2-(1-Methylpyrrolidin-2-yl)-ethyl(5-chloro-4'-fluoro-[1,1'-biphenyl]-2-yl)-carbamate | $^1$H NMR (CDCl$_3$): δ 8.02(s, 1H), 7.31-7.28(m, 3H), 7.18-7.14(m, 3H), 6.44(s, 1H), 4.17-4.13(m, 2H), 3.04-3.01(m, 1H), 2.28(s, 3H), 2.10-2.00(m, 2H), 1.98-1.87(m, 2H), 1.78-1.65(m, 2H), 1.57-1.44(m, 2H) |
| 69 | 2-(1-Methylpyrrolidin-2-yl)-ethyl(5-chloro-3',5'-difluoro-[1,1'-biphenyl]-2-yl)carbamate | $^1$H NMR (CDCl$_3$): δ 7.99(s, 1H), 7.34-7.31(m, 2H), 7.17-7.16(m, 1H), 6.88-6.84(m, 2H), 6.51(s, 1H), 4.18-4.10(m, 2H), 3.16-3.13(m, 1H), 2.36(s, 3H), 2.32-2.29(m, 2H), 2.08-1.96(m, 2H), 1.82-1.61(m, 2H), 1.57-1.49(m, 2H) |
| 70 | 2-(1-Methylpyrrolidin-2-yl)-ethyl(3',5-dichloro-[1,1'-biphenyl]-2-yl)carbamate | $^1$H NMR (CDCl$_3$): δ 8.01(s, 1H), 7.43-7.38(m, 2H), 7.32-7.30(m, 2H), 7.23-7.21(m, 1H), 7.17(d, 1H, J = 2.4 Hz), 6.47(s, 1H), 4.18-4.13(m, 2H), 3.06-3.04(m, 1H), 2.25(s, 3H), 2.19-2.06(m, 2H), 2.05-1.90(m, 2H), 1.80-1.59(m, 2H), 1.58-1.44(m, 2H) |
| 71 | 2-(1-(Methylpyrrolidin-2-yl)-ethyl(3',5,5'-trichloro-[1,1'-biphenyl]-2-yl)-carbamate | $^1$H NMR (CDCl$_3$): δ 7.98(s, 1H), 7.41(s, 1H), 7.33(dd, 1H, J = 8.8 Hz, J = 2.4 Hz), 7.23-7.22(m, 2H), 7.15(d, 1H, J = 2.4 Hz), 6.39(s, 1H), 4.19-4.14(m, 2H), 3.09-3.05(m, 1H), 2.30(s, 3H), 2.19-2.07(m, 2H), 2.04-1.91(m, 2H), 1.77-1.61(m, 2H), 1.59-1.43(m, 2H) |

TABLE 6-continued

Compounds of Examples

| Example | Compound | NMR Value |
|---|---|---|
| 72 | 2-(1-Methylpyrrolidin-2-yl)-ethyl(3',5-dichloro-5'-fluoro-[1,1'-biphenyl]-2-yl)-carbamate | $^1$H NMR (CDCl$_3$): δ 7.99(s, 1H), 7.33(dd, 1H, J = 8.8 Hz, J = 2.4 Hz), 7.21-7.13(m, 3H), 6.96(dd, 1H, J = 8.8 Hz, J = 2.4 Hz), 6.46(s, 1H), 4.20-4.12(m, 2H), 3.11-3.07(m, 1H), 2.32(s, 3H), 2.20-2.14(m, 2H), 2.06-1.91(m, 2H), 1.79-1.62(m, 2H), 1.60-1.45(m, 2H) |
| 73 | 2-(1-Methylpyrrolidin-2-yl)-ethyl(3',5-dichloro-4'-fluoro-[1,1'-biphenyl]-2-yl)-carbamate | $^1$H NMR (CDCl$_3$): δ 7.98(s, 1H), 7.39-7.37(m, 1H), 7.32-7.26(m, 1H), 7.23-7.21(m, 2H), 7.19(d, 1H, J = 2.8 Hz), 6.41(s, 1H), 4.17-4.13 (m, 2H), 3.06-3.03(m, 1H), 2.26(s, 3H), 2.39-2.10(m, 2H), 2.03-1.89(m, 2H), 1.80-1.59(m, 2H), 1.57-1.43(m, 2H) |
| 74 | (R)-(1-methylpyrrolidin-3-yl)methyl(3'-fluoro-4'-formyl[1,1'-biphenyl]-2-yl)-carbamate | $^1$H NMR (CDCl$_3$): δ 8.00-7.93(m, 2H), 7.41-7.37(t, 1H, J = 15.2 Hz), 7.29-7.27(d, 1H, J = 8.0 Hz), 7.23-7.15(m, 3H), 6.51(s, 1H), 4.08-3.97(m, 2H), 2.60-2.56(t, 1H, J = 17.2 Hz), 2.49-2.45(m, 3H), 2.29-2.24(m, 4H), 1.96-1.91(m, 1H), 1.48-1.43(m, 1H) |
| 75 | 2-(1-Methylpyrrolidin-2-yl)-ethyl(3',5'-difluoro-5-hydroxy-[1,1'-biphenyl]-2-yl)carbamate | $^1$H NMR (CD$_3$OD): δ 7.19-7.17(m, 1H), 6.92-6.90(m, 2H), 6.85-6.76(m, 2H), 6.72-6.71(m, 1H), 4.10-4.02(m, 2H), 3.70-3.61(m, 1H), 3.16-3.10(m, 2H), 2.83(s, 3H), 2.27-2.13(m, 2H), 2.13-2.02(m, 2H), 1.77-1.72(m, 2H) |

TABLE 6-continued

Compounds of Examples

| Example Compound | NMR Value |
|---|---|
| 76 2-(1-Methylpyrrolidin-2-yl)-ethyl(3',5'-dichloro-5-hydroxy-[1,1'-biphenyl]-2-yl)carbamate | $^1$H NMR (CD$_3$OD): δ 7.33-7.32(m, 1H), 7.27-7.23(m, 1H), 7.17-7.15(m, 1H), 7.05-7.01(m, 1H), 6.82-6.79(m, 1H), 6.72-6.71(m, 1H), 4.11-4.07(m, 2H), 3.50-3.47(m, 1H), 3.04-3.01(m, 2H), 2.70(s, 3H), 2.20-2.16(m, 2H), 1.95-1.90(m, 2H), 1.75-1.70(m, 2H) |
| 77 2-(1-Methylpyrrolidin-2-yl)-ethyl(3'-chloro-4'-fluoro-5-hydroxy-[1,1'-biphenyl]-2-yl)carbamate | $^1$H NMR (CD$_3$OD): δ 7.44-7.42(m, 1H), 7.27-7.22(m, 2H), 7.16-7.14(m, 1H), 6.77-6.75(m, 1H), 6.70-6.69(m, 1H), 4.08-4.02(m, 2H), 3.64-3.57(m, 1H), 3.13-3.09(m, 2H), 2.86(s, 3H), 2.27-2.22(m, 2H), 1.97-1.93(m, 2H), 1.75-1.70(m, 2H) |
| 78 (R)-pyrrolidin-3-ylmethyl-[1,1'-biphenyl]-2-ylcarbamate | $^1$H NMR (CDCl$_3$): δ 8.17-7.98(bs, 1H), 7.60-7.29(m, 6H), 7.26-7.06(m, 2H), 6.78-6.61(bs, 1H), 4.17-3.94(m, 2H), 3.09-2.81(m, 3H), 2.75-2.59(m, 1H), 2.56-2.33(m, 2H), 1.98-1.80(m, 1H), 1.54-1.35(m, 1H) |
| 79 (S)-pyrrolidin-3-ylmethyl-[1,1'-biphenyl]-2-ylcarbamate | $^1$H NMR (CDCl$_3$): δ 8.07-7.89(bs, 1H), 7.58-7.32(m, 6H), 7.32-7.13(m, 2H), 7.01-6.85(bs, 1H), 4.28-3.98(m, 3H), 3.47-3.17(m, 3H), 3.13-2.95(m, 1H), 2.80-2.62(m, 1H), 2.25-2.08(m, 1H), 1.89-1.70(m, 1H) |

TABLE 6-continued

Compounds of Examples

| Example | Compound | NMR Value |
|---|---|---|
| 80 | (R)-pyrrolidin-3-ylmethyl-(3',5'-dichloro-[1,1'-biphenyl]-2-yl)carbamate | $^1$H NMR (CDCl$_3$): δ 8.10-7.93(bs, 1H), 7.45-7.30(m, 1H), 7.21-7.08(m, 2H), 6.98-6.79(m, 3H), 6.67-6.51(bs, 1H), 4.15-3.90(m, 2H), 3.11-2.76(m, 3H), 2.71-2.53(m, 8H), 2.48-2.29(m, 1H), 2.02-2.72(m, 2H), 1.49-1.29(m, 1H) |
| 81 | (S)-pyrrolidin-3-ylmethyl-(3',5'-difluoro-[1,1'-biphenyl]-2-yl)carbamate | $^1$H NMR (CDCl$_3$): δ 8.10-7.89(m, 1H), 7.49-7.30(m, 1H), 7.22-7.04(m, 2H), 6.98-6.75(m, 3H), 6.68-6.50(bs, 1H), 4.19-3.85(m, 2H), 3.12-2.75(m, 3H), 2.72-2.52(bs, 1H), 2.52-2.27(m, 1H), 2.07-1.72(m, 2H), 1.50-1.31(m, 1H) |
| 82 | (S)-pyrrolidin-3-ylmethyl(5-fluoro-[1,1'-biphenyl]-2-yl)-carbamate | $^1$H NMR (CDCl$_3$): δ 7.81(s, 1H), 7.45-7.36(m, 3H), 7.33-7.26(m, 2H), 7.06-7.01(m, 1H), 6.97-6.94(m, 1H), 4.12-4.06(m, 2H), 3.35-3.27(m, 1H), 3.23-3.16(m, 1H), 3.05-3.02(m, 1H), 2.69-2.65(m, 1H), 2.17-2.12(m, 1H), 1.82-1.78(m, 2H) |
| 83 | (S)-pyrrolidin-3-ylmethyl(5-fluoro-3'-methyl-[1,1'-biphenyl]-2-yl)carbamate | $^1$H NMR (CDCl$_3$): δ 7.82(s, 1H), 7.35-7.31(m, 1H), 7.20-7.18(m, 1H), 7.18-7.14(m, 1H), 7.13-7.11(m, 1H), 7.07-6.98(m, 1H), 6.95-6.92(m, 1H), 4.13-4.07(m, 2H), 3.38-3.33(m, 2H), 3.25-3.22(m, 1H), 3.09-3.05(m, 1H), 2.69-2.65(m, 1H), 2.38(s, 3H), 2.15-2.13(m, 1H), 1.80-1.76(m, 1H) |

TABLE 6-continued

Compounds of Examples

| Example | Compound | NMR Value |
|---|---|---|
| 84 | (R)-pyrrolidin-3-ylmethyl-(3',5,5'-trifluoro-[1,1'-biphenyl]-2-yl)carbamate | $^1$H NMR (CDCl$_3$): δ 7.98-7.79(bs, 1H), 7.14-7.00(m, 1H), 7.00-6.78(m, 4H), 6.61-6.45(bs, 1H), 4.18-3.90(m, 2H), 3.13-2.80(m, 3H), 2.70-2.57(m, 1H), 2.51-2.21(m, 2H), 1.94-1.80(m, 1H), 1.49-1.35(m, 1H) |
| 85 | (S)-pyrrolidin-3-ylmethyl-(3',5,5'-trifluoro-[1,1'-biphenyl]-2-yl)carbamate | $^1$H NMR (CDCl$_3$): δ 7.96-7.77(bs, 1H), 7.13-6.99(m, 1H), 6.99-6.76(m, 4H), 6.68-6.50(bs, 1H), 4.15-3.92(m, 2H), 3.16-2.90(bs, 3H), 2.90-2.30(m, 3H), 1.99-1.81(m, 1H), 1.53-1.35(m, 1H) |
| 86 | (R)-pyrrolidin-3-ylmethyl(5-methyl-[1,1'-biphenyl]-2-yl)-carbamate | $^1$H NMR (CDCl$_3$): δ 7.77 (s, 1H), 7.44-7.40(m, 2H), 7.37-7.31(m, 2H), 7.20-7.13(m, 2H), 7.04(s, 1H), 6.85(s, 1H), 4.13-4.04(m, 2H), 2.78-2.62(m, 3H), 2.32(s, 3H), 2.16-2.09(m, 2H), 2.03(s, 1H), 1.79-1.70(m, 2H) |
| 87 | (R)-pyrrolidin-3-ylmethyl(3'-fluoro-5-methyl-[1,1'-biphenyl]-2-yl)carbamate | $^1$H NMR (CDCl$_3$): δ 7.84 (s, 1H), 7.43-7.38(m, 1H), 7.17-7.08(m, 2H), 7.04-7.02(m, 2H), 7.01(s, 1H), 6.55(s, 1H), 4.08-3.97(m, 2H), 2.47-2.33(m, 3H), 2.32(s, 3H), 1.94-1.80(m, 2H), 1.51-1.40(m, 2H) |

TABLE 6-continued

Compounds of Examples

| Example | Compound | NMR Value |
|---|---|---|
| 88 | (S)-pyrrolidin-2-ylmethyl(4'-fluoro-[1,1'-biphenyl]-2-yl)-carbamate | $^1$H NMR (CDCl$_3$): δ 8.13-7.94(m, 1H), 7.41-7.23(m, 3H), 7.20-7.02(m, 4H), 6.75-6.57(bs, 1H), 4.23-4.04(m, 1H), 4.02-3.85(m, 1H), 3.47-3.30(m, 1H), 3.02-2.81(m, 2H), 2.57-2.25(bs, 1H), 1.95-1.59(m, 3H), 1.50-1.32(m, 1H) |
| 89 | (R)-(1-methylpyrrolidin-3-yl)methyl[1,1'-biphenyl]-2-ylcarbamate | $^1$H NMR (CDCl$_3$): δ 8.13-7.94(bs, 1H), 7.55-7.27(m, 6H), 7.26-7.03(m, 2H), 6.77-6.59(bs, 1H), 4.18-3.94(m, 2H), 3.00-2.57(m, 4H), 2.54-2.49(m, 1H), 2.47(s, 3H), 2.10-1.98(m, 1H) 1.67-1.55(m, 1H) |
| 90 | (S)-(1-methylpyrrolidin-3-yl)methyl[1,1'-biphenyl]-2-ylcarbamate | $^1$H NMR (CDCl$_3$): δ 8.09-7.94(bs, 1H), 7.56-7.31(m, 6H), 7.30-7.12(m, 2H), 6.86-6.72(bs, 1H), 4.19-4.02(m, 1H), 3.41-3.05(m, 3H), 2.97-2.77(m, 2H), 2.74(s, 3H), 2.29-2.15(m, 1H), 1.89-1.74(m, 1H) |
| 91 | (R)-(1-methylpyrrolidin-3-yl)methyl(3',5'-difluoro-[1,1'-biphenyl]-2-yl)-carbamate | $^1$H NMR (CDCl$_3$): δ 8.08-7.95(bs, 1H), 7.42-7.33(m, 1H), 7.21-7.08(m, 2H), 6.98-6.79(m, 3H), 6.59-6.48(bs, 1H), 4.13-3.95(m, 2H), 2.69-2.43(m, 3H), 2.40-2.14(m, 5H), 2.05-1.90(m, 1H), 1.57-1.42(m, 1H) |

TABLE 6-continued

| Example | Compound | NMR Value |
|---|---|---|
| 92 | (S)-(1-methylpyrrolidin-3-yl)methyl(3',5'-difluoro-[1,1'-carbamate]-2-yl)-carbamate | $^1$H NMR (CDCl$_3$): δ 8.08-7.95(bs, 1H), 7.42-7.33(m, 1H), 7.21-7.08(m, 2H), 6.98-6.79(m, 3H), 6.59-6.48(bs, 1H), 4.13-3.95(m, 2H), 2.69-2.43(m, 3H), 2.40-2.14(m, 5H), 2.05-1.90(m, 1H), 1.57-1.42(m, 1H) |
| 93 | (S)-(1-methylpyrrolidin-3-yl)methyl(5-fluoro-[1,1'-biphenyl]-2-yl)carbamate | $^1$H NMR (CDCl$_3$): δ 7.98(s, 1H), 7.49-7.39(m, 3H), 7.34-7.32(m, 2H), 7.06-7.01(m, 1H), 6.94-6.91(m, 1H), 6.49(s, 1H), 4.08-3.96(m, 2H), 2.61-2.57(m, 1H), 2.53-2.44(m, 3H), 2.30(s, 3H), 2.27-2.22(m, 1H), 1.98-1.89(m, 1H), 1.49-1.41(m, 1H) |
| 94 | (S)-(1-methylpyrrolidin-3-yl)methyl(5-fluoro-3'-methyl-[1,1'-biphenyl]-2-yl)-carbamate | $^1$H NMR (CDCl$_3$): δ 7.97(s, 1H), 7.37-7.33(m, 1H), 7.30-7.21(m, 2H), 7.13-7.11(m, 1H), 7.04-7.00(m, 1H), 6.95-6.91(m, 1H), 6.58(s, 1H), 4.08-3.98(m, 2H), 2.71-2.66(m, 1H), 2.59-2.46(m, 3H), 2.46-2.33(m, 7H), 2.01-1.97(m, 1H), 1.55-1.48(m, 1H) |
| 95 | (R)-(1-methylpyrrolidin-3-yl)methyl(3',5,5'-trifluoro-[1,1'-biphenyl]-2-yl)-carbamate | $^1$H NMR (CDCl$_3$): δ 7.97-7.81(bs, 1H), 7.13-7.01(m, 1H), 6.99-6.78(m, 4H), 6.57-6.41(bs, 1H), 4.13-3.94(m, 2H), 2.70-2.42(m, 4H), 2.05-2.88(m, 1H), 1.58-1.41(m, 4H) |

TABLE 6-continued

| Compounds of Examples | |
|---|---|
| Example Compound | NMR Value |
| 96 (S)-(1-methylpyrrolidin-3-yl)methyl(3',5,5'-trifluoro-[1,1'-biphenyl]-2-yl)-carbamate | $^1$H NMR (CDCl$_3$): δ 7.97-7.78(bs, 1H), 7.14-7.00(m, 1H), 6.99-6.78(m, 4H), 6.63-6.45(bs, 1H), 4.14-3.93(m, 2H), 2.71-2.42(m, 4H), 2.40-2.23(bs, 4H), 2.05-1.88(m, 1H), 1.59-1.41(m, 1H) |
| 97 (R)-(1-methylpyrrolidin-3-yl)methyl(5-methyl-[1,1'-biphenyl]-2-yl)carbamate | $^1$H NMR (CDCl$_3$): δ 7.89 (s, 1H), 7.47-7.43(m, 2H), 7.39-7.31(m, 2H), 7.22-7.13(m, 2H), 7.02(s, 1H), 6.63(s, 1H), 4.09-4.01(m, 2H), 2.67-2.58(m, 3H), 2.52(s, 3H), 2.32(s, 3H), 2.11-2.01(m, 2H), 1.65-1.58(m, 2H) |
| 98 (R)-(1-methylpyrrolidin-3-yl)methyl(3'-fluoro-5-methyl-[1,1'-biphenyl]-2-yl)-carbamate | $^1$H NMR (CDCl$_3$): δ 7.88 (s, 1H), 7.44-7.38(m, 1H), 7.17-7.10(m, 2H), 7.09-7.05(m, 2H), 7.01(s, 1H), 6.55(s, 1H), 4.09-3.98(m, 2H), 2.38(s, 3H), 2.32(s, 3H), 2.61-2.40(m, 3H), 2.15-1.97(m, 2H), 1.56-1.51(m, 2H) |
| 99 (S)-(1-methylpyrrolidin-2-yl)methyl(4'-fluoro-[1,1'-biphenyl]-2-yl)carbamate | $^1$H NMR (CDCl$_3$): δ 8.13-7.96(m, 1H), 7.41-7.23(m, 3H), 7.20-7.02(m, 4H), 6.62-6.45(bs, 1H), 4.24-3.97(m, 2H), 3.10-2.96(m, 1H), 2.50-2.27(m, 4H), 2.27-2.13(m, 1H) 1.96-1.80(m, 1H), 1.80-1.51(m, 3H) |

TABLE 6-continued

Compounds of Examples

| Example | Compound | NMR Value |
|---|---|---|
| 100 | (R)-(1-methylpyrrolidin-3-yl)methyl(3'-methyl-[1,1'-biphenyl]-2-yl)carbamate | $^1$H NMR (CDCl$_3$): δ 8.13-7.96(bs, 1H), 7.41-7.30(m, 2H), 7.30-7.03(m, 5H), 6.71-6.59(bs, 1H), 4.13-3.95(m, 2H), 2.72-2.59(m, 1H), 2.59-2.43(m, 3H), 2.40(s, 3H), 2.14-2.22(m, 4H), 2.06-1.87(m, 1H), 1.55-1.42(m, 1H) |
| 101 | (S)-(1-methylpyrrolidin-3-yl)methyl(3'-methyl-[1,1'-biphenyl]-2-yl)carbamate | $^1$H NMR (CDCl$_3$): δ 8.15-7.99(bs, 1H), 7.46-7.29(m, 2H), 7.28-7.02(m, 5H), 6.74-6.58(bs, 1H), 4.15-3.93(m, 2H), 2.70-2.43(m, 4H), 2.40(s, 3H), 2.31(s, 3H), 2.15-2.17(m, 1H) 2.03-1.86(m, 1H), 1.57-1.40(m, 1H) |
| 102 | (R)-(1-ethylpyrrolidin-3-yl)-methyl[1,1'-biphenyl]-2-yl-carbamate | $^1$H NMR (CDCl$_3$): δ 8.13-7.96(bs, 1H), 7.54-7.26(m, 6H), 7.25-7.02(m, 2H), 6.72-6.55(bs, 1H), 4.15-3.92(m, 2H), 2.91-2.69(m, 1H), 2.69-2.35(m, 5H), 2.33-2.17(m, 1H), 2.04-1.87(m, 1H) 1.60-1.42(m, 1H), 1.00(t, 3H, J = 7.2 Hz) |
| 103 | (S)-(1-ethylpyrrolidin-3-yl)-methyl[1,1'-biphenyl]-2-yl-carbamate | $^1$H NMR (CDCl$_3$): δ 8.15-7.97(bs, 1H), 7.55-7.27(m, 6H), 7.24-7.05(m, 2H), 6.72-6.59(bs, 1H), 4.14-3.94(m, 2H), 2.92-2.71(bs, 1H), 2.71-2.39(m, 5H), 2.38-2.22(m, 1H), 2.04-1.86(m, 1H), 1.59-1.44(m, 1H), 1.11(t, 3H, J = 7.2 Hz) |

TABLE 6-continued

Compounds of Examples

| Example | Compound | NMR Value |
|---|---|---|
| 104 | (R)-(1-ethylpyrrolidin-3-yl)-methyl(3'-methyl-[1,1'-biphenyl]-2-yl)carbamate | $^1$H NMR (CDCl$_3$): δ 8.13-8.00(bs, 1H), 7.42-7.27(m, 2H), 7.25-7.03(m, 5H), 6.69-6.59(bs, 1H), 4.13-3.95(m, 2H), 2.80-2.68(m, 1H), 2.68-2.32(m, 9H), 2.30-2.17(m, 1H), 2.03-1.89(m, 1H), 1.58-1.41(m, 1H), 1.18-1.04(t, 3H, J = 7.6 Hz) |
| 105 | (S)-(1-ethylpyrrolidin-3-yl)-methyl(3'-methyl-[1,1'-biphenyl]-2-yl)carbamate | $^1$H NMR (CDCl$_3$): δ 8.13-7.99(m, 1H), 7.43-7.27(m, 2H), 7.27-7.02(m, 5H), 6.72-6.58(bs, 1H), 4.13-3.94(m, 2H), 2.89-2.66(m, 1H), 2.66-2.15(m, 9H), 2.06-1.87(m, 1H), 1.57-1.40(m, 1H), 1.09(t, 3H, J = 7.6 Hz) |
| 106 | (S)-(1-ethylpyrrolidin-2-yl)-methyl[1,1'-biphenyl]-2-yl-carbamate | $^1$H NMR (CDCl$_3$): δ 8.15-8.01(m, 1H), 7.54-7.26(m, 6H), 7.22-7.05(m, 2H), 6.72-6.58(bs, 1H), 4.22-4.07(m, 1H), 4.07-3.93(m, 1H), 3.21-3.02(m, 1H), 2.92-2.59(m, 2H), 2.41-2.12(m, 2H), 1.95-1.50(m, 5H), 1.08(t, 3H, J = 7.2 Hz) |
| 107 | (S)-(1-isobutylpyrrolidin-2-yl)methyl[1,1'-biphenyl]-2-ylcarbamate | $^1$H NMR (CDCl$_3$): δ 8.18-8.02(m, 1H), 7.53-7.27(m, 6H), 7.22-7.03(m, 2H), 6.69-6.54(bs, 1H), 4.18-3.83(m, 2H), 3.15-2.95(bs, 1H), 2.71-2.53(bs, 1H), 2.48-2.30(m, 1H), 2.23-2.02(m, 2H), 1.92-1.45(m, 5H), 0.84(t, 6H, J = 6.8 Hz) |

TABLE 6-continued

Compounds of Examples

| Example | Compound | NMR Value |
|---|---|---|
| 108 | (S)-(1-methylpyrrolidin-3-yl)methyl(3',5-difluoro-[1,1'-biphenyl]-2-yl)-carbamate | ¹H NMR (CDCl₃): δ 7.85(s, 1H), 7.46-7.41(m, 1H), 7.15-7.03(m, 4H), 6.96-6.93(m, 1H), 4.11-4.03(m, 2H), 2.92-2.90(m, 1H), 2.82-2.68(m, 2H), 2.42(s, 3H), 2.12-2.10(m, 2H), 1.71-1.69(m, 2H) |
| 109 | (R)-(1-methylpyrrolidin-2-yl)methyl[1,1'-biphenyl]-2-ylcarbamate | ¹H NMR (CDCl₃): δ 8.18-7.99(m, 1H), 7.49-7.27(m, 6H), 7.22-7.15(m, 1H), 7.15-7.06(m, 1H), 6.72-6.60(bs, 1H), 4.24-3.98(m, 2H), 3.10-2.95(m, 1H), 2.52-2.40(m, 1H), 2.35(s, 3H) 2.26-2.12(m, 1H), 1.97-1.50(m, 4H) |
| 110 | (R)-(1-methylpyrrolidin-2-yl)methyl(3'-methyl-[1,1'-biphenyl]-2-yl)carbamate | ¹H NMR (CDCl₃): δ 8.18-7.97(bs, 1H), 7.41-7.28(m, 2H), 7.23-7.01(m, 5H), 6.78-6.62(bs, 1H), 4.12-3.97(m, 2H), 3.05-2.90(m, 1H), 2.52-2.11(m, 8H), 1.95-1.47(m, 4H) |
| 111 | (R)-(1-methylpyrrolidin-2-yl)methyl(5-fluoro-3'-methyl-[1,1'-biphenyl]-2-yl)-carbamate | ¹H NMR (CDCl₃): δ 8.00(s, 1H), 7.34-7.31(m, 1H), 7.21-7.19(m, 1H), 7.12-7.06(m, 2H), 7.04-6.99(m, 1H), 6.92-6.89(m, 1H), 6.59(s, 1H), 4.18-4.04(m, 2H), 3.06-3.02(m, 1H), 2.38(s, 3H), 2.35(s, 3H), 2.22-2.15(m, 2H), 1.92-1.76(m, 2H), 1.68-1.54(m, 2H) |

TABLE 6-continued

Compounds of Examples

| Example | Compound | NMR Value |
|---|---|---|
| 112 | (S)-(1-isopropylpyrrolidin-2-yl)methyl[1,1'-biphenyl]-2-ylcarbamate | ¹H NMR (CDCl₃): δ 8.15-8.01(m, 1H), 7.51-7.27(m, 6H), 7.21-7.06(m, 2H), 6.69-6.56(bs, 1H), 4.12-4.00(m, 1H), 3.87-3.76(m, 1H), 3.04-2.78(m, 3H), 2.53-2.40(m, 1H), 1.80-1.62(m, 4H), 1.08(d, 3H, J = 6.4 Hz), 0.99(d, 3H, J = 6.4 Hz) |
| 113 | (R)-(1-methylpyrrolidin-3-yl)methyl(3'-fluoro-[1,1'-biphenyl]-2-yl)carbamate | ¹H NMR (CDCl₃): δ 8.13-7.98(m, 1H), 7.50-7.31(m, 2H), 7.21-7.00(m, 5H), 6.62-6.49(bs, 1H), 4.14-3.95(m, 2H), 2.75-2.42(m, 4H), 2.42-2.22(m, 4H), 2.03-1.87(m, 1H), 1.58-1.42(m, 1H) |
| 114 | (R)-(1-methylpyrrolidin-3-yl)methyl(4'-fluoro-[1,1'-biphenyl]-2-yl)carbamate | ¹H NMR (CDCl₃): δ 8.11-7.97(bs, 1H), 7.42-7.27(m, 3H), 7.01-7.03(m, 4H), 6.57-6.42(bs, 1H), 4.13-3.92(m, 2H), 2.70-2.41(m, 4H), 2.41-2.20(m, 4H), 2.06-1.94(m, 1H), 1.56-1.41(m, 1H) |
| 115 | (R)-(1-methylpyrrolidin-3-yl)methyl(3',4'-difluoro-[1,1'-biphenyl]-2-yl)-carbamate | ¹H NMR (CDCl₃) δ 8.02-8.01(s, 1H), 7.38-7.06(m, 5H), 6.47(s, 1H), 4.09-3.98(m, 2H), 2.62-2.58(t, 1H, J = 17.2 Hz), 2.55-2.46(m, 3H), 2.37-2.25(m, 4H), 2.04-1.91(m, 2H), 1.51-1.43(m, 1H) |

TABLE 6-continued

| Compounds of Examples | |
|---|---|
| Example Compound | NMR Value |
| 116 (S)-(1-methylpyrrolidin-3-yl)methyl(3'-fluoro-[1,1'-biphenyl]-2-yl)carbamate | $^1$H NMR (CDCl$_3$): δ 8.12-7.98(bs, 1H), 7.50-7.31(m, 2H), 7.24-7.02(m, 5H), 6.70-6.54(bs, 1H), 4.16-3.97(m, 2H), 2.77-2.65(m, 1H), 2.64-2.47(m, 3H), 2.45-2.28(m, 4H), 2.06-1.93(m, 1H), 1.61-1.47(m, 1H) |
| 117 (R)-(1-methylpyrrolidin-3-yl)methyl(3'-chloro-[1,1'-biphenyl]-2-yl)carbamate | $^1$H NMR (CDCl$_3$): δ 8.08-7.93(bs, 1H), 7.47-7.27(m, 4H), 7.21-7.05(m, 3H), 6.67-6.53(bs, 1H), 4.15-3.93(m, 2H), 2.80-2.50(m, 4H), 2.50-2.24(bs, 4H), 2.09-1.92(m, 1H), 1.62-1.46(m, 1H) |
| 118 (S)-(1-methylpyrrolidin-3-yl)methyl(3'-chloro-[1,1'-biphenyl]-2-yl)carbamate | $^1$H NMR (CDCl$_3$): δ 8.07-7.92(bs, 1H), 7.42-7.31(m, 4H), 7.27-7.21(m, 1H), 7.20-7.09(m, 2H), 6.66-6.56(bs, 1H), 4.13-3.97(m, 2H), 2.85-2.53(m, 4H), 2.52-2.35(m, 4H), 2.08-1.97(m, 1H), 1.63-1.52(m, 1H) |
| 119 (S)-(1-methylpyrrolidin-3-yl)methyl(3',5'-dichloro-[1,1'-biphenyl]-2-yl)carbamate | $^1$H NMR (CDCl$_3$): δ 8.02-7.83(bs, 1H), 7.48-7.32(m, 2H), 7.33-7.21(m, 2H), 7.20-7.08(m, 2H), 6.77-6.56(bs, 1H), 4.15-3.95(m, 2H), 2.80-2.54(m, 4H), 2.54-2.30(m, 4H), 2.12-1.92(m, 1H), 1.67-1.49(m, 1H) |

TABLE 6-continued

Compounds of Examples

| Example | Compound | NMR Value |
|---|---|---|
| 120 | (S)-(1-methylpyrrolidin-3-yl)methyl(3'-chloro-5'-fluoro-[1,1'-biphenyl]-2-yl)carbamate | ¹H NMR (CDCl₃): δ 8.03-7.89(bs, 1H), 7.45-7.33(m, 1H), 7.23-7.07(m, 4H), 7.05-6.95(m, 1H), 6.72-6.56(bs, 1H), 4.16-3.96(m, 2H), 2.78-2.50(m, 4H), 2.50-2.29(m, 4H), 2.10-1.92(m, 1H), 1.65-1.47(m, 1H) |
| 121 | (S)-(1-methylpyrrolidin-3-yl)methyl(3'-chloro-4'-fluoro-[1,1'-biphenyl]-2-yl)carbamate | ¹H NMR (CDCl₃): δ 8.06-7.96(bs, 1H), 7.49-7.32(m, 2H), 7.25-7.19(m, 2H), 7.18-7.10(m, 2H), 6.65-6.47(bs, 1H), 4.17-3.95(m, 2H), 2.78-2.50(m, 4H), 2.50-2.25(m, 4H), 2.08-1.91(m, 1H), 1.62-1.47(m, 1H) |
| 122 | (S)-(1-methylpyrrolidin-3-yl)methyl(5-fluoro-3',5'-dimethyl-[1,1'-biphenyl]-2-yl)carbamate | ¹H NMR (CDCl₃): δ 8.03-7.88(bs, 1H), 7.05-6.96(m, 2H), 6.95-6.87(m, 3H), 6.64-6.58(bs, 1H), 4.12-3.92(m, 2H), 2.68-2.57(m, 1H) 2.57-2.43(m, 3H), 2.34(s, 6H), 2.33-2.15(m, 4H), 2.00-1.77(m, 1H), 1.55-1.45(m, 1H) |
| 123 | (S)-(1-methylpyrrolidin-3-yl)methyl(3'-chloro-5-fluoro-5'-hydroxy-[1,1'-biphenyl]-2-yl)carbamate | ¹H NMR (CDCl₃): δ 7.77-7.60(bs, 1H), 7.13-6.86(m, 3H), 6.79(s, 1H), 6.70(s, 1H), 6.53(s, 1H), 5.03-4.50(bs, 1H), 4.33-4.18(m, 1H), 4.18-3.98(m, 1H), 3.08-2.95(bs, 1H), 2.95-2.78(bs, 1H), 2.70-2.31(m, 5H), 2.08-1.90(bs, 1H), 1.90-1.70(bs, 1H) |

TABLE 6-continued

Compounds of Examples

| Example | Compound | NMR Value |
|---|---|---|
| 124 | (S)-(1-methylpyrrolidin-3-yl)methyl(4',5-difluoro-[1,1'-biphenyl]-2-yl)-carbamate | $^1$H NMR (CDCl$_3$): δ 8.00-7.85(bs, 1H), 7.38-7.25(m, 2H), 7.20-7.19(m, 2H), 7.03(td, 1H, J = 8.4 Hz, 2.8 Hz), 6.90(dd, 1H, J = 8.8 Hz, 2.8 Hz), 6.51-6.39(bs, 1H), 4.12-3.90(m, 2H), 2.63-2.55(m, 1H) 2.55-2.39(m, 3H), 2.37-2.18(m, 4H), 1.99-1.85(m, 1H), 1.54-1.38(m, 1H) |
| 125 | (S)-(1-methylpyrrolidin-3-yl)methyl(3'-chloro-5-fluoro-[1,1'-biphenyl]-2-yl)-carbamate | $^1$H NMR (CDCl$_3$): δ 8.02-7.81(bs, 1H), 7.53-7.30(m, 3H), 7.26-7.19(m, 1H), 7.05(td, 1H, J = 8.0 Hz, 2.8 Hz), 6.91(dd, 1H, J = 8.8 Hz, 2.8 Hz), 6.54-6.45(bs, 1H), 4.13-3.86(m, 2H), 2.65-2.54(m, 1H) 2.54-2.42(m, 3H), 2.37-2.19(m, 4H), 2.00-1.86(m, 1H), 1.55-1.37(m, 1H) |
| 126 | (S)-(1-methylpyrrolidin-3-yl)methyl(3',5'-dichloro-5-fluoro-[1,1'-biphenyl]-2-yl)-carbamate | $^1$H NMR (CDCl$_3$): δ 7.92-7.76(bs, 1H), 7.42-7.36(m, 1H), 7.28-7.17(m, 2H), 7.06(td, 1H, J = 8.8 Hz, 2.8 Hz), 6.90(dd, 1H, J = 8.8 Hz, 2.8 Hz), 6.51-6.36(bs, 1H), 4.12-3.90(m, 2H), 2.63-2.55(m, 1H) 2.55-2.39(m, 3H), 2.37-2.18(m, 4H), 2.00-1.85(m, 1H), 1.54-1.38(m, 1H) |
| 127 | (S)-(1-methylpyrrolidin-3-yl)methyl(4'-chloro-5-fluoro-[1,1'-biphenyl]-2-yl carbamate | $^1$H NMR (CDCl$_3$): δ 7.98-7.82(bs, 1H), 7.49-7.38(m, 2H), 7.34-7.20(m, 2H), 7.03(td, 1H, J = 8.4 Hz, 2.8 Hz), 6.90(dd, 1H, J = 8.8 Hz, 2.8 Hz), 6.60-6.49(bs, 1H), 4.14-3.87(m, 2H), 2.66-2.59(m, 1H) 2.59-2.45(m, 3H), 2.42-2.15(m, 4H), 2.04-1.89(m, 1H), 1.57-1.42(m, 1H) |

TABLE 6-continued

Compounds of Examples

| Example | Compound | NMR Value |
|---|---|---|
| 128 | (S)-(1-methylpyrrolidin-3-yl)methyl(3',4'-dichloro-5-fluoro-[1,1'-biphenyl]-2-yl)-carbamate | $^1$H NMR (CDCl$_3$): δ 7.86-7.65(bs, 1H), 7.58-7.39(m, 2H), 7.26-7.16(m, 1H), 7.04(td, 1H, J = 8.4 Hz, 3.2 Hz), 6.89(dd, 1H, J = 8.8 Hz, 3.2 Hz), 6.89-6.79(bs, 1H), 4.15-3.94(m, 2H), 2.90-2.73(m, 2H), 2.73-2.54(m, 3H), 2.52-2.19(m, 3H), 2.14-1.96(m, 1H), 1.70-1.54(m, 1H) |
| 129 | (S)-(1-methylpyrrolidin-3-yl)methyl(3'-chloro-5,5'-difluoro-[1,1'-biphenyl]-2-yl)carbamate | $^1$H NMR (CDCl$_3$): δ 7.97-7.76(bs, 1H), 7.18-7.02(m, 3H), 7.03-6.86(m, 2H), 6.54-6.42(bs, 1H), 4.03-3.85(m, 2H), 2.65-2.57(m, 1H) 2.57-2.41(m, 3H), 2.37-2.18(m, 4H), 2.02-1.87(m, 1H), 1.55-1.41(m, 1H) |
| 130 | (R)-(1-methylpyrrolidin-3-yl)methyl(3',4'-dichloro-[1,1'-biphenyl]-2-yl)-carbamate | $^1$H NMR (CDCl$_3$) δ 8.01-7.99(m, 1H), 7.54-7.51(d, 1H, J = 8 Hz), 7.46(m, 1H), 7.38-7.34(m, 1H), 7.21-7.11(m, 2H), 6.46(s, 1H), 4.09-3.98(m, 2H), 2.63-2.59(t, 1H, J = 17.2 Hz), 2.54-2.47(m, 3H), 2.36-2.26(m, 4H), 2.00-1.93(m, 1H), 1.50-1.45(m, 1H) |
| 131 | (R)-(1-methylpyrrolidin-3-yl)methyl(3',5'-dichloro-[1,1'-dichloro]-2-yl)-carbamate | $^1$H NMR (CDCl$_3$) δ 8.01-7.97(m, 1H), 7.43-7.35(m, 2H), 7.26-7.25(m, 2H), 7.18-7.11(m, 2H), 6.46(s, 1H), 4.10-3.99(m, 2H), 2.67-2.61(t, 1H, J = 17.2 Hz), 2.57-2.50(m, 3H), 2.38-2.28(m, 4H), 2.01-1.93(m, 1H), 1.52-1.48(m, 1H) |

TABLE 6-continued

Compounds of Examples

| Example | Compound | NMR Value |
|---|---|---|
| 132 | (R)-(1-methylpyrrolidin-3-yl)methyl(3'-chloro-5'-fluoro-[1,1'-biphenyl]-2-yl)-carbamate | $^1$H NMR (CDCl$_3$) δ 8.01-7.99(m, 1H), 7.39-7.35(m, 1H), 7.18-7.11(m, 3H), 6.99-6.97(m, 1H), 6.48(s, 1H), 4.10-3.99(m, 2H), 2.63-2.59(t, 1H, J = 17.2 Hz), 2.53-2.48(m, 3H), 2.36-2.27(m, 4H), 2.00-1.92(m, 1H), 1.51-1.46(m, 1H) |
| 133 | (R)-(1-methylpyrrolidin-3-yl)methyl(5-fluoro-3'-amino-[1,1'-biphenyl]-2-yl)-carbamate | $^1$H NMR (CDCl$_3$) δ 8.03(m, 1H), 7.25-7.21(m, 1H), 7.03-6.98(m, 1H), 6.92-6.90(m, 1H), 6.72-6.61(m, 3H), 4.08-3.97(m, 2H), 3.80(s, 1H), 2.66-2.62(t, 1H, J = 17.2 Hz), 2.53-2.46(m, 3H), 2.33-2.28(m, 4H), 2.01-1.93(m, 1H), 1.51-1.48(m, 1H) |
| 134 | (R)-(1-methylpyrrolidin-3-yl)methyl(3'-chloro-5-fluoro-5'-hydroxy-[1,1'-biphenyl]-2-yl)carbamate | $^1$H NMR (CDCl$_3$) δ 7.67(m, 1H), 7.06-7.01(m, 1H), 6.97-6.94(m, 3H), 6.73-6.72(m, 1H), 6.54(s, 1H), 4.35-4.05(m, 2H), 3.01-3.00(m, 1H), 2.89-2.88(m, 1H), 2.59-2.57(m, 2H), 2.47-2.41(m, 4H), 1.97-1.96(m, 1H), 1.80(m, 1H) |
| 135 | (R)-(1-methylpyrrolidin-3-yl)methyl(3',5'-dichloro-5-fluoro-[1,1'-biphenyl]-2-yl)carbamate | $^1$H NMR (CDCl$_3$) δ 7.85(s, 1H), 7.41-7.40(t, 1H, J = 4.0 Hz), 7.23(s, 2H), 7.10-7.05(m, 2H), 6.93-6.90(m, 2H), 6.36(s, 1H), 4.09-3.99(m, 2H), 2.63-2.59(t, 1H, J = 17.2 Hz), 2.56-2.45(m, 3H), 2.32-2.28(m, 4H), 2.01-1.93(m, 1H), 1.50-1.46(m, 1H) |

TABLE 6-continued

Compounds of Examples

| Example Compound | | NMR Value |
|---|---|---|
| 136 | (R)-(1-(methylpyrrolidin-3-yl)methyl(3'-chloro-4'-fluoro-[1,1'-biphenyl]-2-yl)-carbamate | ¹H NMR (CDCl₃) δ 8.03-7.98(m, 1H), 7.41-7.34(m, 2H), 7.26-7.21(m, 2H), 7.17-7.10(m, 2H), 6.49(s, 1H), 4.09-3.98(m, 2H), 2.63-2.59(t, 1H, J = 17.2 Hz), 2.51-2.46(m, 3H), 2.36-2.26(m, 4H), 2.00-1.91(m, 1H), 1.51-1.46(m, 1H) |
| 137 | (R)-(1-methylpyrrolidin-3-yl)methyl(3'-hydroxy-[1,1'-biphenyl]-2-yl)carbamate | ¹H NMR (CDCl₃): δ 7.95-7.81(m, 1H), 7.40-7.19(m, 3H), 7.18-7.06(m, 1H), 6.89-6.65(m, 4H), 4.34-4.18(m, 1H), 4.09-3.94(m, 1H), 2.89-2.51(m, 5H), 2.42(s, 3H), 2.07-1.95(m, 1H), 1.78-1.60(m, 1H) |
| 138 | (R)-(1-methylpyrrolidin-3-yl)methyl(3'-chloro-5'-(trifluoromethyl)-[1,1'-biphenyl]-2-yl)carbamate | ¹H NMR (CDCl₃) δ 7.96-7.94(m, 1H), 7.63(s, 1H), 7.55-7.52(m, 2H), 7.42-7.37(m, 2H), 7.21-7.17(m, 2H), 6.40(s, 1H), 4.09-3.99(m, 2H), 2.64-2.60(t, 1H, J = 17.2 Hz), 2.55-2.47(m, 3H), 2.36-2.31(m, 4H), 2.00-1.91(m, 1H), 1.51-1.46(m, 1H) |
| 139 | (R)-(1-methylpyrrolidin-3-yl)methyl(3'-chloro-5-fluoro-5'-methoxy-[1,1'-biphenyl]-2-yl)carbamate | ¹H NMR (CDCl₃) δ 7.97(m, 1H), 7.07-7.03(m, 1H), 6.94-6.89(m, 2H), 6.74-6.73(m, 1H), 6.45(s, 1H), 4.08-3.99(m, 2H), 3.83-3.79(m, 3H), 2.63-2.59(t, 1H, J = 17.2 Hz), 2.54-2.47(m, 3H), 2.36-2.27(m, 4H), 2.00-1.91(m, 1H), 1.49-1.45(m, 1H) |

TABLE 6-continued

Compounds of Examples

| Example | Compound | NMR Value |
|---|---|---|
| 140 | (R)-(1-methylpyrrolidin-3-yl)methyl(3'-chloro-5-fluoro-5'-(trifluoromethyl)-[1,1'-biphenyl]-2-yl)carbamate | $^1$H NMR (CDCl$_3$) δ 7.82(m, 1H), 7.65(s, 1H), 7.54-7.51(m, 2H), 7.13-7.08(m, 1H), 6.96-6.93(m, 2H), 6.34(s, 1H), 4.07-3.97(m, 2H), 2.60-2.56(t, 1H, J = 17.2 Hz), 2.53-2.43(m, 3H), 2.34-2.35(m, 4H), 1.98-1.90(m, 1H), 1.49-1.44(m, 1H) |
| 141 | (R)-(1-methylpyrrolidin-3-yl)methyl(4',5-difluoro-[1,1'-biphenyl]-2-yl)-carbamate | $^1$H NMR (CDCl$_3$) δ 7.93(m, 1H), 7.31-7.29(m, 2H), 7.23-7.13(m, 2H), 7.06-7.01(m, 1H), 6.91-6.89(m, 1H), 6.42(s, 1H), 4.07-3.96(m, 2H), 2.61-2.56(t, 1H, J = 17.2 Hz), 2.53-2.43(m, 3H), 2.35-2.25(m, 4H), 2.00-1.89(m, 1H), 1.51-1.41(m, 1H) |
| 142 | (R)-(1-methylpyrrolidin-3-yl)methyl(3'-chloro-5,5'-difluoro-[1,1'-biphenyl]-2-yl)carbamate | $^1$H NMR (CDCl$_3$) δ 7.85(m, 1H), 7.14-7.13(m, 2H), 7.10-7.05(m, 1H), 6.98-6.96(m, 1H), 6.93-6.90(m, 1H), 6.43(s, 1H), 4.09-3.99(m, 2H), 2.65-2.60(t, 1H, J = 17.2 Hz), 2.55-2.47(m, 3H), 2.36-2.31(m, 4H), 2.02-1.95(m, 1H), 1.52-1.47(m, 1H) |
| 143 | (R)-(1-methylpyrrolidin-3-yl)methyl(3'-chloro-4',5-difluoro-[1,1'-biphenyl]-2-yl)carbamate | $^1$H NMR (CDCl$_3$) δ 7.85(m, 1H), 7.40-7.38(m, 1H), 7.26-7.19(m, 2H), 7.08-7.03(m, 1H), 6.91-6.88(m, 1H), 6.34(s, 1H), 4.08-3.97(m, 2H), 2.61-2.57(t, 1H, J = 17.2 Hz), 2.55-2.47(m, 3H), 2.36-2.25(m, 4H), 2.00-1.90(m, 1H), 1.51-1.44(m, 1H) |

TABLE 6-continued

Compounds of Examples

| Example Compound | | NMR Value |
|---|---|---|
| 144 | (R)-(1-methylpyrrolidin-3-yl)methyl(2',5-difluoro-[1,1'-biphenyl]-2-yl)-carbamate | $^1$H NMR (CDCl$_3$) δ 8.05(m, 1H), 7.44-7.40(m, 1H), 7.31-7.23(m, 2H), 7.21-7.17(m, 2H), 6.98-6.96(m, 1H), 4.13-4.07(m, 2H), 3.10-3.08(m, 1H), 2.49-2.45(m, 1H), 2.39(s, 3H), 2.29-2.21(m, 1H), 1.95-1.59(m, 4H) |
| 145 | (R)-(1-methylpyrrolidin-3-yl)methyl(3',5-dichloro-[1,1'-biphenyl]-2-yl)-carbamate | $^1$H NMR (CDCl$_3$) δ 7.87-7.85(m, 1H), 7.55-7.17(m, 5H), 6.99(m, 1H), 6.55(s, 1H), 4.11-4.02(m, 2H), 3.06-3.02(m, 2H), 2.95-2.89(m, 1H), 2.85-2.81(m, 1H), 2.76-2.66(m, 1H), 2.62(s, 3H), 2.18-2.09(m, 1H), 1.78-1.69(m, 1H) |
| 146 | (R)-(1-(methylpyrrolidin-3-yl)methyl(3',5-dichloro-4'-fluoro-[1,1'-biphenyl]-2-yl)carbamate | $^1$H NMR (CDCl$_3$) δ 7.86-7.83(m, 1H), 7.53-7.15(m, 4H), 6.99(m, 1H), 6.50(s, 1H), 4.10-4.02(m, 2H), 3.05-3.02(m, 2H), 2.97-2.90(m, 1H), 2.84-2.82(m, 1H), 2.77-2.67(m, 1H), 2.60(s, 3H), 2.18-2.10(m, 1H), 1.79-1.69(m, 1H) |
| 147 | (R)-1-methylpyrrolidin-3-yl)methyl(3'-chloro-4'-fluoro-5-methoxy-[1,1'-biphenyl]-2-yl)carbamate | $^1$H NMR (CDCl$_3$) δ 7.70(s, 1H), 7.44-7.42(d, 1H, J = 7.2 Hz), 7.26-7.20(m, 2H), 6.93-6.90(m, 1H), 6.75(m, 1H), 6.66(s, 1H), 4.15-4.00(m, 2H), 3.81(s, 3H), 3.42-3.40(m, 1H), 2.81-2.47(m, 2H), 2.34(s, 3H), 2.06-1.60(m, 4H) |

TABLE 6-continued

Compounds of Examples

| Example | Compound | NMR Value |
|---|---|---|
| 148 | (S)-(1-methylpyrrolidin-2-yl)methyl(3'-chloro-5'-fluoro-[1,1'-biphenyl]-2-yl)-carbamate 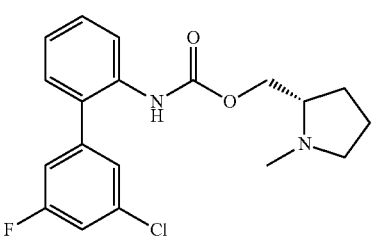 [SMILES: CN1CCC[C@H]1COC(=O)Nc1ccccc1-c1cc(F)cc(Cl)c1] | $^1$H NMR (CDCl$_3$) δ 7.92(s, 1H), 7.43-7.27(m, 2H), 7.23-7.08(m, 3H), 7.03-6.95(m, 1H), 6.79(s, 1H), 4.33-4.19(m, 2H), 3.28-3.26(m, 1H), 2.75(m, 1H), 2.49-2.28(m, 4H), 1.98-1.59(m, 4H) |
| 149 | (S)-(1-methylpyrrolidin-2-yl)methyl(3'-chloro-4'-fluoro-[1,1'-biphenyl]-2-yl)-carbamate 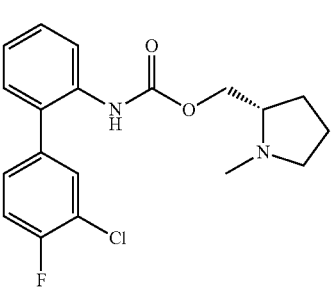 [SMILES: CN1CCC[C@H]1COC(=O)Nc1ccccc1-c1ccc(F)c(Cl)c1] | $^1$H NMR (CDCl$_3$) δ 7.90(s, 1H), 7.39-7.31(m, 2H), 7.22-7.05(m, 3H), 7.03-6.97(m, 1H), 6.72(s, 1H), 4.26-4.11(m, 2H), 3.19-3.14(m, 1H), 2.70-2.64(m, 1H), 2.42-2.30(m, 4H), 1.99-1.58(m, 4H) |
| 150 | (R)-(1-ethylpyrrolidin-3-yl)methyl(3'-chloro-4'-fluoro-[1,1'-biphenyl]-2-yl)-carbamate 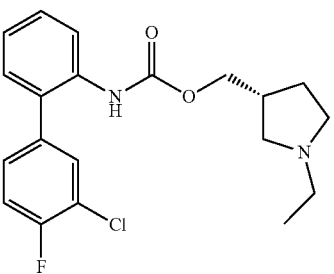 [SMILES: CCN1CC[C@@H](COC(=O)Nc2ccccc2-c2ccc(F)c(Cl)c2)C1] | $^1$H NMR (CDCl$_3$): δ 7.97(s, 1H), 7.41-7.33(m, 2H), 7.23-7.21(m, 2H), 7.16-7.10(m, 2H), 6.60(s, 1H), 4.10-4.01(m, 2H), 2.74-2.72(m, 1H), 2.65-2.45 (m, 5H), 2.37-2.34(m, 1H), 2.02-1.93(m, 1H), 1.57-1.49(m, 1H), 1.11(t, 3H, J = 7.2 Hz) |
| 151 | (R)-(1-isopropylpyrrolidin-3-yl)methyl(3'-chloro-4'-fluoro-[1,1'-biphenyl]-2-yl)-carbamate 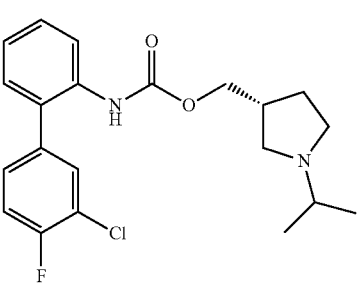 [SMILES: CC(C)N1CC[C@@H](COC(=O)Nc2ccccc2-c2ccc(F)c(Cl)c2)C1] | $^1$H NMR (CDCl$_3$): δ 7.95(s, 1H), 7.41-7.34(m, 2H), 7.23-7.21(m, 2H), 7.18-7.12(m, 2H), 6.68(s, 1H), 4.14-4.04(m, 2H), 3.07-3.05(m, 1H), 2.93-2.90(m, 1H), 2.76-2.74(m, 1H), 2.67-2.64(m, 2H), 2.09-2.02(m, 1H), 1.70-1.65(m, 2H), 1.23(s, 6H) |

TABLE 6-continued

Compounds of Examples

| Example | Compound | NMR Value |
|---|---|---|
| 152 | (R)-(1-methylpyrrolidin-3-yl)methyl(3'-(hydroxymethyl)-[1,1'-biphenyl]-2-yl)-carbamate | ¹H NMR (CDCl₃): δ 8.10-7.92(bs, 1H), 7.57-6.90(m, 7H), 4.71(s, 1H), 4.21-3.91(m, 3H), 2.73-2.16(m, 9H), 2.08-1.84(m, 1H), 1.64-1.39(m, 1H) |
| 153 | (R)-(1-methylpyrrolidin-3-yl)methyl(3'-carbamoyl-[1,1'-biphenyl]-2-yl)carbamate | ¹H NMR (DMSO): δ 8.78(s, 1H), 8.20-7.78(m, 3H), 7.78-7.20(m, 7H), 3.99-3.65(bs, 2H), 3.55-3.26(bs, 1H), 2.60-1.97(m, 7H), 1.88-1.63(bs, 1H), 1.41-1.14(bs, 1H) |
| 154 | (R)-(1-methylpyrrolidin-3-yl)methyl(3'-amino-[1,1'-biphenyl]-2-yl)carbamate | ¹H NMR (CDCl₃): δ 8.15-8.00(bs, 1H), 7.43-7.13(m, 3H), 7.12-6.99(m, 1H), 6.82-6.55(m, 4H), 4.18-3.93(m, 2H), 3.87-3.67(bs, 2H), 2.72-2.41(m, 4H), 2.41-2.19(m, 4H), 2.03-1.83(m, 1H), 1.55-1.40(m, 1H) |
| 155 | (R)-(1-methylpyrrolidin-3-yl)methyl(3'-cyano-[1,1'-biphenyl]-2-yl)carbamate | ¹H NMR (CDCl₃): δ 8.03-7.85(m, 1H), 7.74-7.50(m, 4H), 7.47-7.32(m, 1H), 7.26-7.08(m, 2H), 6.71-6.47(bs, 1H), 4.15-3.90(m, 2H), 2.77-2.48(m, 4H), 2.48-2.25(bs, 4H), 2.09-1.88(m, 1H), 1.63-1.44(m, 1H) |

TABLE 6-continued

Compounds of Examples

| Example | Compound | NMR Value |
|---|---|---|
| 156 | (R)-(1-methylpyrrolidin-3-yl)methyl(2'-fluoro-[1,1'-biphenyl]-2-yl)carbamate | $^1$H NMR (CDCl$_3$): δ 7.98(m, 1H), 7.43-7.38(m, 3H), 7.31-7.29(m, 1H), 7.26-7.25(m, 1H), 7.23-7.16(m, 2H), 6.48(s, 1H), 4.11-4.02(m, 2H), 2.94-2.80(m, 1H), 2.51-2.48(m, 1H), 2.44(s, 3H), 2.14-2.01(m, 1H), 1.89-1.55(m, 4H) |
| 157 | (R)-(1-methylpyrrolidin-3-yl)methyl(2',4'-difluoro-[1,1'-biphenyl]-2-yl)-carbamate | $^1$H NMR (CDCl$_3$): δ 7.91(m, 1H), 7.39-7.36(m, 1H), 7.30-7.26(m, 1H), 7.19-7.17(m, 2H), 7.00-6.97(m, 2H), 6.95-6.92(m, 1H), 6.70(s, 1H), 4.12-4.06(m, 2H), 3.00-2.97(m, 1H), 2.75-2.70(m, 1H), 2.60(s, 3H), 2.18-2.14(m, 1H), 1.90-1.52(m, 4H) |
| 158 | (R)-(1-methylpyrrolidin-3-yl)methyl(2',3'-difluoro-[1,1'-biphenyl]-2-yl)-carbamate | $^1$H NMR (CDCl$_3$): δ 7.84(m, 1H), 7.41-7.39(m, 1H), 7.23-7.17(m, 4H), 7.09-7.07(m, 1H), 4.18-4.11(m, 2H), 3.27-3.14(m, 1H), 2.89-2.85(m, 1H), 2.74(s, 3H), 2.28-2.23(m, 1H), 1.93-1.48(m, 4H) |
| 159 | (R)-(1-methylpyrrolidin-3-yl)methyl(3'-chloro-6'-fluoro-[1,1'-biphenyl]-2-yl)carbamate | $^1$H NMR (CDCl$_3$): δ 7.94(m, 1H), 7.55-7.42(m, 1H), 7.30-7.22(m, 2H), 7.19-7.15(m, 2H), 7.04-7.00(m, 1H), 4.20-4.08(m, 2H), 3.29-3.17(m, 1H), 2.88-2.85(m, 1H), 2.54(s, 3H), 2.33-2.28(m, 1H), 2.01-1.66(m, 4H) |

TABLE 6-continued

Compounds of Examples

| Example | Compound | NMR Value |
|---|---|---|
| 160 | (S)-(1-methylpyrrolidin-2-yl)methyl(3'-fluoro-[1,1'-biphenyl]-2-yl)carbamate 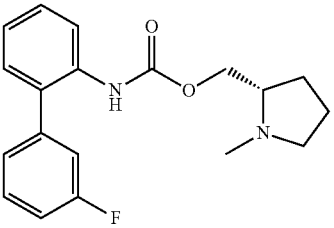 [SMILES: CN1CCC[C@H]1COC(=O)Nc1ccccc1-c1cccc(F)c1] | ¹H NMR (CDCl₃): δ 8.10-8.03(m, 1H), 7.36-7.02(m, 6H), 6.89-6.85(m, 1H), 6.63(s, 1H), 4.22-4.02(m, 2H), 3.07-2.98(m, 1H), 2.51-2.41(m, 1H), 2.39(s, 3H), 2.49-2.14(m, 1H), 1.96-1.52(m, 4H) |
| 161 | (S)-(1-methylpyrrolidin-2-yl)methyl(3',5'-difluoro-[1,1'-biphenyl]-2-yl)-carbamate 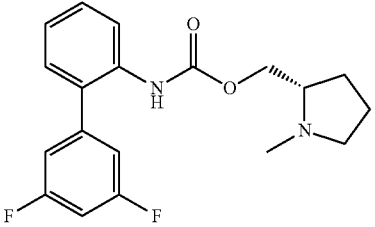 [SMILES: CN1CCC[C@H]1COC(=O)Nc1ccccc1-c1cc(F)cc(F)c1] | ¹H NMR (CDCl₃): δ 8.02-8.00(m, 1H), 7.37-7.25(m, 2H), 7.17-7.08(m, 2H), 6.90-6.78(m, 2H), 6.60(s, 1H), 4.23-4.03(m, 2H), 3.08-2.99(m, 1H), 2.51-2.36(m, 1H), 2.34(s, 3H), 2.29-2.15(m, 1H), 1.99-1.54(m, 4H) |
| 162 | (S)-(1-methylpyrrolidin-2-yl)methyl(3',4'-difluoro-[1,1'-biphenyl]-2-yl)-carbamate 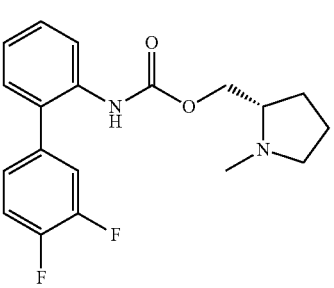 [SMILES: CN1CCC[C@H]1COC(=O)Nc1ccccc1-c1ccc(F)c(F)c1] | ¹H NMR (CDCl₃): δ 8.10-8.08(d, 1H, J = 8.0 Hz), 7.39-7.10(m, 3H), 6.92-6.83(m, 1H), 6.66-6.61(m, 1H), 6.59(s, 1H), 6.52-6.48(m, 1H), 4.28-4.08(m, 2H), 3.14-3.07(m, 1H), 2.59-2.47(m, 1H), 2.38(s, 3H), 2.33-2.21(m, 1H), 2.02-1.58(m, 4H) |
| 163 | (S)-(1-methylpyrrolidin-2-yl)methyl(2',4',5'-trifluoro-[1,1'-biphenyl]-2-yl)-carbamate 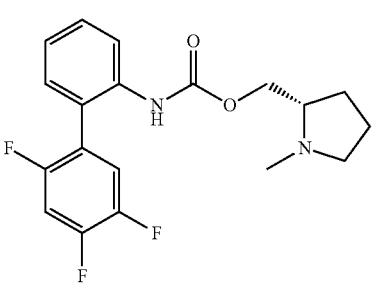 [SMILES: CN1CCC[C@H]1COC(=O)Nc1ccccc1-c1cc(F)c(F)cc1F] | ¹H NMR (CDCl₃): δ 8.11-8.09(d, 1H, J = 8.0 Hz), 7.33-7.23(m, 2H), 7.18-7.14(m, 1H), 7.13-7.10(m, 1H), 6.91-6.87(m, 1H), 6.48(s, 1H), 4.26-4.06(m, 2H), 3.12-3.08(m, 1H), 2.53-2.43(m, 1H), 2.37(s, 3H), 2.30-2.20(m, 1H), 1.98-1.63(m, 4H) |

TABLE 6-continued

Compounds of Examples

| Example | Compound | NMR Value |
|---|---|---|
| 164 | (S)-(1-methylpyrrolidin-2-yl)methyl(4'-chloro-[1,1'-biphenyl]-2-yl)carbamate | $^1$H NMR (CDCl$_3$): δ 8.02-8.00(d, 1H, J = 7.6 Hz), 7.30-7.23(m, 2H), 7.21-7.09(m, 1H), 7.06-7.04(d, 2H, J = 8.8 Hz), 6.77-6.75(d, 2H, J = 8.8 Hz), 6.60(s, 1H), 4.28-4.08(m, 2H), 3.13-3.06(m, 1H), 2.57-2.45(m, 1H), 2.38(s, 3H), 2.33-2.22(m, 1H), 1.99-1.59(m, 4H) |
| 165 | (S)-(1-methylpyrrolidin-2-yl)methyl(3'-chloro-[1,1'-biphenyl]-2-yl)carbamate | $^1$H NMR (CDCl$_3$): δ 8.12-7.99(m, 1H), 7.49-7.28(m, 4H), 7.28-7.02(m, 3H), 6.62-6.49(bs, 1H), 4.26-3.99(m, 2H), 3.12-2.98(m, 1H), 2.53-2.40(m, 1H), 2.36(s, 3H), 2.27-2.14(m, 1H), 1.98-1.81(m, 1H), 1.80-1.55(m, 2H) |
| 166 | (S)-(1-methylpyrrolidin-2-yl)methyl(3',4'-dichloro-[1,1'-biphenyl]-2-yl)-carbamate | $^1$H NMR (CDCl$_3$): δ 8.10-8.08(d, 1H, J = 8.0 Hz), 7.65-7.61(dd, 2H), J = 12.0 Hz), 7.55-7.42(m, 3H), 7.19-7.10(m, 1H), 6.57(s, 1H), 4.27-4.07(m, 2H), 3.13-3.05(m, 1H), 2.57-2.47(m, 1H), 2.38(s, 3H), 2.33-2.21(m, 1H), 2.01-1.60(m, 4H) |
| 167 | (S)-(1-methylpyrrolidin-2-yl)methyl(2',4'-dichloro-[1,1'-biphenyl]-2-yl)-carbamate | $^1$H NMR (CDCl$_3$): δ 8.11-8.09(d, 1H, J = 8.0 Hz), 7.39-7.08(m, 5H), 6.92-6.88(m, 1H), 6.32(s, 1H), 4.27-4.12(m, 2H), 3.14-3.08(m, 1H), 2.57-2.53(m, 1H), 2.44(s, 3H), 2.31-2.21(m, 1H), 2.01-1.58(m, 4H) |

TABLE 6-continued

Compounds of Examples

| Example | Compound | NMR Value |
|---|---|---|
| 168 | (S)-(1-methylpyrrolidin-2-yl)methyl(3'-hydroxy-[1,1'-biphenyl]-2-yl)carbamate | $^1$H NMR (CDCl$_3$): δ 7.98-7.96(d, 1H, J = 7.6 Hz), 7.30-7.26(m, 1H), 7.22-7.14(m, 2H), 7.11-7.05(m, 1H), 6.81-6.77(t, 2H, J = 16.8 Hz), 6.73-6.71(t, 1H, J = 4.4 Hz), 4.23-4.08(m, 2H), 3.09-3.05(m, 1H), 2.57-2.50(m, 1H), 2.38(s, 3H), 2.36-2.22(m, 1H), 1.99-1.59(m, 4H) |
| 169 | (S)-(1-methylpyrrolidin-2-yl)methyl(3'-cyano-[1,1'-biphenyl]-2-yl)carbamate | $^1$H NMR (CDCl$_3$): δ 8.02-8.00(d, 1H, J = 7.2 Hz), 7.68-7.65(m, 2H), 7.60-7.54(m, 2H), 7.41-7.37(m, 1H), 7.17-7.16(d, 2H, J = 4.4 Hz), 6.42(s, 1H), 4.22-4.04(m, 2H), 3.06-3.02(m, 1H), 2.35(s, 3H), 2.30-2.24(q, 1H, J = 16.0 Hz), 2.02-1.55(m, 4H) |
| 170 | (S)-(1-methylpyrrolidin-2-yl)methyl(3'-amino-[1,1'-biphenyl]-2-yl)carbamate | $^1$H NMR (CDCl$_3$): δ 8.09-8.07(d, 1H, J = 7.6 Hz), 7.41-7.15(m, 4H), 7.08-7.00(m, 1H), 6.94(s, 2H), 6.82(s, 1H), 6.42(s, 1H), 6.69-6.66(t, 1H, J = 14.8 Hz), 6.61(s, 1H), 4.24-4.03(m, 2H), 3.11-3.02(m, 1H), 2.56-2.44(m, 1H), 2.40(s, 3H), 2.30-2.17(m, 1H), 1.96-1.58(m, 4H) |
| 171 | (S)-(1-methylpyrrolidin-2-yl)methyl(3',4',5-trifluoro-[1,1'-biphenyl]-2-yl)-carbamate | $^1$H NMR (CDCl$_3$): δ 7.75(s, 1H), 7.23-6.97(m, 4H), 6.90-6.85(m, 1H), 6.83(s, 1H), 4.31-4.15(m, 2H), 3.26(m, 1H), 2.81(m, 1H), 2.54(m, 1H), 2.47(s, 3H), 2.03-1.64(m, 4H) |

TABLE 6-continued

| Example Compound | NMR Value |
|---|---|
| 172 (S)-(1-methylpyrrolidin-2-yl)methyl(3',5,5'-trifluoro-[1,1'-biphenyl]-2-yl)-carbamate | ¹H NMR (CDCl₃): δ 7.88(s, 1H), 7.06-7.01(m, 2H), 6.90-6.78(m, 3H), 6.61(s, 1H), 4.18-3.94(m, 2H), 3.05-3.00(m, 1H), 2.45-2.36(m, 1H), 2.33(s, 3H), 2.28-2.12(m, 1H), 1.90-1.52(m, 4H) |
| 173 (S)-(1-methylpyrrolidin-2-yl)methyl(2',4',5,5'-tetrafluoro-[1,1'-biphenyl]-2-yl)carbamate | ¹H NMR (CDCl₃): δ 7.82(s, 1H), 7.16-6.98(m, 3H), 6.93-6.90(m, 1H), 6.60(s, 1H), 4.29-4.07(m, 2H), 3.24(m, 1H), 2.51-2.32(m, 2H), 2.15(s, 3H), 2.07-1.69(m, 4H) |
| 174 (S)-(1-methylpyrrolidin-2-yl)methyl(3'-chloro-5-fluoro-[1,1'-biphenyl]-2-yl)-carbamate | ¹H NMR (CDCl₃): δ 7.94(s, 1H), 7.23-7.16(m, 2H), 7.07-7.02(m, 2H), 6.92-6.89(m, 2H), 6.56(s, 1H), 4.20-4.04(m, 2H), 3.07-3.03(m, 1H), 2.48-2.39(m, 1H), 2.36(s, 3H), 2.31-2.19(m, 1H), 1.93-1.55(m, 4H) |
| 175 (S)-(1-methylpyrrolidin-2-yl)methyl(4'-chloro-5-fluoro-[1,1'-biphenyl]-2-yl)-carbamate | ¹H NMR (CDCl₃): δ 7.89(s, 1H), 7.24(s, 1H), 7.22(s, 1H), 7.03-6.98(m, 2H), 6.88-6.85(m, 2H), 6.55(s, 1H), 4.16-4.00(m, 2H), 3.04-3.00(m, 1H), 2.47-2.35(m, 1H), 2.32(s, 3H), 2.27-2.16(m, 1H), 1.90-1.51(m, 4H) |

TABLE 6-continued

Compounds of Examples

| Example | Compound | NMR Value |
|---|---|---|
| 176 | (S)-(1-methylpyrrolidin-2-yl)methyl(2',4'-dichloro-5-fluoro-[1,1'-biphenyl]-2-yl)-carbamate | $^1$H NMR (CDCl$_3$): δ 7.89(s, 1H), 7.31-7.28(m, 1H), 7.18(s, 1H), 7.16(s, 1H), 7.13-7.04(m, 1H), 6.83-6.81(m, 1H), 6.30(s, 1H), 4.16-4.00(m, 2H), 3.04-3.00(m, 1H), 2.47-2.35(m, 1H), 2.32(s, 3H), 2.27-2.16(m, 1H), 1.90-1.51(m, 4H) |
| 177 | (S)-(1-methylpyrrolidin-2-yl)methyl(3',4'-dichloro-5-fluoro-[1,1'-biphenyl]-2-yl)-carbamate | $^1$H NMR (CDCl$_3$) δ 7.88(s, 1H), 7.41-7.37(m, 1H), 7.21-7.16(m, 1H), 7.08-7.01(m, 2H), 6.91-6.88(m, 1H), 6.52(s, 1H), 4.24-4.05(m, 2H), 3.12-3.07(m, 1H), 2.53-2.44(m, 1H), 2.38(s, 3H), 2.36-2.22(m, 1H), 1.94-1.56(m, 4H) |
| 178 | (S)-(1-methylpyrrolidin-2-yl)methyl(3'-cyano-5-fluoro-[1,1'-biphenyl]-2-yl)-carbamate | $^1$H NMR (CDCl$_3$): δ 7.86(s, 1H), 7.53-7.49(m, 1H), 7.45-7.40(m, 2H), 7.11-7.05(m, 2H), 6.91-6.88(m, 1H), 6.42(s, 1H), 4.18-4.02(m, 2H), 3.06-3.02(m, 1H), 2.45-2.39(m, 1H), 2.34(s, 3H), 2.28-2.13(m, 1H), 1.91-1.53(m, 4H) |
| 179 | (S)-(1-methylpyrrolidin-2-yl)methyl(3'-hydroxy-5-fluoro-[1,1'-biphenyl]-2-yl)-carbamate | $^1$H NMR (CDCl$_3$): δ 7.85(s, 1H), 7.26-7.19(m, 1H), 7.02-6.96(m, 1H), 6.93-6.90(m, 1H), 6.78-6.74(m, 3H), 6.71(s, 1H), 4.21-4.18(m, 2H), 3.15-3.11(m, 1H), 2.62-2.56(m, 1H), 2.41(s, 3H), 2.34-2.27(m, 1H), 1.98-1.62(m, 4H) |

TABLE 6-continued

Compounds of Examples

| Example | Compound | NMR Value |
|---|---|---|
| 180 | (S)-(1-methylpyrrolidin-2-yl)methyl(5-fluoro-3'-(trifluoromethyl)-[1,1'-biphenyl]-2-yl)carbamate | $^1$H NMR (CDCl$_3$): δ 7.81(s, 1H), 7.25-7.22(m, 1H), 7.11(s, 1H), 7.07-6.91(m, 4H), 6.67(s, 1H), 4.30-4.09(m, 2H), 3.21-3.13(m, 1H), 2.71-2.58(m, 1H), 2.39(s, 3H), 2.03-1.56(m, 4H) |
| 181 | (S)-(1-methylpyrrolidin-2-yl)methyl(3'-chloro-4,4',5-trifluoro-[1,1'-biphenyl]-2-yl)carbamate | $^1$H NMR (CDCl$_3$): δ 8.02(m, 1H), 7.39-7.38(dd, 1H, J = 4.4 Hz), 7.27-7.25(m, 1H), 7.21-7.18(m, 1H), 7.01-6.98(dd, 1H, J = 7.2 Hz), 6.50(s, 1H), 4.23-4.10(m, 2H), 3.10-3.07(m, 1H), 2.50-2.46(m, 1H), 2.39(s, 3H), 2.28-2.23(m, 1H), 1.95-1.60(m, 4H) |
| 182 | (R)-(1-methylpyrrolidin-3-yl)methyl(3'-chloro-4,5-difluoro-[1,1'-biphenyl]-2-yl)carbamate | $^1$H NMR (CDCl$_3$): δ 8.00(m, 1H), 7.41-7.39(m, 1H), 7.28-7.23(m, 1H), 7.20-7.19(m, 1H), 7.00-6.96(dd, 1H, J = 7.2 Hz), 6.61(s, 1H), 4.22-4.10(m, 2H), 3.11-3.09(m, 1H), 2.50-2.46(m, 1H), 2.38(s, 3H), 2.29-2.21(m, 1H), 1.95-1.59(m, 4) |
| 183 | 2-(1-Methylpyrrolidin-2-yl)-ethyl(2',4'-difluoro-[1,1'-biphenyl]-2-yl)carbamate | $^1$H NMR (CDCl$_3$): δ 7.96(m, 1H), 7.41-7.38(m, 1H), 7.30-7.26(m, 2H), 7.19-7.15(m, 2H), 7.01-6.93(m, 2H), 6.38(s, 1H), 4.21-4.14(m, 2H), 3.35(m, 1H), 3.00-2.64(m, 1H), 2.48(s, 3H), 2.26-2.03(m, 3H), 1.94-1.67(m, 4H) |

TABLE 6-continued

Compounds of Examples

| Example | Compound | NMR Value |
|---|---|---|
| 184 | 2-(1-Methylpyrrolidin-2-yl)ethyl(2',3'-difluoro-[1,1'-biphenyl]-2-yl)-carbamate 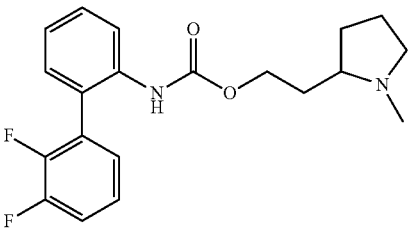 [SMILES: CN1CCCC1CCOC(=O)Nc1ccccc1-c1cccc(F)c1F] | $^1$H NMR (CDCl$_3$): δ 7.90(m, 1H), 7.44-7.41(m, 1H), 7.26-7.19(m, 4H), 7.09-7.06(m, 1H), 6.46(s, 1H), 4.25(m, 2H), 3.80(m, 1H), 2.98(m, 1H), 2.73(s, 3H), 2.29-2.15(m, 3H), 2.02-1.57(m, 4H) |
| 185 | 2-(1-Methylpyrrolidin-2-yl)ethyl(2',6'-difluoro-[1,1'-biphenyl]-2-yl)-carbamate 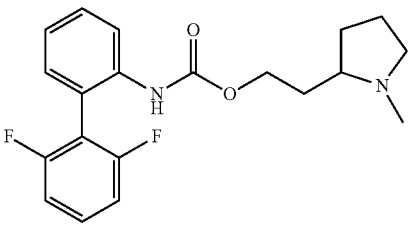 [SMILES: CN1CCCC1CCOC(=O)Nc1ccccc1-c1c(F)cccc1F] | $^1$H NMR (CDCl$_3$): δ 7.94(m, 1H), 7.60-7.37(m, 2H), 7.26-7.21(m, 2H), 7.06-6.99(m, 2H), 6.40(s, 1H), 4.22-4.20(m, 2H), 3.83(m, 1H), 2.99(m, 1H), 2.73(s, 3H), 2.31-2.15(m, 3H), 2.02-1.59(m, 4H) |
| 186 | 2-(1-Methylpyrrolidin-2-yl)ethyl(5'-chloro-2'-fluoro-[1,1'-biphenyl]-2-yl)-carbamate 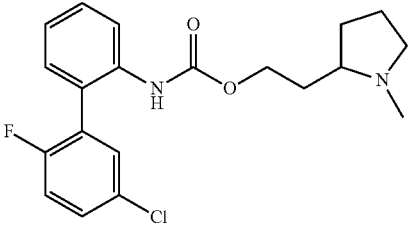 [SMILES: CN1CCCC1CCOC(=O)Nc1ccccc1-c1cc(Cl)ccc1F] | $^1$H NMR (CDCl$_3$): δ 7.92(m, 1H), 7.42-7.39(m, 1H), 7.37-7.34(m, 1H), 7.29-7.28(m, 1H), 7.22-7.17(m, 2H), 7.14-7.11(m, 1H), 6.45(s, 1H), 4.22-4.14(m, 2H), 3.80(m, 1H), 3.47-3.45(m, 1H), 2.53(s, 3H), 2.16-2.11(m, 3H), 1.98-1.72(m, 4H) |
| 187 | (S)-(1-methylpyrrolidin-2-yl)methyl(2'-fluoro-[1,1'-biphenyl]-2-yl)carbamate 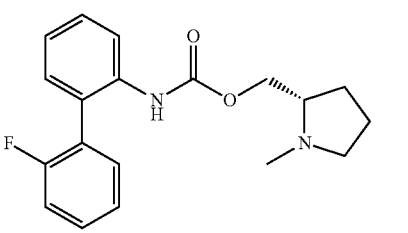 [SMILES: CN1CCC[C@H]1COC(=O)Nc1ccccc1-c1ccccc1F] | $^1$H NMR (CDCl$_3$): δ 8.00(m, 1H), 7.41-7.37(m, 3H), 7.33-7.27(m, 1H), 7.25-7.20(m, 1H), 7.19-7.14(m, 2H), 6.61(s, 1H), 4.08-4.01(m, 2H), 2.88-2.79(m, 1H), 2.49-2.45(m, 1H), 2.40(s, 3H), 2.28-2.14(m, 1H), 1.94-1.61(m, 4H) |

TABLE 6-continued

Compounds of Examples

| Example | Compound | NMR Value |
|---|---|---|
| 188 | (S)-(1-methylpyrrolidin-2-yl)methyl(2',4'-difluoro-[1,1'-biphenyl]-2-yl)-carbamate | ¹H NMR (CDCl₃): δ 7.98(m, 1H), 7.41-7.37(m, 1H), 7.29-7.23(m, 1H), 7.17-7.14(m, 2H), 6.99-6.89(m, 2H), 6.44(s, 1H), 4.23-4.05(m, 2H), 3.10-3.07(m, 1H), 2.49(m, 1H), 2.38(s, 3H), 2.28-2.22(m, 3H), 1.93-1.60(m, 4H) |
| 189 | (S)-(1-methylpyrrolidin-2-yl)methyl(2',3'-difluoro-[1,1'-biphenyl]-2-yl)-carbamate | ¹H NMR (CDCl₃): δ 8.00(m, 1H), 7.38-7.34(m, 1H), 7.29-7.23(m, 2H), 7.20-7.14(m, 2H), 7.02-6.89(m, 1H), 6.51(s, 1H), 4.20-4.05(m, 2H), 3.08-3.05(m, 1H), 2.58-2.44(m, 1H), 2.39(s, 3H), 2.30-2.24(m, 3H), 1.99-1.64(m, 4H) |
| 190 | (S)-(1-methylpyrrolidin-2-yl)methyl(3'-chloro-6'-fluoro-[1,1'-biphenyl]-2-yl)-carbamate | ¹H NMR (CDCl₃): δ 7.97(m, 1H), 7.43-7.39(m, 1H), 7.23-7.08(m, 4H), 7.04-6.98(m, 1H), 6.52(s, 1H), 4.27-4.15(m, 2H), 3.17-3.07(m, 1H), 2.62(m, 1H), 2.44(s, 3H), 2.34-2.30(m, 3H), 1.95-1.58(m, 4H) |
| 191 | (R)-(1-methylpyrrolidin-2-yl)methyl(3',5'-dimethyl-[1,1'-biphenyl]-2-yl)-carbamate | ¹H NMR (CDCl₃): δ 8.07-8.05(m, 1H), 7.33-7.30(m, 1H), 7.18-7.16(m, 1H), 7.10-7.06(m, 1H), 7.03(s, 1H), 6.95(s, 2H), 6.69(s, 1H), 4.09-3.99(m, 2H), 2.69-2.65(t, 1H, J = 17.2 Hz), 2.59-2.40(m, 3H), 2.35-2.27(m, 4H), 2.01-1.95(m, 1H), 1.54-1.48(m, 1H) |

TABLE 6-continued

| Compounds of Examples | |
|---|---|
| Example Compound | NMR Value |
| 192 (R)-(1-methylpyrrolidin-3-yl)methyl(5-fluoro-3'-methyl-[1,1'-biphenyl]-2-yl)-carbamate | $^1$H NMR (CDCl$_3$): δ 8.07-7.89(bs, 1H), 7.40-7.29(m, 1H), 7.29-7.19(m, 1H), 7.19-7.07(m, 2H), 7.07-6.97(m, 1H), 6.97-6.86(m, 1H), 6.61-6.45(bs, 1H), 4.13-3.92(m, 2H), 2.68-2.43(m, 4H), 2.39(s, 3H), 2.36-2.20(m, 4H), 2.04-1.88(m, 1H), 1.53-1.39(m, 1H) |
| 193 (R)-(1-methylpyrrolidin-3-yl)methyl(5-fluoro-3',5'-dimethyl-[1,1'-biphenyl]-2-yl)carbamate | $^1$H NMR (CDCl$_3$): δ 7.98(m, 1H), 7.89-7.04(m, 6H), 6.55(s, 1H), 4.08-3.97(m, 2H), 2.63-2.59(t, 1H, J = 17.2 Hz), 2.53-2.40(m, 2H), 2.35-2.31(m, 3H), 2.31(s, 1H), 2.27-2.23(m, 1H), 1.99-1.92(m, 1H), 1.51-1.44(m, 1H) |
| 194 (R)-(1-methylpyrrolidin-3-yl)methyl(3',5-difluoro-[1,1'-biphenyl]-2-yl)-carbamate | $^1$H NMR (CDCl$_3$): δ 7.95(m, 1H), 7.47-7.41(m, 2H), 7.12-7.04(m, 4H), 6.93-6.91(m, 1H), 6.48(s, 1H), 4.08-3.97(m, 2H), 2.63-2.59(t, 1H, J = 17.2 Hz), 2.52-2.49(m, 3H), 2.34-2.27(m, 4H), 2.00-1.93(m, 1H), 1.50-1.46(m, 1H) |
| 195 (R)-(1-methylpyrrolidin-3-yl)methyl(3'-chloro-5-fluoro-[1,1'-biphenyl]-2-yl)-carbamate | $^1$H NMR (CDCl$_3$): δ 7.92(m, 1H), 7.42-7.33(m, 2H), 7.23-7.21(m, 2H), 7.07-7.03(m, 1H), 6.93-6.90(m, 1H), 6.27(s, 1H), 4.08-3.97(m, 2H), 2.65-2.60(t, 1H, J = 17.2 Hz), 2.53-2.45(m, 3H), 2.35-2.29(m, 4H), 2.01-1.93(m, 1H), 1.53-1.46(m, 1H) |

TABLE 6-continued

Compounds of Examples

| Example | Compound | NMR Value |
|---|---|---|
| 196 | (R)-(1-ethylpyrrolidin-3-yl)methyl(3'-chloro-4',5-difluoro-[1,1'-biphenyl]-2-yl)carbamate 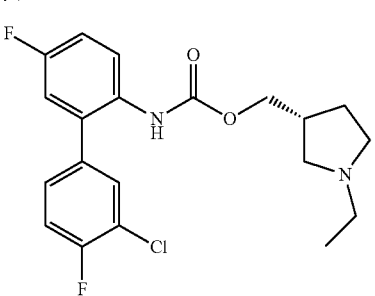 | ¹H NMR (CDCl₃): δ 7.87(s, 1H), 7.40-7.38(m, 1H), 7.25-7.21(m, 2H), 7.08-7.03(m, 1H), 6.90(dd, 1H, J = 8.8 Hz, 2.8 Hz), 6.50(s, 1H), 4.09-3.98(m, 2H), 2.72(t, 1H, J = 8.8 Hz), 2.64-2.44(m, 5H), 2.36-2.33(m, 1H), 2.02-1.92(m, 1H), 1.55-1.47(m, 1H), 1.09(t, 3H, J = 7.2 Hz) |
| 197 | (S)-(1-methylpyrrolidin-2-yl)methyl[1,1'-biphenyl]-2-ylcarbamate 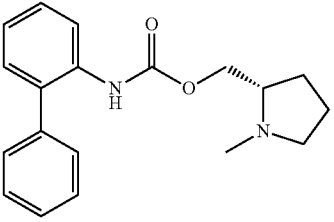 [SMILES: CN1CCC[C@H]1COC(=O)Nc1ccccc1-c1ccccc1] | ¹H NMR (CDCl₃): δ 8.14-8.01(m, 1H), 7.51-7.29(m, 6H), 7.23-7.05(m, 2H), 6.75-6.60(bs, 1H), 4.24-4.00(m, 2H), 3.10-2.98(m, 1H), 2.53-2.29(m, 4H), 2.28-2.15(m, 1H), 1.97-1.52(m, 4H) |
| 198 | (S)-(1-methylpyrrolidin-2-yl)methyl(4'-fluoro-[1,1'-biphenyl]-2-yl)carbamate 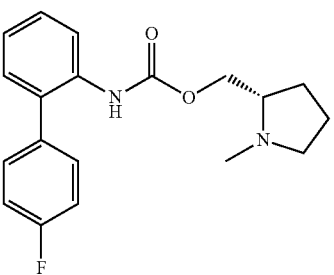 [SMILES: CN1CCC[C@H]1COC(=O)Nc1ccccc1-c1ccc(F)cc1] | ¹H NMR (CDCl₃): δ 8.14-8.01(m, 1H), 7.51-7.29(m, 5H), 7.23-7.05(m, 2H), 6.75-6.60(bs, 1H), 4.24-4.00(m, 2H), 3.10-2.98(m, 1H), 2.53-2.29(m, 4H), 2.28-2.15(m, 1H), 1.97-1.52(m, 4H) |
| 199 | (S)-(1-methylpyrrolidin-2-yl)methyl(3'-methyl-[1,1'-biphenyl]-2-yl)carbamate 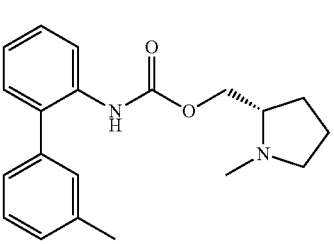 [SMILES: Cc1cccc(-c2ccccc2NC(=O)OC[C@@H]2CCCN2C)c1] | ¹H NMR (CDCl₃): δ 8.17-8.01(m, 1H), 7.41-7.27(m, 2H), 7.22-7.02(m, 5H), 6.76-6.63(bs, 1H), 4.22-4.00(m, 2H), 3.09-2.98(m, 1H), 2.52-2.30(m, 7H), 2.29-2.12(m, 1H), 1.97-1.80(m, 1H), 1.80-1.50(m, 3H) |

TABLE 6-continued

| Example | Compound | NMR Value |
|---|---|---|
| 200 | (S)-(1-methylpyrrolidin-2-yl)methyl(5-fluoro-[1,1'-biphenyl]-2-yl)carbamate | ¹H NMR (CDCl₃): δ 7.97(s, 1H), 7.45-7.37(m, 3H), 7.32-7.25(m, 3H), 7.05-7.00(m, 1H), 6.94-6.91(m, 1H), 6.59(s, 1H), 4.19-4.04(m, 2H), 3.06-3.04(m, 1H), 2.35(s, 3H), 2.28-2.18(m, 2H), 1.90-1.76(m, 2H), 1.61-1.57(m, 2H) |
| 201 | (S)-(1-methylpyrrolidin-2-yl)methyl(5-fluoro-3'-methyl-[1,1'-biphenyl]-2-yl)-carbamate | ¹H NMR (CDCl₃): δ 7.82(s, 1H), 7.30-7.11(m, 3H), 7.01-6.85(m, 3H), 4.30-4.07(m, 2H), 3.24-3.21(m, 1H), 2.43(s, 3H), 2.35(s, 3H), 1.96-1.84(m, 2H), 1.79-1.72(m, 2H), 1.67-1.51(m, 2H) |
| 202 | (S)-(1-methylpyrrolidin-2-yl)methyl(3',5-difluoro-[1,1'-biphenyl]-2-yl)-carbamate | ¹H NMR (CDCl₃): δ 7.97(s, 1H), 7.43-7.39(m, 1H), 7.11-7.03(m, 4H), 6.91(d, 1H, J = 8.4 Hz), 6.48(s, 1H), 4.19-4.04(m, 2H), 3.05-3.02(m, 1H), 2.35(s, 3H), 2.26-2.17(m, 2H), 1.88-1.83(m, 2H), 1.71-1.69(m, 2H) |
| 203 | (S)-(1-methylpyrrolidin-2-yl)methyl(4',5-difluoro-[1,1'-biphenyl]-2-yl)-carbamate | ¹H NMR (CDCl₃): δ 7.97(s, 1H), 7.31-7.26(m, 1H), 7.22-7.12(m, 2H), 7.06-7.00(m, 2H), 6.91-6.88(m, 1H), 6.43(s, 1H), 4.21-4.03(m, 2H), 3.06-3.02(m, 1H), 2.35(s, 3H), 2.28-2.15(m, 2H), 1.95-1.83(m, 2H), 1.70-1.67(m, 2H) |

TABLE 6-continued

Compounds of Examples

| Example | Compound | NMR Value |
|---|---|---|
| 204 | (S)-(1-methylpyrrolidin-2-yl)methyl(4-fluoro-[1,1'-biphenyl]-2-yl)carbamate 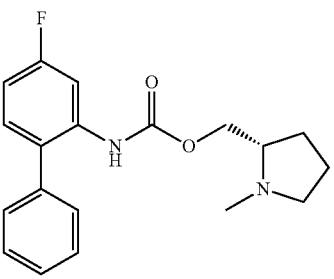 [SMILES: CN1CCC[C@H]1COC(=O)Nc1cc(F)ccc1-c1ccccc1] | $^1$H NMR (CDCl$_3$): δ 7.96(s, 1H), 7.47-7.43(m, 2H), 7.40-7.36(m, 1H), 7.33-7.25(m, 2H), 7.18-7.10(m, 1H), 6.81-6.75(m, 2H), 4.18-4.05(m, 2H), 3.03-3.01(m, 1H), 2.35(s, 3H), 2.22-2.17(m, 2H), 1.93-1.86(m, 2H), 1.61-1.57(m, 2H) |
| 205 | (S)-(1-methylpyrrolidin-2-yl)methyl(3',4-difluoro-[1,1'-biphenyl]-2-yl)-carbamate 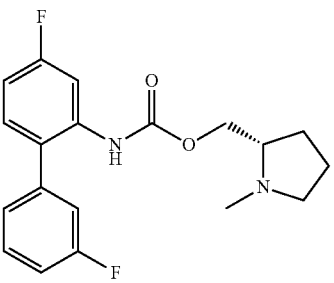 [SMILES: CN1CCC[C@H]1COC(=O)Nc1cc(F)ccc1-c1cccc(F)c1] | $^1$H NMR (CDCl$_3$): δ 7.96(s, 1H), 7.45-7.39(m, 2H), 7.25-7.23(m, 1H), 7.16-7.07(m, 2H), 7.03-7.01(m, 1H), 6.83-6.78(m, 1H), 6.65(s, 1H), 4.19-4.06(m, 2H), 3.05-3.02(m, 1H), 2.36(s, 3H), 2.26-2.18(m, 2H), 1.93-1.84(m, 2H), 1.59-1.50(m, 2H) |
| 206 | (S)-(1-methylpyrrolidin-2-yl)methyl(5-methyl-[1,1'-biphenyl]-2-yl)carbamate 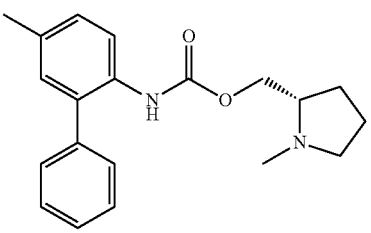 [SMILES: Cc1ccc(NC(=O)OC[C@@H]2CCCN2C)c(-c2ccccc2)c1] | $^1$H NMR (CDCl$_3$): δ 7.92(s, 1H), 7.45-7.41(m, 2H), 7.33-7.25(m, 2H), 7.16-7.13(m, 1H), 7.02(s, 1H), 6.59(s, 1H), 4.21-4.05(m, 2H), 3.09-3.07(m, 1H), 2.38(s, 3H), 2.32(s, 3H), 2.27-2.23(m, 2H), 1.90-1.87(m, 2H), 1.78-1.72(m, 2H) |
| 207 | (S)-(1-methylpyrrolidin-2-yl)methyl(3'-fluoro-5-methyl-[1,1'-biphenyl]-2-yl)-carbamate 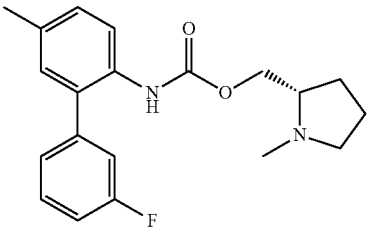 [SMILES: Cc1ccc(NC(=O)OC[C@@H]2CCCN2C)c(-c2cccc(F)c2)c1] | $^1$H NMR (CDCl$_3$): δ 7.88(s, 1H), 7.42-7.36(m, 1H), 7.21-7.20(m, 1H), 7.17-7.15(m, 1H), 7.10-7.03(m, 2H), 7.00(m, 1H), 6.55(s, 1H), 4.22-4.06(m, 2H), 3.10-3.06(m, 1H), 2.38(s, 3H), 2.31(s, 3H), 2.27-2.21(m, 2H), 1.94-1.85(m, 2H), 1.78-1.69(m, 2H) |

TABLE 6-continued

Compounds of Examples

| Example | Compound | NMR Value |
|---|---|---|
| 208 | (S)-(1-methylpyrrolidin-2-yl)methyl(5-fluoro-3',5'-dimethyl-[1,1'-biphenyl]-2-yl)carbamate | ¹H NMR (CDCl₃): δ 7.95(s, 1H), 7.15(m, 2H), 7.04-6.98(m, 2H), 6.93-6.90(m, 2H),, 6.72(s, 1H), 4.31-4.17(m, 2H), 3.14(m, 1H), 2.82(m, 1H), 2.61-2.03(m, 10H), 1.99-1.62(m, 4H) |
| 209 | (S)-(1-methylpyrrolidin-2-yl)methyl(4'-(tert-butyl)-5-fluoro-[1,1'-biphenyl]-2-yl)-carbamate | ¹H NMR (CDCl₃): δ 7.83(s, 1H), 7.72-7.70(m, 2H), 7.67-7.52(m, 2H), 7.03-6.91(m, 2H), 6.76(s, 1H), 4.35-4.22(m, 2H), 3.20(m, 1H), 2.96(m, 1H), 2.68-2.65(m, 1H), 2.48(s, 3H), 1.99-1.63(m, 4H), 1.51-1.29(m, 9H) |
| 210 | (S)-(1-methylpyrrolidin-2-yl)methyl(3'-chloro-5,5'-difluoro-[1,1'-biphenyl]-2-yl)carbamate | ¹H NMR (CDCl₃): δ 7.84(s, 1H), 7.24-7.15(m, 1H), 7.12-6.89(m, 4H), 6.64(s, 1H), 4.26-4.10(m, 2H), 3.16-3.15(m, 1H), 2.62(m, 1H), 2.42(s, 3H), 2.38-2.32(m, 1H), 1.99-1.60(m, 4H) |
| 211 | (S)-(1-methylpyrrolidin-2-yl)methyl(3'-chloro-4',5-difluoro[1,1'-biphenyl]-2-yl)carbamate | ¹H NMR (CDCl₃): δ 8.05(m, 1H), 7.57-7.48(m, 1H), 7.22-7.14(m, 2H), 7.12-7.00(m, 2H), 6.61(s, 1H), 4.23-4.16(m, 2H), 3.22-3.10(m, 1H), 2.58-2.47(m, 1H), 2.38(s, 3H), 2.35-2.30(m, 3H), 1.98-1.60(m, 4H) |

TABLE 6-continued

Compounds of Examples

| Example | Compound | NMR Value |
|---|---|---|
| 212 | (S)-(1-methylpyrrolidin-2-yl)methyl(4'-chloro-3',5-difluoro-[1,1'-biphenyl]-2-yl)carbamate | ¹H NMR (CDCl₃): δ 7.39-7.31(m, 3H), 7.20-7.00(m, 2H), 6.98-6.88(d, 1H, J = 2.8 Hz), 4.34-4.23(m, 2H), 3.45(m, 1H), 3.16(m, 1H), 2.57-2.54(m, 4H), 2.11-1.70(m, 4H). |
| 213 | (S)-(1-methylpyrrolidin-2-yl)methyl(3'-amino-5-fluoro-[1,1'-biphenyl]-2-yl)-carbamate | ¹H NMR (CDCl₃): δ 7.99(s, 1H), 7.23-7.19(m, 1H), 7.03-6.98(m, 1H), 6.93-6.90(m, 1H), 6.74(m, 1H), 6.70-6.66(m, 1H), 6.63(s, 1H), 4.24-4.07(m, 2H), 3.46(s, 1H), 3.14(m, 1H), 2.59(m, 1H), 2.42(s, 3H), 2.33-2.29(m, 1H), 1.98-1.63(m, 4H) |
| 214 | (S)-(1-methylpyrrolidin-2-yl)methyl(2',5-difluoro-3'-(trifluoromethyl)-[1,1'-biphenyl]-2-yl)carbamate | ¹H NMR (CDCl₃): δ 7.84(s, 1H), 7.69-7.66(m, 1H), 7.53-7.50(m, 1H), 7.37-7.33(m, 1H), 7.15-7.10(m, 1H), 6.98-6.95(m, 1H), 6.61(s, 1H), 4.29-4.15(m, 2H), 3.27(s, 1H), 2.78-2.70(m, 1H), 2.48-2.35(m, 4H), 1.98-1.70(m, 4H) |
| 215 | (S)-(1-methylpyrrolidin-2-yl)methyl(3'-chloro-5-fluoro-5'-(trifluoromethyl)-[1,1'-biphenyl]-2-yl)carbamate | ¹H NMR (CDCl₃): δ 7.96(s, 1H), 7.79(s, 1H), 7.61(s, 1H), 7.50-7.47(d, 1H, J = 11.6 Hz), 7.11-7.06(m, 1H), 6.94-6.91(m, 1H), 6.58(s, 1H), 4.27-4.11(m, 2H), 3.22-3.17(m, 1H), 2.67-2.66(m, 1H), 2.42-2.32(m, 4H), 2.02-1.60(m, 4H) |

TABLE 6-continued

Compounds of Examples

| Example | Compound | NMR Value |
|---|---|---|
| 216 | (S)-(1-methylpyrrolidin-2-yl)methyl(3'-chloro-5-fluoro-5'-hydroxy-[1,1'-biphenyl]-2-yl)carbamate 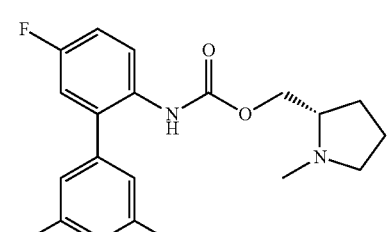 | $^1$H NMR (CDCl$_3$): δ 7.82(s, 1H), 7.02-6.64(m, 5H), 4.17-4.09(m, 2H), 3.10-3.06(m, 1H), 2.53(m, 1H), 2.37(s, 3H), 2.34-2.21(m, 1H), 1.96-1.62(m, 4H) |
| 217 | (S)-(1-methylpyrrolidin-2-yl)methyl(3'-chloro-5-fluoro-5'-methoxy-[1,1'-biphenyl]-2-yl)carbamate 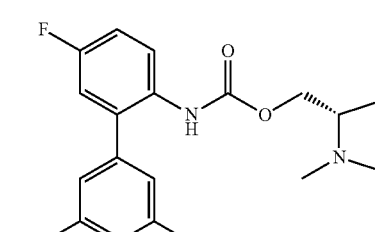 | $^1$H NMR (CDCl$_3$): δ 7.94(s, 1H), 7.66-7.44(m, 4H), 6.91-6.89(d, 1H, J = 8.4 Hz), 6.62(s, 1H), 4.23-4.08(m, 2H), 3.86-3.85(m, 3H), 3.11(m, 1H), 2.53(m, 1H), 2.34(s, 3H), 2.29-2.28(m, 1H), 1.93-1.63(m, 4H) |
| 218 | (S)-(1-methylpyrrolidin-2-yl)methyl(5-fluoro-2',4'-bis(trifluoromethyl)-[1,1'-biphenyl]-2-yl)carbamate 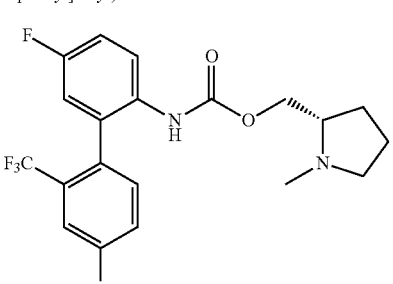 | $^1$H NMR (CDCl$_3$): δ 8.11(m, 1H), 7.44-7.36(m, 1H), 7.20-7.17(m, 2H), 7.10-6.99(m, 2H), 6.54(s, 1H), 4.27-4.21(m, 2H), 3.31-3.15(m, 1H), 2.44-2.40(m, 1H), 2.39(s, 1H), 2.30-2.25(m, 3H), 2.01-1.55(m, 4H) |
| 219 | (S)-(1-methylpyrrolidin-2-yl)methyl(3'-ethoxy-5-fluoro-[1,1'-biphenyl]-2-yl)-carbamate 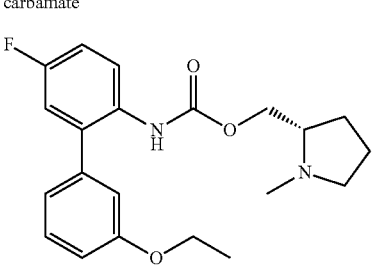 | $^1$H NMR (CDCl$_3$): δ 7.58-7.53(m, 1H), 7.48-7.44(m, 2H), 7.29-7.15(m, 2H), 6.95-6.92(m, 1H), 6.84-6.79(m, 1H), 4.27-4.23(m, 2H), 4.14-4.07(q, 2H, J = 6.8 Hz), 3.28(m, 1H), 2.89(m, 1H), 2.50(m, 4H), 1.98-1.59(m, 4H), 1.46-1.40(t, 3H, J = 14.0 Hz) |

TABLE 6-continued

Compounds of Examples

| Example Compound | NMR Value |
|---|---|
| 220 (S)-(1-methylpyrrolidin-2-yl)methyl(5-fluoro-3',4'-dimethoxy-[1,1'-biphenyl]-2-yl)carbamate | ¹H NMR (CDCl₃): δ 7.65-7.61(m, 1H), 7.54-7.52(m, 1H), 7.47-7.43(m, 2H), 7.33(m, 1H), 6.68-6.65(m, 1H), 4.29-4.15(m, 2H), 3.87(s, 6H), 3.28-3.25(m, 1H), 2.78-2.70(m, 1H), 2.48-2.35(m, 4H), 1.98-1.63(m, 4H) |
| 221 (S)-(1-methylpyrrolidin-2-yl)methyl(5-fluoro-3',5'-dimethoxy-[1,1'-biphenyl]-2-yl)carbamate | ¹H NMR (CDCl₃): δ 7.93(s, 1H), 7.03-6.91(m, 4H), 6.46-6.42(m, 1H), 6.38(s, 1H), 4.22-4.08(m, 2H), 3.77(s, 6H), 3.15(m, 1H), 2.61(m, 1H), 2.41(s, 3H), 2.36-2.24(m, 1H), 1.93-1.58(m, 4H) |
| 222 (S)-(1-methylpyrrolidin-2-yl)methyl(5-methoxy-[1,1'-biphenyl]-2-yl)carbamate | ¹H NMR (CDCl₃): δ 7.81(s, 1H), 7.43-7.28(m, 4H), 7.20-7.19(d, 1H, J = 4.4 Hz), 6.87-6.86(dd, 1H, J = 9.2 Hz), 6.76-6.75(d, 1H, J = 2.8 Hz), 6.61(s, 1H), 4.20-4.06(m, 2H), 3.77(s, 3H), 3.13-3.10(m, 1H), 2.58-2.43(m, 1H), 2.38(s, 3H), 2.32-2.25(m, 1H), 1.92-1.56(m, 4H) |
| 223 (S)-(1-methylpyrrolidin-2-yl)methyl(3'-fluoro-5-methoxy-[1,1'-biphenyl]-2-yl)carbamate | ¹H NMR (CDCl₃): δ 7.74(s, 1H), 7.39-7.33(m, 1H), 7.10-7.01(m, 2H), 6.88-6.85(m, 1H), 6.73-6.72(m, 1H), 6.59(s, 1H), 4.17-4.03(m, 2H), 3.76(s, 3H), 3.76(m, 1H), 2.49(m, 1H), 2.36(s, 3H), 2.28-2.21(m, 1H), 1.99-1.56(m, 4H) |

TABLE 6-continued

Compounds of Examples

| Example | Compound | NMR Value |
|---|---|---|
| 224 | (S)-(1-methylpyrrolidin-2-yl)methyl(3'-chloro-5-methoxy-[1,1'-biphenyl]-2-yl)carbamate | ¹H NMR (CDCl₃): δ 7.79(s, 1H), 7.37-7.33(m, 2H), 7.26-7.20(m, 2H), 6.91-6.88(m, 1H), 6.73-6.72(m, 1H), 6.38(s, 1H), 4.22-4.05(m, 2H), 3.79(s, 3H), 3.11-3.07(m, 1H), 2.50-2.38(m, 1H), 2.33(s, 3H), 2.29-2.22(m, 1H), 1.94-1.57(m, 4H) |
| 225 | (S)-(1-methylpyrrolidin-2-yl)methyl(3',4'-dichloro-5-methoxy-[1,1'-biphenyl]-2-yl)carbamate | ¹H NMR (CDCl₃): δ 7.69(s, 1H), 7.48-7.43(m, 2H), 7.21-7.17(m, 1H), 6.90-6.87(m, 1H), 6.71-6.70(m, 1H), 6.51(s, 1H), 4.21-4.05(m, 2H), 3.78(s, 3H), 3.13(m, 1H), 2.52-2.45(m, 1H), 2.32(s, 3H), 2.30-2.22(m, 1H), 1.97-1.59(m, 4H) |
| 226 | (S)-(1-methylpyrrolidin-2-yl)methyl(3',5'-dichloro-5-methoxy-[1,1'-biphenyl]-2-yl)carbamate | ¹H NMR (CDCl₃): δ 7.79(s, 1H), 7.64(m, 1H), 7.35-7.34(m, 1H), 7.23-7.22(m, 1H), 7.07-7.02(m, 1H), 6.90-6.87(m, 1H), 6.63(s, 1H), 4.26-4.05(m, 2H), 3.20-3.15(m, 1H), 2.66(m, 1H), 2.42-2.32(m, 4H), 1.99-1.61(m, 4H) |

[Example 1] Synthesis of 2-(1-methylpyrrolidin-2-yl)ethyl (4'-fluoro-[1,1'-biphenyl]-2-yl)carbamate

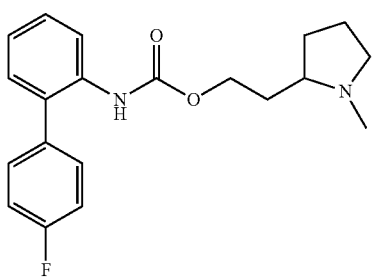 [SMILES: CN1CCCC1CCOC(=O)Nc1ccccc1-c1ccc(F)cc1]

4'-Fluoro-[1,1'-biphenyl]-2-carboxylic acid (747 mg, 3.46 mmol) (Synthesis Example 1) was dissolved in toluene (20 mL), and then biphenylphosphoryl azide (958 µL, 4.15 mmol) and triethylamine (486 µL, 3.46 mmol) were added thereto. The same was stirred at room temperature for 30 minutes, and then stirred again under reflux for 1 hour. The reactant was cooled to room temperature. 2-(2-Hydroxyethyl)-1-methylpyrrolidine (558 µL, 4.15 mmol) was added thereto and stirred under reflux for 12 hours. The reactant was cooled to room temperature. The solvent was removed by concentrating under reduced pressure, and then the same was extracted with water and ethyl acetate. The organic layer was dried with anhydrous magnesium sulfate, filtered and concentrated. The resulting residue was purified with column chromatography to prepare the titled compound (280 mg, 24%).

Examples 2-16

The starting materials in Table 7 were used instead of 4'-fluoro-[1,1'-biphenyl]-2-carboxylic acid (747 mg, 3.46 mmol) (Synthesis Example 1) to prepare compounds of Examples 2-16 in the same manner as Example 1.

TABLE 7

Examples 2-16

| Example | Chemical Name | Starting Material |
|---|---|---|
| 2 | 2-(1-Methylpyrrolidin-2-yl)ethyl (3',5'-difluoro-[1,1'-biphenyl]-2-yl)-carbamate (290 mg, 23%) | 3',5'-Difluoro-[1,1'-biphenyl]-2-carboxylic acid (820 mg) (Synthesis Example 2) |
| 3 | 2-(1-Methylpyrrolidin-2-yl)ethyl (3',4',5'-trifluoro-[1,1'-biphenyl]-2-yl)carbamate (300 mg, 41%) | 3',4',5'-Trifluoro-[1,1'-biphenyl]-2-carboxylic acid (492 mg) (Synthesis Example 3) |
| 4 | 2-(1-Methylpyrrolidin-2-yl)ethyl (3'-fluoro-[1,1'-biphenyl]-2-yl)-carbamate (326 mg, 41%) | 3'-Fluoro-[1,1'-biphenyl]-2-carboxylic acid (500 mg) (Synthesis Example 4) |
| 5 | 2-(1-Methylpyrrolidin-2-yl)ethyl (4'-methoxy-[1,1'-biphenyl]-2-yl)-carbamate (350 mg, 36%) | 4'-Methoxy-[1,1'-biphenyl]-2-carboxylic acid (630 mg) (Synthesis Example 5) |
| 6 | 2-(1-Methylpyrrolidin-2-yl)ethyl [1,1'-biphenyl]-2-ylcarbamate (400 mg, 50%) | [1,1'-Biphenyl]-2-carboxylic acid (500 mg) |
| 7 | 2-(1-Methylpyrrolidin-2-yl)ethyl (4'-chloro-[1,1'-biphenyl]-2-yl)-carbamate (230 mg, 30%) | 4'-Chloro-[1,1'-biphenyl]-2-carboxylic acid (500 mg) (Synthesis Example 6) |
| 8 | 2-(1-Methylpyrrolidin-2-yl)ethyl (3'-chloro-[1,1'-biphenyl]-2-yl)-carbamate (170 mg, 22%) | 3'-Chloro-[1,1'-biphenyl]-2-carboxylic acid (500 mg) (Synthesis Example 7) |
| 9 | 2-(1-Methylpyrrolidin-2-yl)ethyl (3',5'-dichloro-[1,1'-biphenyl]-2-yl)-carbamate (125 mg, 28%) | 3',5'-Dichloro-[1,1'-biphenyl]-2-carboxylic acid (300 mg) (Synthesis Example 8) |
| 10 | 2-(1-Methylpyrrolidin-2-yl)ethyl (4'-trifluoromethoxy-[1,1'-biphenyl]-2-yl)carbamate (370 mg, 57%) | 4'-Trifluoromethoxy-[1,1'-biphenyl]-2-carboxylic acid (450 mg) (Synthesis Example 9) |
| 11 | 2-(1-Methylpyrrolidin-2-yl)ethyl (4'-nitro-[1,1'-biphenyl]-2-yl)carbamate (410 mg, 82%) | 4'-Nitro-[1,1'-biphenyl]-2-carboxylic acid (330 mg) (Synthesis Example 10) |
| 12 | 2-(1-Methylpyrrolidin-2-yl)ethyl (3'-trifluoromethyl-[1,1'-biphenyl]-2-yl)carbamate (476 mg, 65%) | 3'-Trifluoromethyl-[1,1'-biphenyl]-2-carboxylic acid (500 mg) (Synthesis Example 11) |
| 13 | 2-(1-Methylpyrrolidin-2-yl)ethyl (4'-trifluoromethyl-[1,1'-biphenyl]-2-yl)carbamate (45 mg, 6%) | 4'-Trifluoromethyl-[1,1'-biphenyl]-2-carboxylic acid (500 mg) (Synthesis Example 12) |
| 14 | 2-(1-Methylpyrrolidin-2-yl)ethyl ((3'-fluoro-4'-methyl)-[1,1'-biphenyl]-2-yl)carbamate (306 mg, 46%) | 3'-Fluoro-4'-methyl-[1,1'-biphenyl]-2-carboxylic acid (430 mg) (Synthesis Example 13) |
| 15 | 2-(1-Methylpyrrolidin-2-yl)ethyl (3'-methyl-[1,1'-biphenyl]-2-yl)-carbamate (105 mg, 16%) | 3'-Methyl-[1,1'-biphenyl]-2-carboxylic acid (400 mg) (Synthesis Example 14) |
| 16 | 2-(1-Methylpyrrolidin-2-yl)ethyl (3'-ethoxy-[1,1'-biphenyl]-2-yl)-carbamate (250 mg, 52%) | 3'-Ethoxy-[1,1'-biphenyl]-2-carboxylic acid (315 mg) (Synthesis Example 15) |

[Example 17] Synthesis of 2-(1-methylpyrrolidin-2-yl)ethyl (3'-chloro-5-fluoro-[1,1'-biphenyl]-2-yl) carbamate

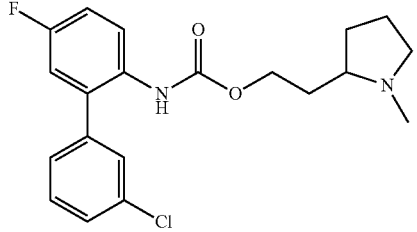 [SMILES: CN1CCCC1CCOC(=O)Nc1ccc(F)cc1-c1cccc(Cl)c1]

3'-Chloro-5-fluoro-[1,1'-biphenyl]-2-carboxylic acid (300 mg, 1.20 mmol) (Synthesis Example 16) was dissolved in toluene (20 mL), and then biphenylphosphoryl azide (310 µL, 1.44 mmol) and triethylamine (202 µL, 1.44 mmol) was added thereto. The same was stirred at room temperature for 30 minutes, and then stirred again under reflux for 1 hour. The reactant was cooled to room temperature. 2-(2-Hydroxyethyl)-1-methylpyrrolidine (194 µL, 1.44 mmol) were added thereto and then stirred under reflux for 12 hours. The reactant was cooled to room temperature. The solvent was removed by concentrating under reduced pressure, and then the same was extracted with water and ethyl acetate. The organic layer was dried with anhydrous magnesium sulfate, filtered and concentrated. The resulting residue was purified with column chromatography to prepare the titled compound (93 mg, 21%).

Examples 18-27

The starting materials in Table 8 were used instead of 3'-chloro-5-fluoro-[1,1'-biphenyl]-2-carboxylic acid (300 mg, 1.20 mmol)(Synthesis Example 16) to prepare compounds of Examples 18-27 in the same manner as Example 17.

TABLE 8

Examples 18-27

| Example | Chemical Name | Starting Material |
|---|---|---|
| 18 | 2-(1-Methylpyrrolidin-2-yl)ethyl (3',5-difluoro-[1,1'-biphenyl]-2-yl)-carbamate (465 mg, 76%) | 3',5-Difluoro-[1,1'-biphenyl]-2-carboxylic acid (400 mg, 1.71 mmol) (Synthesis Example 17) |
| 19 | 2-(1-Methylpyrrolidin-2-yl)ethyl (4',5-difluoro-[1,1'-biphenyl]-2-yl)-carbamate (184 mg, 30%) | 4',5-Difluoro-[1,1'-biphenyl]-2-carboxylic acid (400 mg, 1.71 mmol) (Synthesis Example 18) |
| 20 | 2-(1-Methylpyrrolidin-2-yl)ethyl (3',5,5'-trifluoro-[1,1'-biphenyl]-2-yl)carbamate (362 mg, 48%) | 3',5,5'-Trifluoro-[1,1'-biphenyl]-2-carboxylic acid (500 mg, 1.98 mmol) (Synthesis Example 19) |
| 21 | 2-(1-Methylpyrrolidin-2-yl)ethyl (5-fluoro-[1,1'-biphenyl]-2-yl)carbamate (297 mg, 19%) | 5-Fluoro-[1,1'-biphenyl]-2-carboxylic acid (1 g, 4.63 mmol) (Synthesis Example 20) |
| 22 | 2-(1-Methylpyrrolidin-2-yl)ethyl (5-fluoro-3'-methyl-[1,1'-biphenyl]-2-yl)carbamate (152 mg, 26%) | 5-Fluoro-3'-methyl-[1,1'-biphenyl]-2-carboxylic acid (380 mg, 1.65 mmol) (Synthesis Example 21) |
| 23 | 2-(1-Methylpyrrolidin-2-yl)ethyl (4-fluoro-[1,1'-biphenyl]-2-yl)carbamate (400 mg, 51%) | 4-Fluoro-[1,1'-biphenyl]-2-carboxylic acid (500 mg, 2.31 mmol) (Synthesis Example 22) |

TABLE 8-continued

Examples 18-27

| Example | Chemical Name | Starting Material |
|---|---|---|
| 24 | 2-(1-Methylpyrrolidin-2-yl)ethyl (3',4-difluoro-[1,1'-biphenyl]-2-yl)carbamate (84 mg, 14%) | 3',4-Difluoro-[1,1'-biphenyl]-2-carboxylic acid (400 mg, 1.71 mmol) (Synthesis Example 23) |
| 25 | 2-(1-Methylpyrrolidin-2-yl)ethyl (4-methoxy-[1,1'-biphenyl]-2-yl)carbamate (170 mg, 34%) | 4-Methoxy-[1,1'-biphenyl]-2-carboxylic acid (320 mg, 1.40 mmol) (Synthesis Example 24) |
| 26 | 2-(1-Methylpyrrolidin-2-yl)ethyl (5-methyl-[1,1'-biphenyl]-2-yl)carbamate (123 mg, 26%) | 5-Methyl-[1,1'-biphenyl]-2-carboxylic acid (300 mg, 1.41 mmol) (Synthesis Example 25) |
| 27 | 2-(1-Methylpyrrolidin-2-yl)ethyl (3'-fluoro-5-methyl-[1,1'-biphenyl]-2-yl)carbamate (279 mg, 90%) | 3'-Fluoro-5-methyl-[1,1'-biphenyl]-2-carboxylic acid (200 mg, 0.87 mmol) (Synthesis Example 26) |

[Example 28] Synthesis of 2-(1-methylpyrrolidin-2-yl)ethyl (4'-cyano-[1,1'-biphenyl]-2-yl)carbamate

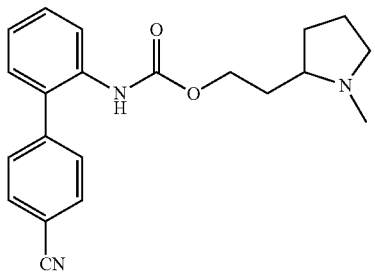

2-(1-Methylpyrrolidin-2-yl)ethyl (2-iodophenyl)carbamate (600 mg, 1.6 mmol) (Synthesis Example A) was dissolved in a mixed solution of toluene (20 mL) and ethanol (4 mL). 4-Cyanophenyl boronic acid (259 mg, 1.76 mmol), potassium carbonate (442 mg, 3.2 mmol) and tetrakis triphenylphosphine palladium (370 mg, 0.32 mmol) were added thereto. The reactant was stirred at 110° C. for 12 hours and cooled to room temperature. The same was filtered through celite and the solvent was removed by concentrating under reduced pressure. The same was extracted with water and ethyl acetate, and then the organic layer was dried with anhydrous magnesium sulfate, filtered and concentrated. The resulting residue was purified with column chromatography to prepare the titled compound (193 mg, 35%).

Examples 29-32

2-(1-Methylpyrrolidin-2-yl)ethyl (2-iodophenyl)carbamate of Synthesis Example A as a starting material and reaction materials in Table 9 were used to prepare compounds of Examples 29-32 in the same manner as Example 28.

TABLE 9

Examples 29-32

| Example | Chemical Name | Starting Material (Synthesis Example A) | Reacting Material |
|---|---|---|---|
| 29 | 2-(1-Methyl-pyrrolidin-2-yl)-ethyl (3'-(3-hydroxypropyl)-[1,1'-biphenyl]-2-yl)carbamate (52 mg, 5%) | 1 g, 2.67 mmol | 3-(3-Hydroxy-propyl)phenyl boronic acid (530 mg, 2.94 mmol) |
| 30 | 2-(1-Methyl-pyrrolidin-2-yl)-ethyl (4'-(dimethylamino)-[1,1'-biphenyl]-2-yl)carbamate (71 mg, 36%) | 200 mg, 0.53 mmol | 4-(Dimethyl-amino)-phenyl boronic acid (131 mg, 0.80 mmol) |
| 31 | 2-(1-Methylpyrrolidin-2-yl)ethyl (4'-(tert-butyl)-[1,1'-biphenyl]-2-yl)-carbamate (33 mg, 22%) | 150 mg, 0.40 mmol | 4-Tert-butylphenyl boronic acid (110 mg, 0.60 mmol) |
| 32 | 2-(1-Methylpyrrolidin-2-yl)ethyl (2'-amino-[1,1'-biphenyl]-2-yl)-carbamate (37 mg, 10%) | 400 mg, 1.07 mmol | 2-Aminophenyl boronic acid pinacol ester (353 mg, 1.61 mmol) |

[Example 33] Synthesis of 2-(1-methylpyrrolidin-2-yl)ethyl (3'-amino-[1,1'-biphenyl]-2-yl)carbamate

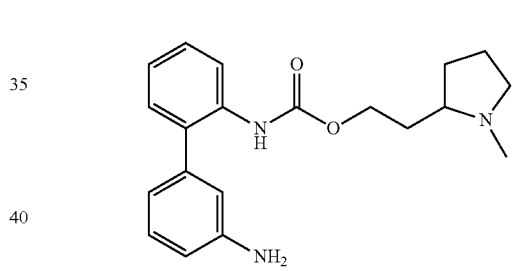

2-(1-Methylpyrrolidin-2-yl)ethyl (2-iodophenyl)carbamate (1.36 g, 3.63 mmol) (Synthesis Example A) was dissolved in a mixed solution of acetonitrile (15 mL) and water (15 mL). 3-Aminophenyl boronic acid (995 mg, 7.26 mmol), sodium carbonate (772 mg, 7.26 mmol) and dichlorobis triphenylphosphine palladium (127 mg, 0.18 mmol) were added thereto. The reactant was stirred at 110° C. in a microwave oven for 10 minutes and cooled to room temperature. The same was filtered through celite and the solvent was removed by concentrating under reduced pressure. The same was extracted with water and ethyl acetate. The organic layer was dried with anhydrous magnesium sulfate, filtered and concentrated. The resulting residue was purified with column chromatography to prepare the titled compound (192 mg, 16%).

Examples 34-41

2-(1-Methylpyrrolidin-2-yl)ethyl (2-iodophenyl)carbamate of Synthesis Example A as a starting material and reacting materials in Table 10 were used to prepare compounds of Examples 34-41 in the same manner as Example 33.

TABLE 10

Examples 34-41

| Example | Chemical Name | Starting Material (Synthesis Example A) | Reacting Material |
|---|---|---|---|
| 34 | 2-(1-Methylpyrrolidin-2-yl)ethyl (2'-fluoro-[1,1'-biphenyl]-2-yl)carbamate (126 mg, 30%) | 400 mg, 1.07 mmol | 2-Fluorophenyl-boronic acid (300 mg, 2.14 mmol) |
| 35 | 2-(1-Methylpyrrolidin-2-yl)ethyl (2'-chloro-[1,1'-biphenyl]-2-yl)carbamate (80 mg, 18%) | 400 mg, 1.07 mmol | 2-Chlorophenyl-boronic acid (335 mg, 2.14 mmol) |
| 36 | 2-(1-Methyl-pyrrolidin-2-yl)ethyl (2'-hydroxy-[1,1'-biphenyl]-2-yl)-carbamate (65 mg, 16%) | 400 mg, 1.07 mmol | 2-Hydroxyphenyl boronic acid pinacol ester (471 mg, 2.14 mmol) |
| 37 | 2-(1-Methyl-pyrrolidin-2-yl)ethyl (3'-tert-butyl-5'-methyl-[1,1'-biphenyl]-2-yl)-carbamate (155 mg, 49%) | 300 mg, 0.80 mmol | (3-tert-Butyl-5-methyl)phenyl-boronic acid (307 mg, 1.60 mmol) |
| 38 | 2-(1-Methyl-pyrrolidin-2-yl)ethyl (4'-fluoro-3'-(trifluoromethyl)-[1,1'-biphenyl]-2-yl)carbamate (66 mg, 20%) | 297 mg, 0.79 mmol | (4-Fluoro-3-(trifluoromethyl)phenyl)boronic acid (330 mg, 1.58 mmol) |
| 39 | 2-(1-Methyl-pyrrolidin-2-yl)ethyl (4'-amino-3'-chloro-[1,1'-biphenyl]-2-yl)carbamate (81 mg, 27%) | 300 mg, 0.80 mmol | (4-Amino-3-chlorophenyl)boronic acid pinacol ester (406 mg, 1.6 mmol) |
| 40 | 2-(1-Methyl-pyrrolidin-2-yl)ethyl (3'-hydroxy-[1,1'-biphenyl]-2-yl)-carbamate (48 mg, 9%) | 300 mg, 0.80 mmol | 3-Hydroxyphenyl boronic acid (221 mg, 1.6 mmol) |
| 41 | 2-(1-Methyl-pyrrolidin-2-yl)ethyl (3'-chloro-4'-fluoro-[1,1'-biphenyl]-2-yl)carbamate (150 mg, 43%) | 300 mg, 0.80 mmol | 3-Chloro-4-fluorophenyl-boronic acid (240 mg, 1.38 mmol) |

[Example 42] Synthesis of 2-(1-methylpyrrolidin-2-yl)ethyl (3',4',5-trifluoro-[1,1'-biphenyl]-2-yl)carbamate

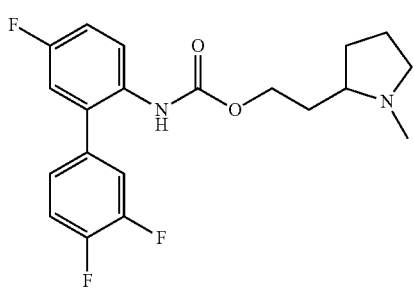 [SMILES: CN1CCCC1CCOC(=O)Nc1ccc(F)cc1-c1ccc(F)c(F)c1]

2-(1-Methylpyrrolidin-2-yl)ethyl(2-bromo-4-fluoro-phenyl)carbamate (400 mg, 1.16 mmol)(Synthesis Example B) was dissolved in toluene (20 mL). 3,4-Fluorophenyl diboronic acid (280 mg, 1.74 mmol), potassium carbonate (321 mg, 2.32 mmol) and tetrakis triphenylphosphine palladium (140 mg, 0.12 mmol) were added thereto. The reactant was stirred at 120° C. for 12 hours and cooled to room temperature. The same was filtered through celite and the solvent was removed by concentrating under reduced pressure. The same was extracted with water and ethyl acetate. The organic layer was dried with anhydrous magnesium sulfate, filtered and concentrated. The resulting residue was purified with column chromatography to prepare the titled compound (15 mg, 3%).

Examples 43-46

2-(1-Methylpyrrolidin-2-yl)ethyl(2-bromo-4-fluoro-phenyl)carbamate of Synthesis Example B as a starting material and reacting materials in Table 11 were used to prepare compounds of Examples 43-46 in the same manner as Example 42.

TABLE 11

Examples 43-46

| Example | Chemical Name | Starting Material (Synthesis Example B) | Reacting Material |
|---|---|---|---|
| 43 | 2-(1-Methyl-pyrrolidin-2-yl)ethyl (3',4'-dichloro-5-fluoro-[1,1'-biphenyl]-2-yl)carbamate (24 mg, 5%) | 400 mg, 1.16 mmol | 3,4-Dichloro-phenyl boronic acid (332 mg, 1.74 mmol) |
| 44 | 2-(1-Methyl-pyrrolidin-2-yl)ethyl (3'-ethyl-5-fluoro-[1,1'-biphenyl]-2-yl)carbamate (40 mg, 12%) | 300 mg, 0.87 mmol | 3-Ethylphenyl boronic acid (200 mg, 1.31 mmol) |
| 45 | 2-(1-Methyl-pyrrolidin-2-yl)ethyl (5-fluoro-3',5'-dimethyl-[1,1'-biphenyl]-2-yl)-carbamate (18 mg, 4%) | 400 mg, 1.16 mmol | 3,5-Dimethyl-phenyl boronic acid (261 mg, 1.74 mmol) |
| 46 | 2-(1-Methyl-pyrrolidin-2-yl)ethyl (3'-amino-5-fluoro-[1,1'-biphenyl]-2-yl)carbamate (50 mg, 5%) | 1 g, 2.90 mmol | 3-Aminophenyl boronic acid (600 mg, 4.35 mmol) |

Examples 47-51

2-(1-Methylpyrrolidin-2-yl)ethyl(2-bromo-4-(trifluoromethyl)phenyl)carbamate of Synthesis Example C as a starting material instead of 2-(1-methylpyrrolidin-2-yl)ethyl (2-bromo-4-fluorophenyl)carbamate of Synthesis Example B and reacting materials in Table 12 were used to prepare compounds of Examples 47-51 in the same manner as Example 42.

TABLE 12

Examples 47-51

| Example | Chemical Name | Starting Material (Synthesis Example C) | Reacting Material |
|---|---|---|---|
| 47 | 2-(1-Methyl-pyrrolidin-2-yl)-ethyl(5-(tri-fluoromethyl)-[1,1'-biphenyl]-2-yl)carbamate (26 mg, 9%) | 300 mg, 0.76 mmol | Phenylboronic acid (102 mg, 0.84 mmol) |
| 48 | 2-(1-Methyl-pyrrolidin-2-yl)-ethyl(4'-fluoro-5-(trifluoro-methyl)-[1,1'-biphenyl]-2-yl)-carbamate (14 mg, 4%) | 300 mg, 0.76 mmol | 4-Fluorophenyl-boronic acid (118 mg, 0.84 mmol) |

TABLE 12-continued

Examples 47-51

| Example | Chemical Name | Starting Material (Synthesis Example C) | Reacting Material |
|---|---|---|---|
| 49 | 2-(1-Methyl-pyrrolidin-2-yl)-ethyl(3'-fluoro-5-(trifluoromethyl)-[1,1'-biphenyl]-2-yl)carbamate (19 mg, 6%) | 300 mg, 0.76 mmol | 3-Fluorophenyl-boronic acid (118 mg, 0.84 mmol) |
| 50 | 2-(1-Methyl-pyrrolidin-2-yl)-ethyl (3',5'-difluoro-5-(trifluoromethyl)-[1,1'-biphenyl]-2-yl)carbamate (12 mg, 4%) | 260 mg, 0.66 mmol | 3,5-Difluoro-phenylboronic acid (115 mg, 0.73 mmol) |
| 51 | 2-(1-Methyl-pyrrolidin-2-yl)-ethyl(3'-chloro-5-(trifluoromethyl)-[1,1'-biphenyl]-2-yl)carbamate (14 mg, 4%) | 300 mg, 0.76 mmol | 3-Chlorophenyl-boronic acid (131 mg, 0.84 mmol) |

[Example 52] Synthesis of 2-(1-methylpyrrolidin-2-yl)ethyl (3'-chloro-5,5'-difluoro-[1,1'-biphenyl]-2-yl) carbamate

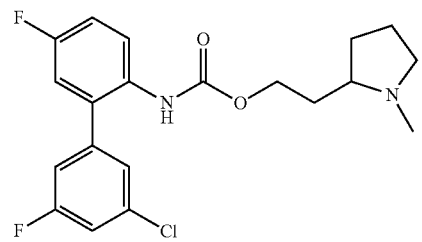 [SMILES: CN1CCCC1CCOC(=O)Nc1ccc(F)cc1-c1cc(F)cc(Cl)c1]

2-(1-Methylpyrrolidin-2-yl)ethyl(2-bromo-4-fluoro-phenyl)carbamate (300 mg, 0.87 mmol)(Synthesis Example B) was dissolved in a mixed solution of acetonitrile (10 mL) and water (10 mL). (3-Chloro-5-fluorophenyl)boronic acid (303 mg, 1.74 mmol), sodium carbonate (184 mg, 1.74 mmol) and dichlorobis triphenylphosphine palladium (31 mg, 0.04 mmol) were added thereto. The reactant was stirred at 110° C. in a microwave oven for 10 minutes and cooled to room temperature. The same was filtered through celite and the solvent was removed by concentrating under reduced pressure. The same was extracted with water and ethyl acetate. The organic layer was dried with anhydrous magnesium sulfate, filtered and concentrated. The resulting residue was purified with column chromatography to prepare the titled compound (51 mg, 15%).

Examples 53-59

2-(1-Methylpyrrolidin-2-yl)ethyl(2-bromo-4-fluoro-phenyl)carbamate of Synthesis Example B as a starting material and reacting materials in Table 13 were used to prepare compounds of Examples 53-59 in the same manner as Example 52.

TABLE 13

Examples 53-59

| Example | Chemical Name | Starting Material (Synthesis Example B) | Reacting Material |
|---|---|---|---|
| 53 | 2-(1-Methyl-pyrrolidin-2-yl)-ethyl(3'-chloro-4',5-difluoro-[1,1'-biphenyl]-2-yl)carbamate (81 mg, 24%) | 300 mg, 0.87 mmol | (3-Chloro-4-fluoro-phenyl)boronic acid (303 mg, 1.74 mmol) |
| 54 | 2-(1-Methyl-pyrrolidin-2-yl)-ethyl(4'-chloro-3',5-difluoro-[1,1'-biphenyl]-2-yl)carbamate (173 mg, 38%) | 400 mg, 1.16 mmol | (3-Fluoro-4-chloro-phenyl)boronic acid (405 mg, 2.32 mmol) |
| 55 | 2-(1-Methyl-pyrrolidin-2-yl)-ethyl(3',5'-dichloro-5-fluoro-[1,1'-biphenyl]-2-yl)-carbamate (71 mg, 15%) | 400 mg, 1.16 mmol | 3,5-Dichlorophenyl boronic acid (443 mg, 2.32 mmol) |
| 56 | 2-(1-Methyl-pyrrolidin-2-yl)-ethyl(3',5'-dichloro-4',5-difluoro-[1,1'-biphenyl]-2-yl)-carbamate (99 mg, 20%) | 400 mg, 1.16 mmol | 3,5-Dichloro-4-fluoro-phenyl boronic acid (484 mg, 2.32 mmol) |
| 57 | 2-(1-Methyl-pyrrolidin-2-yl)-ethyl(3'-chloro-5-fluoro-5'-hydroxy-[1,1'-biphenyl]-2-yl)-carbamate (97 mg, 28%) | 300 mg, 0.87 mmol | (3-Chloro-5-hydroxy-phenyl)boronic acid (300 mg, 1.74 mmol) |
| 58 | 2-(1-Methyl-pyrrolidin-2-yl)-ethyl(3'-chloro-5-fluoro-4'-hydroxy-[1,1'-biphenyl]-2-yl)-carbamate (176 mg, 39%) | 400 mg, 1.16 mmol | (3-Chloro-4-hydroxy-phenyl)boronic acid (400 mg, 2.32 mmol) |
| 59 | 2-(1-Methyl-pyrrolidin-2-yl)ethyl(5-fluoro-3',4'-dimethyl-[1,1'-biphenyl]-2-yl)-carbamate (129 mg, 30%) | 400 mg, 1.16 mmol | (3,4-Dimethyl-phenyl)boronic acid (348 mg, 2.32 mmol) |

Examples 60-65

2-(1-Methylpyrrolidin-2-yl)ethyl(2-bromo-4-methoxyphenyl)carbamate of Synthesis Example D instead of 2-(1-methylpyrrolidin-2-yl)ethyl (2-bromo-4-fluorophenyl)carbamate of Synthesis Example B as a starting material and reacting materials in Table 14 were used to prepare compounds of Examples 60-65 in the same manner as Example 52.

TABLE 14

Examples 60-65

| Example | Chemical Name | Starting Material (Synthesis Example D) | Reacting Material |
|---|---|---|---|
| 60 | 2-(1-Methyl-pyrrolidin-2-yl)-ethyl(5-methoxy-[1,1'-biphenyl]-2-yl)carbamate (25 mg, 8%) | 300 mg, 0.84 mmol | Phenylboronic acid (154 mg, 1.26 mmol) |
| 61 | 2-(1-Methyl-pyrrolidin-2-yl)-ethyl(3'-fluoro-5-methoxy-[1,1'-biphenyl]-2-yl)-carbamate (112 mg, 36%) | 300 mg, 0.84 mmol | 3-Fluorophenylboronic acid (176 mg, 1.26 mmol) |
| 62 | 2-(1-Methyl-pyrrolidin-2-yl)-ethyl(3',5'-difluoro-5-methoxy-[1,1'-biphenyl]-2-yl)-carbamate (161 mg, 37%) | 400 mg, 1.12 mmol | 3,5-Difluoro-phenylboronic acid (354 mg, 2.24 mmol) |
| 63 | 2-(1-Methyl-pyrrolidin-2-yl)-ethyl(3'-chloro-5-methoxy-[1,1'-biphenyl]-2-yl)-carbamate (112 mg, 31%) | 330 mg, 0.92 mmol | 3-Chlorophenyl-boronic acid (289 mg, 1.85 mmol) |
| 64 | 2-(1-Methyl-pyrrolidin-2-yl)-ethyl(3',5'-dichloro-5-methoxy-[1,1'-biphenyl]-2-yl)-carbamate (92 mg, 19%) | 400 mg, 1.12 mmol | 3,5-Dichloro-phenylboronic acid (427 mg, 2.24 mmol) |
| 65 | 2-(1-Methyl-pyrrolidin-2-yl)-ethyl(3'-chloro-4'-fluoro-5-methoxy-[1,1'-biphenyl]-2-yl)-carbamate (155 mg, 34%) | 400 mg, 1.12 mmol | (3-Chloro-4-fluoro)phenylboronic acid (390 mg, 2.24 mmol) |

Examples 66-73

2-(1-Methylpyrrolidin-2-yl)ethyl(2-bromo-4-chloro-phenyl)carbamate of Synthesis Example E instead of 2-(1-methylpyrrolidin-2-yl)ethyl (2-bromo-4-fluorophenyl)carbamate of Synthesis Example B as a starting material and reacting materials in Table 15 were used to prepare compounds of Examples 66-73 in the same manner as Example 52.

TABLE 15

Examples 66-73

| Example | Chemical Name | Starting Material (Synthesis Example E) | Reacting Material |
|---|---|---|---|
| 66 | 2-(1-Methyl-pyrrolidin-2-yl)-ethyl (5-chloro-[1,1'-biphenyl]-2-yl)carbamate (94 mg, 24%) | 400 mg, 1.11 mmol | Phenylboronic acid (271 mg, 2.22 mmol) |
| 67 | 2-(1-Methyl-pyrrolidin-2-yl)-ethyl(5-chloro-3'-fluoro-[1,1'-biphenyl]-2-yl)-carbamate (187 mg, 45%) | 400 mg, 1.11 mmol | 3-Fluorophenyl-boronic acid (311 mg, 2.22 mmol) |
| 68 | 2-(1-Methyl-pyrrolidin-2-yl)-ethyl(5-chloro-4'-fluoro-[1,1'-biphenyl]-2-yl)-carbamate (38 mg, 9%) | 400 mg, 1.11 mmol | 4-Fluorophenyl-boronic acid (311 mg, 2.22 mmol) |
| 69 | 2-(1-Methyl-pyrrolidin-2-yl)-ethyl(5-chloro-3',5'-difluoro-[1,1'-biphenyl]-2-yl)carbamate (162 mg, 37%) | 400 mg, 1.11 mmol | 3,5-Difluorophenyl boronic acid (351 mg, 2.22 mmol) |
| 70 | 2-(1-Methyl-pyrrolidin-2-yl)-ethyl(3',5-dichloro-[1,1'-biphenyl]-2-yl)-carbamate (111 mg, 25%) | 400 mg, 1.11 mmol | 3-Chlorophenyl-boronic acid (347 mg, 2.22 mmol) |
| 71 | 2-(1-Methyl-pyrrolidin-2-yl)-ethyl (3',5,5'-trichloro-[1,1'-biphenyl]-2-yl)-carbamate (58 mg, 12%) | 400 mg, 1.11 mmol | 3,5-Dichlorophenyl boronic acid (424 mg, 2.22 mmol) |
| 72 | 2-(1-Methyl-pyrrolidin-2-yl)-ethyl (3',5-dichloro-5'-fluoro-[1,1'-biphenyl]-2-yl)-carbamate (119 mg, 26%) | 400 mg, 1.11 mmol | (3-Chloro-5-fluoro-phenyl)boronic acid (387 mg, 2.22 mmol) |
| 73 | 2-(1-Methyl-pyrrolidin-2-yl)-ethyl(3',5-dichloro-4'-fluoro-[1,1'-biphenyl]-2-yl)-carbamate (88 mg, 19%) | 400 mg, 1.11 mmol | (3-Chloro-4-fluorophenyl)boronic acid (387 mg, 2.22 mmol) |

[Example 74] Synthesis of (R)-(1-methylpyrrolidin-3-yl)methyl (3'-fluoro-4'-formyl-[1,1'-biphenyl]-2-yl)carbamate (R)-(1-methylpyrrolidin-3-yl)methyl(2-bromophenyl)-carbamate (220 mg, 0.70 mmol) (Synthesis Example F) and 3-fluoro-4-formylphenylboronic acid (237 mg, 1.41 mmol) were used as starting materials to prepare titled compound (124 mg, 50%) in the same manner as Example 52.

[Example 75] Synthesis of 2-(1-methylpyrrolidin-2-yl)ethyl (3',5'-difluoro-5-hydroxy-[1,1'-biphenyl]-2-yl)carbamate

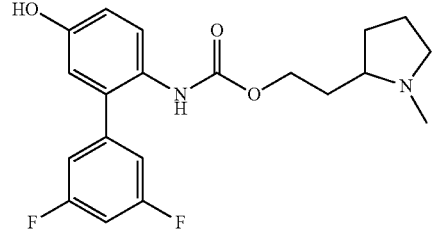

2-(1-Methylpyrrolidin-2-yl)ethyl(3',5'-difluoro-5-methoxy-[1,1'-biphenyl]-2-yl)carbamate (130 mg, 0.33 mmol) (Example 62) was dissolved in dichloromethane (10 mL). A boron trichloride solution (1.0M dichloromethane, 0.99 ml, 0.99 mmol) was added thereto and stirred at room temperature for 2 hours. After reaction was terminated, the reactant was extracted with water and dichloromethane. The organic layer was dried with anhydrous magnesium sulfate, filtered and concentrated. The resulting residue was purified with column chromatography to prepare the titled compound (68 mg, 55%).

[Example 76] Synthesis of 2-(1-methylpyrrolidin-2-yl)ethyl (3',5'-dichloro-5-hydroxy-[1,1'-biphenyl]-2-yl)carbamate 2-(1-Methylpyrrolidin-2-yl)ethyl(3',5'-dichloro-5-methoxy-[1,1'-biphenyl]-2-yl)carbamate (90 mg, 0.21 mmol) (Example 64) was used instead of Example 62 to prepare titled compound (10 mg, 12%) in the same manner as Example 75.

[Example 77] Synthesis of 2-(1-methylpyrrolidin-2-yl)ethyl (3'-chloro-4'-fluoro-5-hydroxy-[1,1'-biphenyl]-2-yl)carbamate 2-(1-Methylpyrrolidin-2-yl)ethyl (3'-chloro-4'-fluoro-5-methoxy-[1,1'-biphenyl]-2-yl)carbamate (140 mg, 0.34 mmol) (Example 65) was used instead of Example 62 to prepare titled compound (130 mg, 96%) in the same manner as Example 75.

[Example 78] Synthesis of (R)-pyrrolidin-3-ylmethyl [1,1'-biphenyl]-2-ylcarbamate

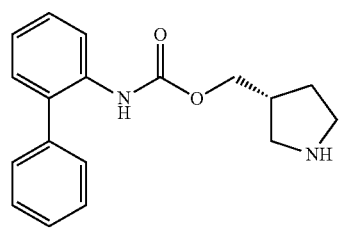 [SMILES: O=C(Nc1ccccc1-c1ccccc1)OC[C@@H]1CCNC1]

[Step 1] (R)-tert-butyl 3-((([1,1'-biphenyl]-2-ylcarbamoyl)-oxy)methyl)pyrrolidine-1-carboxylate

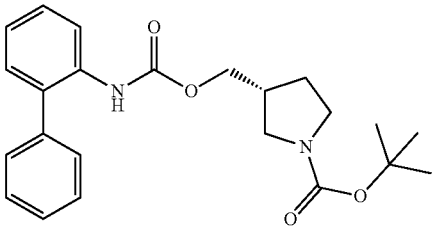 [SMILES: CC(C)(C)OC(=O)N1CC[C@@H](COC(=O)Nc2ccccc2-c2ccccc2)C1]

[1,1'-Biphenyl]-2-carboxylic acid (2 g, 10.09 mmol) was dissolved in toluene (50 mL), and then biphenylphosphoryl azide (2.61 mL, 12.11 mmol) and triethylamine (1.42 mL, 10.09 mmol) were added thereto. The same was stirred at room temperature for 30 minutes and then stirred again under reflux for 1 hour. The reactant was cooled to room temperature. (R)-tert-butyl 3-(hydroxymethyl)pyrrolidine-1-carboxylate (2.44 g, 12.11 mmol) was added thereto and stirred under reflux for 12 hours. The reactant was cooled to room temperature. The solvent was removed by concentrating under reduced pressure, and then the same was extracted with water and dichloromethane. The organic layer was dried with anhydrous magnesium sulfate, filtered and concentrated. The resulting residue was purified with column chromatography to prepare the titled compound (3 g, 75%).

$^1$H NMR(CDCl$_3$): δ 8.15-7.97 (bs, 1H), 7.55-7.26 (m, 6H), 7.26-7.05 (m, 2H), 6.67-6.52 (bs, 1H), 4.19-3.90 (m, 2H), 3.57-3.18 (m, 2H), 3.13-2.73 (bs, 1H), 2.57-2.38 (m, 1H), 2.00-1.83 (m, 1H), 1.70-1.53 (m, 2H) 1.43 (s, 9H)

[Step 2] Synthesis of (R)-pyrrolidin-3-ylmethyl [1,1'-biphenyl]-2-ylcarbamate

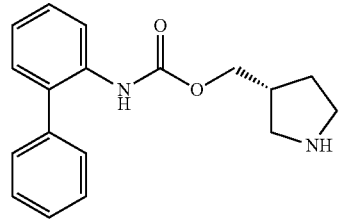 [SMILES: O=C(Nc1ccccc1-c1ccccc1)OC[C@@H]1CCNC1]

(R)-tert-butyl 3-((([1,1'-biphenyl]-2-ylcarbamoyl)oxy)methyl)pyrrolidine-1-carboxylate (3 g, 7.57 mmol) was dissolved in dichloromethane (80 mL). Trifluoroacetic acid (40 mL) was added thereto and stirred at room temperature for 2 hours. The solvent was removed by concentrating the reactant under reduced pressure and the same was extracted with 2N-sodium hydroxide solution and dichloromethane. The organic layer was dried with anhydrous magnesium sulfate, filtered and concentrated. The resulting residue was purified with column chromatography to prepare the titled compound (1.73 g, 77%).

Examples 79-88

Starting materials and reacting materials in Table 16 were used to prepare compounds of Examples 79-88 in the same manner as Example 78.

TABLE 16

| Examples 79-88 | | | |
|---|---|---|---|
| Example | Chemical Name | Starting Material | Reacting Material |
| 79 | (S)-pyrrolidin-3-ylmethyl-[1,1'-biphenyl]-2-yl-carbamate (1.53 g, 51%) | [1,1'-Biphenyl]-2-carboxylic acid (2 g, 10.09 mmol) | (S)-tert-butyl-3-(hydroxymethyl)-pyrrolidine-1-carboxylate (2.44 g, 12.11 mmol) |
| 80 | (R)-pyrrolidin-3-ylmethyl-(3',5'-difluoro-[1,1'-biphenyl]-2-yl)carbamate (435 mg, 63%) | 3',5'-Difluoro-[1,1'-biphenyl]-2-carboxylic acid (500 mg, 2.13 mmol) (Synthesis Example 2) | (R)-tert-butyl-3-(hydroxymethyl)-pyrrolidine-1-carboxylate (516 mg, 2.56 mmol) |
| 81 | (S)-pyrrolidin-3-ylmethyl-(3',5'-difluoro-[1,1'-biphenyl]-2-yl)carbamate (416 mg, 59%) | 3',5'-Difluoro-[1,1'-biphenyl]-2-carboxylic acid (500 mg, 2.13 mmol) (Synthesis Example 2) | (S)-tert-butyl-3-(hydroxymethyl)-pyrrolidine-1-carboxylate (516 mg, 2.56 mmol) |
| 82 | (S)-pyrrolidin-3-ylmethyl-(5-fluoro-[1,1'-biphenyl]-2-yl)carbamate (712 mg, 51%) | 5-Fluoro-[1,1'-biphenyl]-2-carboxylic acid (1 g, 4.63 mmol) (Synthesis Example 20) | (S)-tert-butyl-3-(hydroxymethyl)pyrrolidine-1-carboxylate (1.12 g, 5.56 mmol) |
| 83 | (S)-pyrrolidin-3-ylmethyl (5-fluoro-3'-methyl-[1,1'- | 5-Fluoro-3'-methyl-[1,1'-biphenyl]-2-carboxylic acid | (S)-tert-butyl 3-(hydroxymethyl)pyrrolidine-1-carboxylate |

TABLE 16-continued

Examples 79-88

| Example | Chemical Name | Starting Material | Reacting Material |
|---|---|---|---|
|  | biphenyl]-2-yl)carbamate (260 mg, 18%) | (1 g, 4.34 mmol) (Synthesis Example 21) | (1.05 g, 5.21 mmol) |
| 84 | (R)-pyrrolidin-3-ylmethyl (3',5,5'-trifluoro-[1,1'-biphenyl]-2-yl)carbamate (470 mg, 67%) | 3',5,5'-Trifluoro-[1,1'-biphenyl]-2-carboxylic acid (500 mg, 1.98 mmol) (Synthesis Example 19) | (R)-tert-butyl 3-(hydroxymethyl)pyrrolidine-1-carboxylate (479 mg, 2.38 mmol) |
| 85 | (S)-pyrrolidin-3-ylmethyl (3',5,5'-trifluoro-[1,1'-biphenyl]-2-yl)carbamate (400 mg, 58%) | 3',5,5'-Trifluoro-[1,1'-biphenyl]-2-carboxylic acid (500 mg, 1.98 mmol) (Synthesis Example 19) | (S)-tert-butyl 3-(hydroxymethyl)pyrrolidine-1-carboxylate (479 mg, 2.38 mmol) |
| 86 | (R)-pyrrolidin-3-ylmethyl (5-methyl-[1,1'-biphenyl]-2-yl)carbamate (222 mg, 25%) | 5-Methyl-[1,1'-biphenyl]-2-carboxylic acid (600 mg, 2.83 mmol) (Synthesis Example 25) | (R)-tert-butyl 3-(hydroxymethyl)pyrrolidine-1-carboxylate (684 mg, 3.40 mmol) |
| 87 | (R)-pyrrolidin-3-ylmethyl (3'-fluoro-5-methyl-[1,1'-biphenyl]-2-yl)carbamate (346 mg, 61%) | 3'-Fluoro-5-methyl-[1,1'-biphenyl]-2-carboxylic acid (400 mg, 1.74 mmol) (Synthesis Example 26) | (R)-tert-butyl 3-(hydroxymethyl)pyrrolidine-1-carboxylate (420 mg, 2.09 mmol) |
| 88 | (S)-pyrrolidin-2-ylmethyl (4'-fluoro-[1,1'-biphenyl]-2-yl)carbamate (915 mg, 84%) | 4'-Fluoro-[1,1'-biphenyl]-2-carboxylic acid (750 mg, 3.47 mmol) (Synthesis Example 1) | (S)-tert-butyl 2-(hydroxymethyl)pyrrolidine-1-carboxylate (837 mg, 4.16 mmol) |

[Example 89] Synthesis of (R)-(1-methylpyrrolidin-3-yl)methyl [1,1'-biphenyl]-2-ylcarbamate

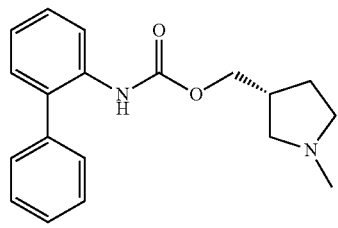 [SMILES: CN1CC[C@@H](COC(=O)Nc2ccccc2-c2ccccc2)C1]

(R)-pyrrolidin-3-ylmethyl [1,1'-biphenyl]-2-ylcarbamate (727 mg, 2.45 mmol) (Example 78) was dissolved in water (50 mL). Acetic acid (1 mL), formaldehyde solution (3 mL) and zinc powder (300 mg) were sequentially added thereto and stirred at room temperature for 12 hours. The reactant was filtered, neutralized with 2N-sodium hydroxide and extracted with water and dichloromethane. The organic layer was dried with anhydrous magnesium sulfate, filtered and concentrated. The resulting residue was purified with column chromatography to prepare the titled compound (209 mg, 28%).

Examples 90-99

Starting materials in Table 17 were used instead of (R)-pyrrolidin-3-ylmethyl [1,1'-biphenyl]-2-ylcarbamate to prepare compounds of Examples 90-99 in the same manner as Example 89

TABLE 17

Examples 90-99

| Example | Chemical Name | Starting Material |
|---|---|---|
| 90 | (S)-(1-methylpyrrolidin-3-yl)methyl [1,1'-biphenyl]-2-ylcarbamate (285 mg, 52%) | (S)-pyrrolidin-3-ylmethyl [1,1'-biphenyl]-2-yl-carbamate (523 mg, 1.76 mmol) (Example 79) |
| 91 | (R)-(1-methylpyrrolidin-3-yl)methyl (3',5'-difluoro-[1,1'-biphenyl]-2-yl)carbamate (138 mg, 33%) | (R)-pyrrolidin-3-ylmethyl (3',5'-difluoro-[1,1'-biphenyl]-2-yl)carbamate (400 mg, 1.2 mmol) (Example 80) |
| 92 | (S)-(1-methylpyrrolidin-3-yl)methyl (3',5'-difluoro-[1,1'-biphenyl]-2-yl)carbamate (78 mg, 19%) | (S)-pyrrolidin-3-ylmethyl (3',5'-difluoro-[1,1'-biphenyl]-2-yl)carbamate (377 mg, 1.13 mmol) (Example 81) |
| 93 | (S)-(1-methylpyrrolidin-3-yl)methyl (5-fluoro-[1,1'-biphenyl]-2-yl)-carbamate (230 mg, 67%) | (S)-pyrrolidin-3-ylmethyl (5-fluoro-[1,1'-biphenyl]-2-yl)carbamate (330 mg, 1.05 mmol) (Example 82) |

TABLE 17-continued

Examples 90-99

| Example | Chemical Name | Starting Material |
|---|---|---|
| 94 | (S)-(1-methylpyrrolidin-3-yl)methyl (5-fluoro-3'-methyl-[1,1'-biphenyl]-2-yl)carbamate (24 mg, 9%) | (S)-pyrrolidin-3-ylmethyl (5-fluoro-3'-methyl-[1,1'-biphenyl]-2-yl)carbamate (260 mg, 0.79 mmol) (Example 83) |
| 95 | (R)-(1-methylpyrrolidin-3-yl)methyl (3',5,5'-trifluoro-[1,1'-biphenyl]-2-yl)carbamate (58 mg, 14%) | (R)-pyrrolidin-3-ylmethyl (3',5,5'-trifluoro-[1,1'-biphenyl]-2-yl)carbamate (400 mg, 1.14 mmol) (Example 84) |
| 96 | (S)-(1-methylpyrrolidin-3-yl)methyl (3',5,5'-trifluoro-[1,1'-biphenyl]-2-yl)carbamate (144 mg, 35%) | (S)-pyrrolidin-3-ylmethyl (3',5,5'-trifluoro-[1,1'-biphenyl]-2-yl)carbamate (400 mg, 1.14 mmol) (Example 85) |
| 97 | (R)-(1-methylpyrrolidin-3-yl)methyl (5-methyl-[1,1'-biphenyl]-2-yl)-carbamate (24 mg, 16%) | (R)-pyrrolidin-3-ylmethyl (5-methyl-[1,1'-biphenyl]-2-yl)carbamate (145 mg, 0.47 mmol) (Example 86) |
| 98 | (R)-(1-methylpyrrolidin-3-yl)methyl (3'-fluoro-5-methyl-[1,1'-biphenyl]-2-yl)carbamate (15 mg, 5%) | (R)-pyrrolidin-3-ylmethyl (3'-fluoro-5-methyl-[1,1'-biphenyl]-2-yl)-carbamate (320 mg, 0.97 mmol) (Example 87) |
| 99 | (S)-(1-methylpyrrolidin-2-yl)methyl (4'-fluoro-[1,1'-biphenyl]-2-yl)-carbamate (87 mg, 10%) | (S)-pyrrolidin-2-ylmethyl (4'-fluoro-[1,1'-biphenyl]-2-yl)carbamate (850 mg, 2.70 mmol) (Example 88) |

[Example 100] Synthesis of (R)-(1-methylpyrrolidin-3-yl)methyl(3'-methyl-[1,1'-biphenyl]-2-yl)carbamate

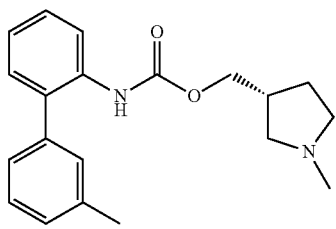 [SMILES: Cc1cccc(-c2ccccc2NC(=O)OC[C@@H]2CCN(C)C2)c1]

[Step 1] Synthesis of (R)-pyrrolidin-3-ylmethyl(3'-methyl-[1,1'-biphenyl]-2-yl)carbamate

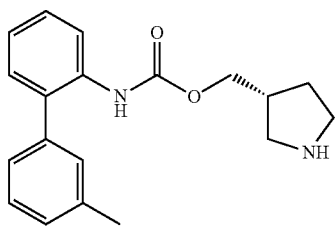 [SMILES: Cc1cccc(-c2ccccc2NC(=O)OC[C@@H]2CCNC2)c1]

3'-Methyl-[1,1'-biphenyl]-2-carboxylic acid (Synthesis Example 14) and (R)-tert-butyl 3-(hydroxymethyl)pyrrolidine-1-carboxylate were used as starting materials to prepare the titled compound in the same manner as Example 78.

$^1$H NMR(CDCl$_3$): δ 8.13-7.97 (bs, 1H), 7.41-7.28 (m, 2H), 7.26-7.02 (m, 5H), 6.77-6.62 (bs, 1H), 4.13-3.92 (m, 2H), 3.09-2.82 (m, 3H), 2.72-2.49 (m, 2H), 2.47-2.30 (m, 4H), 1.97-1.81 (m, 1H), 1.50-1.36 (m, 1H)

[Step 2] Synthesis of (R)-(1-methylpyrrolidin-3-yl)methyl-(3'-methyl-[1,1'-biphenyl]-2-yl)carbamate

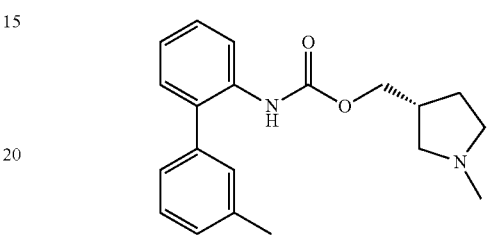

(R)-pyrrolidin-3-ylmethyl(3'-methyl-[1,1'-biphenyl]-2-yl)carbamate (600 mg, 1.93 mmol) prepared in Step 1 was used to prepare the titled compound (30 mg, 5%) in the same manner as Example 89.

[Example 101] Synthesis of (S)-(1-methylpyrrolidin-3-yl)-methyl(3'-methyl-[1,1'-biphenyl]-2-yl)carbamate

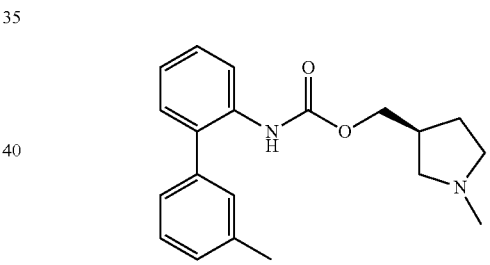

[Step 1] Synthesis of (S)-pyrrolidin-3-ylmethyl(3'-methyl-[1,1'-biphenyl]-2-yl)carbamate

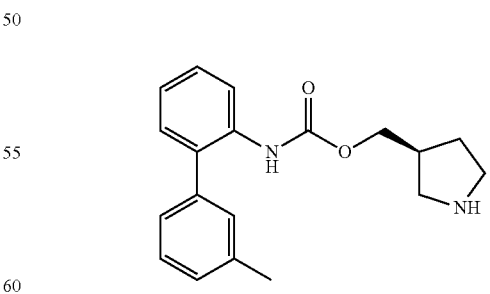

3'-Methyl-[1,1'-biphenyl]-2-carboxylic acid (Synthesis Example 14) and (S)-tert-butyl 3-(hydroxymethyl)pyrrolidine-1-carboxylate were used as starting materials to prepare the titled compound in the same manner as Example 78.

$^1$H NMR(CDCl$_3$): δ 8.15-7.99 (bs, 1H), 7.45-7.29 (m, 2H), 7.27-7.06 (m, 5H), 6.74-6.59 (bs, 1H), 4.15-3.92 (m,

2H), 3.07-2.79 (m, 4H), 2.69-2.57 (m, 1H), 2.39 (s, 3H), 2.07-1.92 (bs, 1H) 1.92-1.79 (m, 1H), 1.48-1.33 (m, 1H)

[Step 2] Synthesis of (S)-(1-methylpyrrolidin-3-yl) methyl (3'-methyl-[1,1'-biphenyl]-2-yl)carbamate

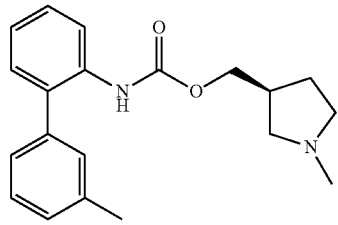 [SMILES: Cc1cccc(-c2ccccc2NC(=O)OC[C@H]2CCN(C)C2)c1]

(S)-pyrrolidin-3-ylmethyl (3'-methyl-[1,1'-biphenyl]-2-yl)carbamate (900 mg, 2.90 mmol) prepared in Step 1 was used to prepare the titled compound (208 mg, 22%) in the same manner as Example 89.

[Example 102] Synthesis of (R)-(1-ethylpyrrolidin-3-yl)methyl [1,1'-biphenyl]-2-ylcarbamate

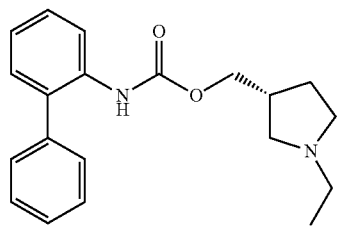 [SMILES: CCN1CC[C@@H](COC(=O)Nc2ccccc2-c2ccccc2)C1]

(R)-pyrrolidin-3-ylmethyl [1,1'-biphenyl]-2-ylcarbamate (1 g, 3.37 mmol) (Example 78) was dissolved in dimethylformamide (20 mL). Potassium carbamate (652 mg, 4.72 mmol), potassium iodide (112 mg, 0.67 mmol), triethylamine (1.42 mL, 10.11 mmol) and iodoethane (323 μL, 4.04 mmol) were sequentially added thereto and stirred at 120° C. for 12 hours. The reactant was cooled to room temperature and extracted with water and ethyl acetate. The organic layer was dried with anhydrous magnesium sulfate, filtered and concentrated. The resulting residue was purified with column chromatography to prepare the titled compound (142 mg, 13%).

Examples 103-105

Starting materials in Table 18 were used instead of (R)-pyrrolidin-3-ylmethyl [1,1'-biphenyl]-2-ylcarbamate to prepare compounds of Examples 103-105 in the same manner as Example 102.

TABLE 18

Examples 103-105

| Example | Chemical Name | Starting Material |
|---|---|---|
| 103 | (S)-(1-ethylpyrrolidin-3-yl)methyl [1,1'-biphenyl]-2-ylcarbamate (89 mg, 8%) | (S)-pyrrolidin-3-ylmethyl [1,1'-biphenyl]-2-yl-carbamate (1 g, 3.37 mmol) (Example 79) |
| 104 | (R)-(1-ethylpyrrolidin-3-yl)methyl (3'-methyl-[1,1'-biphenyl]-2-yl)-carbamate (109 mg, 16%) | (R)-pyrrolidin-3-ylmethyl (3'-methyl-[1,1'-biphenyl]-2-yl)carbamate (623 mg, 2.01 mmol) (Example 100, Step 1) |
| 105 | (S)-(1-ethylpyrrolidin-3-yl)methyl (3'-methyl-[1,1'-biphenyl]-2-yl)-carbamate (40 mg, 6%) | (S)-pyrrolidin-3-ylmethyl (3'-methyl-[1,1'-biphenyl]-2-yl)carbamate (600 mg, 1.93 mmol) (Example 101, Step 1) |

[Example 106] Synthesis of (S)-(1-ethylpyrrolidin-2-yl)methyl [1,1'-biphenyl]-2-ylcarbamate

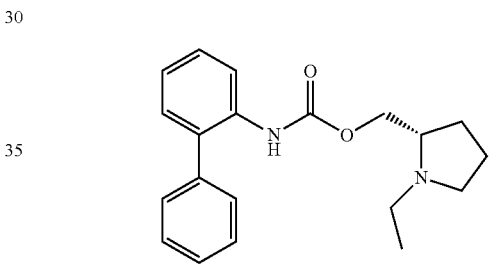

(S)-pyrrolidin-2-ylmethyl [1,1'-biphenyl]-2-ylcarbamate (1 g, 3.37 mmol) and 2-iodoethane (323 μL, 4.04 mmol) were used as starting materials to prepare titled compound (385 mg, 35%) in the same manner as Example 102.

[Example 107] Synthesis of (S)-(1-isobutylpyrrolidin-2-yl)-methyl [1,1'-biphenyl]-2-ylcarbamate

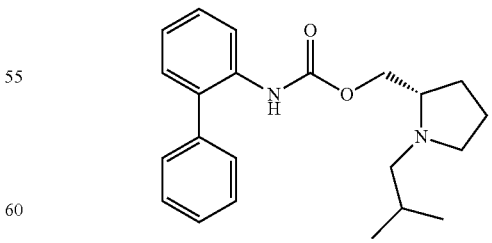

(S)-pyrrolidin-2-ylmethyl [1,1'-biphenyl]-2-ylcarbamate (940 mg, 3.17 mmol) and 1-iodo-2-methylpropane (438 μL, 3.08 mmol) were used as starting materials to prepare titled compound (47 mg, 4%) in the same manner as Example 102.

[Example 108] Synthesis of (S)-(1-methylpyrrolidin-3-yl)-methyl(3',5-difluoro-[1,1'-biphenyl]-2-yl)carbamate

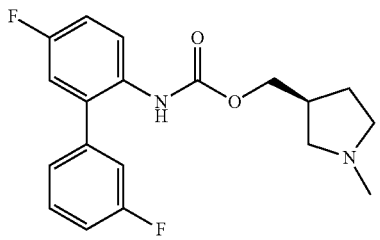

3',5-Difluoro-[1,1'-biphenyl]-2-carboxylic acid (800 mg, 3.42 mmol) (Synthesis Example 17) and (S)-tert-butyl 3-(hydroxymethyl)pyrrolidine-1-carboxylate (825 mg, 4.10 mmol) were used as starting materials to prepare titled compound (50 mg, 5%) in the same manner as Example 78 and Example 89.

[Example 109] Synthesis of (R)-(1-methylpyrrolidin-2-yl)-methyl [1,1'-biphenyl]-2-ylcarbamate

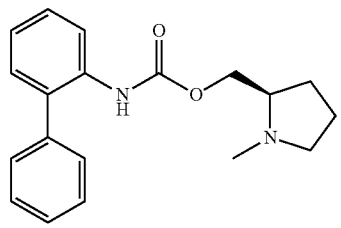 [SMILES: CN1CCC[C@@H]1COC(=O)Nc1ccccc1-c1ccccc1]

[Step 1] Synthesis of (R)-pyrrolidin-2-ylmethyl [1,1'-biphenyl]-2-ylcarbamate

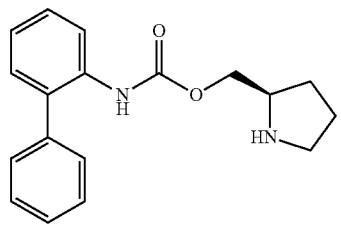 [SMILES: O=C(Nc1ccccc1-c1ccccc1)OC[C@H]1CCCN1]

[1,1'-Biphenyl]-2-carboxylic acid (821 mg, 4.14 mmol) and (R)-tert-butyl-2-(hydroxymethyl)pyrrolidine-1-carboxylate (1 g, 4.97 mmol) were used as starting materials to prepare titled compound (730 mg, 60%) in the same manner as Example 78.

$^1$H NMR (CDCl$_3$): δ 8.09-8.08 (m, 1H), 7.49-7.47 (m, 1H), 7.29-7.26 (m, 1H), 7.17 (m, 1H), 6.92-6.89 (m, 1H), 4.15-4.04 (m, 2H), 3.12-3.08 (m, 1H), 2.99-2.94 (m, 2H), 2.74-2.72 (m, 1H), 2.51-2.44 (m, 1H), 1.98-1.89 (m, 1H), 1.51-1.44 (m, 1H)

[Step 2] Synthesis of (R)-(1-methylpyrrolidin-2-yl) methyl [1,1'-biphenyl]-2-ylcarbamate

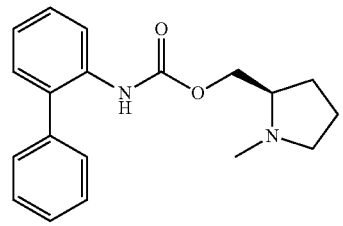 [SMILES: CN1CCC[C@@H]1COC(=O)Nc1ccccc1-c1ccccc1]

(R)-pyrrolidin-2-ylmethyl [1,1'-biphenyl]-2-ylcarbamate (730 mg, 2.46 mmol) was used as a starting material to prepare titled compound (183 mg, 24%) in the same manner as Example 89.

[Example 110] Synthesis of (R)-(1-methylpyrrolidin-2-yl)-methyl (3'-methyl-[1,1'-biphenyl]-2-yl)carbamate

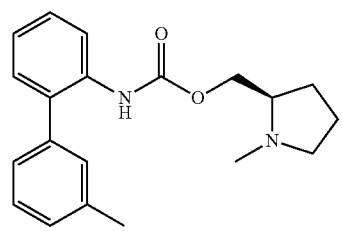 [SMILES: Cc1cccc(-c2ccccc2NC(=O)OC[C@H]2CCCN2C)c1]

3'-Methyl-[1,1'-biphenyl]-2-carboxylic acid (700 mg, 3.3 mmol) (Synthesis Example 14) and (R)-tert-butyl 2-(hydroxymethyl)pyrrolidine-1-carboxylate (797 mg, 3.96 mmol) were used as starting materials to prepare titled compound (258 mg, 24%) in the same manner as Example 78 and Example 89.

[Example 111] Synthesis of (R)-(1-methylpyrrolidin-2-yl)-methyl (5-fluoro-3'-methyl-[1,1'-biphenyl]-2-yl)carbamate

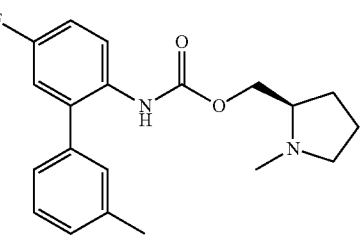

5-Fluoro-3'-methyl-[1,1'-biphenyl]-2-carboxylic acid (1 g, 4.34 mmol) (Synthesis Example 21) and (R)-tert-butyl 2-(hydroxymethyl)pyrrolidine-1-carboxylate (1.05 g, 5.21 mmol) were used as starting materials to prepare titled compound (52 mg, 4%) in the same manner as Example 78 and Example 89.

[Example 112] Synthesis of (S)-(1-isopropylpyrrolidin-2-yl)-methyl [1,1'-biphenyl]-2-ylcarbamate

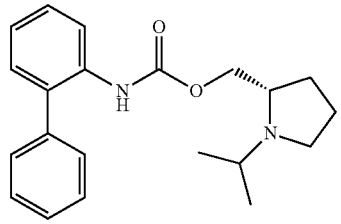 [SMILES: CC(C)N1CCC[C@H]1COC(=O)Nc1ccccc1-c1ccccc1]

[Step 1] Synthesis of (S)-pyrrolidin-2-ylmethyl [1,1'-biphenyl]-2-ylcarbamate

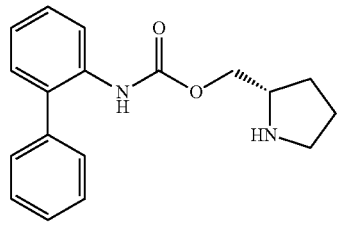

[1,1'-Biphenyl]-2-carboxylic acid (2.5 g, 12.61 mmol) and (S)-tert-butyl-2-(hydroxymethyl)pyrrolidine-1-carboxylate (3.05 g, 15.14 mmol) were used as starting materials to prepare titled compound (3.06 g, 82%) in the same manner as Example 78.

$^1$H NMR (CDCl$_3$) δ 7.88 (m, 1H), 7.48-7.42 (m, 1H), 7.15-7.05 (m, 4H), 7.04-6.92 (m, 1H), 6.40 (s, 1H), 4.78-4.76 (m, 1H), 3.23-3.21 (m, 1H), 2.87-2.73 (m, 4H), 2.06-2.05 (m, 3H), 2.04-1.67 (m, 1H), 1.66-1.54 (m, 1H), 1.53-1.35 (m, 1H)

[Step 2] Synthesis of (S)-(1-isopropylpyrrolidin-2-yl)methyl [1,1'-biphenyl]-2-ylcarbamate

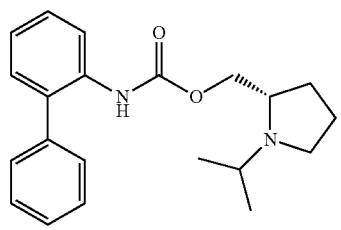 [SMILES: CC(C)N1CCC[C@H]1COC(=O)Nc1ccccc1-c1ccccc1]

(S)-pyrrolidin-2-ylmethyl [1,1'-biphenyl]-2-ylcarbamate (1 g, 3.37 mmol) and 2-iodopropyl (404 μL, 4.04 mmol) were used as starting materials to prepare titled compound (78 mg, 7%) in the same manner as Example 102.

[Example 113] Synthesis of (R)-(1-methylpyrrolidin-3-yl)-methyl (3'-fluoro-[1,1'-biphenyl]-2-yl)carbamate

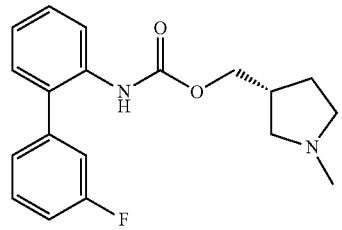

(R)-(1-methylpyrrolidin-3-yl)methyl(2-bromophenyl)-carbamate (230 mg, 0.73 mmol) (Synthesis Example F) was dissolved in a mixed solution of ethanol (5 mL) and water (5 mL). 3-Fluorophenylboronic acid (123 mg, 0.88 mmol), potassium carbonate (203 mg, 1.47 mmol), di(acetato)dicyclo-hexylphenylphosphine palladium(II) and Polymer-bound FibreCat™ (30 mg) were added thereto. The reactant was stirred at 110° C. for 12 hours and then cooled to room temperature. The same was filtered through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (60 mg, 25%).

Examples 114-115

Reacting materials in Table 19 was used instead of 3-fluorophenylboronic acid to prepare compounds of Examples 114-115.

TABLE 19

| Example 114-115 | | | |
|---|---|---|---|
| Example | Chemical Name | Starting Material (Synthesis Example F) | Reacting Material |
| 114 | (R)-(1-methyl-pyrrolidin-3-yl)-methyl(4'-fluoro-[1,1'-biphenyl]-2-yl)carbamate (58 mg, 24%) | 230 mg, 0.73 mmol | 4-Fluorophenyl-boronic acid (123 mg, 0.88 mmol) |
| 115 | (R)-(1-methyl-pyrrolidin-3-yl)-methyl(3',4'-difluoro-[1,1'-biphenyl]-2-yl)-carbamate (132 mg, 55%) | 220 mg, 0.70 mmol | 3,4-Difluoro-phenylboronic acid (222 mg, 1.40 mmol) |

[Examples 116] Synthesis of (S)-(1-methylpyrrolidin-3-yl)-methyl (3'-fluoro-[1,1'-biphenyl]-2-yl)carbamate

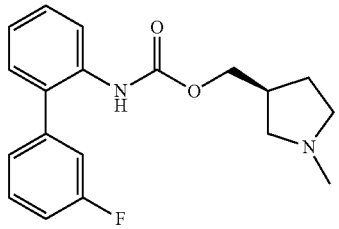 [SMILES: CN1CC[C@H](COC(=O)Nc2ccccc2-c2cccc(F)c2)C1]

(S)-(1-methylpyrrolidin-3-yl)methyl(2-bromophenyl)-carbamate (200 mg, 0.64 mmol) (Synthesis Example G) was dissolved in toluene (10 mL). 3-Fluorophenylboronic acid (179 mg, 1.28 mmol), potassium carbonate (177 mg, 1.28 mmol) and tetrakis triphenylphosphine palladium (74 mg, 0.064 mmol) were added thereto. The reactant was stirred at 110° C. for 12 hours and cooled to room temperature. The same was filtered through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (102 mg, 49%).

Examples 117-129

Starting materials and reacting materials in Table 20 were used to prepare compounds of Examples 117-129 in the same manner as Example 116.

TABLE 20

| | Examples 117-129 | | |
|---|---|---|---|
| Example | Chemical Name | Starting Material | Reacting Material |
| 117 | (R)-(1-methyl-pyrrolidin-3-yl)methyl(3'-chloro-[1,1'-biphenyl]-2-yl)-carbamate (160 mg, 63%) | (R)-(1-methyl-pyrrolidin-3-yl)-methyl(2-bromo-phenyl)carbamate (230 mg, 0.73 mmol) (Synthesis Example F) | 3-Chlorophenyl-boronic acid (138 mg, 0.88 mmol) |
| 118 | (S)-(1-methyl-pyrrolidin-3-yl)methyl(3'-chloro-[1,1'-biphenyl]-2-yl)-carbamate (130 mg, 39%) | (S)-(1-methyl-pyrrolidin-3-yl)-methyl(2-bromo-phenyl)carbamate (305 mg, 0.97 mmol) (Synthesis Example G) | 3-Chlorophenyl-boronic acid (305 mg, 1.95 mmol) |
| 119 | (S)-(1-methyl-pyrrolidin-3-yl)methyl(3',5'-dichloro-[1,1'-biphenyl]-2-yl)-carbamate (170 mg, 51%) | (S)-(1-methyl-pyrrolidin-3-yl)-methyl(2-bromo-phenyl)carbamate (274 mg, 0.88 mmol) (Synthesis Example G) | 3,5-Dichloro-phenylboronic acid (334 mg, 1.75 mmol) |
| 120 | (S)-(1-methyl-pyrrolidin-3-yl)methyl(3'-chloro-5'-fluoro-[1,1'-biphenyl]-2-yl)-carbamate (66 mg, 18%) | (S)-(1-methyl-pyrrolidin-3-yl)-methyl(2-bromo-phenyl)carbamate (312 mg, 1.00 mmol) (Synthesis Example G) | 3-Chloro-5-fluorophenyl-boronic acid (348 mg, 1.99 mmol) |
| 121 | (S)-(1-methyl-pyrrolidin-3-yl)methyl(3'-chloro-4'-fluoro-[1,1'-biphenyl]-2-yl)-carbamate (107 mg, 47%) | (S)-(1-methyl-pyrrolidin-3-yl)-methyl(2-bromo-phenyl)carbamate (200 mg, 0.63 mmol) (Synthesis Example G) | (3-Chloro-4-fluoro)phenyl-boronic acid (223 mg, 1.28 mmol) |
| 122 | (S)-(1-methyl-pyrrolidin-3-yl)methyl(5-fluoro-3',5'-dimethyl-[1,1'-biphenyl]-2-yl)-carbamate (160 mg, 73%) | (S)-(1-methyl-pyrrolidin-3-yl)-methyl(2-bromo-4-fluorophenyl)-carbamate (190 mg, 0.57 mmol) (Synthesis Example I) | 3,5-Dimethyl-phenylboronic acid (172 mg, 1.15 mmol) |
| 123 | (S)-(1-methyl-pyrrolidin-3-yl)methyl(3'-chloro-5-fluoro-5'-hydroxy-[1,1'-biphenyl]-2-yl)carbamate (150 mg, 64%) | (S)-(1-methyl-pyrrolidin-3-yl)-methyl(2-bromo-4-fluorophenyl)-carbamate (205 mg, 0.62 mmol) (Synthesis Example I) | (3-Chloro-5-hydroxyphenyl)-boronic acid (213 mg, 1.24 mmol) |

TABLE 20-continued

Examples 117-129

| Example | Chemical Name | Starting Material | Reacting Material |
|---|---|---|---|
| 124 | (S)-(1-methyl-pyrrolidin-3-yl)methyl(4',5-difluoro-[1,1'-biphenyl]-2-yl)carbamate (78 mg, 33%) | (S)-(1-methyl-pyrrolidin-3-yl)-methyl(2-bromo-4-fluorophenyl)-carbamate (225 mg, 0.68 mmol) (Synthesis Example I) | 4-Fluorophenyl-boronic acid (114 mg, 0.82 mmol) |
| 125 | (S)-(1-methyl-pyrrolidin-3-yl)methyl(3'-chloro-5-fluoro-[1,1'-biphenyl]-2-yl)carbamate (153 mg, 64%) | (S)-(1-methyl-pyrrolidin-3-yl)-methyl(2-bromo-4-fluorophenyl)-carbamate (220 mg, 0.66 mmol) (Synthesis Example I) | 3-Chlorophenyl-boronic acid (125 mg, 0.80 mmol) |
| 126 | (S)-(1-methyl-pyrrolidin-3-yl)methyl(3',5'-dichloro-5-fluoro-[1,1'-biphenyl]-2-yl)-carbamate (74 mg, 22%) | (S)-(1-methyl-pyrrolidin-3-yl)-methyl(2-bromo-4-fluorophenyl)-carbamate (280 mg, 0.85 mmol) (Synthesis Example I) | 3,5-Dichloro-phenylboronic acid (460 mg, 1.69 mmol) |
| 127 | (S)-(1-methyl-pyrrolidin-3-yl)methyl(4'-chloro-5-fluoro-[1,1'-biphenyl]-2-yl)carbamate (37 mg, 17%) | (S)-(1-methyl-pyrrolidin-3-yl)-methyl(2-bromo-4-fluorophenyl)carbamate (195 mg, 0.59 mmol) (Synthesis Example I) | 4-Chlorophenyl-boronic acid (111 mg, 0.71 mmol) |
| 128 | (S)-(1-methyl-pyrrolidin-3-yl)methyl(3',4'-dichloro-5-fluoro-[1,1'-biphenyl]-2-yl)-carbamate (50 mg, 19%) | (S)-(1-methyl-pyrrolidin-3-yl)-methyl(2-bromo-4-fluorophenyl)carbamate (220 mg, 0.66 mmol) (Synthesis Example I) | 3,4-Dichloro-phenylboronic acid (152 mg, 0.80 mmol) |
| 129 | (S)-(1-methyl-pyrrolidin-3-yl)methyl(3'-chloro-5,5'-difluoro-[1,1'-biphenyl]-2-yl)-carbamate (130 mg, 54%) | (S)-(1-methyl-pyrrolidin-3-yl)-methyl (2-bromo-4-fluorophenyl)-carbamate (210 mg, 0.63 mmol) (Synthesis Example I) | (3-Chloro-5-fluorophenyl)-boronic acid (221 mg, 1.27 mmol) |

[Example 130] Synthesis of (R)-(1-methylpyrrolidin-3-yl)-methyl (3',4'-dichloro-[1,1'-biphenyl]-2-yl) carbamate

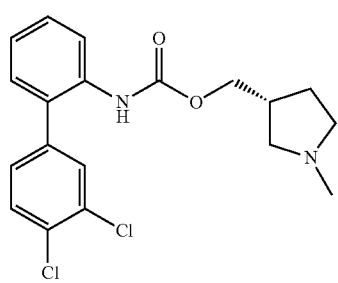

(R)-(1-methylpyrrolidin-3-yl)methyl(2-bromophenyl)-carbamate (225 mg, 0.72 mmol) (Synthesis Example F) was dissolved in a mixed solution of ethanol (5 mL) and water (5 mL). 3,4-Dichlorophenylboronic acid (274 mg, 1.44 mmol), potassium carbonate (199 mg, 1.44 mmol) and tetrakis triphenylphosphine palladium (83 mg, 0.072 mmol) were added thereto. The reactant was stirred at 110° C. for 6 hours and cooled to room temperature. The same was filtered through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (151 mg, 56%).

Examples 131-135

Starting materials and reacting materials in Table 21 were used to prepare compounds of Examples 131-135 in the same manner as Example 130.

TABLE 21

Examples 131-135

| Example | Chemical Name | Starting Material | Reacting Material |
|---|---|---|---|
| 131 | (R)-(1-methyl-pyrrolidin-3-yl)-methyl(3',5'-dichloro-[1,1'-biphenyl]-2-yl)-carbamate (101 mg, 40%) | (R)-(1-methyl-pyrrolidin-3-yl)-methyl(2-bromo-phenyl)carbamate (206 mg, 0.66 mmol) (Synthesis Example F) | 3,5-Dichloro-phenylboronic acid (251 mg, 1.32 mmol) |
| 132 | (R)-(1-methyl-pyrrolidin-3-yl)methyl(3'-chloro-5'-fluoro-[1,1'-biphenyl]-2-yl)carbamate | (R)-(1-methyl-pyrrolidin-3-yl)-methyl(2-bromo-phenyl)carbamate (206 mg, 0.66 mmol) (Synthesis Example F) | 3-Chloro-5-fluorophenyl-boronic acid (251 mg, 1.32 mmol) |
| 133 | (R)-(1-methyl-pyrrolidin-3-yl)-methyl(5-fluoro-3'-amino-[1,1'-biphenyl]-2-yl)-carbamate (63 mg, 28%) | (R)-(1-methyl-pyrrolidin-3-yl)-methyl(2-bromo-4-fluorophenyl)-carbamate (215 mg, 0.65 mmol) (Synthesis Example H) | 3-Aminophenyl-boronic acid (178 mg, 1.30 mmol) |
| 134 | (R)-(1-methyl-pyrrolidin-3-yl)-methyl(3'-chloro-5-fluoro-5'-hydroxy-[1,1'-biphenyl]-2-yl)-carbamate (143 mg, 53%) | (R)-(1-methyl-pyrrolidin-3-yl)-methyl(2-bromo-4-fluorophenyl)-carbamate (236 mg, 0.71 mmol) (Synthesis Example H) | (3-Chloro-5-hydroxyphenyl)-boronic acid (246 mg, 1.43 mmol) |
| 135 | (R)-(1-methyl-pyrrolidin-3-yl)-methyl(3',5'-dichloro-5-fluoro-[1,1'-biphenyl]-2-yl)-carbamate (65 mg, 25%) | (R)-(1-methyl-pyrrolidin-3-yl)-methyl(2-bromo-4-fluorophenyl)-carbamate (220 mg, 0.66 mmol) (Synthesis Example H) | 3,5-Dichloro-phenylboronic acid (254 mg, 1.33 mmol) |

[Example 136] Synthesis of (R)-(1-methylpyrrolidin-3-yl)-methyl (3'-chloro-4'-fluoro-[1,1'-biphenyl]-2-yl)carbamate

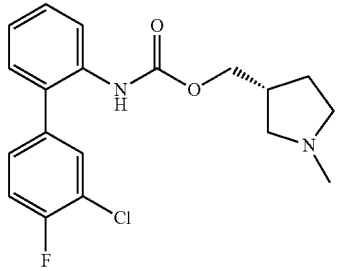

(R)-(1-methylpyrrolidin-3-yl)methyl(2-bromophenyl)-carbamate (250 mg, 0.80 mmol) (Synthesis Example F) was dissolved in a mixed solution of acetonitrile (6 mL) and water (6 mL). (3-Chloro-4-fluorophenyl)boronic acid (279 mg, 1.60 mmol), sodium carbonate (170 mg, 1.60 mmol) and dichlorobistriphenylphosphine palladium (28 mg, 0.04 mmol) were added thereto. The reactant was stirred in a microwave oven at 110° C. for 30 minutes and cooled to room temperature. The same was filtered through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (23 mg, 70%).

Examples 137-149

Starting materials and reacting materials in Table 22 were used to prepare compounds of Examples 137-149 in the same manner as Example 136.

TABLE 22

Examples 137-149

| Example | Chemical Name | Starting Material | Reacting Material |
|---|---|---|---|
| 137 | (R)-(1-methyl-pyrrolidin-3-yl)methyl(3'-hydroxy-[1,1'-biphenyl]-2-yl)carbamate (156 mg, 65%) | (R)-(1-methyl-pyrrolidin-3-yl)-methyl(2-bromo-phenyl)carbamate (230 mg, 0.73 mmol) (Synthesis Example F) | 3-Hydroxyphenyl-boronic acid (111 mg, 0.81 mmol) |
| 138 | (R)-(1-methyl-pyrrolidin-3-yl)methyl(3'-chloro-5'-(trifluoro-methyl)-[1,1'-biphenyl]-2-yl)carbamate (208 mg, 43%) | (R)-(1-methyl-pyrrolidin-3-yl)-methyl(2-bromo-phenyl)carbamate (365 mg, 0.17 mmol) (Synthesis Example F) | (3-Chloro-5-(trifluoromethyl)-phenyl)boronic acid (523 mg, 2.33 mmol) |
| 139 | (R)-(1-methyl-pyrrolidin-3-yl)methyl(3'-chloro-5-fluoro-5'-methoxy-[1,1'-biphenyl]-2-yl)carbamate (184 mg, 73%) | (R)-(1-methyl-pyrrolidin-3-yl)-methyl(2-bromo-4-fluorophenyl)-carbamate (213 mg, 0.64 mmol) (Synthesis Example H) | (3-Chloro-5-methoxyphenyl)-boronic acid (240 mg, 1.29 mmol) |
| 140 | (R)-(1-methyl-pyrrolidin-3-yl)methyl(3'-chloro-5-fluoro-5'-(trifluoro-methyl)-[1,1'-biphenyl]-2-yl)carbamate (135 mg, 47%) | (R)-(1-methyl-pyrrolidin-3-yl)-methyl(2-bromo-4-fluorophenyl)-carbamate (227 mg, 0.69 mmol) (Synthesis Example H) | (3-Chloro-5-(trifluoromethyl)-phenyl)boronic acid (307 mg, 1.37 mmol) |
| 141 | (R)-(1-methyl-pyrrolidin-3-yl)methyl(4',5-difluoro-[1,1'-biphenyl]-2-yl)carbamate (208 mg, 62%) | (R)-(1-methyl-pyrrolidin-3-yl)-methyl(2-bromo-4-fluorophenyl)-carbamate (320 mg, 0.97 mmol) (Synthesis Example H) | 4-Fluorophenyl-boronic acid (270 mg, 1.93 mmol) |
| 142 | (R)-(1-methyl-pyrrolidin-3-yl)methyl(3'-chloro-5,5'-difluoro-[1,1'-biphenyl]-2-yl)carbamate (108 mg, 42%) | (R)-(1-methyl-pyrrolidin-3-yl)methyl(2-bromo-4-fluoro-phenyl)carbamate (226 mg, 0.68 mmol) (Synthesis Example H) | (3-Chloro-5-fluorophenyl)-boronic acid (238 mg, 1.37 mmol) |

TABLE 22-continued

Examples 137-149

| Example | Chemical Name | Starting Material | Reacting Material |
|---|---|---|---|
| 143 | (R)-(1-methyl-pyrrolidin-3-yl)methyl(3'-chloro-4',5-difluoro-[1,1'-biphenyl]-2-yl)carbamate (150 mg, 54%) | (R)-(1-methyl-pyrrolidin-3-yl)-methyl(2-bromo-4-fluorophenyl)-carbamate (240 mg, 0.73 mmol) (Synthesis Example H) | (3-Chloro-4-fluorophenyl)-boronic acid (253 mg, 1.45 mmol) |
| 144 | (R)-(1-methyl-pyrrolidin-3-yl)methyl(2',5-difluoro-[1,1'-biphenyl]-2-yl)carbamate (134 mg, 43%) | (R)-(1-methyl-pyrrolidin-3-yl)-methyl(2-bromo-4-fluorophenyl)-carbamate (300 mg, 0.91 mmol) (Synthesis Example H) | 2-Fluorophenyl boronic acid (254 mg, 1.812 mmol) |
| 145 | (R)-(1-methyl-pyrrolidin-3-yl)methyl(3',5-dichloro-[1,1'-biphenyl]-2-yl)carbamate (69 mg, 22%) | (R)-(1-methyl-pyrrolidin-3-yl)-methyl(2-bromo-4-chlorophenyl)-carbamate (290 mg, 0.84 mmol) (Synthesis Example J) | 3-Chlorophenyl-boronic acid (197 mg, 1.26 mmol) |
| 146 | (R)-(1-methyl-pyrrolidin-3-yl)methyl(3',5-dichloro-4'-fluoro-[1,1'-biphenyl]-2-yl)carbamate | (R)-(1-methyl-pyrrolidin-3-yl)-methyl(2-bromo-4-chlorophenyl)-carbamate (300 mg, 0.84 mmol) (Synthesis Example J) | (3-Chloro-4-fluorophenyl)-boronic acid (300 mg, 1.72 mmol) |
| 147 | (R)-(1-methyl-pyrrolidin-3-yl)methyl(3'-chloro-4'-fluoro-5-methoxy-[1,1'-biphenyl]-2-yl)carbamate | (R)-(1-methyl-pyrrolidin-3-yl)-methyl(2-bromo-4-methoxyphenyl)-carbamate (270 mg, 0.78 mmol) (Synthesis Example K) | (3-Chloro-4-fluorophenyl)-boronic acid (274 mg, 1.57 mmol) |
| 148 | (S)-(1-methyl-pyrrolidin-2-yl)methyl(3'-chloro-5'-fluoro-[1,1'-biphenyl]-2-yl)carbamate (150 mg, 65%) | (S)-(1-methyl-pyrrolidin-2-yl)-methyl(2-bromo-phenyl)carbamate (200 mg, 0.64 mmol) (Synthesis Example M) | (3-Chloro-5-fluorophenyl)-boronic acid (223 mg, 1.28) |
| 149 | (S)-(1-methyl-pyrrolidin-2-yl)methyl(3'-chloro-4'-fluoro-[1,1'-biphenyl]-2-yl)carbamate (151 mg, 26%) | (S)-(1-methyl-pyrrolidin-2-yl)-methyl(2-bromo-phenyl)carbamate (500 mg, 1.59 mmol) (Synthesis Example M) | (3-Chloro-4-fluorophenyl)-boronic acid (555 mg, 3.18 mmol) |

[Example 150] Synthesis of (R)-(1-ethylpyrrolidin-3-yl)methyl (3'-chloro-4'-fluoro-[1,1'-biphenyl]-2-yl)carbamate

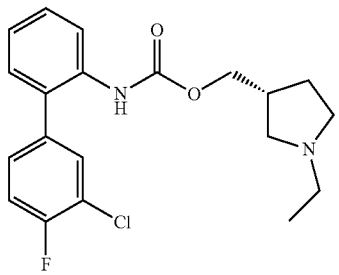 [SMILES: CCN1CC[C@@H](COC(=O)Nc2ccccc2-c2ccc(F)c(Cl)c2)C1]

[Step 1] Synthesis of (R)-tert-butyl 3-((((3'-chloro-4'-fluoro-[1,1'-biphenyl]-2-yl)carbamoyl)oxy)methyl)pyrrolidine-1-carboxylate

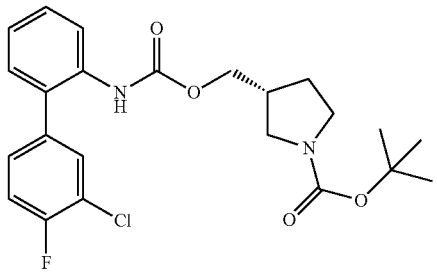 [SMILES: CC(C)(C)OC(=O)N1CC[C@@H](COC(=O)Nc2ccccc2-c2ccc(F)c(Cl)c2)C1]

(R)-tert-butyl-3-((((2-bromophenyl)carbamoyl)oxy)methyl)pyrrolidine-1-carboxylate (4 g, 10.02 mmol) (Synthesis Example F, Step 1) and (3-chloro-4-fluoro)phenylboronic acid (3.5 g, 20.04 mmol) were used as starting materials to prepare titled compound (3.4 g, 76%) in the same manner as Example 42.

$^1$H NMR (CDCl$_3$): δ 8.01 (s, 1H), 7.41-7.35 (m, 2H), 7.31-7.22 (m, 2H), 7.20-7.13 (m, 2H), 6.34 (s, 1H), 4.15-4.07 (m, 2H), 3.48-3.29 (m, 3H), 3.15-2.99 (s, 1H), 2.51-2.48 (m, 1H), 1.98-1.94 (m, 1H), 1.44-1.38 (m, 10H)

[Step 2] Synthesis of (R)-pyrrolidin-3-ylmethyl (3'-chloro-4'-fluoro-[1,1'-biphenyl]-2-yl)carbamate

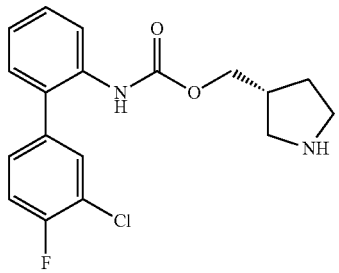 [SMILES: O=C(Nc1ccccc1-c1ccc(F)c(Cl)c1)OC[C@@H]1CCNC1]

(R)-tert-butyl-3-((((3'-chloro-4'-fluoro-[1,1'-biphenyl]-2-yl)carbamoyl)oxy)methyl)pyrrolidine-1-carboxylate (3.4 g, 7.57 mmol) prepared in Step 1 was used as a starting material to prepare titled compound (2.3 g, 87%) in the same manner as Example 78.

$^1$H NMR (CDCl$_3$): δ 7.98 (s, 1H), 7.41-7.34 (m, 2H), 7.23-7.17 (m, 2H), 7.16-7.11 (m, 2H), 6.55 (s, 1H), 4.10-4.01 (m, 2H), 3.99-2.86 (m, 3H), 2.70-2.66 (s, 1H), 2.45-2.39 (m, 1H), 1.95-1.86 (m, 1H), 1.47-1.41 (m, 1H)

[Step 3] Synthesis of (R)-pyrrolidin-3-ylmethyl (3'-chloro-4'-fluoro-[1,1'-biphenyl]-2-yl)carbamate (R)-pyrrolidin-3-ylmethyl-(3'-chloro-4'-fluoro-[1,1'-biphenyl]-2-yl)carbamate (345 mg, 0.99 mmol) prepared in Step 2 was dissolved in tetrahydrofuran (20 mL). Triethylamine (150 μL, 1.09 mmol) and bromoethane (118 μL, 1.58 mmol) were sequentially added thereto and stirred at room temperature for 3 days. The reactant was concentrated under reduced pressure and extracted with water and dichloromethane. The organic layer was dried with anhydrous magnesium sulfate, filtered and concentrated. The resulting residue was purified with column chromatography to prepare the titled compound (74 mg, 20%).

[Example 151] Synthesis of (R)-(1-isopropyl pyrrolidin-3-yl)-methyl (3'-chloro-4'-fluoro-[1,1'-biphenyl]-2-yl)carbamate

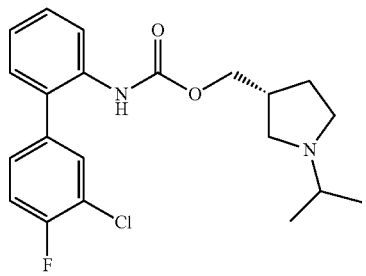 [SMILES: CC(C)N1CC[C@@H](COC(=O)Nc2ccccc2-c2ccc(F)c(Cl)c2)C1]

(R)-pyrrolidin-3-ylmethyl-(3'-chloro-4'-fluoro-[1,1'-biphenyl]-2-yl)carbamate (347 mg, 1.00 mmol) (Example 150, Step 2) was dissolved in tetrahydrofuran (20 mL). Triethylamine (150 μL, 1.10 mmol) and 2-bromopropane (100 μL, 1.10 mmol) were sequentially added thereto and stirred at room temperature for 3 days. The reactant was concentrated under reduced pressure and extracted with water and dichloromethane. The organic layer was dried with anhydrous magnesium sulfate, filtered and concentrated. The resulting residue was purified with column chromatography to prepare the titled compound (17 mg, 4%).

[Example 152] Synthesis of (R)-(1-methylpyrrolidin-3-yl)-methyl (3'-(hydroxymethyl)-[1,1'-biphenyl]-2-yl)carbamate

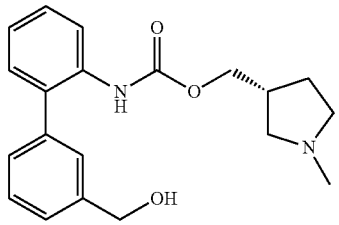 [SMILES: CN1CC[C@@H](COC(=O)Nc2ccccc2-c2cccc(CO)c2)C1]

(R)-(1-methylpyrrolidin-3-yl)methyl-(2-bromophenyl)-carbamate (395 mg, 1.26 mmol) (Synthesis Example F) was dissolved in a mixed solution of toluene (15 mL) and ethanol (2 mL). 3-(Hydroxymethyl)phenylboronic acid (211 mg, 1.39 mmol), potassium carbonate (348 mg, 2.52 mmol) and tetrakis triphenylphosphine palladium (146 mg, 0.13 mmol) were added thereto. The reactant was stirred at 110° C. for 12 hours and cooled to room temperature. The same was filtered through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (126 mg, 29%).

Examples 153-190

Starting materials and reacting materials in Table 23 were used to prepare compounds of Examples 153-190 in the same manner as Example 152.

TABLE 23

Examples 153-190

| Example | Chemical Name | Starting Material | Reacting Material |
|---|---|---|---|
| 153 | (R)-(1-methyl-pyrrolidin-3-yl)methyl(3'-carbamoyl-[1,1'-biphenyl]-2-yl)carbamate (125 mg, 28%) | (R)-(1-methyl-pyrrolidin-3-yl)-methyl(2-bromo-phenyl)carbamate (395 mg, 1.26 mmol) (Synthesis Example F) | (3-Carbamoyl-phenyl)boronic acid (229 mg, 1.39 mmol) |
| 154 | (R)-(1-methyl-pyrrolidin-3-yl)methyl(3'-amino-[1,1'-biphenyl]-2-yl)carbamate (102 mg, 45%) | (R)-(1-methyl-pyrrolidin-3-yl)-methyl(2-bromo-phenyl)carbamate (220 mg, 0.70 mmol) (Synthesis Example F) | 3-Aminophenyl-boronic acid (115 mg, 0.84 mmol) |
| 155 | (R)-(1-methyl-pyrrolidin-3-yl)methyl(3'-cyano-[1,1'-biphenyl]-2-yl)carbamate (77 mg, 34%) | (R)-(1-methyl-pyrrolidin-3-yl)-methyl(2-bromo-phenyl)carbamate (210 mg, 0.67 mmol) (Synthesis Example F) | 3-Cyanophenyl-boronic acid (118 mg, 0.80 mmol) |
| 156 | (R)-(1-methyl-pyrrolidin-3-yl)methyl(2'-fluoro-[1,1'-biphenyl]-2-yl)carbamate (210 mg, 67%) | (R)-(1-methyl-pyrrolidin-3-yl)-methyl(2-bromo-phenyl)carbamate (300 mg, 0.958 mmol) (Synthesis Example F) | 2-Fluorophenyl boronic acid (201 mg, 1.437 mmol) |
| 157 | (R)-(1-methyl-pyrrolidin-3-yl)methyl-(2',4'-difluoro-[1,1'-biphenyl]-2-yl)carbamate (115 mg, 52%) | (R)-(1-methyl-pyrrolidin-3-yl)-methyl(2-bromo-phenyl)carbamate (200 mg, 0.639 mmol) (Synthesis Example F) | 2,4-Difluoro-phenyl boronic acid (202 mg, 1.277 mmol) |
| 158 | (R)-(1-methyl-pyrrolidin-3-yl)methyl(2',3'-difluoro-[1,1'-biphenyl]-2-yl)carbamate (145 mg, 66%) | (R)-(1-methyl-pyrrolidin-3-yl)-methyl(2-bromo-phenyl)carbamate (200 mg, 0.639 mmol) (Synthesis Example F) | 2,3-Difluoro-phenyl boronic acid (202 mg, 1.277 mmol) |

TABLE 23-continued

Examples 153-190

| Example | Chemical Name | Starting Material | Reacting Material |
|---|---|---|---|
| 159 | (R)-(1-methyl-pyrrolidin-3-yl)methyl(3'-chloro-6'-fluoro-[1,1'-biphenyl]-2-yl)carbamate (130 mg, 56%) | (R)-(1-methyl-pyrrolidin-3-yl)methyl(2-bromo-phenyl)carbamate (200 mg, 0.639 mmol) (Synthesis Example F) | 3-Chloro-6-fluorophenyl boronic acid (223 mg, 1.277 mmol) |
| 160 | (S)-(1-methyl-pyrrolidin-2-yl)methyl(3'-fluoro-[1,1'-biphenyl]-2-yl)carbamate (183 mg, 87%) | (S)-(1-methyl-pyrrolidin-2-yl)-methyl(2-bromo-phenyl)carbamate (200 mg, 0.64 mmol) (Synthesis Example M) | 3-Fluorophenyl-boronic acid (107 mg, 0.77 mmol) |
| 161 | (S)-(1-methyl-pyrrolidin-2-yl)methyl(3',5'-difluoro-[1,1'-biphenyl]-2-yl)carbamate (163 mg, 74%) | (S)-(1-methyl-pyrrolidin-2-yl)-methyl(2-bromo-phenyl)carbamate (200 mg, 0.64 mmol) (Synthesis Example M) | 3,5-Difluoro-phenylboronic acid (121 mg, 0.77 mmol) |
| 162 | (S)-(1-methyl-pyrrolidin-2-yl)methyl(3',4'-difluoro-[1,1'-biphenyl]-2-yl)carbamate (105 mg, 95%) | (S)-(1-methyl-pyrrolidin-2-yl)-methyl(2-bromo-phenyl)carbamate (100 mg, 0.32 mmol) (Synthesis Example M) | 3,4-Difluoro-phenylboronic acid (101 mg, 0.64 mmol) |
| 163 | (S)-(1-methyl-pyrrolidin-2-yl)methyl (2',4',5'-trifluoro-[1,1'-biphenyl]-2-yl)carbamate (79 mg, 68%) | (S)-(1-methyl-pyrrolidin-2-yl)methyl(2-bromo-phenyl)carbamate (100 mg, 0.32 mmol) (Synthesis Example M) | 2,4,5-Trifluoro-phenylboronic acid (113 mg, 0.64 mmol) |
| 164 | (S)-(1-methyl-pyrrolidin-2-yl)methyl(4'-chloro-[1,1'-biphenyl]-2-yl)carbamate (103 mg, 94%) | (S)-(1-methyl-pyrrolidin-2-yl)-methyl(2-bromo-phenyl)carbamate (100 mg, 0.32 mmol) (Synthesis Example M) | 4-Chlorophenyl-boronic acid (100 mg, 0.64 mmol) |
| 165 | (S)-(1-methyl-pyrrolidin-2-yl)methyl(3'-chloro-[1,1'-biphenyl]-2-yl)carbamate (70 mg, 64%) | (S)-(1-methyl-pyrrolidin-2-yl)-methyl(2-bromo-phenyl)carbamate (100 mg, 0.32 mmol) (Synthesis Example M) | 3-Chlorophenyl-boronic acid (100 mg, 0.64 mmol) |
| 166 | (S)-(1-methyl-pyrrolidin-2-yl)methyl(3',4'-dichloro-[1,1'-biphenyl]-2-yl)carbamate (96 mg, 79%) | (S)-(1-methyl-pyrrolidin-2-yl)-methyl(2-bromo-phenyl)carbamate (100 mg, 0.32 mmol) (Synthesis Example M) | 3,4-Dichloro-phenylboronic acid (122 mg, 0.64 mmol) |
| 167 | (S)-(1-methyl-pyrrolidin-2-yl)methyl(2',4'-dichloro-[1,1'-biphenyl]-2-yl)carbamate (83 mg, 69%) | (S)-(1-methyl-pyrrolidin-2-yl)-methyl(2-bromo-phenyl)carbamate (100 mg, 0.32 mmol) (Synthesis Example M) | 2,4-Dichloro-phenylboronic acid (122 mg, 0.64 mmol) |
| 168 | (S)-(1-methyl-pyrrolidin-2-yl)methyl(3'-hydroxy-[1,1'-biphenyl]-2-yl)carbamate (160 mg, 77%) | (S)-(1-methyl-pyrrolidin-2-ylmethyl(2-bromo-phenyl)carbamate (200 mg, 0.64 mmol) (Synthesis Example M) | 3-Hydroxyphenyl-boronic acid (106 mg, 0.77 mmol) |

TABLE 23-continued

Examples 153-190

| Example | Chemical Name | Starting Material | Reacting Material |
|---|---|---|---|
| 169 | (S)-(1-methyl-pyrrolidin-2-yl)methyl(3'-cyano-[1,1'-biphenyl]-2-yl)carbamate (17 mg, 13%) | (S)-(1-methyl-pyrrolidin-2-yl)-methyl(2-bromo-phenyl)carbamate (200 mg, 0.64 mmol) (Synthesis Example M) | 3-Cyanophenyl-boronic acid (113 mg, 0.77 mmol) |
| 170 | (S)-(1-methyl-pyrrolidin-2-yl)methyl(3'-amino-[1,1'-biphenyl]-2-yl)carbamate (78 mg, 38%) | (S)-(1-methyl-pyrrolidin-2-yl)-methyl(2-bromo-phenyl)carbamate (200 mg, 0.64 mmol) (Synthesis Example M) | 3-Aminophenyl-boronic acid (105 mg, 0.77 mmol) |
| 171 | (S)-(1-methyl-pyrrolidin-2-yl)methyl (3',4',5-trifluoro-[1,1'-biphenyl]-2-yl)carbamate (88 mg, 81%) | (S)-(1-methyl-pyrrolidin-2-yl)-methyl(2-bromo-4-fluorophenyl)-carbamate (100 mg, 0.30 mmol) (Synthesis Example N) | 3,4-Difluoro-phenylboronic acid (95 mg, 0.60 mmol) |
| 172 | (S)-(1-methyl-pyrrolidin-2-yl)methyl(3',5,5'-trifluoro-[1,1'-biphenyl]-2-yl)carbamate (180 mg, 83%) | (S)-(1-methyl-pyrrolidin-2-yl)-methyl(2-bromo-4-fluorophenyl)-carbamate (200 mg, 0.60 mmol) (Synthesis Example N) | 3,5-Difluoro-phenylboronic acid (190 mg, 1.20 mmol) |
| 173 | (S)-(1-methyl-pyrrolidin-2-yl)methyl (2',4',5,5'-tetrafluoro-[1,1'-biphenyl]-2-yl)carbamate (188 mg, 82%) | (S)-(1-methyl-pyrrolidin-2-yl)-methyl(2-bromo-4-fluorophenyl)-carbamate (200 mg, 0.60 mmol) (Synthesis Example N) | 2,4,5-Trifluoro-phenylboronic acid (211 mg, 1.20 mmol) |
| 174 | (S)-(1-methyl-pyrrolidin-2-yl)methyl(3'-chloro-5-fluoro-[1,1'-biphenyl]-2-yl)carbamate (171 mg, 79%) | (S)-(1-methyl-pyrrolidin-2-yl)-methyl(2-bromo-4-fluorophenyl)-carbamate (200 mg, 0.60 mmol) (Synthesis Example N) | 3-Chlorophenyl-boronic acid (188 mg, 1.20 mmol) |
| 175 | (S)-(1-methyl-pyrrolidin-2-yl)methyl (4'-chloro-5-fluoro-[1,1'-biphenyl]-2-yl)carbamate (198 mg, 91%) | (S)-(1-methyl-pyrrolidin-2-yl)-methyl(2-bromo-4-fluorophenyl)-carbamate (200 mg, 0.60 mmol) (Synthesis Example N) | 4-Chlorophenyl-boronic acid (188 mg, 1.20 mmol) |
| 176 | (S)-(1-methyl-pyrrolidin-2-yl)methyl (2',4'-dichloro-5-fluoro-[1,1'-biphenyl]-2-yl)carbamate (146 mg, 61%) | (S)-(1-methyl-pyrrolidin-2-yl)-methyl(2-bromo-4-fluorophenyl)-carbamate (200 mg, 0.60 mmol) (Synthesis Example N) | 2,4-Dichlorophenyl-boronic acid (230 mg, 1.20 mmol) |
| 177 | (S)-(1-methyl-pyrrolidin-2-yl)methyl (3',4'-dichloro-5-fluoro-[1,1'-biphenyl]-2-yl)carbamate (76 mg, 64%) | (S)-(1-methyl-pyrrolidin-2-yl)-methyl(2-bromo-4-fluorophenyl)-carbamate (100 mg, 0.30 mmol) (Synthesis Example N) | 3,4-Dichlorophenyl-boronic acid (115 mg, 0.60 mmol) |

TABLE 23-continued

Examples 153-190

| Example | Chemical Name | Starting Material | Reacting Material |
|---|---|---|---|
| 178 | (S)-(1-methyl-pyrrolidin-2-yl)methyl (3'-cyano-5-fluoro-[1,1'-biphenyl]-2-yl)carbamate (117 mg, 55%) | (S)-(1-methyl-pyrrolidin-2-yl)-methyl(2-bromo-4-fluorophenyl)-carbamate (200 mg, 0.60 mmol) (Synthesis Example N) | 3-Cyanophenyl-boronic acid (176 mg, 1.20 mmol) |
| 179 | (S)-(1-methyl-pyrrolidin-2-yl)methyl(3'-hydroxy-5-fluoro-[1,1'-biphenyl]-2-yl)carbamate (66 mg, 64%) | (S)-(1-methyl-pyrrolidin-2-yl)-methyl(2-bromo-4-fluorophenyl)-carbamate (100 mg, 0.30 mmol) (Synthesis Example N) | 3-Hydroxyphenyl-boronic acid (83 mg, 0.60 mmol) |
| 180 | (S)-(1-methyl-pyrrolidin-2-yl)methyl(5-fluoro-3'-(trifluoromethyl)-[1,1'-biphenyl]-2-yl)carbamate (43 mg, 36%) | (S)-(1-methyl-pyrrolidin-2-yl)-methyl(2-bromo-4-fluorophenyl)-carbamate (100 mg, 0.30 mmol) (Synthesis Example N) | 3-(Trifluoro-methyl)phenyl-boronic acid (115 mg, 0.60 mmol) |
| 181 | (S)-(1-methyl-pyrrolidin-2-yl)methyl(3'-chloro-4,4',5-trifluoro-[1,1'-biphenyl]-2-yl)carbamate (57 mg, 25%) | (S)-(1-methyl-pyrrolidin-2-yl)-methyl(2-bromo-4,5-difluorophenyl)-carbamate (200 mg, 0.57 mmol) (Synthesis Example P) | 3-Chloro-4-fluorophenyl boronic acid (200 mg, 1.15 mmol) |
| 182 | (R)-(1-methyl-pyrrolidin-3-yl)methyl (3'-chloro-4,5-difluoro-[1,1'-biphenyl]-2-yl)carbamate (50 mg, 25%) | (R)-(1-methyl-pyrrolidin-3-yl)-methyl(2-bromo-4,5-difluorophenyl)-carbamate (180 mg, 1.52 mmol) (Synthesis Example L) | 3-Chlorophenyl boronic acid (161 mg, 1.03 mmol) |
| 183 | 2-(1-Methyl-pyrrolidin-2-yl)ethyl (2',4'-difluoro-[1,1'-biphenyl]-2-yl)carbamate (50 mg, 15%) | 2-(1-Methyl-pyrrolidin-2-yl)-ethyl(2-iodo-phenyl)carbamate (300 mg, 0.917 mmol) (Synthesis Example A) | 2,4-Difluoro-phenyl boronic acid (290 mg, 1.834 mmol) |
| 184 | 2-(1-Methyl-pyrrolidin-2-yl)ethyl(2',3'-difluoro-[1,1'-biphenyl]-2-yl)carbamate (50 mg, 15%) | 2-(1-Methyl-pyrrolidin-2-yl)-ethyl(2-iodo-phenyl)carbamate (300 mg, 0.917 mmol) (Synthesis Example A) | 2,3-Difluoro-phenyl boronic acid (290 mg, 1.834 mmol) |
| 185 | 2-(1-Methyl-pyrrolidin-2-yl)ethyl(2',6'-difluoro-[1,1'-biphenyl]-2-yl)carbamate (50 mg, 15%) | 2-(1-Methyl-pyrrolidin-2-yl)-ethyl(2-iodo-phenyl)carbamate (300 mg, 0.917 mmol) (Synthesis Example A) | 2,6-Difluoro-phenyl boronic acid (290 mg, 1.834 mmol) |
| 186 | 2-(1-Methyl-pyrrolidin-2-yl)ethyl (5'-chloro-2'-fluoro-[1,1'-biphenyl]-2-yl)carbamate (160 mg, 46%) | 2-(1-Methyl-pyrrolidin-2-yl)-ethyl(2-iodo-phenyl)carbamate (300 mg, 0.917 mmol) (Synthesis Example A) | 5-Chloro-2-fluorophenyl boronic acid (320 mg, 1.834 mmol) |
| 187 | (S)-(1-methyl-pyrrolidin-2-yl)methyl(2'-fluoro-[1,1'- | (S)-(1-methyl-pyrrolidin-2-yl)-methyl(2-bromo-phenyl)carbamate | 2-Fluorophenyl boronic acid (268 mg, 1.916 mmol) |

TABLE 23-continued

Examples 153-190

| Example | Chemical Name | Starting Material | Reacting Material |
|---|---|---|---|
| | biphenyl]-2-yl)carbamate (205 mg, 65%) | (300 mg, 0.958 mmol) (Synthesis Example M) | |
| 188 | (S)-(1-methyl-pyrrolidin-2-yl)methyl(2',4'-difluoro-[1,1'-biphenyl]-2-yl)carbamate (250 mg, 75%) | (S)-(1-methyl-pyrrolidin-2-yl)-methyl(2-bromo-phenyl)carbamate (300 mg, 0.958 mmol) (Synthesis Example M) | 2,4-Difluoro-phenyl boronic acid (303 mg, 1.916 mmol) |
| 189 | (S)-(1-methyl-pyrrolidin-2-yl)methyl(2',3'-difluoro-[1,1'-biphenyl]-2-yl)carbamate (100 mg, 30%) | (S)-(1-methyl-pyrrolidin-2-yl)-methyl(2-bromo-phenyl)carbamate (300 mg, 0.958 mmol) (Synthesis Example M) | 2,3-Difluoro-phenyl boronic acid (303 mg, 1.916 mmol) |
| 190 | (S)-(1-methyl-pyrrolidin-2-yl)methyl(3'-chloro-6'-fluoro-[1,1'-biphenyl]-2-yl)carbamate (150 mg, 43%) | (S)-(1-methyl-pyrrolidin-2-yl)-methyl(2-bromo-phenyl)carbamate (300 mg, 0.958 mmol) (Synthesis Example M) | 3-Chloro-6-fluorophenyl boronic acid (334 mg, 1.916 mmol) |

[Example 191] Synthesis of (R)-(1-methylpyrrolidin-3-yl)-methyl (3',5'-dimethyl-[1,1'-biphenyl]-2-yl)carbamate

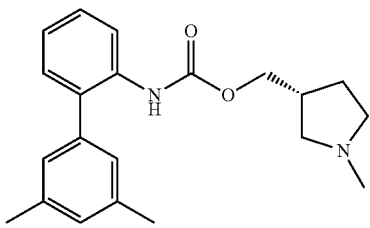 [SMILES: Cc1cc(C)cc(-c2ccccc2NC(=O)OC[C@@H]2CCN(C)C2)c1]

(R)-(1-methylpyrrolidin-3-yl)methyl(2-bromophenyl)-carbamate (220 mg, 0.70 mmol) (Synthesis Example F) was dissolved in a mixed solution of ethanol (5 mL) and water (5 mL). 3,5-Dimethylboronic acid (211 mg, 1.41 mmol), potassium carbonate (194 mg, 1.41 mmol), di(acetato)dicyclohexylphenyl-phosphine palladium(II) and Polymer-bound FibreCat™ (28 mg) were added thereto. The reactant was stirred in a microwave oven at 110° C. for 30 minutes and cooled to room temperature. The same was filtering through celite and the solvent was removed by concentrating under reduced pressure. The same was extracted with water and dichloromethane. The organic layer was dried with anhydrous magnesium sulfate, filtered and concentrated. The resulting residue was purified with column chromatography to prepare the titled compound (134 mg, 56%).

Examples 192-195

Starting materials and reacting materials in Table 24 were used to prepare compounds of Examples 192-195 in the same manner as Example 191.

TABLE 24

Examples 192-195

| Example | Chemical Name | Starting Material | Reacting Material |
|---|---|---|---|
| 192 | (R)-(1-methyl-pyrrolidin-3-yl)methyl(5-fluoro-3'-methyl-[1,1'-biphenyl]-2-yl)carbamate (158 mg, 73%) | (R)-(1-methyl-pyrrolidin-3-yl)-methyl(2-bromo-4-fluorophenyl)-carbamate (210 mg, 0.63 mmol) (Synthesis Example H) | 3-Methylphenyl-boronic acid (172 mg, 1.27 mmol) |
| 193 | (R)-(1-methyl-pyrrolidin-3-yl)methyl(5-fluoro-3',5'-dimethyl-[1,1'-biphenyl]-2-yl)carbamate (82 mg, 39%) | (R)-(1-methyl-pyrrolidin-3-yl)-methyl(2-bromo-4-fluorophenyl)-carbamate (206 mg, 0.62 mmol) (Synthesis Example H) | 3,5-Dimethyl-phenylboronic acid (187 mg, 1.24 mmol) |
| 194 | (R)-(1-methyl-pyrrolidin-3-yl)methyl(3',5-difluoro-[1,1'-biphenyl]-2-yl)carbamate (124 mg, 55%) | (R)-(1-methyl-pyrrolidin-3-yl)-methyl(2-bromo-4-fluoro-phenyl-)carbamate (215 mg, 0.65 mmol) (Synthesis Example H) | 3-Fluorophenyl-boronic acid (182 mg, 1.30 mmol) |
| 195 | (R)-(1-methyl-pyrrolidin-3-yl)methyl(3'-chloro-5-fluoro-[1,1'-biphenyl]-2-yl)carbamate (151 mg, 66%) | (R)-(1-methyl-pyrrolidin-3-yl)-methyl(2-bromo-4-fluorophenyl)-carbamate (210 mg, 0.63 mmol) (Synthesis Example H) | 3-Chlorophenyl-boronic acid (198 mg, 1.27 mmol) |

[Example 196] Synthesis of (R)-(1-ethylpyrrolidin-3-yl)methyl (3'-chloro-4',5-difluoro-[1,1'-biphenyl]-2-yl)carbamate

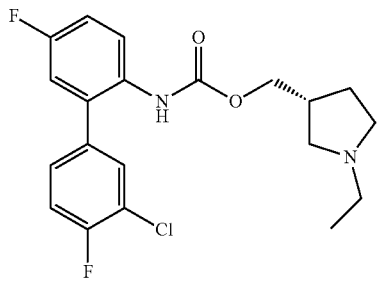 [SMILES: CCN1CC[C@@H](COC(=O)Nc2ccc(F)cc2-c2ccc(F)c(Cl)c2)C1]

[Step 1] Synthesis of (R)-(1-ethylpyrrolidin-3-yl) methyl (2-bromo-4-fluorophenyl)carbamate

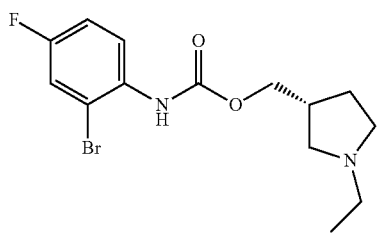 [SMILES: CCN1CC[C@@H](COC(=O)Nc2ccc(F)cc2Br)C1]

2-Bromo-4-fluorobenzoic acid (3 g, 13.70 mmol) and (R)-tert-butyl 3-(hydroxymethyl)pyrrolidine-1-carboxylate (3.31 g, 16.44 mmol) were used as starting materials to prepare titled compound (4.5 g, 79%) in the same manner as Synthesis Example F.

$^1$H NMR (CDCl$_3$): δ 8.00 (s, 1H), 7.28-7.24 (m, 1H), 7.05-7.00 (m, 1H), 4.21-4.10 (m, 2H), 3.06-3.03 (m, 1H), 2.90-2.87 (m, 1H), 2.84-2.71 (m, 5H), 2.17-2.12 (m, 1H), 1.76-1.71 (m, 1H), 1.24 (t, 3H, J=7.2 Hz)

[Step 2] Synthesis of (R)-(1-ethylpyrrolidin-3-yl) methyl (3'-chloro-4',5-difluoro-[1,1'-biphenyl]-2-yl)carbamate

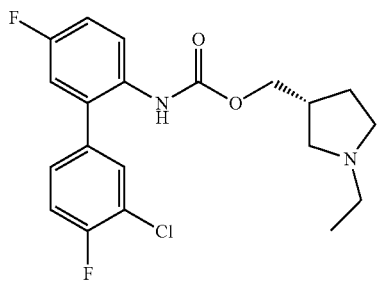 [SMILES: CCN1CC[C@@H](COC(=O)Nc2ccc(F)cc2-c2ccc(F)c(Cl)c2)C1]

(R)-(1-ethylpyrrolidin-3-yl)methyl(2-bromo-4-fluorophenyl)carbamate (165 mg, 0.48 mmol) and (3-chloro-4-fluoro-phenyl)boronic acid (167 mg, 0.96 mmol) were used as starting materials to prepare titled compound (143 mg, 76%) in the same manner as Example 136.

[Example 197] Synthesis of (S)-(1-methylpyrrolidin-2-yl)-methyl [1,1'-biphenyl]-2-ylcarbamate

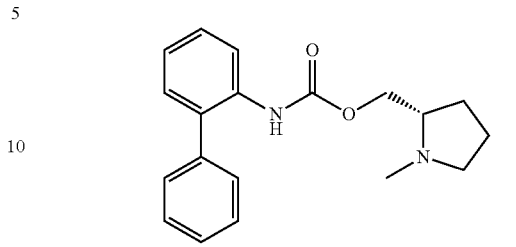

[1,1'-Biphenyl]-2-carboxylic acid (1 g, 5.05 mmol) was dissolved in toluene (20 mL). Biphenylphosphoryl azide (1.4 mL, 6.05 mmol) and triethylamine (0.71 mL, 5.05 mmol) were added thereto. The same was stirred at room temperature for minutes, and then stirred again under reflux at room temperature for 1 hour. The reactant was cooled to room temperature and (S)-(1-methylpyrrolidin-2-yl)methanol (0.72 mL, 6.05 mmol) was added thereto, and then stirred under reflux for 12 hours. The reactant was cooled to room temperature. The solvent was removed by concentrating under reduced pressure. The same was extracted with water and ethyl acetate. The organic layer was dried with anhydrous magnesium sulfate, filtered and concentrated. The resulting residue was purified with column chromatography to prepare the titled compound (458 mg, 29%).

Examples 198-207

Starting materials and reacting materials in Table 25 were used to prepare compounds of Examples 198-207 in the same manner as Example 197.

TABLE 25

Examples 198-207

| Example | Chemical Name | Starting Material | Reacting Material |
|---|---|---|---|
| 198 | (S)-(1-methyl-pyrrolidin-2-yl)methyl(4'-fluoro-[1,1'-biphenyl]-2-yl)carbamate (97 mg, 13%) | 4'-Fluoro-[1,1'-biphenyl]-2-carboxylic acid (482 mg, 2.23 mmol) (Synthesis Example 1) | (S)-(1-methyl-pyrrolidin-2-yl)-methanol (318 μL, 2.68 mmol) |
| 199 | (S)-(1-methyl-pyrrolidin-2-yl)methyl(3'-methyl-[1,1'-biphenyl]-2-yl)carbamate (379 mg, 51%) | 3'-Methyl-[1,1'-biphenyl]-2-carboxylic acid (488 mg, 2.3 mmol) (Synthesis Example 14) | (S)-(1-methyl-pyrrolidin-2-yl)-methanol (328 μL, 2.76 mmol) |
| 200 | (S)-(1-methyl-pyrrolidin-2-yl)methyl(5-fluoro-[1,1'-biphenyl]-2-yl)carbamate (42 mg, 7%) | 5-Fluoro-[1,1'-biphenyl]-2-carboxylic acid (400 mg, 1.85 mmol) (Synthesis Example 20) | (S)-(1-methyl-pyrrolidin-2-yl)-methanol (0.26 mL, 2.22 mmol) |
| 201 | (S)-(1-methyl-pyrrolidin-2-yl)methyl (5-fluoro-3'-methyl-[1,1'-biphenyl]-2-yl)carbamate (98 mg, 14%) | 5-Fluoro-3'-methyl-[1,1'-biphenyl]-2-carboxylic acid (460 mg, 2.0 mmol) (Synthesis Example 21) | (S)-(1-methyl-pyrrolidin-2-yl)-methanol (0.29 mL, 2.4 mmol) |

TABLE 25-continued

Examples 198-207

| Example | Chemical Name | Starting Material | Reacting Material |
|---|---|---|---|
| 202 | (S)-(1-methyl-pyrrolidin-2-yl)methyl (3',5-difluoro-[1,1'-biphenyl]-2-yl)carbamate (280 mg, 47%) | 3',5-Difluoro-[1,1'-biphenyl]-2-carboxylic acid (400 mg, 1.71 mmol) (Synthesis Example 17) | (S)-(1-methyl-pyrrolidin-2-yl)-methanol (0.24 mL, 2.05 mmol) |
| 203 | (S)-(1-methyl-pyrrolidin-2-yl)methyl (4',5-difluoro-[1,1'-biphenyl]-2-yl)carbamate (312 mg, 53%) | 4',5-Difluoro-[1,1'-biphenyl]-2-carboxylic acid (400 mg, 1.71 mmol) (Synthesis Example 18) | (S)-(1-methyl-pyrrolidin-2-yl)-methanol (0.24 mL, 2.05 mmol) |
| 204 | (S)-(1-methyl-pyrrolidin-2-yl)methyl (4-fluoro-[1,1'-biphenyl]-2-yl)carbamate (140 mg, 51%) | 4-Fluoro-[1,1'-biphenyl]-2-carboxylic acid (180 mg, 0.83 mmol) (Synthesis Example 22) | (S)-(1-methyl-pyrrolidin-2-yl)-methanol (0.12 mL, 1.0 mmol) |
| 205 | (S)-(1-methyl-pyrrolidin-2-yl)methyl(3',4-difluoro-[1,1'-biphenyl]-2-yl)carbamate (200 mg, 34%) | 3',4-Difluoro-[1,1'-biphenyl]-2-carboxylic acid (400 mg, 1.71 mmol) (Synthesis Example 23) | (S)-(1-methyl-pyrrolidin-2-yl)-methanol (0.24 mL, 2.05 mmol) |
| 206 | (S)-(1-methyl-pyrrolidin-2-yl)methyl(5-methyl-[1,1'-biphenyl]-2-yl)carbamate (189 mg, 41%) | 5-Methyl-[1,1'-biphenyl]-2-carboxylic acid (300 mg, 1.41 mmol) (Synthesis Example 25) | (S)-(1-methyl-pyrrolidin-2-yl)-methanol (201 μL, 1.7 mmol) |
| 207 | (S)-(1-methyl-pyrrolidin-2-yl)methyl(3'-fluoro-5-methyl-[1,1'-biphenyl]-2-yl)carbamate (265 mg, 89%) | 3'-Fluoro-5-methyl-[1,1'-biphenyl]-2-carboxylic acid (200 mg, 0.87 mmol) (Synthesis Example 26) | (S)-(1-methyl-pyrrolidin-2-yl)-methanol (124 μL, 1.04 mmol) |

[Example 208] Synthesis of (S)-(1-methylpyrrolidin-2-yl)-methyl(5-fluoro-3',5'-dimethyl-[1,1'-biphenyl]-2-yl)-carbamate

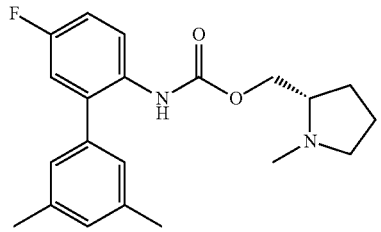 [SMILES: Cc1cc(C)cc(-c2cc(F)ccc2NC(=O)OC[C@@H]2CCCN2C)c1]

(S)-(1-methylpyrrolidin-2-yl)methyl(2-bromo-4-fluorophenyl)carbamate (200 mg, 0.60 mmol)(Synthesis Example N) was dissolved in a mixed solution of acetonitrile (3 mL) and water (3 mL). 3,5-Dimethylphenylboronic acid (181 mg, 1.20 mmol), sodium carbonate (95 mg, 0.90 mmol) and dichlorobistriphenylphosphine palladium (2 mg, 0.003 mmol) were added thereto. The reactant was stirred in a microwave oven at 150° C. for 10 minutes and cooled to room temperature. The same was filtered through celite and the solvent was removed by concentrating under reduced pressure. The same was extracted with water and ethyl acetate. The organic layer was dried with anhydrous magnesium sulfate, filtered and concentrated. The resulting residue was purified with column chromatography to prepare the titled compound (98 mg, 46%).

Examples 209-226

Starting materials and reacting materials in Table 26 were used to prepare compounds of Examples 209-226 in the same manner as Example 208.

TABLE 26

Examples 209-226

| Example | Chemical Name | Starting Material | Reacting Material |
|---|---|---|---|
| 209 | (S)-(1-methyl-pyrrolidin-2-yl)methyl (4'-(tert-butyl)-5-fluoro-[1,1'-biphenyl]-2-yl)carbamate (68 mg, 30%) | (S)-(1-methyl-pyrrolidin-2-yl)-methyl(2-bromo-4-fluorophenyl)-carbamate (200 mg, 0.60 mmol) (Synthesis Example N) | 4-tert-Butylphenyl-boronic acid (213 mg, 1.20 mmol) |
| 210 | (S)-(1-methyl-pyrrolidin-2-yl)methyl(3'-chloro-5,5'-difluoro-[1,1'- | (S)-(1-methyl-pyrrolidin-2-yl)-methyl(2-bromo-4-fluorophenyl)-carbamate (150 mg, 0.45 mmol) | (3-Chloro-5-fluoro)phenyl-boronic acid (158 mg, 0.90 mmol) |

TABLE 26-continued

Examples 209-226

| Example | Chemical Name | Starting Material | Reacting Material |
|---|---|---|---|
| | biphenyl]-2-yl)carbamate (55 mg, 32%) | (Synthesis Example N) | |
| 211 | (S)-(1-methyl-pyrrolidin-2-yl)methyl(3'-chloro-4',5-difluoro-[1,1'-biphenyl]-2-yl)carbamate (56 mg, 16%) | (S)-(1-methyl-pyrrolidin-2-yl)methyl(2-bromo-4-fluorophenyl)-carbamate (300 mg, 0.91 mmol) (Synthesis Example N) | (3-Chloro-4-fluoro)phenyl-boronic acid (316 mg, 1.81 mmol) |
| 212 | (S)-(1-methyl-pyrrolidin-2-yl)methyl(4'-chloro-3',5-difluoro-[1,1'-biphenyl]-2-yl)carbamate (140 mg, 40%) | (S)-(1-methyl-pyrrolidin-2-yl)methyl(2-bromo-4-fluoro-phenyl)carbamate (300 mg, 0.91 mmol) (Synthesis Example N) | (3-Fluoro-4-chloro)phenyl-boronic acid (316 mg, 1.81 mmol) |
| 213 | (S)-(1-methyl-pyrrolidin-2-yl)methyl (3'-amino-5-fluoro-[1,1'-biphenyl]-2-yl)carbamate (46 mg, 45%) | (S)-(1-methyl-pyrrolidin-2-yl)-methyl(2-bromo-4-fluorophenyl)-carbamate (150 mg, 0.45 mmol) (Synthesis Example N) | 3-Aminophenyl-boronic acid (68 mg, 0.50 mmol) |
| 214 | (S)-(1-methyl-pyrrolidin-2-yl)methyl(2',5-difluoro-3'-(trifluoromethyl)-[1,1'-biphenyl]-2-yl)carbamate (17 mg, 10%) | (S)-(1-methyl-pyrrolidin-2-yl)-methyl(2-bromo-4-fluorophenyl)-carbamate (150 mg, 0.45 mmol) (Synthesis Example N) | (2-Fluoro-3-(trifluoromethyl)phenyl)boronic acid (187 mg, 0.90 mmol) |
| 215 | (S)-(1-methyl-pyrrolidin-2-yl)methyl(3'-chloro-5-fluoro-5'-(trifluoromethyl)-[1,1'-biphenyl]-2-yl)carbamate (80 mg, 41%) | (S)-(1-methyl-pyrrolidin-2-yl)-methyl(2-bromo-4-fluorophenyl)-carbamate (150 mg, 0.45 mmol) (Synthesis Example N) | (3-Chloro-5-(trifluoromethyl)phenyl)boronic acid (202 mg, 0.90 mmol) |
| 216 | (S)-(1-methyl-pyrrolidin-2-yl)methyl(3'-chloro-5-fluoro-5'-hydroxy-[1,1'-biphenyl]-2-yl)carbamate (35 mg, 24%) | (S)-(1-methyl-pyrrolidin-2-yl)-methyl(2-bromo-4-fluorophenyl)-carbamate (130 mg, 0.39 mmol) (Synthesis Example N) | (3-Chloro-5-hydroxyphenyl)-boronic acid (135 mg, 0.79 mmol) |
| 217 | (S)-(1-methyl-pyrrolidin-2-yl)methyl (3'-chloro-5-fluoro-5'-methoxy-[1,1'-biphenyl]-2-yl)carbamate (55 mg, 31%) | (S)-(1-methyl-pyrrolidin-2-yl)-methyl(2-bromo-4-fluorophenyl)-carbamate (150 mg, 0.45 mmol) (Synthesis Example N) | (3-Chloro-5-methoxyphenyl)-boronic acid (168 mg, 0.90 mmol) |
| 218 | (S)-(1-methyl-pyrrolidin-2-yl)methyl(5-fluoro-2',4'-bis(trifluoromethyl)-[1,1'-biphenyl]-2-yl)carbamate (85 mg, 41%) | (S)-(1-methyl-pyrrolidin-2-yl)-methyl(2-bromo-4-fluorophenyl)-carbamate (150 mg, 0.45 mmol) (Synthesis Example N) | (2,4-Bis-(trifluoromethyl)phenyl)boronic acid (230 mg, 0.90 mmol) |

TABLE 26-continued

Examples 209-226

| Example | Chemical Name | Starting Material | Reacting Material |
|---|---|---|---|
| 219 | (S)-(1-methyl-pyrrolidin-2-yl)methyl(3'-ethoxy-5-fluoro-[1,1'-biphenyl]-2-yl)carbamate (94 mg, 42%) | (S)-(1-methyl-pyrrolidin-2-yl)methyl(2-bromo-4-fluorophenyl)-carbamate (200 mg, 0.60 mmol) (Synthesis Example N) | 3-Ethoxyphenyl-boronic acid (200 mg, 1.20 mmol) |
| 220 | (S)-(1-methyl-pyrrolidin-2-yl)methyl (5-fluoro-3',4'-dimethoxy-[1,1'-biphenyl]-2-yl)carbamate (54 mg, 23%) | (S)-(1-methyl-pyrrolidin-2-yl)methyl(2-bromo-4-fluorophenyl)-carbamate (200 mg, 0.60 mmol) (Synthesis Example N) | 3,4-Dimethoxy-phenylboronic acid (218 mg, 1.20 mmol) |
| 221 | (S)-(1-methyl-pyrrolidin-2-yl)methyl(5-fluoro-3',5'-dimethoxy-[1,1'-biphenyl]-2-yl)carbamate (140 mg, 60%) | (S)-(1-methyl-pyrrolidin-2-yl)methyl(2-bromo-4-fluorophenyl)-carbamate (200 mg, 0.60 mmol) (Synthesis Example N) | 3,5-Dimethoxy-phenylboronic acid (218 mg, 1.20 mmol) |
| 222 | (S)-(1-methyl-pyrrolidin-2-yl)methyl(5-methoxy-[1,1'-biphenyl]-2-yl)carbamate (66 mg, 34%) | (S)-(1-methyl-pyrrolidin-2-yl)methyl(2-bromo-4-methoxyphenyl)-carbamate (200 mg, 0.58 mmol) (Synthesis Example O) | Phenylboronic acid (142 mg, 1.16 mmol) |
| 223 | (S)-(1-methyl-pyrrolidin-2-yl)methyl(3'-fluoro-5-methoxy-[1,1'-biphenyl]-2-yl)carbamate (99 mg, 55%) | (S)-(1-methyl-pyrrolidin-2-yl)methyl(2-bromo-4-methoxy-phenyl)carbamate (200 mg, 0.58 mmol) (Synthesis Example O) | 3-Fluorophenyl-boronic acid (162 mg, 1.16 mmol) |
| 224 | (S)-(1-methyl-pyrrolidin-2-yl)methyl(3'-chloro-5-methoxy-[1,1'-biphenyl]-2-yl)carbamate (117 mg, 54%) | (S)-(1-methyl-pyrrolidin-2-yl)methyl(2-bromo-4-methoxyphenyl)-carbamate (200 mg, 0.58 mmol) (Synthesis Example O) | 3-Chlorophenyl-boronic acid (181 mg, 1.16 mmol) |
| 225 | (S)-(1-methyl-pyrrolidin-2-yl)methyl (3',4'-dichloro-5-methoxy-[1,1'-biphenyl]-2-yl)carbamate (90 mg, 38%) | (S)-(1-methyl-pyrrolidin-2-yl)methyl(2-bromo-4-methoxyphenyl)-carbamate (200 mg, 0.58 mmol) (Synthesis Example O) | 3,4-Dichloro-phenylboronic acid (221 mg, 1.16 mmol) |
| 226 | (S)-(1-methyl-pyrrolidin-2-yl)methyl (3',5'-dichloro-5-methoxy-[1,1'-biphenyl]-2-yl)carbamate (110 mg, 46%) | (S)-(1-methyl-pyrrolidin-2-yl)methyl(2-bromo-4-methoxyphenyl)-carbamate (200 mg, 0.58 mmol) (Synthesis Example O) | 3,5-Dichloro-phenylboronic acid (221 mg, 1.16 mmol) |

[Experimental Example 1] Binding Assay on Human Muscarinic M3 Receptor

Cell membrane proteins (Perkin Elmer) wherein human muscarinic M3 receptor was overexpressed, [$^3$H]-methyl scopolamine and test compounds in various concentration were cultured in 0.2 ml of Tris-HCl buffer at 25° C. for 120 minutes. The same was filtered under suction through glass fiber filter (Whatman GF/B), and then the filter was washed 5 times with 1 ml of Tris-HCl buffer. The radioactivity of

[³H]-methyl scopolamine adsorbed on the filter was measured by a liquid scintillation counter. Non-specific binding was evaluated under existence of 5 μM of atropine. Affinity of the compound of the present invention to muscarinic M3 receptor was calculated as the dissociation constant ($K_i$), which can be calculated from concentration ($IC_{50}$) of test compounds inhibiting 50% of binding of [³H]-methyl scopolamine (i.e. labeled ligand) according to Cheng and Prusoff [Cheng and Prusoff, Biochem. Pharmacol., 22, 3099, 1973]. In following Table, compounds having stronger binding affinity to human muscarinic M3 receptor have lower dissociation constant ($K_i$).

TABLE 27

Binding affinity to human muscarine M3 receptor

| Example | Binding Affinity to M3 Receptor, $K_i$ (nM) |
|---|---|
| 1 | 4.42 |
| 2 | 8.69 |
| 3 | 11.58 |
| 4 | 2.93 |
| 5 | 1101.45 |
| 6 | 2.47 |
| 7 | 31.84 |
| 8 | 1.33 |
| 9 | 9.10 |
| 10 | 401.05 |
| 11 | 467.04 |
| 12 | 88.00 |
| 13 | 80.10 |
| 14 | 12.39 |
| 15 | 2.27 |
| 16 | 1056.28 |
| 17 | 1.00 |
| 18 | 6.98 |
| 19 | 4.17 |
| 20 | 20.72 |
| 21 | 2.25 |
| 22 | 3.79 |
| 23 | 6.40 |
| 24 | 31.01 |
| 25 | 115.46 |
| 26 | 18.52 |
| 27 | 56.72 |
| 28 | 844.79 |
| 29 | 931.06 |
| 30 | 830.16 |
| 31 | 311.47 |
| 32 | >1000 |
| 33 | 16.84 |
| 34 | 19.64 |
| 35 | 434.72 |
| 36 | >1000 |
| 37 | >1000 |
| 38 | 574.03 |
| 39 | 28.04 |
| 40 | 118.89 |
| 41 | 2.45 |
| 42 | 9.21 |
| 43 | 1.48 |
| 44 | 95.47 |
| 45 | 69.57 |
| 46 | 37.51 |
| 47 | 136.47 |
| 48 | 257.54 |
| 49 | 303.01 |
| 50 | >1000 |
| 51 | 101.48 |
| 52 | 10.02 |
| 53 | 1.34 |
| 54 | 125.95 |
| 55 | 38.76 |
| 56 | 12.52 |
| 57 | 34.83 |
| 58 | 26.31 |
| 59 | 6.42 |
| 60 | 118.72 |
| 61 | 217.94 |
| 62 | >1000 |
| 63 | 58.09 |
| 64 | >1000 |
| 65 | 71.32 |
| 66 | 6.98 |
| 67 | 16.32 |
| 68 | 13.23 |
| 69 | 108.98 |
| 70 | 8.17 |
| 71 | 134.09 |
| 72 | 58.83 |
| 73 | 4.84 |
| 74 | >1000 |
| 75 | 471.30 |
| 76 | >1000 |
| 77 | 22.00 |
| 78 | 4.62 |
| 80 | 27.38 |
| 81 | 30.35 |
| 82 | 18.89 |
| 83 | 18.29 |
| 84 | 34.94 |
| 86 | 111.04 |
| 87 | 94.38 |
| 88 | 99.67 |
| 89 | 2.43 |
| 90 | 1.97 |
| 91 | 4.50 |
| 92 | 10.66 |
| 93 | 4.12 |
| 94 | 6.18 |
| 95 | 6.27 |
| 96 | 17.57 |
| 97 | 35.17 |
| 98 | 46.18 |
| 99 | 8.10 |
| 100 | 2.43 |
| 101 | 3.79 |
| 102 | 12.86 |
| 103 | 12.96 |
| 104 | 14.18 |
| 105 | 19.55 |
| 106 | 0.80 |
| 107 | 752.18 |
| 108 | 3.95 |
| 109 | 5.33 |
| 110 | 9.13 |
| 111 | 10.79 |
| 112 | 3.77 |
| 113 | 1.92 |
| 114 | 4.23 |
| 115 | 7.49 |
| 116 | 12.60 |
| 117 | 1.60 |
| 118 | 2.42 |
| 119 | 42.34 |
| 120 | 9.70 |
| 121 | 1.75 |
| 122 | 87.80 |
| 123 | 52.84 |
| 124 | 8.12 |
| 125 | 2.67 |
| 126 | 24.79 |
| 127 | 69.36 |
| 128 | 3.41 |
| 129 | 12.56 |
| 130 | 2.10 |
| 131 | 12.01 |
| 132 | 4.64 |
| 133 | 34.48 |
| 134 | 46.90 |
| 135 | 24.15 |
| 136 | 1.59 |

TABLE 27-continued

Binding affinity to human muscarine M3 receptor

| Example | Binding Affinity to M3 Receptor, $K_i$ (nM) |
|---|---|
| 137 | 27.02 |
| 138 | >1000 |
| 139 | 82.67 |
| 140 | >1000 |
| 141 | 7.57 |
| 142 | 4.88 |
| 143 | 1.12 |
| 144 | 17.16 |
| 145 | 14.27 |
| 146 | 6.85 |
| 147 | 77.41 |
| 148 | 10.20 |
| 149 | 1.57 |
| 150 | 5.60 |
| 151 | 14.95 |
| 152 | 147.11 |
| 153 | >1000 |
| 154 | 16.67 |
| 155 | >1000 |
| 156 | 10.63 |
| 157 | 29.63 |
| 158 | 119.82 |
| 159 | 5.13 |
| 160 | 4.29 |
| 161 | 8.92 |
| 162 | 5.34 |
| 163 | 16.13 |
| 164 | 36.92 |
| 165 | 0.63 |
| 166 | 9.04 |
| 167 | 67.35 |
| 168 | 22.86 |
| 169 | 282.30 |
| 170 | 9.23 |
| 171 | 16.93 |
| 172 | 6.15 |
| 173 | 42.74 |
| 174 | 0.61 |
| 175 | 22.49 |
| 176 | >1000 |
| 177 | 6.32 |
| 178 | >1000 |
| 179 | 241.05 |
| 180 | 9.15 |
| 181 | 3.29 |
| 182 | >1000 |
| 183 | 18.91 |
| 184 | 63.46 |
| 185 | 46.09 |
| 186 | 4.68 |
| 187 | 10.66 |
| 188 | 13.73 |
| 189 | 65.59 |
| 190 | 2.17 |
| 191 | 30.78 |
| 192 | 4.60 |
| 193 | 45.83 |
| 194 | 6.30 |
| 195 | 1.08 |
| 196 | 7.67 |
| 197 | 0.78 |
| 198 | 1.87 |
| 199 | 0.80 |
| 200 | 2.03 |
| 201 | 2.70 |
| 202 | 2.18 |
| 203 | 2.36 |
| 204 | 3.53 |
| 205 | 7.95 |
| 206 | 7.32 |
| 207 | 13.45 |
| 208 | 110.05 |
| 209 | >1000 |
| 210 | 4.60 |
| 211 | 9.91 |
| 212 | >1000 |
| 213 | 53.03 |
| 214 | >1000 |
| 215 | >1000 |
| 216 | 60.13 |
| 217 | 222.89 |
| 218 | >1000 |
| 219 | >1000 |
| 220 | >1000 |
| 221 | >1000 |
| 222 | 28.27 |
| 223 | 120.66 |
| 224 | 15.14 |
| 225 | 53.65 |
| 226 | 16.71 |

[Experimental Example 2] Antagonism Assay on Human Muscarinic M3 Receptor

The antagonism assay for various compounds of the present invention was conducted on antagonism to human M3 receptor in Cos-7 cells that was transfected with plasmid coding human muscarinic M3 receptor. Test compounds in various concentrations were pre-treated to the cells for 3 minutes, and then the changes of intracellular calcium were measured after treating the same with carbachol (i.e. muscarinic receptor agonist). The FLIPR® Calcium 5 assay (Molecular Devices) and Flex3 device (Molecular Devices) were used to measure concentration of calcium. Amounts of calcium before and after carbachol treatment were set as 0% and 100% respectively. Inhibition rates (%) by the compounds for increase in intracellular calcium by carbachol were calculated. The antagonistic potency of the test compounds on human muscarinic M3 receptor was calculated as the functional inhibitory constant ($K_i$), which can be calculated from concentration (IC50) of compound inhibiting 50% of activity of carbachol according to Cheng and Prusoff equation. The compounds used in the experiment were identified as antagonists for human muscarinic M3 receptor, and lower $K_{4i}$ value means superior antagonistic potency

TABLE 28

Antagonistic potency for human muscarinic M3 receptor

| Example | Antagonism for M3 receptor, $K_i$ (nM) |
|---|---|
| 2 | 6.02 |
| 4 | 3.41 |
| 8 | 3.02 |
| 15 | 4.10 |
| 19 | 1.90 |
| 21 | 0.49 |
| 22 | 2.39 |
| 34 | 2.64 |
| 41 | 0.18 |
| 42 | 1.19 |
| 52 | 1.22 |
| 53 | 0.57 |
| 56 | 10.00 |
| 58 | 4.70 |
| 59 | 2.38 |
| 66 | 3.06 |
| 67 | 11.85 |
| 68 | 13.22 |

TABLE 28-continued

Antagonistic potency for human muscarinic M3 receptor

| Example | Antagonism for M3 receptor, $K_i$ (nM) |
|---|---|
| 70 | 1.95 |
| 73 | 4.75 |
| 77 | 10.00 |
| 89 | 0.16 |
| 90 | 0.17 |
| 91 | 1.32 |
| 95 | 0.75 |
| 100 | 0.64 |
| 114 | 0.58 |
| 115 | 0.32 |
| 116 | 1.21 |
| 117 | 0.34 |
| 118 | 0.77 |
| 120 | 1.03 |
| 124 | 2.86 |
| 125 | 0.33 |
| 126 | 17.47 |
| 128 | 1.20 |
| 129 | 6.24 |
| 130 | 1.14 |
| 131 | 1.86 |
| 132 | 0.75 |
| 135 | 16.53 |
| 136 | 0.25 |
| 141 | 0.35 |
| 142 | 1.04 |
| 143 | 0.68 |
| 144 | 1.42 |
| 145 | 2.97 |
| 146 | 1.57 |
| 148 | 2.22 |
| 149 | 0.10 |
| 150 | 1.34 |
| 151 | 2.67 |
| 156 | 1.15 |
| 157 | 3.25 |
| 159 | 0.46 |
| 166 | 1.33 |
| 181 | 0.29 |
| 183 | 2.57 |
| 186 | 0.34 |
| 187 | 0.48 |
| 188 | 2.23 |
| 190 | 0.95 |
| 194 | 0.58 |
| 195 | 0.43 |
| 196 | 1.54 |
| 199 | 0.26 |
| 207 | 3.52 |
| 211 | 10.00 |
| 224 | 7.5 |
| 226 | 4.99 |

[Experimental Example 3] Experiment on Rhythmic Bladder Contractions in Rats (In Vivo)

Female Sprague-Dawley rat was halothane-anesthetized, and a polyethylene catheter was inserted through urethra lay down straight and fixed. Urine in bladder was excreted through the catheter by gently massaging abdomen of the rat, and then removed. A three-way stopcock was connected to the catheter and a pressure transducer was connected to one side of the three-way stopcock to measure pressure, and a syringe was installed at the other side to inject 37° C. of saline solution. The saline solution was slowly injected until regular bladder contractions occurred repeatedly. When regular bladder contractions occurred stably, test compounds were administered intravenously through the tail vein. Inhibitory effect of the test compounds was evaluated by measuring degree of amplitude reduction of bladder contractions. The compounds of the present invention significantly reduced amplitude of bladder contractions when the compounds were administered at least 0.3 mg/kg or more.

TABLE 29

Rhythmic bladder contraction in rats

| Example | Inhibition of Rhythmic bladder contraction in rats (%, 0.3 mpk) |
|---|---|
| 1 | 26.1 ± 5.1 |
| 2 | 20.1 ± 3.1 |
| 3 | 15.9 ± 0.9 |
| 4 | 22.3 ± 4.9 |
| 6 | 28.5 ± 4.6 |
| 8 | 23.2 ± 2.3 |
| 9 | 9.6 ± 1.6 |
| 15 | 25.6 ± 2.2 |
| 17 | 27.9 ± 6.1 |
| 19 | 12.8 ± 3.0 |
| 22 | 16.7 ± 1.7 |
| 26 | 11.0 ± 2.5 |
| 34 | 20.1 ± 1.8 |
| 43 | 8.9 ± 2.3 |
| 52 | 10.8 ± 0.8 |
| 53 | 28.0 ± 5.0 |
| 59 | 11.6 ± 1.9 |
| 66 | 12.0 ± 1.4 |
| 70 | 9.7 ± 4.1 |
| 73 | 10.0 ± 1.0 |
| 78 | 17.9 ± 2.1 |
| 89 | 33.9 ± 3.5 |
| 90 | 27.4 ± 1.9 |
| 91 | 25.2 ± 2.5 |
| 93 | 27.3 ± 1.9 |
| 95 | 15.7 ± 0.8 |
| 99 | 16.3 ± 1.0 |
| 100 | 26.0 ± 6.0 |
| 101 | 20.1 ± 1.7 |
| 108 | 18.1 ± 1.4 |
| 109 | 18.1 ± 1.7 |
| 106 | 32.7 ± 5.2 |
| 112 | 34.8 ± 2.9 |
| 117 | 15.4 ± 0.1 |
| 121 | 31.4 ± 6.1 |
| 124 | 21.2 ± 0.7 |
| 125 | 22.6 ± 5.8 |
| 128 | 15.1 ± 3.4 |
| 129 | 15.7 ± 1.4 |
| 131 | 17.8 ± 2.5 |
| 136 | 33.2 ± 4.0 |
| 142 | 15.1 ± 3.4 |
| 143 | 24.3 ± 5.5 |
| 145 | 13.1 ± 3.0 |
| 146 | 8.2 ± 2.9 |
| 150 | 25.1 ± 2.5 |
| 160 | 15.5 ± 2.4 |
| 165 | 34.5 ± 2.5 |
| 166 | 10.2 ± 1.7 |
| 172 | 12.4 ± 2.7 |
| 177 | 11.3 ± 2.2 |
| 180 | 6.3 ± 1.3 |
| 181 | 18.1 ± 2.6 |
| 192 | 18.6 ± 3.6 |
| 194 | 24.6 ± 2.6 |
| 195 | 20.3 ± 2.6 |
| 197 | 32.8 ± 9.7 |
| 198 | 26.3 ± 2.4 |
| 199 | 27.8 ± 4.5 |
| 201 | 9.1 ± 3.0 |
| 202 | 17.3 ± 1.3 |
| 203 | 19.4 ± 4.0 |
| 204 | 23.3 ± 6.6 |
| 205 | 11.9 ± 3.7 |
| 207 | 18.2 ± 3.7 |

[Experimental Example 4] Acute Toxicity Test for Oral Administration on Rats

In order to confirm acute toxicity of the compounds of the present invention, following experiment was conducted. A low-dose group, a medi-dose group and a high-dose group, wherein the compounds of Examples were administered 100 mg/kg, 300 mg/kg and 1000 mg/kg respectively, were prepared. Methyl cellulose solution (0.5%) was prepared and orally administered to 3 rats of each group (i.e. both sexes of 6-week old Sprague-Dawley (SD) rats; male rats in 142-143 g; female rats in 126.3-127.3 g) in a volume of 10 mL/kg. Mortality, clinical signs and weight and the like were measured for 4 days, and discovered approximate lethal dose (ALD) therefrom were explained in Table 30 below. As shown in Table 30, approximate lethal dose of the test compounds were 1000 mg/kg or more, therefore the compounds were determined as safe drugs.

TABLE 30

Approximate lethal dose

| Example | Approximate Lethal Dose (ALD) |
|---|---|
| 15 | >1000 |
| 53 | >1000 |
| 89 | >1000 |
| 90 | >1000 |
| 91 | >1000 |
| 100 | >1000 |
| 136 | >1000 |
| 143 | >1000 |
| 150 | >1000 |
| 199 | >1000 |

INDUSTRIAL APPLICABILITY

The novel biphenyl derivatives, the isomers or pharmaceutically acceptable salts thereof according to the present invention acts as a muscarinic M3 receptor antagonist, and thus can be useful for the prevention or treatment of a disease selected from the group consisting of chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, and hyper salivation syndrome.

The invention claimed is:
1. A biphenyl derivative represented by Formula 1, a stereoisomer thereof, or a pharmaceutically acceptable salt thereof:

Formula 1 wherein:
$R_1$ is hydrogen, halogen, hydroxy, substituted or unsubstituted $C_1$-$C_6$ alkyl, or $C_1$-$C_6$ alkoxy;
$R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$;
$R_5$ is hydrogen or $C_1$-$C_6$ alkyl;
n is 0 or 1; and
$R_6$ is hydrogen or amino.

2. The biphenyl derivative, stereoisomer thereof or pharmaceutically acceptable salt thereof according to claim 1, wherein $R_1$ is hydrogen or halogen; $R_2$, $R_3$ and $R_4$ are each independently hydrogen, halogen, or $C_1$-$C_6$ alkyl; and $R_5$ is $C_1$-$C_6$ alkyl.

3. The biphenyl derivative, stereoisomer thereof or pharmaceutically acceptable salt thereof according to claim 1, wherein $R_1$ is hydrogen; $R_2$, $R_3$ and $R_4$ are independently hydrogen or halogen; $R_5$ is $C_1$-$C_6$ alkyl; and n is 0 or 1.

4. The biphenyl derivative, stereoisomer thereof or pharmaceutically acceptable salt thereof according to claim 1 selected from the group consisting of the following compounds:

2-(1-methylpyrrolidin-2-yl)ethyl (4'-fluoro-[1,1'-biphenyl]-2-yl)carbamate;
2-(1-methylpyrrolidin-2-yl)ethyl (3',5'-difluoro-[1,1'-biphenyl]-2-yl)carbamate;
2-(1-methylpyrrolidin-2-yl)ethyl (3',4',5'-trifluoro-[1,1'-biphenyl]-2-yl)carbamate;
2-(1-methylpyrrolidin-2-yl)ethyl (3'-fluoro-[1,1'-biphenyl]-2-yl)carbamate;
2-(1-methylpyrrolidin-2-yl)ethyl (4'-methoxy-[1,1'-biphenyl]-2-yl)carbamate;
2-(1-methylpyrrolidin-2-yl)ethyl [1,1'-biphenyl]-2-ylcarbamate;
2-(1-methylpyrrolidin-2-yl)ethyl (4'-chloro-[1,1'-biphenyl]-2-yl)carbamate;
2-(1-methylpyrrolidin-2-yl)ethyl (3'-chloro-[1,1'-biphenyl]-2-yl)carbamate;
2-(1-methylpyrrolidin-2-yl)ethyl (3',5'-dichloro-[1,1'-biphenyl]-2-yl)carbamate;
2-(1-methylpyrrolidin-2-yl)ethyl (4'-trifluoromethoxy-[1,1'-biphenyl]-2-yl)carbamate;
2-(1-methylpyrrolidin-2-yl)ethyl (4'-nitro-[1,1'-biphenyl]-2-yl)carbamate;
2-(1-methylpyrrolidin-2-yl)ethyl (3'-trifluoromethyl-[1,1'-biphenyl]-2-yl)carbamate;
2-(1-methylpyrrolidin-2-yl)ethyl (4'-trifluoromethyl-[1,1'-biphenyl]-2-yl)carbamate;
2-(1-methylpyrrolidin-2-yl)ethyl ((3'-fluoro-4'-methyl)-[1,1'-biphenyl]-2-yl)-carbamate;
2-(1-methylpyrrolidin-2-yl)ethyl (3'-methyl-[1,1'-biphenyl]-2-yl)carbamate;
2-(1-methylpyrrolidin-2-yl)ethyl (3'-ethoxy-[1,1'-biphenyl]-2-yl)carbamate;
2-(1-methylpyrrolidin-2-yl)ethyl (3'-chloro-5-fluoro-[1,1'-biphenyl]-2-yl)carbamate;
2-(1-methylpyrrolidin-2-yl)ethyl (3',5-difluoro-[1,1'-biphenyl]-2-yl)carbamate;
2-(1-methylpyrrolidin-2-yl)ethyl (4',5-difluoro-[1,1'-biphenyl]-2-yl)carbamate;
2-(1-methylpyrrolidin-2-yl)ethyl (3',5,5'-trifluoro-[1,1'-biphenyl]-2-yl)carbamate;
2-(1-methylpyrrolidin-2-yl)ethyl (5-fluoro-[1,1'-biphenyl]-2-yl)carbamate;
2-(1-methylpyrrolidin-2-yl)ethyl (5-fluoro-3'-methyl-[1,1'-biphenyl]-2-yl)carbamate;

2-(1-methylpyrrolidin-2-yl)ethyl (4-fluoro-[1,1'-biphenyl]-2-yl)carbamate;
2-(1-methylpyrrolidin-2-yl)ethyl (3',4-difluoro-[1,1'-biphenyl]-2-yl)carbamate;
2-(1-methylpyrrolidin-2-yl)ethyl (4-methoxy-[1,1'-biphenyl]-2-yl)carbamate;
2-(1-methylpyrrolidin-2-yl)ethyl (5-methyl-[1,1'-biphenyl]-2-yl)carbamate;
2-(1-methylpyrrolidin-2-yl)ethyl (3'-fluoro-5-methyl-[1,1'-biphenyl]-2-yl)carbamate;
2-(1-methylpyrrolidin-2-yl)ethyl (4'-cyano-[1,1'-biphenyl]-2-yl)carbamate;
2-(1-methylpyrrolidin-2-yl)ethyl (3'-(3-hydroxypropyl)-[1,1'-biphenyl]-2-yl)-carbamate;
2-(1-methylpyrrolidin-2-yl)ethyl (4'-(dimethylamino)-[1,1'-biphenyl]-2-yl)carbamate;
2-(1-methylpyrrolidin-2-yl)ethyl (4'-(tert-butyl)-[1,1'-biphenyl]-2-yl)carbamate;
2-(1-methylpyrrolidin-2-yl)ethyl (2'-amino-[1,1'-biphenyl]-2-yl)carbamate;
2-(1-methylpyrrolidin-2-yl)ethyl (3'-amino-[1,1'-biphenyl]-2-yl)carbamate;
2-(1-methylpyrrolidin-2-yl)ethyl (2'-fluoro-[1,1'-biphenyl]-2-yl)carbamate;
2-(1-methylpyrrolidin-2-yl)ethyl (2'-chloro-[1,1'-biphenyl]-2-yl)carbamate;
2-(1-methylpyrrolidin-2-yl)ethyl (2'-hydroxy-[1,1'-biphenyl]-2-yl)carbamate;
2-(1-methylpyrrolidin-2-yl)ethyl (3'-tert-butyl-5'-methyl-[1,1'-biphenyl]-2-yl)-carbamate;
2-(1-methylpyrrolidin-2-yl)ethyl (4'-fluoro-3'-(trifluoromethyl)-[1,1'-biphenyl]-2-yl)-carbamate;
2-(1-methylpyrrolidin-2-yl)ethyl (4'-amino-3'-chloro-[1,1'-biphenyl]-2-yl)carbamate;
2-(1-methylpyrrolidin-2-yl)ethyl (3'-hydroxy-[1,1'-biphenyl]-2-yl)carbamate;
2-(1-methylpyrrolidin-2-yl)ethyl (3'-chloro-4'-fluoro-[1,1'-biphenyl]-2-yl)carbamate;
2-(1-methylpyrrolidin-2-yl)ethyl (3',4,5-trifluoro-[1,1'-biphenyl]-2-yl)carbamate;
2-(1-methylpyrrolidin-2-yl)ethyl (3',4'-dichloro-5-fluoro-[1,1'-biphenyl]-2-yl)-carbamate;
2-(1-methylpyrrolidin-2-yl)ethyl (3'-ethyl-5-fluoro-[1,1'-biphenyl]-2-yl)carbamate;
2-(1-methylpyrrolidin-2-yl)ethyl (5-fluoro-3',5'-dimethyl-[1,1'-biphenyl]-2-yl)-carbamate;
2-(1-methylpyrrolidin-2-yl)ethyl (3'-amino-5-fluoro-[1,1'-biphenyl]-2-yl)carbamate;
2-(1-methylpyrrolidin-2-yl)ethyl (5-(trifluoromethyl)-[1,1'-biphenyl]-2-yl)carbamate;
2-(1-methylpyrrolidin-2-yl)ethyl (4'-fluoro-5-(trifluoromethyl)-[1,1'-biphenyl]-2-yl)-carbamate;
2-(1-methylpyrrolidin-2-yl)ethyl (3'-fluoro-5-(trifluoromethyl)-[1,1'-biphenyl]-2-yl)-carbamate;
2-(1-methylpyrrolidin-2-yl)ethyl (3',5'-difluoro-5-(trifluoromethyl)-[1,1'-biphenyl]-2-yl)carbamate;
2-(1-methylpyrrolidin-2-yl)ethyl (3'-chloro-5-(trifluoromethyl)-[1,1'-biphenyl]-2-yl)-carbamate;
2-(1-methylpyrrolidin-2-yl)ethyl (3'-chloro-5,5'-difluoro-[1,1'-biphenyl]-2-yl)-carbamate;
2-(1-methylpyrrolidin-2-yl)ethyl (3'-chloro-4',5-difluoro-[1,1'-biphenyl]-2-yl)-carbamate;
2-(1-methylpyrrolidin-2-yl)ethyl (4'-chloro-3',5-difluoro-[1,1'-biphenyl]-2-yl)-carbamate;
2-(1-methylpyrrolidin-2-yl)ethyl (3',5'-dichloro-5-fluoro-[1,1'-biphenyl]-2-yl)-carbamate;
2-(1-methylpyrrolidin-2-yl)ethyl (3',5'-dichloro-4',5-difluoro-[1,1'-biphenyl]-2-yl)-carbamate;
2-(1-methylpyrrolidin-2-yl)ethyl (3'-chloro-5-fluoro-5'-hydroxy-[1,1'-biphenyl]-2-yl)-carbamate;
2-(1-methylpyrrolidin-2-yl)ethyl (3'-chloro-5-fluoro-4'-hydroxy-[1,1'-biphenyl]-2-yl)-carbamate;
2-(1-methylpyrrolidin-2-yl)ethyl (5-fluoro-3',4'-dimethyl-[1,1'-biphenyl]-2-yl)-carbamate;
2-(1-methylpyrrolidin-2-yl)ethyl (5-methoxy-[1,1'-biphenyl]-2-yl)carbamate;
2-(1-methylpyrrolidin-2-yl)ethyl (3'-fluoro-5-methoxy-[1,1'-biphenyl]-2-yl)-carbamate;
2-(1-methylpyrrolidin-2-yl)ethyl (3',5'-difluoro-5-methoxy-[1,1'-biphenyl]-2-yl)-carbamate;
2-(1-methylpyrrolidin-2-yl)ethyl (3'-chloro-5-methoxy-[1,1'-biphenyl]-2-yl)-carbamate;
2-(1-methylpyrrolidin-2-yl)ethyl (3',5'-dichloro-5-methoxy-[1,1'-biphenyl]-2-yl)-carbamate;
2-(1-methylpyrrolidin-2-yl)ethyl (3'-chloro-4'-fluoro-5-methoxy-[1,1'-biphenyl]-2-yl)-carbamate;
2-(1-methylpyrrolidin-2-yl)ethyl (5-chloro-[1,1'-biphenyl]-2-yl)carbamate;
2-(1-methylpyrrolidin-2-yl)ethyl (5-chloro-3'-fluoro-[1,1'-biphenyl]-2-yl)carbamate;
2-(1-methylpyrrolidin-2-yl)ethyl (5-chloro-4'-fluoro-[1,1'-biphenyl]-2-yl)carbamate;
2-(1-methylpyrrolidin-2-yl)ethyl (5-chloro-3',5'-difluoro-[1,1'-biphenyl]-2-yl)-carbamate;
2-(1-methylpyrrolidin-2-yl)ethyl (3',5-dichloro-[1,1'-biphenyl]-2-yl)carbamate;
2-(1-methylpyrrolidin-2-yl)ethyl (3',5,5'-trichloro-[1,1'-biphenyl]-2-yl)carbamate;
2-(1-methylpyrrolidin-2-yl)ethyl (3',5-dichloro-5'-fluoro-[1,1'-biphenyl]-2-yl)-carbamate;
2-(1-methylpyrrolidin-2-yl)ethyl (3',5-dichloro-4'-fluoro-[1,1'-biphenyl]-2-yl)-carbamate;
(R)-(1-methylpyrrolidin-3-yl)methyl (3'-fluoro-4'-formyl-[1,1'-biphenyl]-2-yl)-carbamate;
2-(1-methylpyrrolidin-2-yl)ethyl (3',5'-difluoro-5-hydroxy-[1,1'-biphenyl]-2-yl)-carbamate;
2-(1-methylpyrrolidin-2-yl)ethyl (3',5'-dichloro-5-hydroxy-[1,1'-biphenyl]-2-yl)-carbamate;
2-(1-methylpyrrolidin-2-yl)ethyl (3'-chloro-4'-fluoro-5-hydroxy-[1,1'-biphenyl]-2-yl)carbamate;
(R)-pyrrolidin-3-ylmethyl [1,1'-biphenyl]-2-ylcarbamate;
(S)-pyrrolidin-3-ylmethyl [1,1'-biphenyl]-2-ylcarbamate;
(R)-pyrrolidin-3-ylmethyl (3',5'-difluoro-[1,1'-biphenyl]-2-yl)carbamate;
(S)-pyrrolidin-3-ylmethyl (3',5'-difluoro-[1,1'-biphenyl]-2-yl)carbamate;
(S)-pyrrolidin-3-ylmethyl (5-fluoro-[1,1'-biphenyl]-2-yl)carbamate;
(S)-pyrrolidin-3-ylmethyl (5-fluoro-3'-methyl-[1,1'-biphenyl]-2-yl)carbamate;
(R)-pyrrolidin-3-ylmethyl (3',5,5'-trifluoro-[1,1'-biphenyl]-2-yl)carbamate;
(S)-pyrrolidin-3-ylmethyl (3',5,5'-trifluoro-[1,1'-biphenyl]-2-yl)carbamate;
(R)-pyrrolidin-3-ylmethyl (5-methyl-[1,1'-biphenyl]-2-yl)carbamate;
(R)-pyrrolidin-3-ylmethyl (3'-fluoro-5-methyl-[1,1'-biphenyl]-2-yl)carbamate;
(S)-pyrrolidin-2-ylmethyl (4'-fluoro-[1,1'-biphenyl]-2-yl)carbamate;
(R)-(1-methylpyrrolidin-3-yl)methyl [1,1'-biphenyl]-2-ylcarbamate;

(S)-(1-methylpyrrolidin-3-yl)methyl [1,1'-biphenyl]-2-yl-carbamate;
(R)-(1-methylpyrrolidin-3-yl)methyl (3',5'-difluoro-[1,1'-biphenyl]-2-yl)carbamate;
(S)-(1-methylpyrrolidin-3-yl)methyl (3',5'-difluoro-[1,1'-biphenyl]-2-yl)carbamate;
(S)-(1-methylpyrrolidin-3-yl)methyl (5-fluoro-[1,1'-biphenyl]-2-yl)carbamate;
(S)-(1-methylpyrrolidin-3-yl)methyl (5-fluoro-3'-methyl-[1,1'-biphenyl]-2-yl)-carbamate;
(R)-(1-methylpyrrolidin-3-yl)methyl (3',5,5'-trifluoro-[1,1'-biphenyl]-2-yl)carbamate;
(S)-(1-methylpyrrolidin-3-yl)methyl (3',5,5'-trifluoro-[1,1'-biphenyl]-2-yl)carbamate;
(R)-(1-methylpyrrolidin-3-yl)methyl (5-methyl-[1,1'-biphenyl]-2-yl)carbamate;
(R)-(1-methylpyrrolidin-3-yl)methyl (3'-fluoro-5-methyl-[1,1'-biphenyl]-2-yl)-carbamate;
(S)-(1-methylpyrrolidin-2-yl)methyl (4'-fluoro-[1,1'-biphenyl]-2-yl)carbamate;
(R)-(1-methylpyrrolidin-3-yl)methyl (3'-methyl-[1,1'-biphenyl]-2-yl)carbamate;
(S)-(1-methylpyrrolidin-3-yl)methyl (3'-methyl-[1,1'-biphenyl]-2-yl)carbamate;
(R)-(1-ethylpyrrolidin-3-yl)methyl [1,1'-biphenyl]-2-yl-carbamate;
(S)-(1-ethylpyrrolidin-3-yl)methyl [1,1'-biphenyl]-2-yl-carbamate;
(R)-(1-ethylpyrrolidin-3-yl)methyl (3'-methyl-[1,1'-biphenyl]-2-yl)carbamate;
(S)-(1-ethylpyrrolidin-3-yl)methyl (3'-methyl-[1,1'-biphenyl]-2-yl)carbamate;
(S)-(1-ethylpyrrolidin-2-yl)methyl [1,1'-biphenyl]-2-yl-carbamate;
(S)-(1-isobutylpyrrolidin-2-yl)methyl [1,1'-biphenyl]-2-ylcarbamate;
(S)-(1-methylpyrrolidin-3-yl)methyl (3',5-difluoro-[1,1'-biphenyl]-2-yl)carbamate;
(R)-(1-methylpyrrolidin-2-yl)methyl [1,1'-biphenyl]-2-ylcarbamate;
(R)-(1-methylpyrrolidin-2-yl)methyl (3'-methyl-[1,1'-biphenyl]-2-yl)carbamate;
(R)-(1-methylpyrrolidin-2-yl)methyl (5-fluoro-3'-methyl-[1,1'-biphenyl]-2-yl)-carbamate;
(S)-(1-isopropylpyrrolidin-2-yl)methyl [1,1'-biphenyl]-2-ylcarbamate;
(R)-(1-methylpyrrolidin-3-yl)methyl (3'-fluoro-[1,1'-biphenyl]-2-yl)carbamate;
(R)-(1-methylpyrrolidin-3-yl)methyl (4'-fluoro-[1,1'-biphenyl]-2-yl)carbamate;
(R)-(1-methylpyrrolidin-3-yl)methyl (3',4'-difluoro-[1,1'-biphenyl]-2-yl)carbamate;
(S)-(1-methylpyrrolidin-3-yl)methyl (3'-fluoro-[1,1'-biphenyl]-2-yl)carbamate;
(R)-(1-methylpyrrolidin-3-yl)methyl (3'-chloro-[1,1'-biphenyl]-2-yl)carbamate;
(S)-(1-methylpyrrolidin-3-yl)methyl (3'-chloro-[1,1'-biphenyl]-2-yl)carbamate;
(S)-(1-methylpyrrolidin-3-yl)methyl (3',5'-dichloro-[1,1'-biphenyl]-2-yl)carbamate;
(S)-(1-methylpyrrolidin-3-yl)methyl (3'-chloro-5'-fluoro-[1,1'-biphenyl]-2-yl)-carbamate;
(S)-(1-methylpyrrolidin-3-yl)methyl (3'-chloro-4'-fluoro-[1,1'-biphenyl]-2-yl)-carbamate;
(S)-(1-methylpyrrolidin-3-yl)methyl (5-fluoro-3',5'-dimethyl-[1,1'-biphenyl]-2-yl)-carbamate;
(S)-(1-methylpyrrolidin-3-yl)methyl (3'-chloro-5-fluoro-5'-hydroxy-[1,1'-biphenyl]-2-yl)carbamate;
(S)-(1-methylpyrrolidin-3-yl)methyl (4',5-difluoro-[1,1'-biphenyl]-2-yl)carbamate;
(S)-(1-methylpyrrolidin-3-yl)methyl (3'-chloro-5-fluoro-[1,1'-biphenyl]-2-yl)-carbamate;
(S)-(1-methylpyrrolidin-3-yl)methyl (3',5'-dichloro-5-fluoro-[1,1'-biphenyl]-2-yl)-carbamate;
(S)-(1-methylpyrrolidin-3-yl)methyl (4'-chloro-5-fluoro-[1,1'-biphenyl]-2-yl)-carbamate;
(S)-(1-methylpyrrolidin-3-yl)methyl (3',4'-dichloro-5-fluoro-[1,1'-biphenyl]-2-yl)-carbamate;
(S)-(1-methylpyrrolidin-3-yl)methyl (3'-chloro-5,5'-difluoro-[1,1'-biphenyl]-2-yl)-carbamate;
(R)-(1-methylpyrrolidin-3-yl)methyl (3',4'-dichloro-[1,1'-biphenyl]-2-yl)carbamate;
(R)-(1-methylpyrrolidin-3-yl)methyl (3',5'-dichloro-[1,1'-biphenyl]-2-yl)carbamate;
(R)-(1-methylpyrrolidin-3-yl)methyl (3'-chloro-5'-fluoro-[1,1'-biphenyl]-2-yl)-carbamate;
(R)-(1-methylpyrrolidin-3-yl)methyl (5-fluoro-3'-amino-[1,1'-biphenyl]-2-yl)-carbamate;
(R)-(1-methylpyrrolidin-3-yl)methyl (3'-chloro-5-fluoro-5'-hydroxy-[1,1'-biphenyl]-2-yl)carbamate;
(R)-(1-methylpyrrolidin-3-yl)methyl (3',5'-dichloro-5-fluoro-[1,1'-biphenyl]-2-yl)-carbamate;
(R)-(1-methylpyrrolidin-3-yl)methyl (3'-chloro-4'-fluoro-[1,1'-biphenyl]-2-yl)-carbamate;
(R)-(1-methylpyrrolidin-3-yl)methyl (3'-hydroxy-[1,1'-biphenyl]-2-yl)carbamate;
(R)-(1-methylpyrrolidin-3-yl)methyl (3'-chloro-5'-(trifluoromethyl)-[1,1'-biphenyl]-2-yl)carbamate;
(R)-(1-methylpyrrolidin-3-yl)methyl (3'-chloro-5-fluoro-5'-methoxy-[1,1'-biphenyl]-2-yl)carbamate;
(R)-(1-methylpyrrolidin-3-yl)methyl (3'-chloro-5-fluoro-5'-(trifluoromethyl)-[1,1'-biphenyl]-2-yl)carbamate;
(R)-(1-methylpyrrolidin-3-yl)methyl (4',5-difluoro-[1,1'-biphenyl]-2-yl)carbamate;
(R)-(1-methylpyrrolidin-3-yl)methyl (3'-chloro-5,5'-difluoro-[1,1'-biphenyl]-2-yl)-carbamate;
(R)-(1-methylpyrrolidin-3-yl)methyl (3'-chloro-4',5-difluoro-[1,1'-biphenyl]-2-yl)carbamate;
(R)-(1-methylpyrrolidin-3-yl)methyl (2',5-difluoro-[1,1'-biphenyl]-2-yl)carbamate;
(R)-(1-methylpyrrolidin-3-yl)methyl (3',5-dichloro-[1,1'-biphenyl]-2-yl)carbamate;
(R)-(1-methylpyrrolidin-3-yl)methyl (3',5-dichloro-4'-fluoro-[1,1'-biphenyl]-2-yl)-carbamate;
(R)-(1-methylpyrrolidin-3-yl)methyl (3'-chloro-4'-fluoro-5-methoxy-[1,1'-biphenyl]-2-yl)carbamate;
(S)-(1-methylpyrrolidin-2-yl)methyl (3'-chloro-5'-fluoro-[1,1'-biphenyl]-2-yl)-carbamate;
(S)-(1-methylpyrrolidin-2-yl)methyl (3'-chloro-4'-fluoro-[1,1'-biphenyl]-2-yl)-carbamate;
(R)-(1-ethylpyrrolidin-3-yl)methyl (3'-chloro-4'-fluoro-[1,1'-biphenyl]-2-yl)-carbamate;
(R)-(1-isopropylpyrrolidin-3-yl)methyl (3'-chloro-4'-fluoro-[1,1'-biphenyl]-2-yl)-carbamate;
(R)-(1-methylpyrrolidin-3-yl)methyl (3'-(hydroxymethyl)-[1,1'-biphenyl]-2-yl)-carbamate;
(R)-(1-methylpyrrolidin-3-yl)methyl (3'-carbamoyl-[1,1'-biphenyl]-2-yl)carbamate;
(R)-(1-methylpyrrolidin-3-yl)methyl (3'-amino-[1,1'-biphenyl]-2-yl)carbamate;
(R)-(1-methylpyrrolidin-3-yl)methyl (3'-cyano-[1,1'-biphenyl]-2-yl)carbamate;

(R)-(1-methylpyrrolidin-3-yl)methyl (2'-fluoro-[1,1'-biphenyl]-2-yl)carbamate;
(R)-(1-methylpyrrolidin-3-yl)methyl (2',4'-difluoro-[1,1'-biphenyl]-2-yl)carbamate;
(R)-(1-methylpyrrolidin-3-yl)methyl (2',3'-difluoro-[1,1'-biphenyl]-2-yl)carbamate;
(R)-(1-methylpyrrolidin-3-yl)methyl (3'-chloro-6'-fluoro-[1,1'-biphenyl]-2-yl)-carbamate;
(S)-(1-methylpyrrolidin-2-yl)methyl (3'-fluoro-[1,1'-biphenyl]-2-yl)carbamate;
(S)-(1-methylpyrrolidin-2-yl)methyl (3',5'-difluoro-[1,1'-biphenyl]-2-yl)carbamate;
(S)-(1-methylpyrrolidin-2-yl)methyl (3',4'-difluoro-[1,1'-biphenyl]-2-yl)carbamate;
(S)-(1-methylpyrrolidin-2-yl)methyl (2',4',5'-trifluoro-[1,1'-biphenyl]-2-yl)carbamate;
(S)-(1-methylpyrrolidin-2-yl)methyl (4'-chloro-[1,1'-biphenyl]-2-yl)carbamate;
(S)-(1-methylpyrrolidin-2-yl)methyl (3'-chloro-[1,1'-biphenyl]-2-yl)carbamate;
(S)-(1-methylpyrrolidin-2-yl)methyl (3',4'-dichloro-[1,1'-biphenyl]-2-yl)carbamate;
(S)-(1-methylpyrrolidin-2-yl)methyl (2',4'-dichloro-[1,1'-biphenyl]-2-yl)carbamate;
(S)-(1-methylpyrrolidin-2-yl)methyl (3'-hydroxy-[1,1'-biphenyl]-2-yl)carbamate;
(S)-(1-methylpyrrolidin-2-yl)methyl (3'-cyano-[1,1'-biphenyl]-2-yl)carbamate;
(S)-(1-methylpyrrolidin-2-yl)methyl (3'-amino-[1,1'-biphenyl]-2-yl)carbamate;
(S)-(1-methylpyrrolidin-2-yl)methyl (3',4',5-trifluoro-[1,1'-biphenyl]-2-yl)carbamate;
(S)-(1-methylpyrrolidin-2-yl)methyl (3',5,5'-trifluoro-[1,1'-biphenyl]-2-yl)carbamate;
(S)-(1-methylpyrrolidin-2-yl)methyl (2',4',5,5'-tetrafluoro-[1,1'-biphenyl]-2-yl)-carbamate;
(S)-(1-methylpyrrolidin-2-yl)methyl (3'-chloro-5-fluoro-[1,1'-biphenyl]-2-yl)-carbamate;
(S)-(1-methylpyrrolidin-2-yl)methyl (4'-chloro-5-fluoro-[1,1'-biphenyl]-2-yl)-carbamate;
(S)-(1-methylpyrrolidin-2-yl)methyl (2',4'-dichloro-5-fluoro-[1,1'-biphenyl]-2-yl)-carbamate;
(S)-(1-methylpyrrolidin-2-yl)methyl (3',4'-dichloro-5-fluoro-[1,1'-biphenyl]-2-yl)-carbamate;
(S)-(1-methylpyrrolidin-2-yl)methyl (3'-cyano-5-fluoro-[1,1'-biphenyl]-2-yl)-carbamate;
(S)-(1-methylpyrrolidin-2-yl)methyl (3'-hydroxy-5-fluoro-[1,1'-biphenyl]-2-yl)-carbamate;
(S)-(1-methylpyrrolidin-2-yl)methyl (5-fluoro-3'-(trifluoromethyl)-[1,1'-biphenyl]-2-yl)carbamate;
(S)-(1-methylpyrrolidin-2-yl)methyl (3'-chloro-4,4',5-trifluoro-[1,1'-biphenyl]-2-yl)-carbamate;
(R)-(1-methylpyrrolidin-3-yl)methyl (3'-chloro-4,5-difluoro-[1,1'-biphenyl]-2-yl)-carbamate;
2-(1-methylpyrrolidin-2-yl)ethyl (2',4'-difluoro-[1,1'-biphenyl]-2-yl)carbamate;
2-(1-methylpyrrolidin-2-yl)ethyl (2',3'-difluoro-[1,1'-biphenyl]-2-yl)carbamate;
2-(1-methylpyrrolidin-2-yl)ethyl (2',6'-difluoro-[1,1'-biphenyl]-2-yl)carbamate;
2-(1-methylpyrrolidin-2-yl)ethyl (5'-chloro-2'-fluoro-[1,1'-biphenyl]-2-yl)carbamate;
(S)-(1-methylpyrrolidin-2-yl)methyl (2'-fluoro-[1,1'-biphenyl]-2-yl)carbamate;
(S)-(1-methylpyrrolidin-2-yl)methyl (2',4'-difluoro-[1,1'-biphenyl]-2-yl)carbamate;
(S)-(1-methylpyrrolidin-2-yl)methyl (2',3'-difluoro-[1,1'-biphenyl]-2-yl)carbamate;
(S)-(1-methylpyrrolidin-2-yl)methyl (3'-chloro-6'-fluoro-[1,1'-biphenyl]-2-yl)-carbamate;
(R)-(1-methylpyrrolidin-3-yl)methyl (3',5'-dimethyl-[1,1'-biphenyl]-2-yl)carbamate;
(R)-(1-methylpyrrolidin-3-yl)methyl (5-fluoro-3'-methyl-[1,1'-biphenyl]-2-yl)-carbamate;
(R)-(1-methylpyrrolidin-3-yl)methyl (5-fluoro-3',5'-dimethyl-[1,1'-biphenyl]-2-yl)-carbamate;
(R)-(1-methylpyrrolidin-3-yl)methyl (3',5-difluoro-[1,1'-biphenyl]-2-yl)carbamate;
(R)-(1-methylpyrrolidin-3-yl)methyl (3'-chloro-5-fluoro-[1,1'-biphenyl]-2-yl)-carbamate;
(R)-(1-ethylpyrrolidin-3-yl)methyl (3'-chloro-4',5-difluoro-[1,1'-biphenyl]-2-yl)-carbamate;
(S)-(1-methylpyrrolidin-2-yl)methyl [1,1'-biphenyl]-2-yl-carbamate;
(S)-(1-methylpyrrolidin-2-yl)methyl (4'-fluoro-[1,1'-biphenyl]-2-yl)carbamate;
(S)-(1-methylpyrrolidin-2-yl)methyl (3'-methyl-[1,1'-biphenyl]-2-yl)carbamate;
(S)-(1-methylpyrrolidin-2-yl)methyl (5-fluoro-[1,1'-biphenyl]-2-yl)carbamate;
(S)-(1-methylpyrrolidin-2-yl)methyl (5-fluoro-3'-methyl-[1,1'-biphenyl]-2-yl)-carbamate;
(S)-(1-methylpyrrolidin-2-yl)methyl (3',5-difluoro-[1,1'-biphenyl]-2-yl)carbamate;
(S)-(1-methylpyrrolidin-2-yl)methyl (4',5-difluoro-[1,1'-biphenyl]-2-yl)carbamate;
(S)-(1-methylpyrrolidin-2-yl)methyl (4-fluoro-[1,1'-biphenyl]-2-yl)carbamate;
(S)-(1-methylpyrrolidin-2-yl)methyl (3',4-difluoro-[1,1'-biphenyl]-2-yl)carbamate;
(S)-(1-methylpyrrolidin-2-yl)methyl (5-methyl-[1,1'-biphenyl]-2-yl)carbamate;
(S)-(1-methylpyrrolidin-2-yl)methyl (3'-fluoro-5-methyl-[1,1'-biphenyl]-2-yl)-carbamate;
(S)-(1-methylpyrrolidin-2-yl)methyl (5-fluoro-3',5'-dimethyl-[1,1'-biphenyl]-2-yl)-carbamate;
(S)-(1-methylpyrrolidin-2-yl)methyl (4'-(tert-butyl)-5-fluoro-[1,1'-biphenyl]-2-yl)-carbamate;
(S)-(1-methylpyrrolidin-2-yl)methyl (3'-chloro-5,5'-difluoro-[1,1'-biphenyl]-2-yl)-carbamate;
(S)-(1-methylpyrrolidin-2-yl)methyl (3'-chloro-4',5-difluoro-[1,1'-biphenyl]-2-yl)-carbamate;
(S)-(1-methylpyrrolidin-2-yl)methyl (4'-chloro-3',5-difluoro-[1,1'-biphenyl]-2-yl)-carbamate;
(S)-(1-methylpyrrolidin-2-yl)methyl (3'-amino-5-fluoro-[1,1'-biphenyl]-2-yl)-carbamate;
(S)-(1-methylpyrrolidin-2-yl)methyl (2',5-difluoro-3'-(trifluoromethyl)-[1,1'-biphenyl]-2-yl)carbamate;
(S)-(1-methylpyrrolidin-2-yl)methyl (3'-chloro-5-fluoro-5'-(trifluoromethyl)-[1,1'-biphenyl]-2-yl)carbamate;
(S)-(1-methylpyrrolidin-2-yl)methyl (3'-chloro-5-fluoro-5'-hydroxy-[1,1'-biphenyl]-2-yl)carbamate;
(S)-(1-methylpyrrolidin-2-yl)methyl (3'-chloro-5-fluoro-5'-methoxy-[1,1'-biphenyl]-2-yl)carbamate;
(S)-(1-methylpyrrolidin-2-yl)methyl (5-fluoro-2',4'-bis(trifluoromethyl)-[1,1'-biphenyl]-2-yl)carbamate;
(S)-(1-methylpyrrolidin-2-yl)methyl (3'-ethoxy-5-fluoro-[1,1'-biphenyl]-2-yl)-carbamate;
(S)-(1-methylpyrrolidin-2-yl)methyl (5-fluoro-3',4'-dimethoxy-[1,1'-biphenyl]-2-yl)-carbamate;
(S)-(1-methylpyrrolidin-2-yl)methyl (5-fluoro-3',5'-dimethoxy-[1,1'-biphenyl]-2-yl)-carbamate;

(S)-(1-methylpyrrolidin-2-yl)methyl (5-methoxy-[1,1'-biphenyl]-2-yl)carbamate;

(S)-(1-methylpyrrolidin-2-yl)methyl (3'-fluoro-5-methoxy-[1,1'-biphenyl]-2-yl)-carbamate;

(S)-(1-methylpyrrolidin-2-yl)methyl (3'-chloro-5-methoxy-[1,1'-biphenyl]-2-yl)-carbamate;

(S)-(1-methylpyrrolidin-2-yl)methyl (3',4'-dichloro-5-methoxy-[1,1'-biphenyl]-2-yl)-carbamate; and (S)-(1-methylpyrrolidin-2-yl)methyl (3',5'-dichloro-5-methoxy-[1,1'-biphenyl]-2-yl)-carbamate.

5. A method for preparing a compound of Formula 1 or a pharmaceutically acceptable salt thereof:

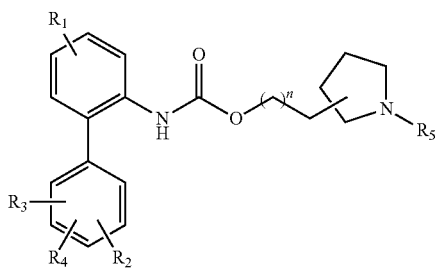

Formula 1 the method comprising a step of:
reacting a compound of Formula 2:

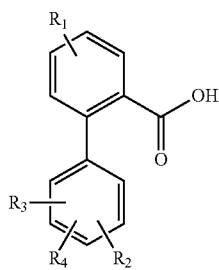

Formula 2 with a compound of Formula 3:

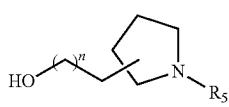

Formula 3 in the presence of a carbamate synthesis reagent, wherein:
the carbamate synthesis reagent is:
a mixture of diphenylphosphoryl azide (DPPA) and triethylamine; or
a mixture of propylphosphonic anhydride (T3P), trimethylsilyl azide (TMSN$_3$) and triethylamine; or
a mixture of sodium azide (NaN$_3$), tetrabutylammonium bromide and zinc(II) triflate;

R$_1$ is hydrogen, halogen, hydroxy, substituted or unsubstituted C$_1$-C$_6$ alkyl, or C$_1$-C$_6$ alkoxy;

R$_2$, R$_3$ and R$_4$ are each independently hydrogen, halogen, substituted or unsubstituted amino, nitro, cyano, hydroxy, substituted or unsubstituted C$_1$-C$_6$ alkyl, substituted or unsubstituted C$_1$-C$_6$ alkoxy, or —C(O)R$_6$;

R$_5$ is hydrogen or C$_1$-C$_6$ alkyl; and
n is 0 or 1.

6. A method for preparing a compound of Formula 1 or a pharmaceutically acceptable salt thereof:

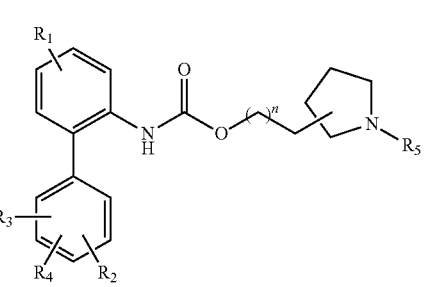

Formula 1 the method comprising the steps of:
(a) reacting a compound of Formula 2:

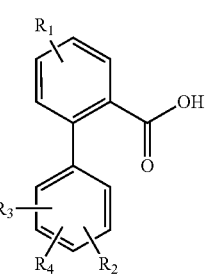

Formula 2 with a compound of Formula 3a:

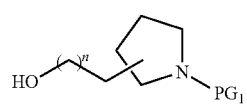

Formula 3a in the presence of a carbamate synthesis reagent to prepare a compound of Formula 4:

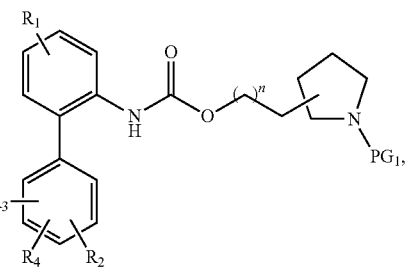

Formula 4 wherein:
the carbamate synthesis reagent is:
a mixture of diphenylphosphoryl azide (DPPA) and triethylamine; or a mixture of propylphosphonic anhydride (T3P), trimethylsilyl azide (TMSN$_3$) and triethylamine; or a mixture of sodium azide (NaN$_3$), tetrabutylammonium bromide and zinc(II) triflate;

(b) removing an amine protecting group from the compound of Formula 4 to prepare a compound of Formula 1a:

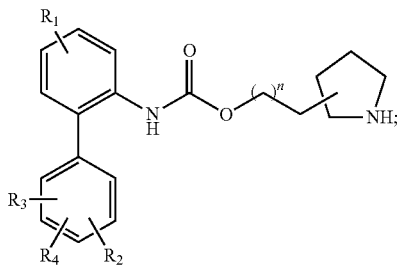

Formula 1a and introducing an R$_5$ substituent into the compound of Formula 1a to yield a compound of Formula 1, wherein:

R$_1$ is hydrogen, halogen, hydroxy, substituted or unsubstituted C$_1$-C$_6$ alkyl, or C$_1$-C$_6$ alkoxy;

R$_2$, R$_3$ and R$_4$ are each independently hydrogen, halogen, substituted or unsubstituted amino, nitro, cyano, hydroxy, substituted or unsubstituted C$_1$-C$_6$ alkyl, substituted or unsubstituted C$_1$-C$_6$ alkoxy, or —C(O)R$_6$;

R$_5$ is hydrogen or C$_1$-C$_6$ alkyl;

n is 0 or 1; and

PG$_1$ is an amine protecting group selected from the group consisting of Boc (tert-butyloxycarbonyl), benzyl, tert-butyl, PMB (4-methoxybenzyl), Fmoc (fluorenylmethyloxycarbonyl), Ts (tosylate), MOM (methoxymethyl), THP (tetrahydropyranyl), TBDMS (tert-butyldimethylsilyl), and TBDPS (tert-butyldiphenylsilyl).

7. The method of claim 5, wherein the compound of Formula 2 is prepared by the steps of:

reacting a compound of Formula 5:

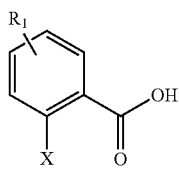

Formula 5 in the presence of an acid to prepare a compound of Formula 6:

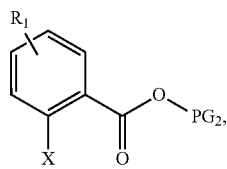

Formula 6 which has a carboxylic acid protecting group introduced therein;

coupling the compound of Formula 6 with a compound of Formula 7:

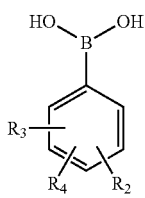

Formula 7 to prepare a compound of Formula 8:

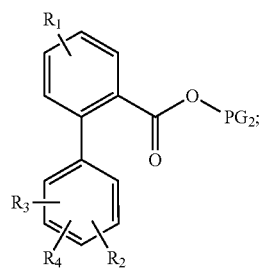

Formula 8 and de-esterifying the compound of Formula 8 in the presence of a base, wherein:

R$_1$ is hydrogen, halogen, hydroxy, substituted or unsubstituted C$_1$-C$_6$ alkyl, or C$_1$-C$_6$ alkoxy;

R$_2$, R$_3$ and R$_4$ are each independently hydrogen, halogen, substituted or unsubstituted amino, nitro, cyano, hydroxy, substituted or unsubstituted C$_1$-C$_6$ alkyl, substituted or unsubstituted C$_1$-C$_6$ alkoxy, or —C(O)R$_6$;

R$_5$ is hydrogen or C$_1$-C$_6$ alkyl;

n is 0 or 1;

X is halogen; and

PG$_2$ is a protecting group selected from the group consisting of a C$_1$-C$_4$ alkyl group, benzyl, PMB (4-methoxybenzyl), THP (tetrahydropyranyl), TBDMS (tert-butyldimethylsilyl), and TBDPS (tert-butyldiphenylsilyl).

8. A method for preparing a compound of Formula 1 or a pharmaceutically acceptable salt thereof:

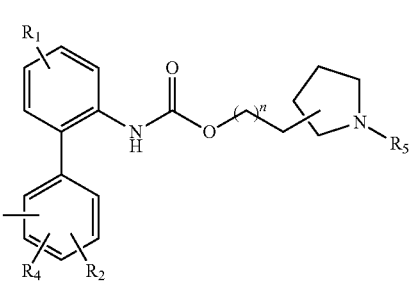

Formula 1 the method comprising the steps of:
 (a) reacting a compound of Formula 5:

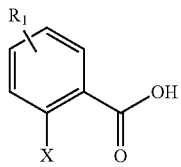

Formula 5 with a compound of Formula 3:

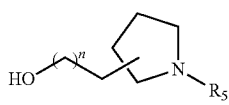

Formula 3 in the presence of a carbamate synthesis reagent to prepare a compound of Formula 9:

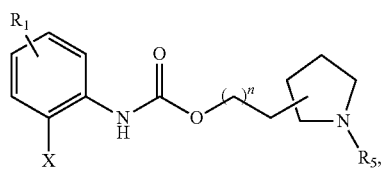

Formula 9 wherein the carbamate synthesis reagent is:
 a mixture of diphenylphosphoryl azide (DPPA) and triethylamine; or
 a mixture of propylphosphonic anhydride (T3P), trimethylsilyl azide (TMSN$_3$) and triethylamine; or
 a mixture of sodium azide (NaN$_3$), tetrabutylammonium bromide and zinc(II) triflate, and
 (b) coupling a compound of Formula 7:

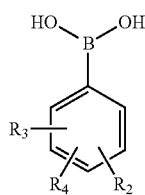

Formula 7 to the compound of formula 9 to yield the compound of Formula 1;
wherein
 $R_1$ is hydrogen, halogen, hydroxy, substituted or unsubstituted $C_1$-$C_6$ alkyl, or $C_1$-$C_6$ alkoxy;
 $R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$;
 $R_5$ is hydrogen or $C_1$-$C_6$ alkyl;
 n is 0 or 1; and
 X is halogen.

9. A method for preparing a compound of Formula 1 or a pharmaceutically acceptable salt thereof:

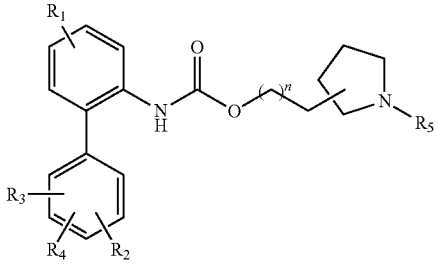

Formula 1 the method comprising the steps of:
 reacting a compound of Formula 5:

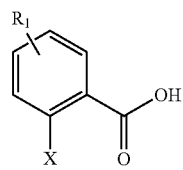

Formula 5 with a compound of Formula 3a:

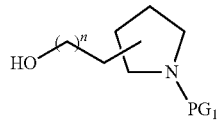

[Formula 3a]

in the presence of a carbamate synthesis reagent to prepare a compound of Formula 9a:

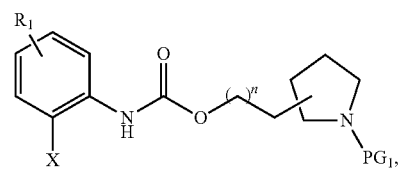

Formula 9a wherein the carbamate synthesis reagent is a mixture of diphenylphosphoryl azide (DPPA) and triethylamine, a mixture of propylphosphonic anhydride (T3P), trimethylsilyl azide (TMSN$_3$) and triethylamine, or a mixture of sodium azide (NaN$_3$), tetrabutylammonium bromide and zinc(II) triflate;
deprotecting the compound of Formula 9a to prepare a compound of Formula 9b:

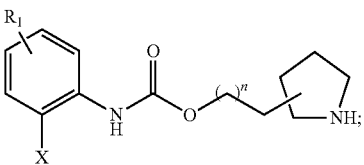

Formula 9b introducing an $R_5$ substituent into the compound of Formula 9b to prepare a compound of Formula 9:

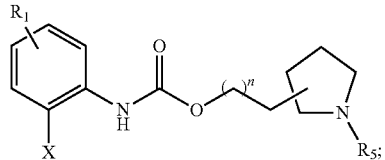
Formula 9 and
coupling a compound of Formula 7:

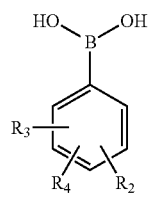
Formula 7 to the compound of Formula 9 to yield the compound of Formula 1,
wherein:
$R_1$ is hydrogen, halogen, hydroxy, substituted or unsubstituted $C_1$-$C_6$ alkyl, or $C_1$-$C_6$ alkoxy;
$R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$;
$R_5$ is hydrogen or $C_1$-$C_6$ alkyl;
n is 0 or 1;
X is halogen; and
$PG_1$ is the same as defined in claim 6.

10. A pharmaceutical composition, comprising the compound of claim 1, a stereoisomer thereof, or a pharmaceutically acceptable salt thereof as an active ingredient; and a pharmaceutically acceptable carrier or diluent.

11. A method for treating a disease responsive to blocking the activity of the muscarinic M3 receptor, wherein the disease is urinary incontinence, urinary urgency or overactive bladder, the method comprising administering a composition containing the compound of claim 1, a stereoisomer thereof, or a pharmaceutically acceptable salt thereof as an active ingredient to a mammal in need thereof.

12. The method of claim 6, wherein the compound of Formula 2 is prepared by the steps of:
reacting a compound of Formula 5:

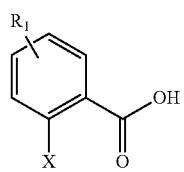
Formula 5 in the presence of an acid to prepare a compound of Formula 6:

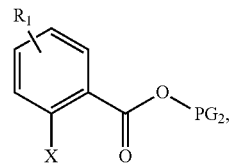
[Formula 6]

which has a carboxylic acid protecting group introduced therein;
coupling the compound of Formula 6 with a compound of Formula 7:

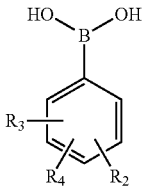
Formula 7 to prepare a compound of Formula 8:

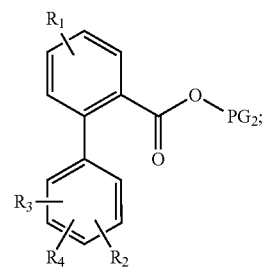
Formula 8 and
de-esterifying the compound of Formula 8 in the presence of a base,
wherein:
$R_1$ is hydrogen, halogen, hydroxy, substituted or unsubstituted $C_1$-$C_6$ alkyl, or $C_1$-$C_6$ alkoxy;
$R_2$, $R_3$ and $R_4$ are each independently hydrogen, halogen, substituted or unsubstituted amino, nitro, cyano, hydroxy, substituted or unsubstituted $C_1$-$C_6$ alkyl, substituted or unsubstituted $C_1$-$C_6$ alkoxy, or —C(O)$R_6$;
$R_5$ is hydrogen or $C_1$-$C_6$ alkyl;
n is 0 or 1;
X is halogen; and
$PG_2$ is a protecting group selected from the group consisting of a $C_1$-$C_4$ alkyl group, benzyl, PMB (4-methoxybenzyl), THP (tetrahydropyranyl), TBDMS (tert-butyldimethylsilyl), and TBDPS (tert-butyldiphenylsilyl).

13. The method of claim 11, wherein the mammal is a human.

* * * * *